United States Patent [19]

Bacus

[11] Patent Number: 5,018,209
[45] Date of Patent: May 21, 1991

[54] ANALYSIS METHOD AND APPARATUS FOR BIOLOGICAL SPECIMENS

[75] Inventor: James W. Bacus, Hinsdale, Ill.

[73] Assignee: Cell Analysis Systems, Inc., Lombard, Ill.

[21] Appl. No.: 927,285

[22] Filed: Nov. 4, 1986

Related U.S. Application Data

[63] Continuation-in-part of Ser. No. 794,937, Nov. 4, 1985, Pat. No. 4,741,043.

[51] Int. Cl.⁵ .............................................. G06K 9/00
[52] U.S. Cl. .................................. 382/6; 364/413.08; 356/39
[58] Field of Search ............... 382/6; 356/39, 40, 432, 356/410; 364/416, 413.07, 413.08, 413.09; 128/653, 665, 633, 653 R, 653 A; 358/101; 250/237 R

[56] References Cited

U.S. PATENT DOCUMENTS

| | | | |
|---|---|---|---|
| 3,297,879 | 3/1963 | Meyer | 250/237 R |
| 3,481,659 | 12/1969 | Rosenberg | 350/94 |
| 3,847,486 | 11/1974 | McCabe | 356/205 |
| 3,907,437 | 9/1975 | Hirschfeld | 356/39 |
| 3,977,791 | 8/1976 | Weber et al. | 356/168 |
| 4,000,417 | 12/1976 | Adkisson et al. | 356/39 |
| 4,017,192 | 4/1977 | Rosenthal | 356/39 |
| 4,045,772 | 8/1977 | Bouton et al. | 340/146.3 |
| 4,048,616 | 9/1977 | Hart et al. | 340/146.3 |
| 4,097,845 | 6/1978 | Bacus | 340/146.3 |
| 4,125,828 | 11/1978 | Resnick et al. | 340/146.3 |
| 4,175,860 | 11/1979 | Bacus | 356/39 |
| 4,199,748 | 4/1980 | Bacus | 340/146.3 |
| 4,213,036 | 7/1980 | Kopp et al. | 382/6 |
| 4,219,440 | 8/1980 | Runck et al. | 252/408 |
| 4,227,814 | 10/1980 | Soodak et al. | 356/410 |
| 4,232,970 | 11/1980 | Sawamura et al. | 356/432 |
| 4,257,709 | 3/1981 | Mostyn, Jr. | 356/40 |
| 4,307,376 | 12/1981 | Miller et al. | 340/146.3 |
| 4,362,386 | 12/1982 | Matsushita et al. | 356/39 |
| 4,389,669 | 6/1983 | Epstein et al. | 358/101 |
| 4,404,683 | 9/1983 | Kobayashi et al. | 382/6 |
| 4,446,871 | 5/1984 | Imura | 128/633 |
| 4,453,266 | 6/1984 | Bacus | 382/6 |
| 4,513,438 | 4/1985 | Graham et al. | 382/6 |
| 4,523,278 | 6/1985 | Reinhardt et al. | 364/413 |
| 4,562,593 | 12/1985 | Ooe et al. | 382/6 |

*Primary Examiner*—Michael Razavi
*Attorney, Agent, or Firm*—Fitch, Even, Tabin & Flannery

[57] ABSTRACT

A method and apparatus are provided for selecting and analyzing a subpopulation of cells or cell objects for a certain parameter such as DNA, estrogen, and then measuring the selected cells. The observer in real time views a field of cells and then gates for selection based on the morphological criteria those cells that have the visual parameter such as colored DNA or colored antigen into a subpopulation that is to be measured. The selected cells are examined by digital image processing and are measured for a parameter such as a true actual measurement of DNA in picograms. A quantitation of the measured parameter is generated and provided.

34 Claims, 12 Drawing Sheets

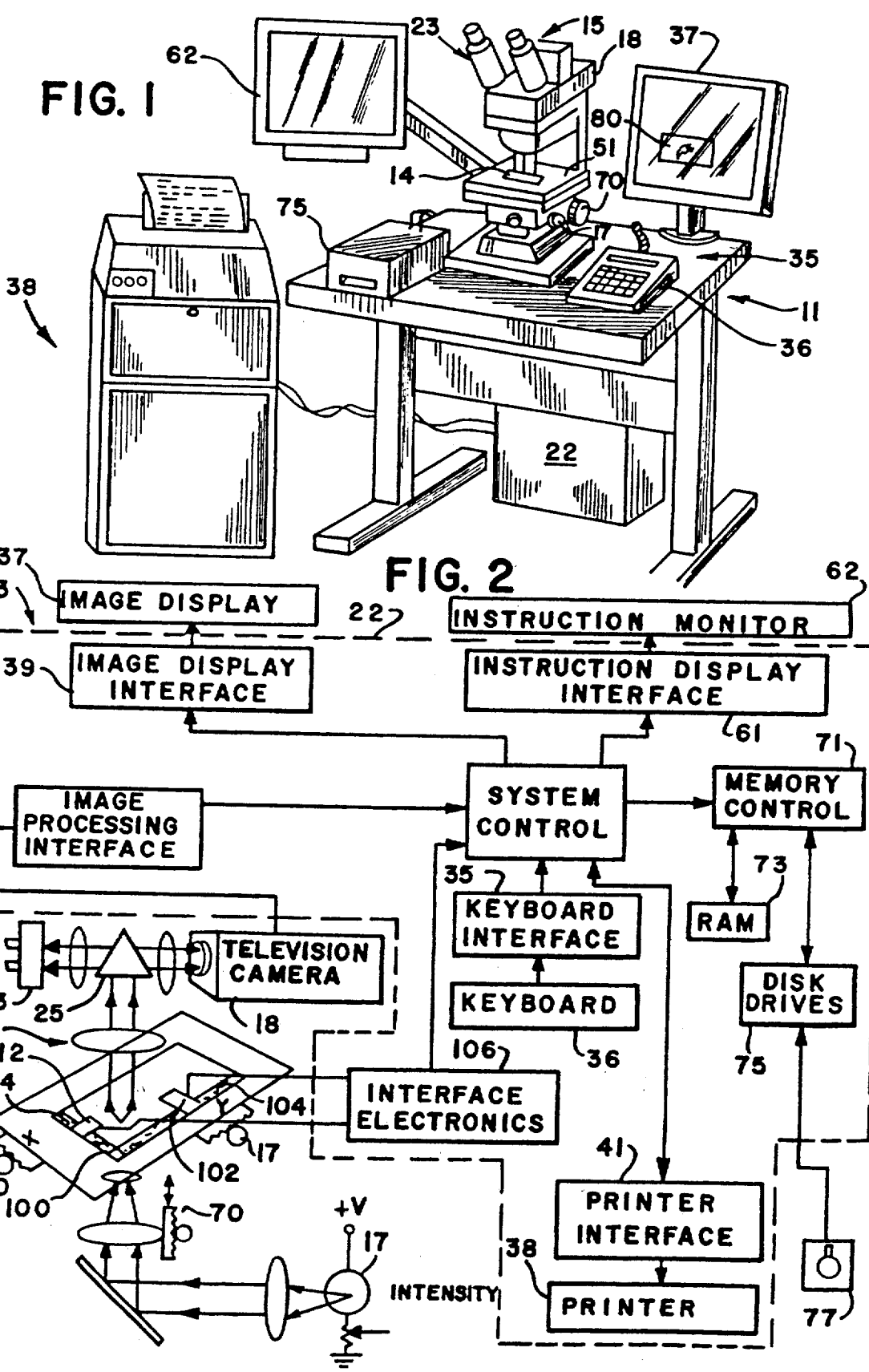

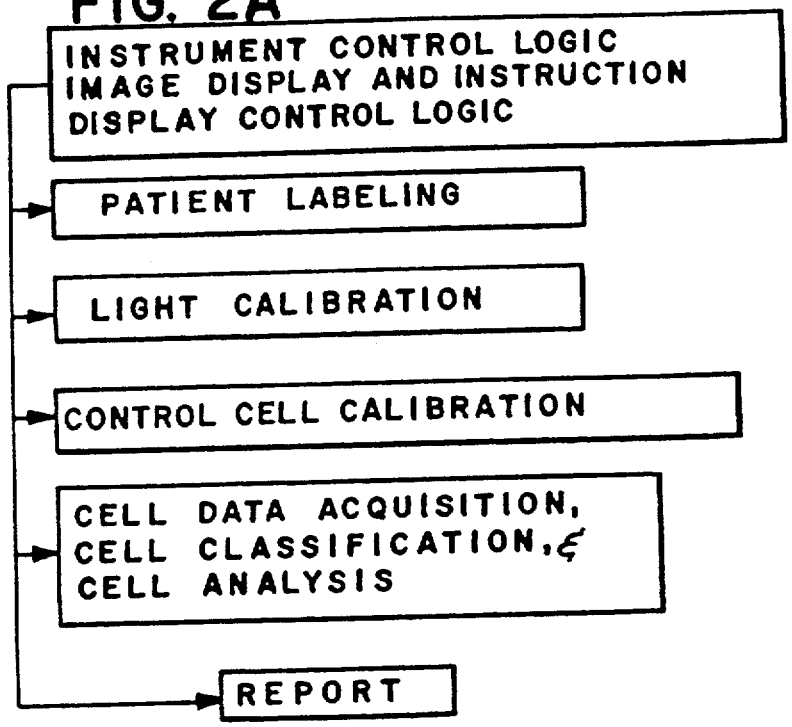
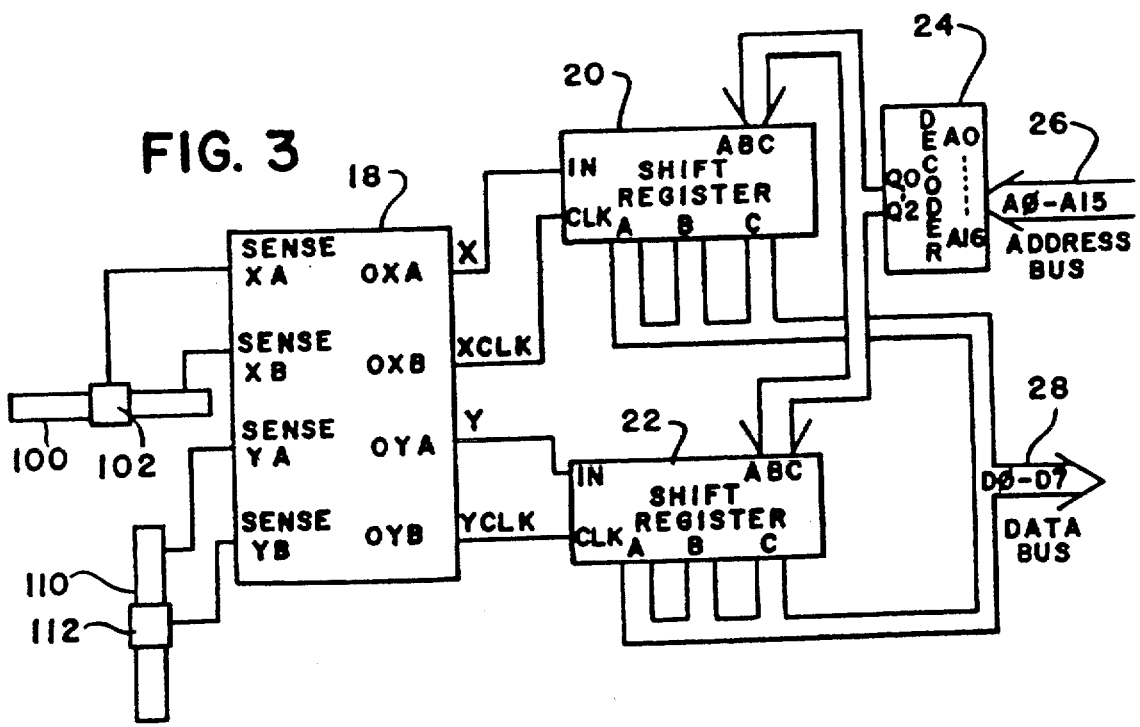

FIG. 11    MAIN SCREEN

```
PATIENT IDENTIFICATION
ACCESSION NUMBER
DNA INDEX BASED ON 7.18 PICOGRAMS

CALIBRATION STATUS          ANALYSIS STATUS              OPTION
                                                          LIST
CELL COUNT         87       CELL COUNT       0

PEAK O.D. VALUE   8400      MAIN PEAK DNA    .0  pg.   A10

LIGHT LEVEL         0       MAIN PEAK INDEX  .0

2ND PEAK DNA     .0  pg.

2ND PEAK INDEX   .0

CONFIRM FUNCTION
                                             YES
                                             NO
```

FIG. 12    CALIBRATION SCREEN

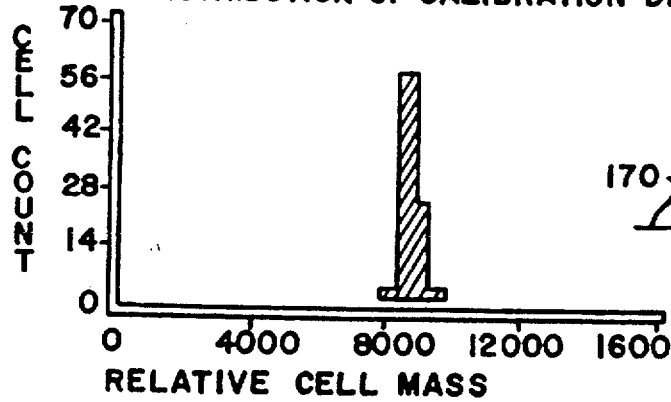

```
PATIENT IDENTIFICATION
ACCESSION NUMBER                                          OPTION
DNA INDEX BASED ON 7.18 PICOGRAMS                          LIST

DISTRIBUTION OF CALIBRATION DNA
                                            CALIBRATION DATA
                                            LIGHT LEVEL    0
                                            CELL COUNT    87
                                            PEAK VALUE  8400

170
                                          MEASURE OPERATIONS 0
                                          0 = ACCEPT CELL
                                          9 = REJECT CELL
                                          (CR) = STOP/SAVE DATA
                                          (ESC) = STOP
                                          CTRL F1 = BACKUP
                                          CTRL F2 = NEXT
                                          CTRL F3 = AUTOMATIC
                                          CTRL F6 = FORWARD
```

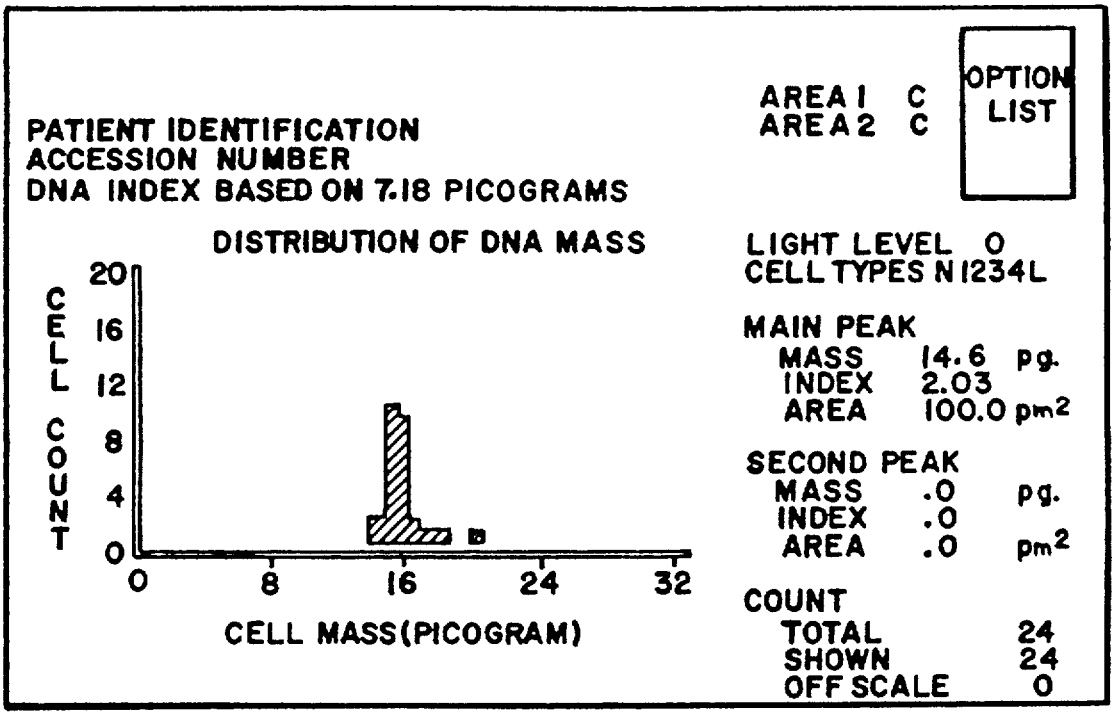
FIG. 13 ANALYSIS SCREEN
FIG. 14 X,Y FIELD COORDINATES SCREEN

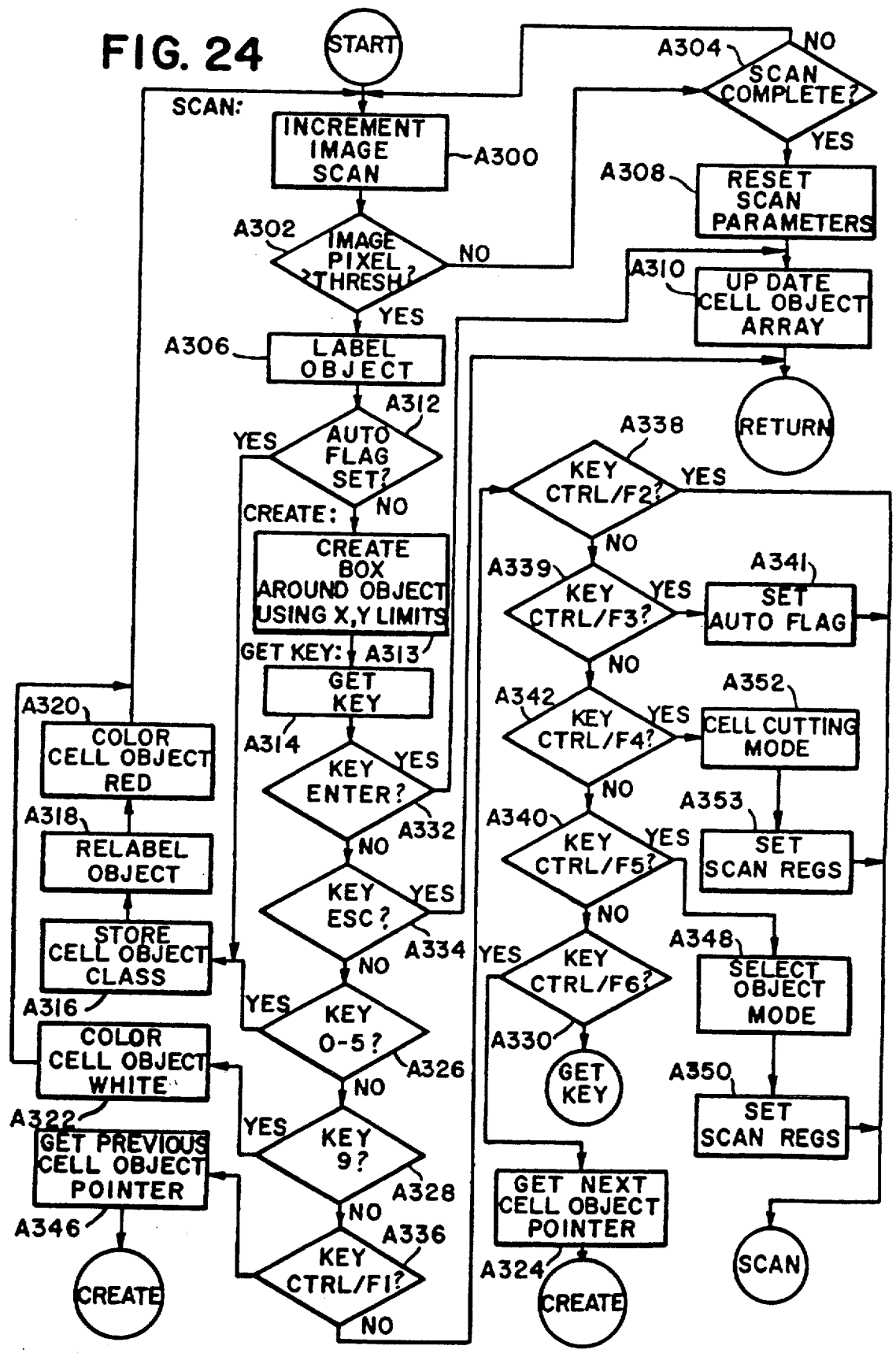

ANALYSIS METHOD AND APPARATUS FOR BIOLOGICAL SPECIMENS

CROSS REFERENCE TO RELATED APPLICATIONS

The present application is a continuation-in-part application of application Ser. No. 794,937 filed Nov. 4, 1985 in the name of James W. Bacus and now U.S. Pat. No. 4,741,043 and entitled "Cell Analysis Apparatus and Method with Calibration and Control Slide" which is commonly assigned with the present application. The disclosure of Bacus is hereby expressly incorporated by reference herein.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates generally to the measurement of cell object features and parameters by image analysis, and is more particularly directed to quantitative measurement methods and apparatus for DNA analysis in small cell populations.

BACKGROUND OF THE INVENTION

The present invention is directed to a quantitative testing apparatus and method which may be used for a wide range of diagnostic and prognostic evaluations of various cells, antigens, or other biological materials taken from the human body. However, for purposes of illustration and ease of understanding, the invention will be disclosed in conjunction with its preferred use, which is the quantitative measurement of cellular DNA for the purpose of cancer diagnosis and prognosis. More specifically, the present invention is directed to a method of interactive image analysis for analyzing and quantifying the DNA in specimen cells taken from a person.

The current state of the art in the pathology laboratory is to measure the DNA content of a cell by the visual observation of the pathologist who observes primarily the shape and texture of suspected cancer cells and who then classifies the cells into a normal category or into one of several abnormal cancer categories. However, such evaluations are very subjective and can not differentiate and quantify small changes in DNA within individual cells or in very small populations of abnormal cells. These small changes may represent an incipient stage of cancer or a change in cell structure due to treatment of the cancer by chemotherapy or radiation. Such small changes are, therefore, important in the diagnosis and prognosis of these diseases.

However, the advantage in diagnosis and/or prognosis of abnormal ploidy distributions that a pathologist viewing a specimen under a microscope has is the discerning expertise of a skilled person in classifying cells as normal or abnormal. There is an innate human ability to make relatively quick infinite gradations of classification, i.e., almost normal, slightly abnormal, etc. On the other hand, the classification and measurement of cell features and parameters by a pathologist on a cell-by-cell basis is extremely tedious and time consuming. Broad statistical analysis of such cell data taken by hand is relatively difficult because each record has to be entered and then processed. For different records, taken at different times, and under varying conditions broad statistical categorizations may be unreliable.

The alternative is automated cell analysis where the pathologist uses specialized equipment to perform the analysis. In automatic cell analysis, such as that accomplished by a flow cytometer, mass tests are performed in gross on a specimen cell population without a researcher being able to exclude or include certain data of the population. The specimen is measured "as is" without really knowing what cells are being measured and how many. Important single cell data or data from relatively small groups of cells are lost in the overall averaging of a specimen. Further, relatively large amounts of a specimen have to be used to provide any accuracy because of the averaging problem. This was considered necessary in the prior art to process large amounts of cell data relatively quickly so that the results will be fairly accurate. Again small changes in individual cells or small cell populations cannot be discerned.

Although there are commercially available general purpose flow cytometers, they are very expensive and can handle only liquid blood specimens or tissue disaggregations. These cytometers are incapable of working on standard tissue sections or using conventional microscope slides which are the preferred specimen forms of pathology laboratories. Additionally, a flow cytometer does not allow for the analysis of morphological features of cells such texture, size and shape of cell nuclei and alterations in the nuclear-to-cytoplasmic ratios of cells.

Moreover, for such cell analysis, either automatic or manual, to be of real value there should be some way of verifying the results. The normal scientific method for accomplishing verification is to save the specimen so that another pathologist can compare his analysis to that of the first. However, for individual cells classified by manual means this indicates either photographs, drawings, or other imprecise mediums because it is extremely difficult to fix a tissue specimen for a long period of time. Further, even with those techniques where such specimens are fixed sufficiently for subsequent viewing, there remains the problem of finding the same cell or small population of cells from which an original evaluation was made and presenting the same conditions for viewing. With automated methods, the sample is consumed and verification can only occur by observing similar tissue from the same area.

SUMMARY OF THE INVENTION

The invention solves these and other problems relating to the image analysis of various features and parameters of cell objects by providing a measurement method and apparatus which can acquire quantitative data concerning a plurality of individual cells very quickly by an interactive process with a pathologist or an operator. The apparatus provides means for displaying an image of a group of cells from a field of a microscope slide. The image is further digitized and stored in a memory of the apparatus. From the digitized image a processor means identifies each possible cell object automatically by pattern recognition technique. An interactive program allows the operator to point to each object or cell in succession and make decisions for classification and measurements concerning each. For quantitative DNA analysis, the measurement is of the optical density of the cell object and the classification is by a pathologist as to whether the cell appears normal or cancerous. The decisions can include whether to accept or reject the particular cell for further processing. The cell object, if selected, can also be classified into one of several classifications for later statistical analysis. The apparatus further has means which provide for the classification and storing of more than one image.

One of the features the present apparatus provides is the enhancement of the image by providing a threshold value for the data prior to its display. The displayed image corresponds to a plurality of pixels which form the digitization of the image field. Below such threshold, a pixel in the display is shown as white or the absence of any information. A grey scale image above the threshold is displayed for the remaining pixels. This feature advantageously reduces background clutter and enhances the visual characteristics of the cell objects in the field. The threshold is variable and can be used to mask certain features while enhancing others. The full scale of grey resolution is used above the threshold for excellent contrast differentiation.

Another feature of the invention provides for the verification of the measured data. When each image or field is digitized and stored, a reference number is stored with the data. Preferably this reference number is the relative X, Y position of the image from a selected coordinate origin on a slide. The invention provides means for displaying the actual position of the area of a slide being viewed. Therefore, to verify a previously stored image, a slide is remounted with respect to a reference and positioned until its actual displayed position matches the stored reference position. Thus, the data and analysis of the study can be verified not only by the data images from a slide, but the actual slide image used in the analysis can be found readily.

When the apparatus is used for DNA analysis, tissue and cell specimens are applied to a slide which is then stained with a specific stain that combines proportionately with the DNA and essentially renders invisible the remainder of the cell so that the image analysis can measure the optical density of the DNA which is concentrated in the nucleus of the cell. The stain associates with the DNA to provide a detailed nuclear structure and pattern which may be visually observed and interpreted by the pathologist using the apparatus for classification. The amount of DNA in the malignant cells is substantially greater than that for normal cells because the malignant cells are usually dividing and replicating rapidly or the malignant cells have abnormal numbers of chromosomes or have defective chromosomes.

The preferred and illustrated apparatus of the present invention can not only detect minute alterations in the nucleus by providing a real and accurate measurement of the DNA mass in picograms but also can measure and quantify the amount of DNA and relate it to stored statistical analyses to aid in the diagnosis. More specifically, the invention allows an iterative analysis of specimen population cells and provides a histogram or other statistical display of the population distribution of the cells with respect to their DNA content and with respect to a standard DNA for normal cells so that subtle shifts in population distribution can be readily understood. To this end cell nuclei images are not only acquired and stored but the data therefrom can be integrated with other statistical data to provide multivariate analysis, discrimination of cells, histograms, and scattergrams of cells or cell populations.

The use of image analysis techniques and equipment for stained specimens by pathologists in a conventional pathology laboratory involves solving a number of problems which have been overcome by the present invention. For example, while there are a number of available staining techniques which can be used, such as an Azure A Feulgen staining technique described hereinafter, the staining of the DNA will vary substantially not only from slide to slide and from batch to batch by the same pathologist but also will vary substantially between different pathologists and different laboratories. Because the present image analysis apparatus measures grey level or optical density and because it is desired to provide a true actual measurement of DNA in picograms, it is important to overcome the problem of different staining factors for different specimens. Also, image analysis techniques which use adjustable microscopes and optical lighting provide different intensities of light when used by the pathologist. Trained researchers, in research laboratories may be equipped to adjust the optical intensity to the desired conditions for image analysis by image pattern techniques but this generally cannot be accomplished with the precision necessary in the usual pathology laboratory. Thus, there is a need to overcome the problem of this light intensity and, therefore, optical density variable.

Additionally, the present invention is directed to overcoming the problem of high costs heretofore associated with automated equipment used for image analysis; and to this end, the present invention provides a facile interactive system in which the pathologist performs a number of tasks and performs the preparation of cells and their selection by manipulation of the equipment. The pathologist also is provided with slides which are specially prepared and calibrated with reference cells to aid in the analysis of the specimen cells and to assist in overcoming the above-described staining problem.

The present invention has particularly been developed to locate cells for examination as to their morphology and to preserve their location for a later or corroborating analysis by a second pathologist when so desired. As will be explained, with respect to nuclei, measurements may be obtained as to their area in microns, total nuclear optical density or nuclear mass in picograms, average nuclear optical density, nuclear texture, and deviation of the nuclear shape from being a round nucleus.

Accordingly, a general object of the invention is to provide a new and improved method and apparatus for analyzing cells or other biological materials by using image analysis techniques.

Another object of the invention is to provide a new and improved method and apparatus for making a quantitative ploidy analysis of cells using image pattern recognition equipment.

A further object of the invention is to provide a new and improved slide or support for specimen cells having control cells or cell objects thereon which are used for calibrating the image analysis equipment.

These and other objects, features, and aspects of the invention will become apparent upon reading the following detailed description when taken in conjunction with the attached drawings wherein:

BRIEF DESCRIPTION OF THE DRAWINGS

FIG. 1 is a pictorial representation of an image analysis system constructed in accordance with the invention;

FIG. 2 is a functional block diagram of the image analysis system illustrated in FIG. 1 which is adapted to perform an image analysis method in accordance with the invention;

FIG. 2A is a functional system diagram illustrating the major operations of the system control illustrated in FIG. 2;

FIG. 3 is an electrical block diagram of an interface electronics for the X, Y position circuitry illustrated in FIG. 2;

FIG. 11 is a pictorial representation of the main screen image which appears on the instruction monitor illustrated in FIG. 1;

FIG. 12 is a pictorial representation of the calibration image screen which appears on the instruction monitor illustrated in FIG. 1;

FIG. 13 is a pictorial representation of the analysis screen image which appears on the instruction monitor illustrated in FIG. 1;

FIG. 14 is a pictorial representation of the X, Y field coordinates image screen which appears on the instruction monitor illustrated in FIG. 1;

DETAILED DESCRIPTION OF THE PREFERRED EMBODIMENTS

The apparatus illustrated in FIGS. 1 and 2 can be used to develop histograms, and other statistical data, of cell populations for the diagnosis and prognosis of malignancies and other diseases. To illustrate the utility of such statistical analysis reference is directed to FIGS. 6-9.

Figure 6:
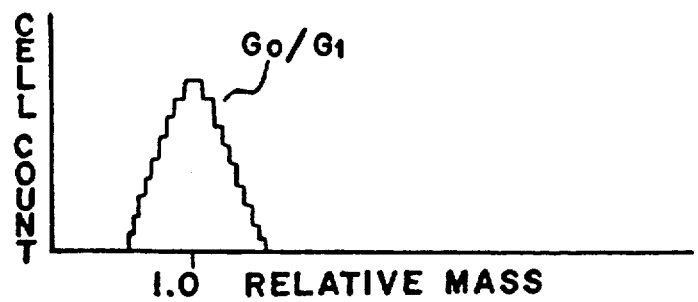
FIGS. 6-9 are pictorial representations of histograms for different normal and abnormal cell populations.
Figure 7:
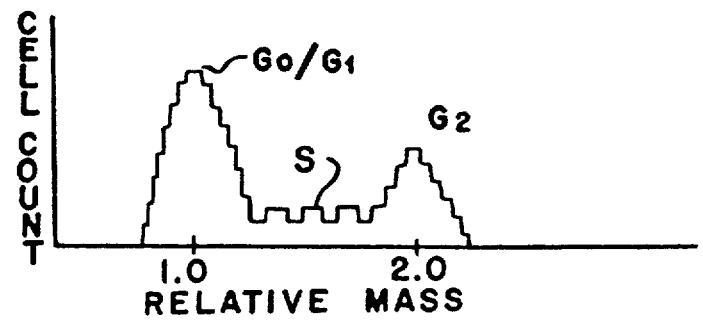

Referring now to FIG. 6 there is shown a normal ploidy histogram having cell number versus mass distribution for healthy, non-dividing cells. The number of cells is provided on the ordinate axis and their nuclear mass on the abscissa. If the cell population shown in the figure is not dividing, the DNA content should be peaked around a normal peak G0/G1 which is the diploid amount, 7.18 picograms/cell. This relative mass of DNA is labelled as 1.0 to normalize the abscissa of the histogram. FIG. 7 also shows a normal cell population which is dividing, where there is a significant G0/G1 peak at 1.0 and a second peak G2 at 2.0. The peak at 2.0 is normal because some of the cells are in division and have double the normal diploid amount of DNA. The saddle S between the two peaks is relatively low and does not indicate any malignancy.

Figure 8:
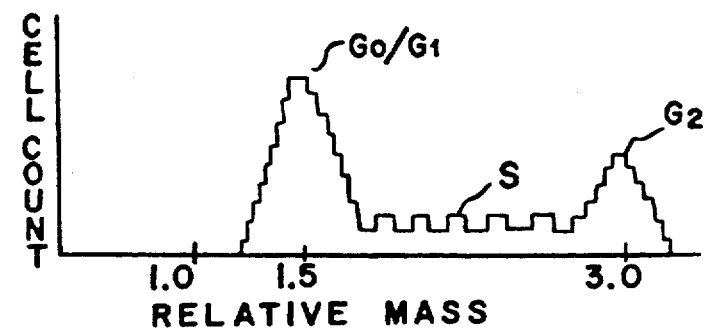
Figure 9:
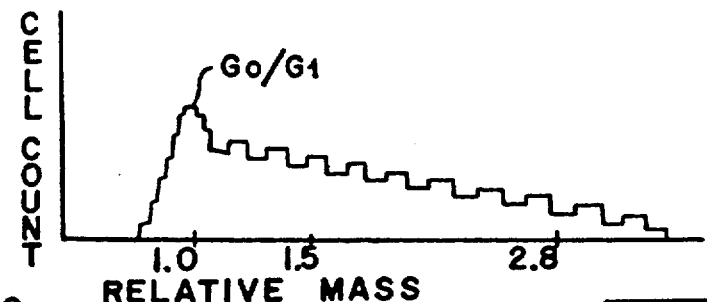

Comparing the histogram in FIG. 8 with the first two, it is seen that this cell population is skewed from normal having a higher first peak around 1.5 and a second peak around 3.0. Further, the saddle S is more pronounced and can be rough in cell count. This histogram may show a malignancy because of the abnormally high DNA content of many of the cells. This high DNA content is likely indicative of the increased ploidy amount of malignant cells which are rapidly dividing. Likewise, in FIG. 9 it is shown that the G0/G1 peak occurs at 1.0 with a normal diploid amount of DNA but has a relatively large trailing saddle from 1.0 to 2.8. A normal G2 second peak is not noted and is indicative of an abnormal cell population. The shape of the histogram is likely due to abnormal DNA amounts in cells and clones of cells indicative of malignancy. Therefore, from the shapes and changes in cell distribution histograms, diagnostic and prognostic information can be obtained.

In the implementation shown, the system is a computerized image analysis system designed to measure a number of cell object features and parameters from their image on a typical glass slide. The instrument includes a sophisticated digital image processing system controlled by software to perform quantitative analysis on individual cells for nuclear DNA content by Feulgen staining as well as measurement of other nuclear features. The imaging system couples the ability of a pathologist to identify cells to be studied with the capability of computer enhanced, high resolution digital video image processing to quantify optical and stain density accurately.

In general, a pathologist first prepares a touch preparation or a needle aspirate of fresh tissue. Alternatively, embedded samples can be visually inspected for areas of interest and then deparaffinized and disaggregated by mincing in the presence of pepsin to produce a single cell suspension that is then placed on a microscope slide. After fixation and staining with Azure A Feulgen stain, the preparation is ready for analysis.

The operator has the option of classifying the cells morphologically into any one of six categories or rejecting inappropriate cells or debris. The cell data are processed by a system control and the cellular elements are characterized by a quantitative DNA analysis for each cell class. The information when compared with either a standard cell calibration or published data allows a pathologist to accurately quantify and classify abnormalities that might ordinarily be described only verbally from the image a person sees.

The addition of quantitative data enables pathologists to perform their work in a more standardized and reproducible manner. The system is of value in classifying lesions that may be malignant and in providing prognostic information for known malignancies based on DNA content. The image identification system is more advantageous than common flow cytometry methods of evaluating DNA content. Flow cytometry permits an operator to classify neoplastic cells based only on cell markers. The pathologist, however, never sees the cells that the instrument has examined. In addition, the cell preparation must be used in a short time frame and is consumed in the course of the study. Although a permanent section of a tumor under study may be examined at the same time, there is no guarantee that the same cells are examined in both areas. Also the quantity of tumor available may not be large enough to permit a flow cytometric examination.

In the invention, the quantitative DNA analysis is performed rapidly for the measurement of DNA and ploidy distribution pattern in a cell population under study. The pathologist advantageously selects the cells which are to be used in the population measurements. The measurement of DNA content is useful and believed to be relevant in diagnosing and determining prognosis for a variety of tumors that involve the breast, colorectum, and prostate. The system takes advantage of the pathologists skill to identify visually abnormal cells and then uses a computer aided imaging analysis to analyze quantitatively those particular cells for the parameters desired. Such instrument extends and augments the recognition and diagnostic skills of the pathologist.

As shown more specifically in the drawings for purposes of illustration, the invention is embodied in a method and apparatus for automatically analyzing "cell objects" which term is used herein to be generic to cells, such as blood cells or cells taken from tumors or the like, which are to be analyzed for the DNA content. The term is also meant to encompass non-biological objects, such as conventional plastic or glass spheres used in biological studies, painted cell images on a slide, or antigens or monoclonal antibodies on cells. The system further finds use where a monoclonal antibody is conjugated with a stain, wherein the stain may be a fluorescent material which is excited at one wavelength and which can then be analyzed at another wavelength where fluorescence occurs. By way of example, the present invention is useful for ploidy analysis, red blood cell analysis, pap smear cell analysis, monoclonal antibody analysis, and the analysis of other infectious diseases which can be diagnosed by DNA probes for viruses. The imaging and analysis system is, therefore, advantageously used in a number of studies where one of the optical characteristics, such as optical density, of a cell object may be used to determine some parameter or feature of that object which is diagnostic or prognostic for a particular condition.

As shown in FIGS. 1 and 2 of the drawings, the invention is embodied as an apparatus 11 which functionally operates as a digital image processing system 13 (FIG. 2). The apparatus 11 comprises a high resolution microscope 15 with which an operator can view specimens on a support, in the preferred embodiment a glass slide 14. The microscope 15 has means 70 for focusing its optics on the slide and a platform 51 movable incrementally by means 11 and 17 in X and Y directions for viewing various areas thereof. The specimens or material on the slide 14 are further viewable by the imaging system 13 which is controlled by a system control 22 in the form of a digital processor such as a personal computer. An operator can communicate with the system control 22 via a keyboard 36 and interacts with the apparatus 11 by viewing two displays. A first display, image display 37, is a RGB monitor which displays through the system control 22 the same image as seen through the microscope 15. A second display, instruction monitor 62, is another RGB monitor and is used to provide the operator with interactive prompts, messages, information, and instructions from the program controlling the system control 22. A printer 38 is provided to produce a reliable hard copy output of data produced by the apparatus 11.

The functional schematic of the apparatus 11 is illustrated in FIG. 2 as image processing system 13. The image processing system 13 is used to analyze a plurality of cell objects on the support or glass slide 14 of the microscope 15. Suitable high resolution microscope optics 16 receive light from a variable intensity source 17 through the slide 14. The optics 16 form an optical image of each of the cell objects on the slide 14 and transmit them to a image splitter 25 which can take the form of a prism.

On one side of the splitter 25, a television camera 18, or other detector, converts the optical images point by point into a scanned electronic signal representing the optical intensity of each point in the image. The output of the camera 18 which is a standard NTSC analog video signal is applied to an analog to digital converter of an image processing interface 21. The image processing interface 21 converts the image signal from the television camera 18 to a digitized signal which is received and stored by the system control 22. Because of the continuous scanning, a real time image of the area the optics 16 are focused on is provided by the image display 37. In general, the image is a $512 \times 512$ array of pixels each having a measured light intensity.

On the other side of the image splitter 25 is located the viewing optics 23 of the microscope 15. This parafocal arrangement allows the same image in the viewing optics 23 to be displayed on the image display 37. This feature allows the positioning of the platform 51 by the manual X, Y adjustment means 11 and 17 until the operator views a field of interest on the slide 14. At that time, a computer enhanced digitized image of the selected field is displayed on the image display 37 for further analysis.

Both of the displays 37 and 62 are controlled by the system control 22 through standard video interface circuitry 39 and 61, respectively. Similarly, the keyboard 36 and printer 38 communicate with the system control 22 through conventional interface circuitry 35 and 41, respectively. In addition, the system control 22 controls a random access memory 73 and bulk storage in the form of floppy and hard disk drives 75 through a memory control 71.

All of the interface circuits 21, 35, 39, 41, 61, 71, and 106 can be selectively embodied on printed circuit boards which are mounted in the backplane or card connector of a conventional personal computer forming the system control 22. Preferably, the personal computer can be one manufactured by the IBM Corporation having a model designation AT. Such system control can be run under a disk operating system such as PC DOS version 3.1 or later. The system software for the image analysis is called as an application program from the disk drive 75, and could, for example, be supplied on a floppy disk 77. The system software is read from disk 77 and loaded into RAM 73. After loading program control is transferred to the analysis software to regulate the various hardware elements previously set forth in a known manner.

The analysis software can be for DNA analysis as hereinafter described or could include other software for various purposes. For example, the analysis of the shape and size as well as hemoglobin content of the cells when examining red blood cells may be accomplished in accordance with the pattern recognition technique and analysis method disclosed in U.S. Pat. Nos. 4,097,845 and 4,199,748 issued to Bacus which are hereby incorporated by reference as if fully reproduced herein.

FIG. 2A illustrates functional operation of the system software where control logic for the instrument hardware, the image display, and the instruction display are used to perform the main system functions. The main system functions are patient labelling, light level calibration, control cell calibration, cell data acquisition, cell classification, cell analysis, and report generation.

The interface circuitry, except the interface electronics 106, can be standard control circuits for the various functions illustrated. The interface electronic 106 is a specialized circuit which is more fully illustrated in FIGS. 3 and 4. The X, Y position sensors allow the field under analysis to be given a position.

Herein the X and Y locations of each field are easily determined for any given location by a novel method and apparatus which includes, as best seen in FIG. 2, an X direction sensing strip 100 which may be fastened to the underside of the microscope stage 51 for movement with the stage 51 past a sensing pad 102, which is secured to a stationary part of the microscope. The sensor provides an analog output to an interface electronics 106 which provides the X coordinate in digital numbers to the system control 22 for storing in memory and for displaying on the monitor screen 62. Likewise, a similar strip 110 is fastened to the stage 51 for movement in the Y direction with the stage past a sensing pad 112 which is secured to a stationary part of the microscope is so that the pad may provide an analog signal to the interface electronics 106 which supplies digital signals to the instrument control logic 122 for storage of the Y coordinate and for showing the Y coordinate on the video monitor adjacent the X coordinate. Manifestly, the system can be reversed with the sense heads fastened to the stage for movement therewith and with the sensor strips 100 and 110 being mounted stationary to provide analog signals as the heads move thereacross.

Figure 4:
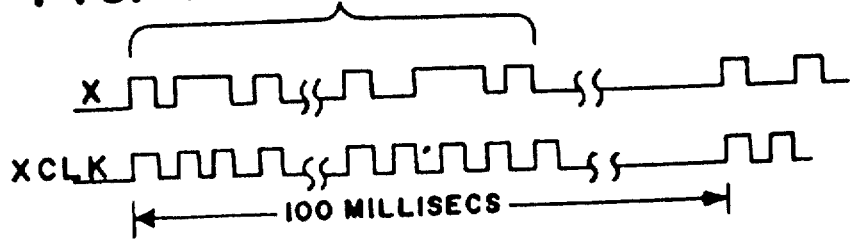
FIG. 4 are representative timing waveforms for the input to the interface electronics illustrated in FIG. 2.

The circuitry for interfacing with the position sensors is more fully detailed in FIGS. 3 and 4. The position sensors are magnetic sensors having the pair of sensor strips 100 and 102 for the X coordinate and the pair of sensor strips 110 and 112 for the Y coordinate. The sensor strips 100 and 110 are affixed orthogonal to each other such that these strips form a reference axes for the coordinate system. The moveable sensor pads 102 and 112 which are affixed to the moveable base of the microscope 15 travel along the strips 100 and 102 sensing the relative movement between the members depending upon the relative position of the moveable pad with respect to the fixed strip. The sensors are connected to a measuring chip 18 which includes circuitry for measuring the relative position between the strips and for generating a digital numbers based on that sensed parameter. The X sensing strips 100 and 102 are connected to the sense XA and sense XB inputs of the measuring circuit 18 and similarly the Y sensing strips 110 and 112 are connected to the sense YA and sense YB inputs of the circuit. The circuit 18 is an internally timed position to digital number generator which outputs a 3 byte serial digital number depending upon the relative position of the moveable pad with respect to the fixed strip from outputs OXA and OYA. This 3 byte number is serial and is accompanied by a clock signals XCLK or YCLK for timing purposes.

Each of these bursts of 24 bits are at a frequency of approximately 24 KHz. and occur every 100 milliseconds. The measurement circuit 18, therefore, produces a 3 byte number for the X position every 100 milliseconds and a 3 byte number representative of the Y position every 100 milliseconds. The outputs OXA and OXB are connected respectively to the serial input IN and clock input CLK of a shift register 20. Similarly the output OYA and output OYB of the circuit 18 are connected respectively to the serial input IN and clock input CLK of shift register 22. The signal XCLK will clock or time the 24 bits of the position number into the shift register 20 every 100 milliseconds. This number is then stored in the shift register 20 until it is to be used by the main control program. The Y position of 24 bits is serially presented to the input of the shift register 22 and clocked in to the device by the signal YCLK every 100 milliseconds. The shift registers 20 and 22 act to hold these position numbers between communication bursts from the measurement circuit 18.

The shift registers 20 and 22 are connected to the system control 22 by the address lines A0–A15 of its address bus and by its data lines T0–T7 of the data bus. The 8 bit data bus is connected in parallel to the byte outputs A, B, and C of the shift register 20 and the byte outputs A, B, and C of the shift register 22. Each output represents one of the bytes of a 24 bit position word for either the X or Y position. The outputs are enabled by the input lines A, B, and C connected to the outputs Q0–Q2 of a decoder 24. The address bus lines A0–A15 are connected to the input lines of the decoder 24.

The decoder 24 translates a specific address assigned for each byte of the position words and enables that byte from the respective shift register so that it can be read in on the data bus 28. For example, to read the X position, the system control 22 would output the address which is used by the decoder 24 to enable the A output of the shift register 20 and then read that byte in through the data bus 28. Thereafter, the system control 22 would output the address which would enable the B output of shift register 20, and then read that byte from the data bus 28. Subsequently, the system control 22 will output the address to enable the C output of shift register 20 and read that byte. The operation is identical for reading the Y position word from the shift register 22.

The reading and loading of the shift registers 20 and 22 is entirely asynchronous. Because the positions of the X and Y coordinate are updated every 100 milliseconds, a relatively simple transfer scheme like this can be implemented. If the shift registers 20 and 22 are shifting when the position words are being read by the computer, then the software will make suitable comparisons to determine whether the input number read is a correct number or the shift register was inputting another number when it was read.

Figure 23:
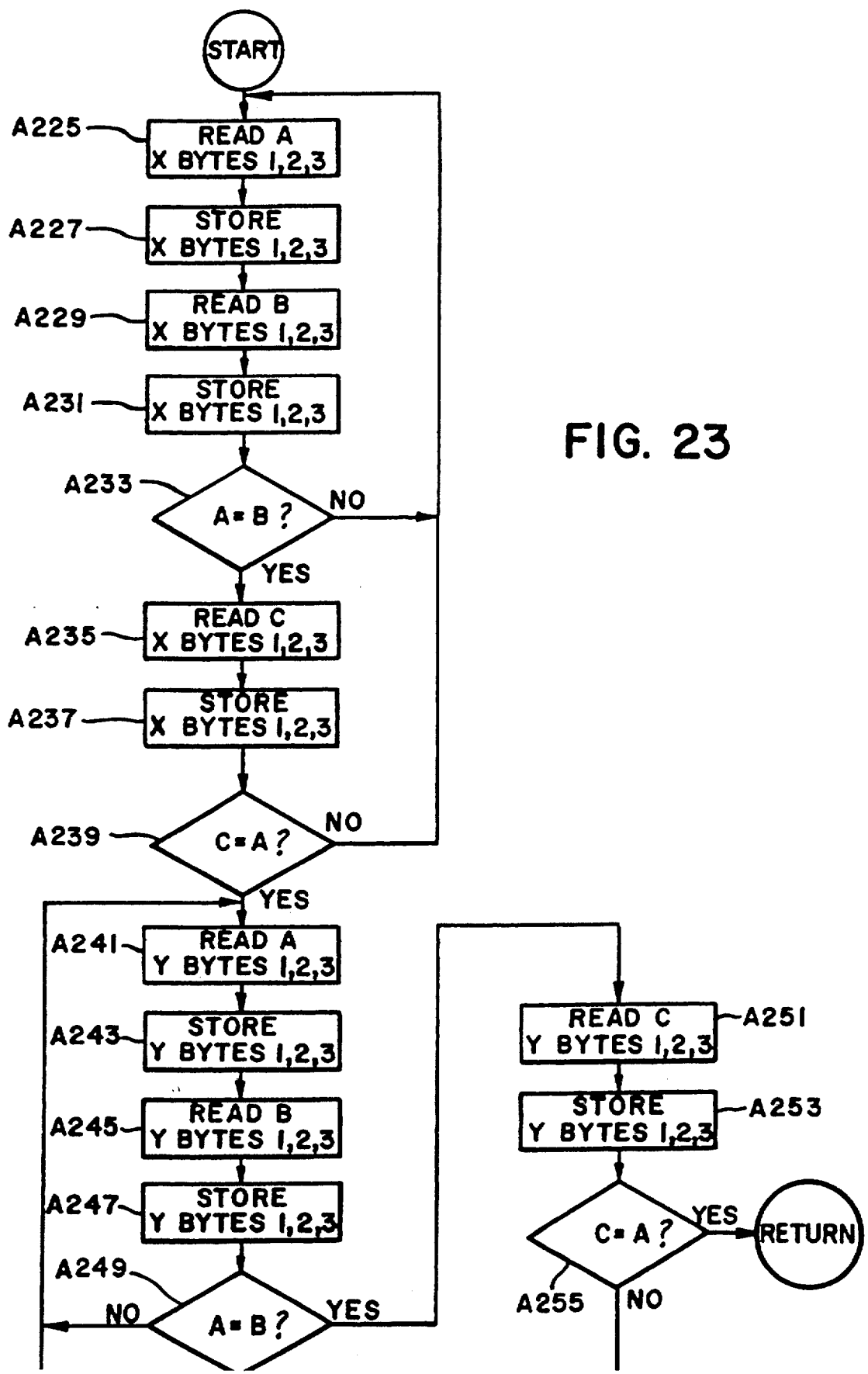
FIG. 23 is a flow chart diagram of the program which reads the X, Y coordinate position of the platform of the microscope illustrated in FIG. 1.

A flow chart of the subroutine which reads the shift registers 20 and 22 is more fully illustrated in FIG. 23. The subroutine may be called periodically to determine the actual X, Y position of platform 51. The program begins by reading and storing the X position twice in blocks A225-A231. A comparison is made to see if the two are equal (A=B) and, if not, loops back to the start. A third read and store in blocks A235 and A237 precedes a comparison of A and C in block A239. A negative branch begins the process once again while a positive branch starts the reading of the Y position in the same manner. The technique requires three reads to match before the number is accepted as the correct position, thereby eliminating the possibility that the table was moved or the shift registers shifted between reads.

Because the apparatus 11 may be used in various offices such as pathology offices having persons of varying degrees of skill and knowledge about image analysis, the microscope light source 17 may be variously adjusted by different operators such that the background may have a different light intensity not only from machine to machine but also at different times depending on the age and nature of the lamp doing the illumination. When the cell objects are DNA nucleus, the stained nuclei appear darker and have high darker gray levels than the cells which have fewer or no DNA content. The particular light intensity level is desired to be known in an accurate and real manner; and hence, it is important that there be a calibration of the light intensity to eliminate errors which might be introduced if differences in light intensity levels are not accounted for.

A further problem with widespread usage of equipment of the foregoing kind is the staining factor by which is meant that the user may be applying either a heavy amount or a light amount of the Azure A stain. This will result in a variation of the gray level being viewed through microscope 15 and by the camera 18 which is then analyzed as to the particular DNA content. Thus, there is a need that the apparatus 11 be calibrated to eliminate differences because of the staining factor so as to provide a true indication of the actual amount of hemoglobin, DNA, or antigens or monoclonal antibodies on cells, etc. being analyzed.

In accordance with the present invention, calibration material 40 (FIG. 5A) is provided on the slide 14 which, when viewed by the operator under a calibration step of the system software allows the operator to adjust and to calibrate the apparatus prior to the measuring and analyzing of specimen cell objects 12 on the slide 14.

In the illustrated embodiment of the invention there are provided two different calibrating materials on the slide 14 with the first calibrating material being the control cell objects 40 which are stained simultaneously with the staining of the specimen cell objects 12. The simultaneous staining permits the analysis of the control cell objects to be compared to a predetermined stored reference light intensity, gray level, or optical density which the control cell objects 40 have after staining. If the cell objects are stained either too lightly or too heavily, the amount of understaining or overstaining can be quantitatively analyzed and adjusted for as will be described hereinafter.

In the preferred embodiment of the invention, the calibration material also includes an optical density reference material 45 which is usually a printed mark on the slide which has a predetermined known optical density, which can be used as a reference to calibrate the instrument. As will be explained in greater detail hereinafter instructions are provided to the operator from the system software to the operator. Following these instructions, the operator manually adjusts the background light intensity of source 17 until the desired intensity is obtained for the reference material 45. As will be explained hereinafter, this step provides the system control 22 with a calibration to read the proper optical density of the objects on slide 14.

Figure 5A:
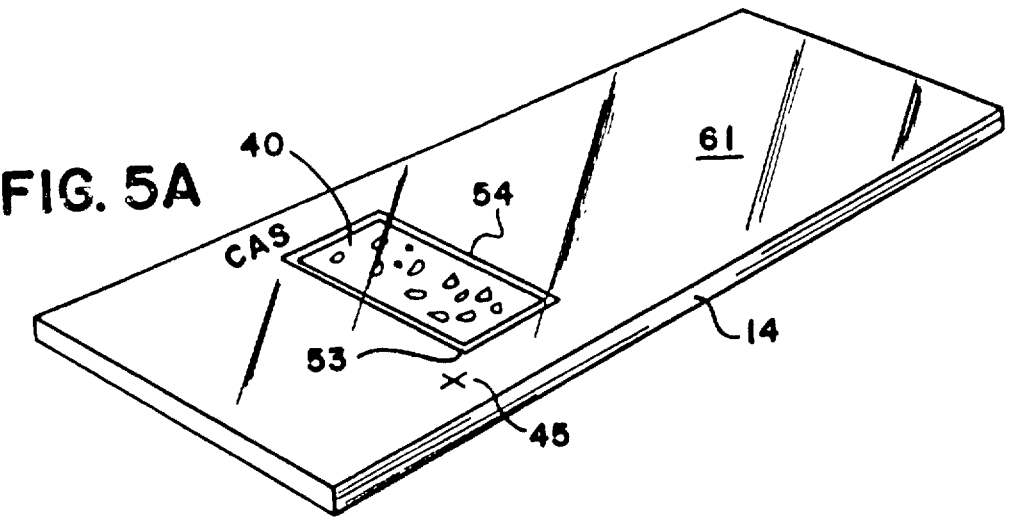
FIGS. 5A, 5B, and 5C are perspective, top, and cross sectional views, respectively, of a slide particularly adapted for use in the image analysis system illustrated in FIG. 1 having separate areas for calibration cell objects and specimen cell objects.
Figure 5B:
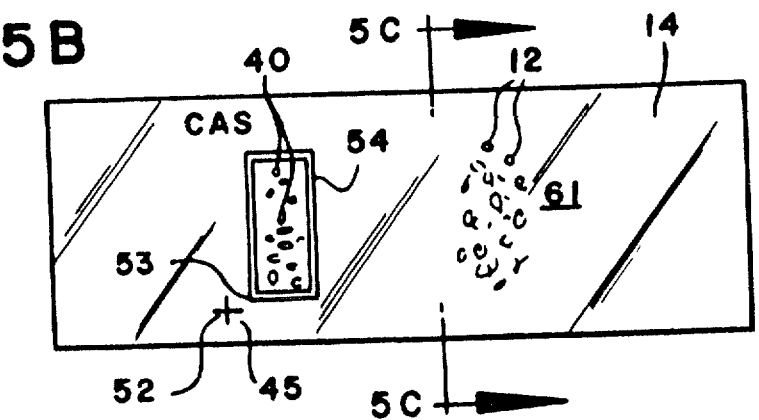
Figure 5C:

As a safeguard to the integrity of the system, it may be desired to provide an integrity check or identification step for the slide 14 by analyzing a predetermined and prefixed optical pattern on the slide which is read and measured as to gray levels and physical dimensions before the analyzing may be begun. Herein, the optical integrity pattern may be in the form of initials CAS located above the control cell objects as seen in FIGS. 5A-5C. Manifestly, the integrity check may be the cross 52 or any other shaped material on the slide 14.

The light calibrating material 45 which is in the form of a cross 52 shown in FIG. 5C may also take a large number of different shapes and forms, and in fact, may be merely the border 54 for the control cell objects or may be a logo CAS or other identifying mark which has been applied to the slide to provide a predetermined optical density when the light source for the microscope 15 is adjusted to the desired intensity.

The present invention is also useful for later analysis of the specimen cells 12 on the slide 14; and to aid in the recall of cell images stored in memory or to allow the operator or another person to return to a given cell for a second review thereof at a later time. To this end, after the slide 14 has been secured on the microscope stage 51 (FIG. 1) in a particular position, a certain location or landmark on the slide, such as the center of the cross 52, is defined as a zero-zero X-Y reference point. This reference point is used to set up a translation table for the position readings from the X, Y sensors. A pair of location registers of the system control 22 for the X and Y distances are zeroed at this point so that subsequently all cell locations may have a specific X and Y coordinate address from the reference point. Another easy landmark to find with the position adjustment means of the microscope stage 51 is a corner such as the righthand lower corner 53 of the box border 54 within which are located the reference cell objects 40. The box border 54 is printed on the slide and it also may be used for the optical density calibration rather than the special cross 45. By suitable logic, any point on the slide and microscope stage at which the classification operation begins may be taken as the zero X and Y location with the location registers. The X and Y coordinates are initially zeroed at this location and then provide a readout for each image field location from this zero location.

The specimen slide 14 may be of any size or shape but because of the familiarity of laboratory technicians and pathologists with glass slides used with microscopes, it is preferred that the support 14 be an actual microscope slide of glass which typically measures 3 inch by 1 inch. The illustrated slide 14 shown in FIG. 4 has a preprinted border 54 within which are located reference or control cell objects 40. The slide also has an area 61 for specimen cell objects.

The control cell objects are, in this illustrated embodiment of the invention, lymphoblastoid cells of a known size and shape, and DNA content. The lymphoblastoid cells may be mostly of the type having normal DNA content, although some cells may have double or other ratios to the normal DNA content which is typical of cancer cells. The control cell objects may be other types of cells having dark centers or nuclei which stain well, such as chicken blood cells or trout cells. On the other hand, the cell objects 40 may be artifacts printed on the slide to have a cell shape. Furthermore, as above explained, the cell objects 40 may be conventional plastic beads of a predetermined size which will react with a particular fluorescent stain or enzyme stain when treated simultaneously with specimen cell objects such as monoclonal antibodies used in the specimen area 61 of the slide. The reference cell objects will vary from test to test and the present invention is not limited to any particular test or cell objects.

A pathologist will take a previously prepared slide such as shown in FIG. 5A having premounted thereon the control cell objects 40 and add thereto the specimen cell objects 12 which are, in this instance, cells from a slice of tissue (such a tumor tissue), or a a needle aspirate of tumor tissue or monolayer of blood cells or other cells, at the area 61 on the slide. The pathologist will then stain or otherwise treat simultaneously the control cell objects and the specimen cell objects for image enhancement. The preferred slides are provided with a kit which have bottles of reagent therein specific to the control cell objects. For DNA analysis, the kit contains bottles of Feulgen Azure A reagent solution and bottles of rinse reagent solution to specifically and quantitatively stain nuclear DNA.

To prepare a slide, the following process is used. The slide 14 has normal control cells on one area and a space for the specimen cells on another area. The slide 14 is fixed within 10% formalin for ten minutes and then put aside while routine paraffin embedded sections are prepared for the area 61. If a malignant or questionable tissue is present on the permanent section, the slide 14 will be processed to analyze the section.

Processing consists of first treating the slide for 65 minutes in 5N hydrochloride to hydrolyze the nuclear DNA. The slide is then transferred to a container of Azure A stain for a two hour staining period. Afterward, he slide is washed in rinse solution, dehydrated with ethanol, cleared with Zylene, cover slipped, and mounted. At this point, the slide is permanently fixed and ready for analysis at any time.

The system software for DNA analysis can now determine the density of the cellular DNA by obtaining the optical density of the specimen cells via the instrument 11. In general, the mass of a stained cell object can be obtained from its optical density by utilizing Beer-Lambert Law which is well known in the art of microspectrophotometry. The equation states:

$$M = \frac{\alpha \Sigma OD}{E\lambda}$$

where
$M$ = mass of the object in picograms
$\alpha$ = spot size in $\mu m^2$
$E\lambda$ = extinction coefficient of the stain at wavelength $\lambda$ in $\mu m^2/pg$.
$OD$ = optical density of each spot (dimensionless)

The instrument uses this law to find the mass distribution of a number of cells or cell objects which can then be analyzed according to a statistical basis, histogram, or other analytical format as will be discussed hereinafter. The spot size $\alpha$ is determined by the number of pixels which are measured by the camera 18. The optical density for each pixel is calibrated by adjusting the light level, focus, and reading a reference optical density from the calibration area on the slide. This calibration allows the conversion of the measured light levels for each pixel into an optical density a dimensionless quantity.

A calibration for the extinction coefficient is accomplished by measuring the optical density for a plurality of the control cells to determine a peak for the distribution in relative mass units. Because the peak DNA content is known for the control cell distribution, the cells in the measurement field can be measured using the relative OD units and then converted directly into picograms by using the control cell calibration. For example, if the control cells are known to contain 5.96 pg of DNA (trout cells) and a group of calibration cells show a peak distribution of 11,000 relative OD units then a normal group of human cells (with a known DNA content of 7.18 pg.) would exhibit a peak in their distribution at approximately 13,250 relative OD units. Further, any other relative OD unit measurement can be converted directly into picograms by determining and using the extinction coefficient found from the group of calibration cells.

Figure 10:
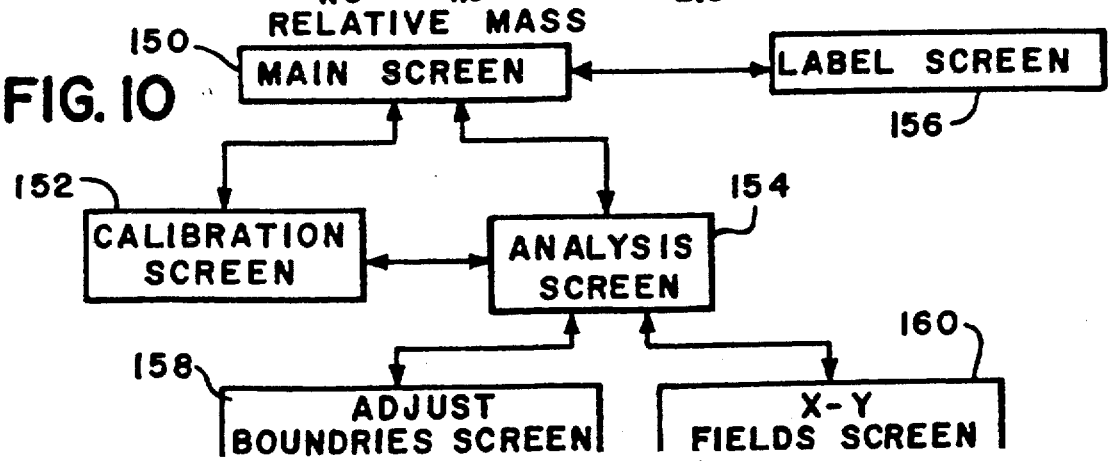
FIG. 10 is a pictorial representation of the different screen images viewable on the instruction monitor illustrated in FIG. 1.

The system software for DNA analysis is a menu driven program that uses interactive information screens on monitor 62 to assist the operator in making the described measurements on several cells or cell subpopulations. In FIG. 10 there is illustrated the visual screen structure of the program which appears on monitor 62. A main screen 150 provides information as to the calibration and analysis status of the apparatus and provides an option list for calling three other primary information screens. A pictorial example of the main screen is shown in FIG. 11. The three primary information screens correspond to the three operational functions of the program where the label screen 156 corresponds to the label function, a calibration screen 152 corresponds to the calibration function (optical density and staining), and an analysis screen 154 corresponds to the analysis function. Each screen 152, 154, and 156 provides an option list or menu wherein one of the options is to exit to the main screen 50.

In addition, the operator can enter the calibration screen 152 from the analysis screen 154, or vice versa. Two other screens are available as options from the analysis screen 154 and are used to adjust the boundary of the viewing field with the adjust boundary screen 158 and to display the X, Y coordinates of the fields that have been measured with the X, Y fields screen 160. A pictorial representation of the calibration screen is illustrated in FIG. 12, while pictorial representations of the analysis screen and the X, Y field coordinates screen are illustrated in FIG. 13 and FIG. 14, respectively.

Figure 15:
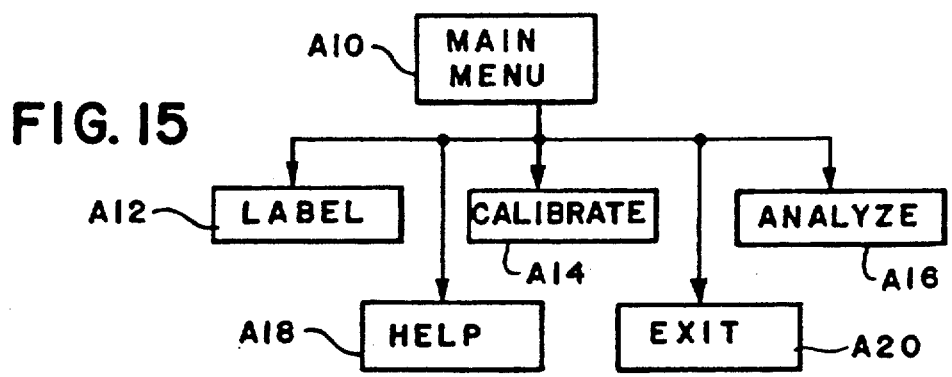
FIG. 15 is a pictorial representation of the option list for the main screen illustrated in FIG. 11.

When the unit is in operation the pathologist has a number of options or functions from a menu on each screen from which he can choose to acquire data and process that data. In general, the program is menu driven from the main screen illustrated in FIG. 11 which provides a main menu of options as shown in FIG. 15. The main menu A10 consists of five main screen functions including a label function A12, a calibrate function A14, an analyze function A16, a help function A18, and an exit function A20.

The label function allows a user to enter information regarding patient identification, accession number, and DNA conversion number. The DNA conversion number is the number that the first and second peak masses are divided by to get the first and second peak indexes (FIG. 11). Initially, the number is set to a standard 7.18 picograms/cell for normal human cells. However, the apparatus may be used to measure non-human cells and the index may be changed to that desired. The DNA index number must be greater than or equal to 1.0 and less than or equal to 99.99. If the conversion number is not within that range, the user is not allowed to select the analyze option in either the main or the calibration screens.

The three lines of information entered during the label function will appear on every screen except the X, Y field coordinate screen. The label operation is exited by pressing either the enter or escape key. Pressing the enter key will save any changes that were made to the three lines of information. Pressing the escape key will ignore any changes that were made to the three lines. The information stored during the label function will not be saved when the program is exited.

Figure 16:
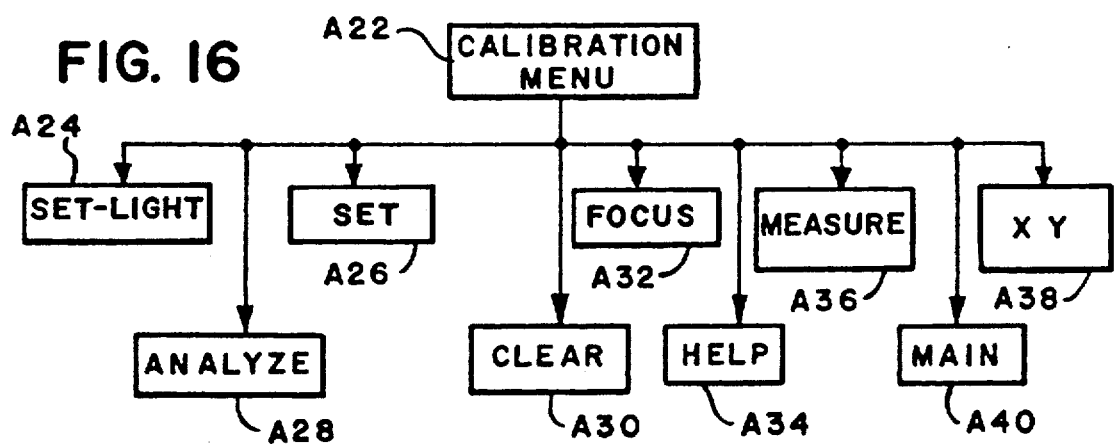
FIG. 16 is a pictorial representation of the option list for the calibration screen illustrated in FIG. 12.

Selecting the calibrate function will cause a change of the display on monitor 62 from the main screen to the calibration screen illustrated in FIG. 12. The calibration screen whose options are shown in FIG. 16 are those necessary to perform calibration of the instrument for optical density and for staining factor on the control cells. A calibration of the apparatus 11 is to be performed every time a new slide is selected to normalize the light level and staining factor.

Selecting the analyze function will cause a change of the display on the main screen on monitor 62 to the analysis screen as illustrated in FIG. 13. The analysis screen contains the menu for the functions that are necessary to perform data acquisition and DNA measurements on the specimen cells. These functions are more fully set forth in FIG. 17. Three criteria must be met in order to select the analyze function. First, the set light function in the calibration screen must have been successfully performed at least once. The set light function is successful when the current image is blank and the light level is between 129 and 131. Secondly, the calibration control cell count must be between 50 and 512. Finally, the DNA conversion number must be greater than or equal to 1.0 and less than or equal to 99.99.

The exit function allows the user to terminate the operation of the program from the main screen. Pressing the escape key is the same as selecting the exit function. When the exit operation is specified, either by selecting exit or pressing escape, the user will be asked to confirm his command to exit. To accept the confirmation, the user selects the yes key. To reject the confirmation, he selects the no key or presses the escape key.

The options for the calibration menu are illustrated in FIG. 16. The calibration menu choices include a set light function A24, a set X, Y function A26, a focus function A32, a measure function A36, an X, Y function A38, an analyze function A28, a clear function A30, a help function A34, and an exit or return to the main screen function A40.

The set light function A24 calculates the background light level for the current image. The light level can be adjusted until it is within a standardized range. The set light function should be successfully performed at least once before selecting the analyze, focus, and measure functions. For the most accurate results, the light level should be exactly equal to 130. The light level value is displayed on the calibration screen by the words "light level." If the light level is successfully set, image noise subtraction will occur in the measurement program.

Figure 22:
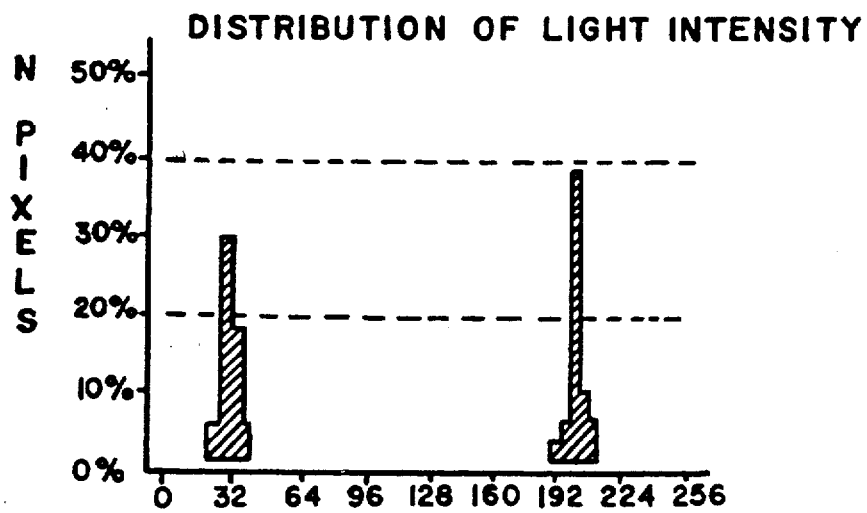
FIG. 22 is a pictorial diagram of a histogram used for light source calibration in the image analysis system illustrated in FIG. 2.

The light source calibration achieves a number of results including assistance in focusing the microscope by providing an update of a gray scale histogram which may be in the form generally shown in FIG. 22 entitled "Distribution of Light Intensity". The illustrated histogram shows a comparison of incident light $I_o$ and transmitted light $I_t$ with the transmitted light having grey level value and the incident light having a grey level value. The operator has moved the platform 51 to view the light calibrating cross 52 on the monitor 37. The operator views the light calibration material 45 and the system calculates a histogram of that pattern by inputting light from the picture elements of that field. The operator then adjusts the intensity level of the source 17 to change the light level reading on the screen. The operator does this by alternatively selecting the function and adjusting the source 17 until the correct reading appears on the screen. When the light source has been adjusted to provide the left and right peaks $I_t$ and $I_o$ for the transmitted and incidental light at the desired grey levels, 130 as the background light intensity, the system is calibrated. The system software of the apparatus 11 uses the $I_o$ and $I_t$ values to set up an internal calibration table for optical density, such that light intensity sensed for each picture element is referred to this table and known to have a particular optical density in the image scene being analyzed.

As is known with digital imaging apparatus the actual optical density for a dark object is known using white $I_o$) as a reference. By calibrating the apparatus for optical density, the incoming image data may be converted by the lookup tables in the image processing board 21 so that output optical density can be linearly added to proportionately reflect directly, in this instance, the amounts of DNA in the specimen objects.

The set X, Y of function A26 provides the setting of the origin for the slide X, Y coordinate system. This function sets the current image or field location as the origin by zeroing a pair of location registers in the software. Generally, the microscope platform 51 is moved until a easily recognized landmark is visible, such as cross 52. This landmark is then used to rezero the coordinate system to provide a means of relocating previously measured fields. The set X, Y function is used every time a new slide is selected. If the set X, Y function has not been executed, then the X, Y functions of the calibration and analysis screens and the functions in the X, Y field coordinates screen will not work properly. The set X, Y function can only be used when the calibration control cell count is equal to zero. If the microscope platform 51 is being moved when the set X, Y operation is in execution, then the coordinate origin will be in error. The program provides a message on the screen to notify the operator when the set X, Y operation is successful. In response to the function not being successful, the operator merely reselects set X, Y from the menu and attempts the function again.

The measure function A36 is used to perform the control cell or control object calibration for normalizing the staining factor. When the measure function is selected, the camera image acquisition will stop and the cursor 170 on the calibration screen will move to the words "measure operations" in FIG. 12. When the cursor 170 is at this location, the user can specify measure operations by activating the numeric lock. An identifier such as a magenta colored box will be placed around an identified cell object. By using a number of key operations illustrated in FIG. 18, the operator can perform an interactive selection and rejection process which will be more fully explained hereinafter.

During control cell calibration, the operator moves the microscope stage by turning the conventional X and Y knobs 11 and 17 (FIG. 1) to shift the control cell objects 40 into view on the monitoring screen 37. When an individual cell object 40 is within a box or indentifier border 75, the operator presses a key on the keyboard 36 to enter measurement of the summed optical density for that control cell object. After a suitable number of control cell objects have been analyzed, the operator will be provided with a histogram such as shown in FIG. 12 on the video monitor 62 which shows the operator the control cell object ploidy distribution as having a relative quantity of DNA. Internally within the system control 22, the summed relative optical density values actually measured for the control cell objects is compared to a predetermined standard or reference amount of DNA which the control cells are known to have. In the present example, if the control cells contain 5.96 picograms of DNA per cell, then an optical density measurement of approximately 8700 relative OD units corresponds to that mass. The actual summed optical density found by the operator is divided into the stored reference DNA value to provide a factor by which to adjust the extinction coefficient for deviations in the stain from a perfect staining.

The X, Y function A38 when selected displays on the calibration screen, the X, Y coordinates of the current image or field, on monitor 37. The coordinates will be continuously displayed until the user presses a key (except CTRL, ALT, or SHFT). Thus, if the same origin for the slide 14 was set, the operator can, by positioning the platform 51 and watching the coordinates change, find the same image which was previously recorded. The set X, Y function A26 must have been successfully performed previously in order for the X, Y function to be selected.

The clear function A30 will cause a purge of all the stored data images. After a clear function has been selected, the user will be asked to confirm the operation. To accept the confirmation, the user selects the yes key to confirm or, to reject the confirmation, the user selects the no key or presses the ESC key.

The focus function A32 provides color enhancement to the image so that the user can perform more precise focusing of the image. The system control 22 automatically provides different colors for gradations in grey level in the image. The operator then adjusts the focusing means of the microscope 15 until the object being focused on, for example an edge of the box, shows a clear color demarkation. This is an indication that the two separate levels or grey scale of the edge are in focus. This is much more difficult without color because the two grey levels may be close together and undiscernible without the color enhancement. The set light function A24 must have been successfully performed at least once in order to select the focus function. To restore the image to its original color, the focus function is selected a second time. If the color enhanced image is present when the user selects the measure function, the image will automatically be returned to its original color.

Selecting the analyze function A28 will change the display from the calibration screen to the analysis screen. The analysis screen provides a menu of functions shown in FIG. 17 that are necessary to perform the DNA measurements on the cellular material. Three criteria must be met in order to select the analyzed function. First, the set light function in the calibration screen must have been successfully performed at least once. Secondly, the calibration control cell count must be between 50 and 512, and finally the DNA conversion number must be greater than or equal to 1.0 and less than or equal to 99.99. The analyze function in the calibration menu works the same way as the analyze function in the main screen.

Figure 17:
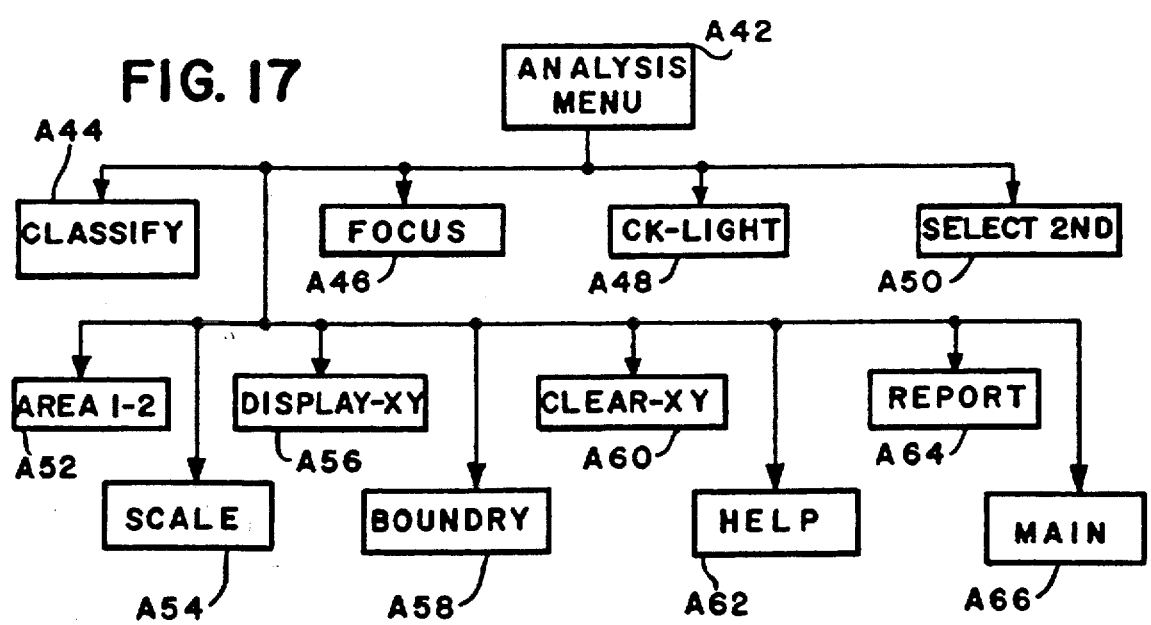
FIG. 17 is a pictorial representation of the option list for the analysis screen illustrated in FIG. 13.

The analyze function options in the analysis menu are more fully shown in FIG. 17. The analysis menu allows the selection of a classify function 44, a focus function 46, a check light function A48, a select 2nd, function A50, an area 1-2 function A52, a scale function A54, a display X, Y function A56, a boundary function A58, a clear X, Y function A60, a help function A62, a report function A64 and a return to the main menu function A66.

The check light function A48 calculates the light level of the current image. The light level value is displayed on the analysis screen by the words "light level" in FIG. 12.

The select-2nd function A50 allows the user to select the second peak on the histogram displayed on the analysis screen. The mass, DNA index, and the area of the second peak are displayed on the screen under the words "second peak." The select-2nd function cannot be selected when the shown cell count is equal to zero. The shown cell count is displayed by the word "shown." After the select-2nd function has been selected, the cursor will move to a set of arrows and the current second peak location on the histogram will be highlighted in yellow. Initially the right most histogram data location is chosen as the second peak. Selecting the left arrow moves the second peak location to the left and the user selects the right arrow to move the second peak location to the right. Every time an arrow is selected, the current peak data on the screen will be updated.

Below the histograms horizontal axis, one of three symbols will appear underneath the second peak location. A "less than" symbol will appear if the second peak lies in area one. A "greater than" symbol will appear if the second peak lies in area two. An up arrow symbol will appear if the second peak lies in neither area one nor area two. The reason for the three symbols is so that the second peak location can be identified after the select-2nd operation is exited. The vertical yellow line disappears once the select-2nd function is exited. The users presses the ESC key to exit the select second operation. The second peak data will also be automatically cleared when one of the following analysis screen functions is selected: clear, report, scale, or main.

The classify function A44 allows the user to classify the cells or objects in the current image. After the classify function has been selected, the user will be asked to confirm the operation. To accept the confirmation, the user will select the yes key, and to reject the confirmation, the user will select the no key or press the ESC key. If the classification is confirmed, the camera acquisitional stop and the cursor will move by the words "classify operation." When the cursor is at this location, the user can specify the classify operations. The numeric lock is activated which enables these functions. As was the case in the measure function, a magenta colored box will be placed around a current cell and the operations allow the user to move this cell identifier through the image to identify and classify the cells therein.

The display X, Y function A56 will change the display from the analysis screen to the X, Y field coordinates screen (FIG. 14). The X, Y field coordinate will display the X, Y coordinates of the first 512 images that are classified and stored. Also, the screen contains the functions that allow the sorting of the image fields by coordinates. The set X, Y function in the calibration screen must have been successfully performed before the display X, Y function is selected.

The X, Y field coordinate screen has several functions. One of the functions, "nearest" sorts the X, Y coordinates according to the distance from the current X, Y field position. The X function will sort the X, Y coordinates according to the X coordinate value. If there is a tie, then the Y coordinate value will determine the sort order. Similarly the Y function will sort the X, Y coordinates according to the Y coordinate value. If there is a tie, then X coordinate value will determine the sort order. The "field#" function will sort the X, Y coordinates according to the coordinates field number. The field number is the order in which the images were classified.

The page up function allows the user to display the previous page of X, Y coordinates, if any, and the page down function allows the use to display the next page of X, Y coordinates, if any. The exit function changes the display from the X, Y field coordinate screen to the analysis screen. Pressing the escape key is the same as selecting the exit function.

Selecting the X, Y function displays the X, Y coordinates of the current field. The coordinates will be continuously displayed until the user presses a key (except CTRL, ALT, and shift). The set X, Y function in the calibration screen must have successfully been performed before the X, Y function is selected. The X, Y function in the X, Y field coordinate screen works the same way as the X, Y function in the calibration and analysis screens.

The clear function A60 will clear all analysis related areas of data. After the clear function has been selected, the user will be asked to confirm the clear operation. To accept the confirmation, the user selects the yes key, or to reject the confirmation, the user will select the no key or press the ESC key.

The focus function A46 provides color enhancement to the image so that the user can perform more precise focusing of the image. The focus function in the analysis screen works the same way as the focus function in the calibration screen previously described.

The area 1-2 function A52 allows the user to specify two areas in the histogram displayed in the analysis screen. The purpose of this function is to identify the cell counts in certain areas in the histogram. The area 1-2 function cannot be selected when the shown cell count is equal to zero. The cell counts are displayed at the lower right portion of the screen. After area 1-2 is selected, the cursor will move to a row of numbers that is below the histograms horizontal axis. The row of numbers allows the user to specify the locations of area 1 and area 2. The user types a "1" to specify that the current histogram position belongs to area 1. The user types a "2" to specify that the position belongs to area 2. The user types a "0" to specify the current histogram position belongs to neither area 1 or 2. The user is allowed to specify an area 1 without an area 2, but cannot specify an area 2 without an area 1. When both areas are specified, area 1 must be specified to the left of area 2. The area must be specified as continuous. To exit the area 1-2 function, the user presses the enter or ESC keys. If the user presses the enter key, area 1 of the histogram will be highlighted in green and the area 2 will be highlighted in magenta. The area cell counts will also be displayed. Pressing the ESC key will cause the program to disregard any of the changes that were made. Area 1 and area 2 data will automatically be cleared when one of the following functions is selected: classify, clear, reports, scale or main.

Figure 20:
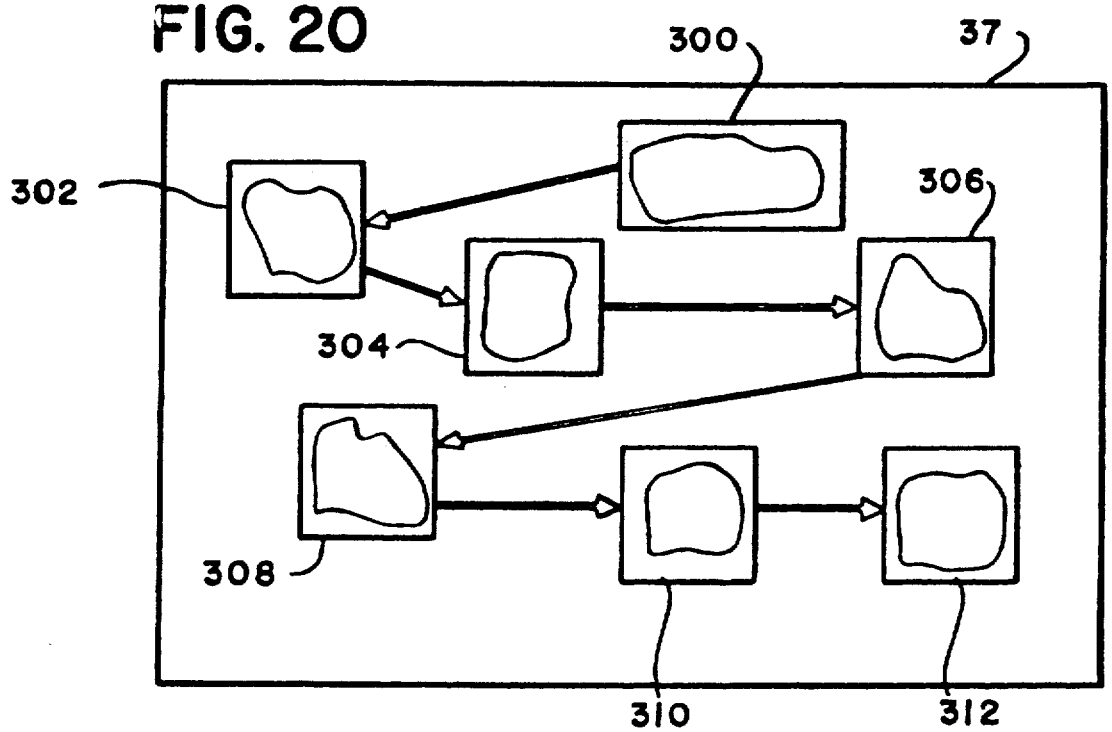
FIG. 20 is a pictorial representation in time sequence of the analysis operation for a field of cell objects as seen on the image display illustrated in FIG. 1.
Figure 21:
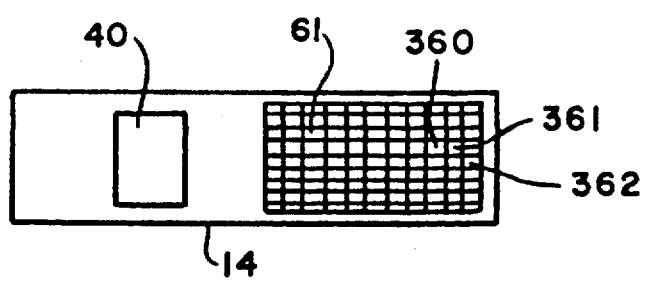
FIG. 21 is a pictorial diagram of a slide used for image analysis which has been divided into a plurality of selectable image fields by the image analysis system illustrated in FIG. 2.

The analysis function A44 is more fully described with respect to FIGS. 20 and 21. The operator will select a number of field locations 360, 361, and 362 in the slide specimen area 61 for analysis. The operator will move the X and Y knobs 11 and 17 for the microscope stage 51 to move into view on the monitor screen 37 a first field of specimen cell objects to be analyzed for DNA content as well as for cell morphology if desired (FIG. 20). The program will place a box, for example at 300, over a particular specimen cell object 12 being displayed on the monitor 37 and then the operator will use a key to cause the scanning of the pixels (picture elements) of the specimen object to classify the cell in a manner similar to that disclosed in U.S. Pat. No. 4,453,266 to give summed optical density for the cell specimen object i.e., a stained cell nucleus, as well as its area, its roundness, and other classification information. Also, the operator has on the keyboard 36 several cell classification keys to be manually operated and the operator depresses one of the keys of a known category such as a type 0 normal cell; a type 1 cancer cell; a type 2 cancer cell; a type 3 cancer cell; and etc. On the monitoring screen 62 there will be an analysis histogram displaying the DNA content of the cells in the field. The operator selects a number of cells in each field or area and then moves the microscope stage to position a number of different fields of specimen cells into view and takes and analyses a number of these specimen cells until the operator feels he has enough cells for a representative sample.

A histogram, such as shown will at this time be displayed on the monitor screen 62 which shows the number of cells of a particular DNA content and shows the DNA content averages for each of the reference peaks, such as shown in FIG. 13. By depressing a print key, on the keyboard 36 the operator may print out the histogram shown in FIG. 13 on the printer 38. The data for the specimen cells is also stored internally within the system control 22 for later recall and comparison with data of any new specimen from the same patient for analysis relating to the progress or regression of a patient.

Figure 19:
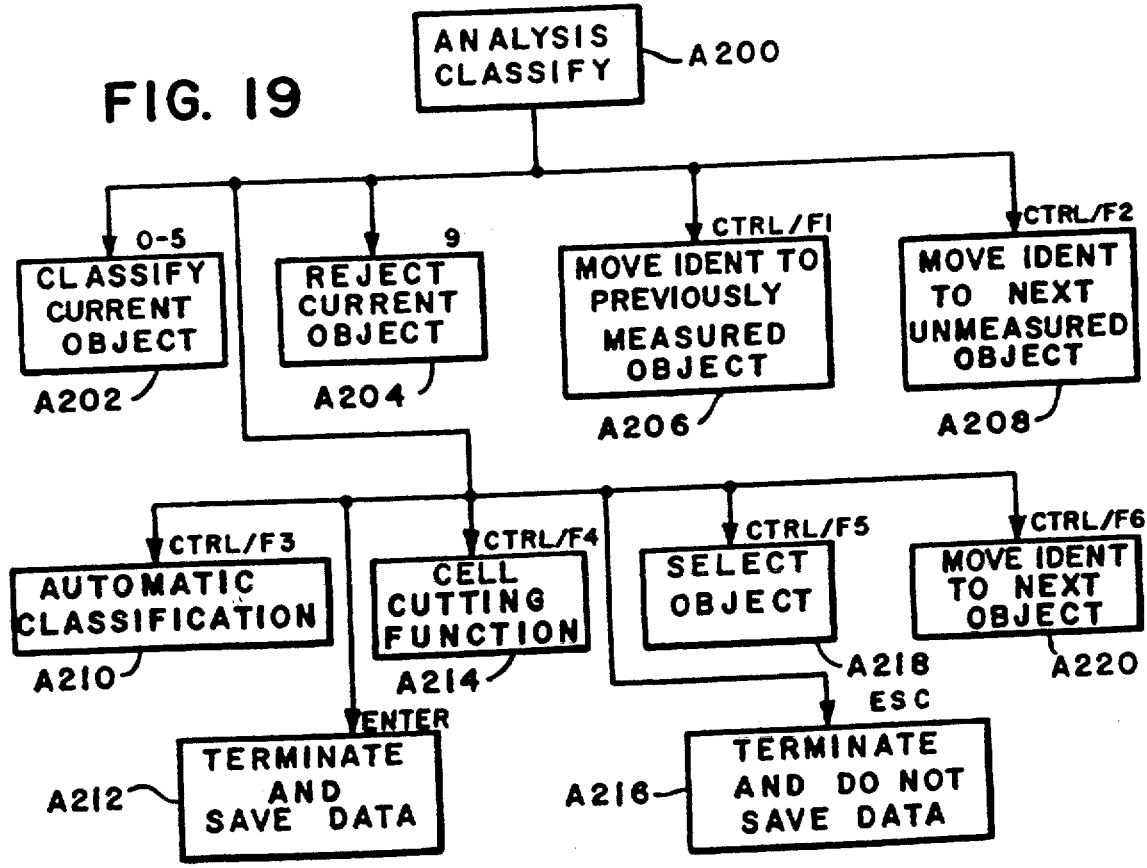
FIG. 19 is a pictorial representation of the analysis operations for the analysis screen illustrated in FIG. 13.

The operation of the analysis function will be now more fully described with respect to FIGS. 19 and 20 whereas there is shown a visual field which has been previously stored in the instrument. The field contains a number of cell objects which are to be classified and measured as to DNA content. When the program initially comes into this mode of operation, the first object in the field will be identified by scanning the pixels of the field in a raster like manner until a cell object is recognized. Once a cell object is recognized, an identification means such as box 300 is drawn around the object. This provides a visual identifier for the operator to determine which cell object is presently being measured. In addition to the measurement, the operator has a number of options in the analysis menu. The primary option that an operator has is to classify a current object in block A202. He accomplishes this by pressing one of the numeric keys 0 through 5 which automatically puts the cell object of the identifying box 300 into the classification 0-5 selected. If the object identified is debris, not an abnormal cell, or not an identifiable cell object, the operator can reject the current object by selecting a 9 on the keyboard as indicated in block A204.

After the classification or rejection of the object in box 300, the operator can move the identification box to the next unmeasured object as determined in block A208. A operator accomplishes this by pressing the keys CTRL/F2 which causes the program to erase the box 300 and search for the next identifiable cell object. This cell object is found and then another identifying box 302 is drawn around it to indicate to the operator the function has been accomplished. In this manner, the entire group of cell objects can be classified and measured or rejected by repeating this process. FIG. 20 illustrates the procedure of scanning for a cell object, putting an identifying box around it, and the classifying or rejecting the object. In this manner, the program steps through the analysis procedure from object 300 to 302, 304, 306, 308, 310, 312, etc.

Further, if one of the cell objects to be classified does not look like the operator thinks it should and cannot be put in one of the previous classifications, or for some other reason the operator believes he has classified a previous object by mistake, then in block A206 by pressing CTRL/F1, he can move the identifying box back to the previously measured object. After identifying all cell objects in the particular field being displayed, the operator has the option of going to another field by manipulating the X, Y positioning mechanism to provide more cells for the particular analysis.

When the operator has determined that enough cell objects had been analyzed, he may either terminate the analysis function by pressing either the enter key or escape key. If he terminates the analysis function by pressing the enter key, as indicated in block A212, then the data assembled for each of the measurements will be saved. However, if the analysis function is terminated by pressing the ESC key, then in block A216 the data will not be saved.

The report function A64 allows the user to specify which cell classifications are to be included in the histogram shown on the screen of the monitor 62. After the report function has been selected, the cursor can be moved to a option list which will allow the operator to specify the cell types. The following table specifies which key the operator presses in order to select a particular cell type.

| CELL TYPE | KEY |
| --- | --- |
| normal | 0 or n |
| 1 | 1 |
| 2 | 2 |

-continued

| CELL TYPE | KEY |
| --- | --- |
| 3 | 3 |
| 4 | 4 |
| lymphocyte | 5 or L |

Any combination of the types for the report data is allowed. The program will ignore any other characters than those listed in the table. The operator exits the report operation by pressing the enter or escape key. If the operator presses the enter key, he will change the types in the histogram to those which were specified. However, if the escape key is selected, the program will ignore any changes that were made and return normally. The functions area one and area two and the second peak data will automatically be cleared when the report operation is performed.

The scale function A54 allows the operator to change the scale of the horizontal axis of the histogram provided on the analysis screen. There are three scales to choose from, 0-16, 0-32, and 0-64. If the scale function is selected when the current scale is 0-16, then the new scale will be 0-32. If the scale function is selected when the current scale is 0-32, then the new scale will be 0-64. Likewise, if the scale function is selected when the current scale is 0-64, then the new scale will be 0-16. In this function the area 1, area 2, and second peak data will automatically be cleared when the scale operation is performed.

The boundary function A58 will change the display on monitor 27 from the analysis screen to the adjust boundary screen. The adjust boundary screen contains functions that are necessary to change the cell boundary, i.e., threshold. While addressing the boundary screen, the camera image acquisition will be halted.

The step function allows the operator to change the amount by which the boundary will change when one of the arrow keys is selected. The value must be in the range of 0-128. After the step size is selected, the cursor will move to the location on the screen where the user can type in a new step size value. To exit the step size function, the enter or escape keys are used. Pressing the enter key will save the step size change where pressing the escape key will ignore any change that was made. Initially, the step size value is equal to one.

The up arrow function will increase the cell boundary by the value of the step size and the down area function will decrease the cell boundary by the value of the step size. The exit function changes the display from the address boundary screen to the analysis screen. Pressing the escape key is the same as selecting the exit function.

In general, an interactive data collection and analysis scheme is used by the apparatus for the collection of specific parameters for both the calibration cell objects and the specimen cell objects. Each field which is selected is displayed on the monitor 37 and either the measure operation of the calibration screen or the classify operation of the analysis screen is chosen.

Figure 18:
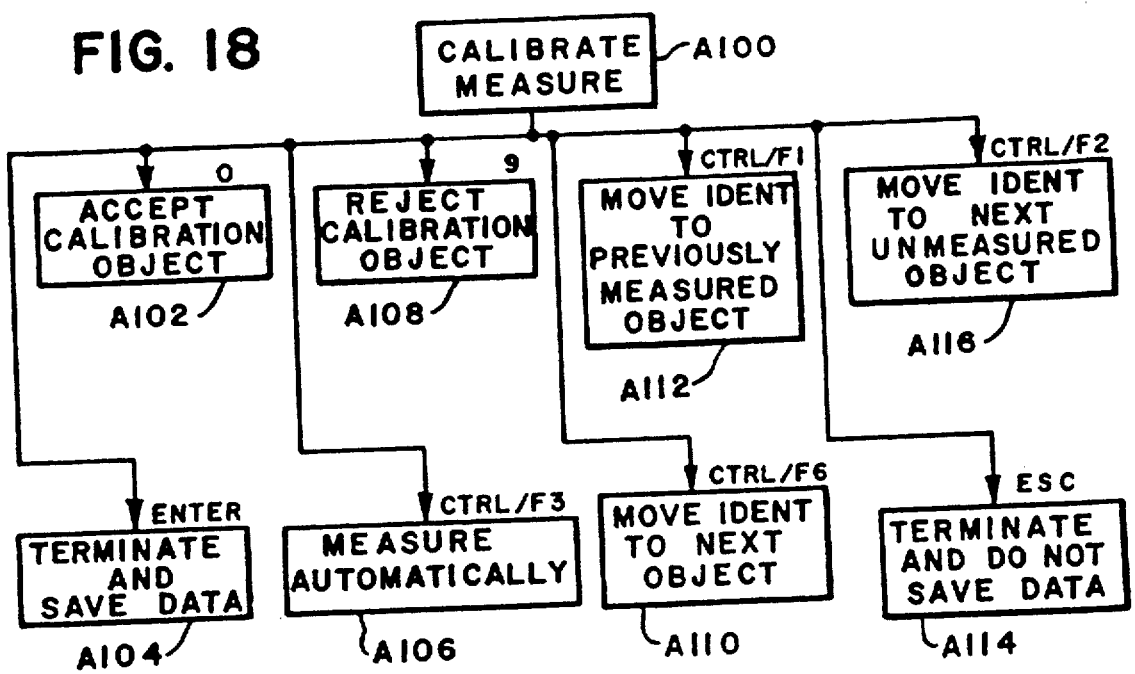
FIG. 18 is a pictorial representation of the measure operations for the calibration screen illustrated in FIG. 12.
Figure 24A:
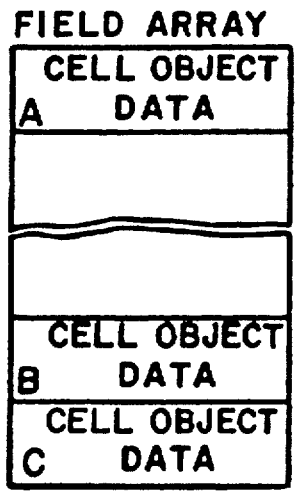
FIG. 24A, B and C is a software flow chart of the program whose function is to process the analysis and measurement operations for the analysis and measurement screens illustrated in FIGS. 12 and 13, respectively.
Figure 24B:
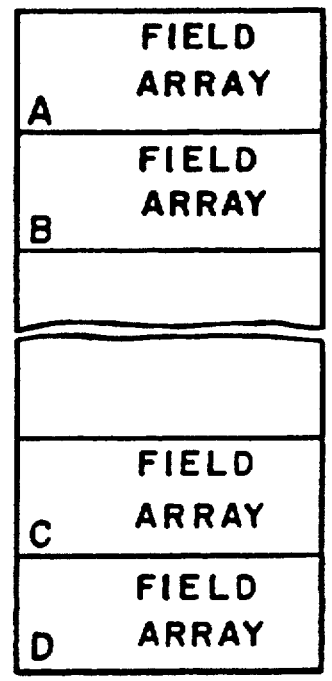
Figure 24C:
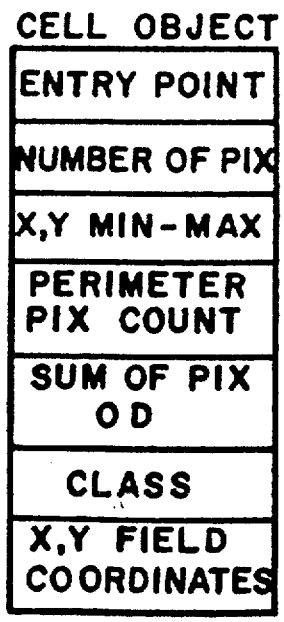

A software flow chart of a subroutine providing the interactive operations for the calibrate key operations and the analysis key operations, FIGS. 18 and 19, is illustrated in FIG. 24. When the operator selects either the measure operations or the classify operations, this program is called to provide the selection process for both the calibration cell objects and the specimen cell objects. The program begins in block A300 by performing a raster scan of the stored image pixel by pixel until it finds a pixel greater than the threshold value. The test for this operation is performed in block A302. If no pixel is found which is greater than the threshold, block A304 determines if the scan is complete. If not, the program loops back to block A300 where the scan is continued until all pixels in the image field are tested. After all pixels have been tested, the scan parameters are reset in block A308 and the cell object array updated in block A310.

At the time an image pixel is determined to be greater than the threshold, the program will label the object in block A306. The operation of labelling will now be more particularly described. The individualized cell objects in the digitized image are located by a scene analysis technique in which the raster scan is made of the digitized image to locate any pixel above the critical threshold. The technique then performs a four neighbor analysis of adjacent pixel elements and continues in a recursive manner locating "neighbors of the neighbors" which are above the threshold until the entire region of a cell object is defined. This technique is preferred to other scene analysis techniques, such as local boundary found from a gradient image, because it is fool proof in distinguishing the true region of a cell, particularly those cells having irregular or spiculed projections.

The four pixels (top, bottom, right side, and left side) surrounding the initially located pixel which are contiguous therewith are examined sequentially to identify the next pixel with a optical density or gray level value above the threshold. For instance, if the pixel located above the first pixel is not above the threshold, it is discarded from the labelling routine. The next pixel (right side) in a clockwise direction is then examined and may be above the threshold. If so, that pixel is then identified and stored in memory with the pixel as being a portion of the region of a cell. Next the address and density of the pixel found is stored in a pushdown list and the four neighboring pixels of that pixel are examined in the same clockwise order. This continues in a recursive manner until no neighbors are found above a threshold for a particular pixel. At this point the prior pixels on the pushdown list are reexamined to continue the neighbor search process until the entire number of pixels defining a region, i.e., the cell object has been identified. Thus, each of the pixels above the threshold of the region are identified and a complete enclosed region has been defined for a cell.

Once a cell object is labelled, a cell object table (FIG. 24C) is set up for the object as shown. The table lists the address of its entry point pixel, the number of pixels in the object, the X, Y points for the minimum and maximum points of the object, a count of the pixels in the perimeter of the object, the sum of the optical density of the object pixels, any classification provided for the object, and the X, Y coordinates of the field to which the object belongs. A plurality of the cell object tables comprise a temporary array, called a field array and shown in FIG. 24A, which is used to store the interactive data developed for the present field image under consideration.

In block A312 the program determines whether an automatic flag has previously been set. If so, the program will branch immediately to block A316 or, if not, negatively branch to block A314. Next, in block A313, a box or identifying border is placed around the object using the X, Y limits. This mode identifies a particular object in the field for the operator. In block A314, a key handler is entered to obtain a key press from the operator to determine which of the key functions of FIGS. 18 or 19 are to be accomplished. The key handler further determines which operation, either for calibration or analysis, is to be performed and only those keys which are associated with the present mode are enabled, all others are locked out. Once a key has been obtained, blocks A326–A342 will determine which function was selected and the progress of the routine.

Keys 0–5 as detected in block A326 provide for the acceptance of a calibration object or the classification of a specimen object. If such key is detected, then an affirmative branch continues the program at block A318. In block A318 the object is relabelled and in block A320 the object is colored (red) to indicate to the operator that it has been accepted or classified. The operator classifies the cell objects into different categories based upon visual clues such as morphology. The cells for analysis can be classified into a normal class 0, or one of several abnormal classes 1–5. The data class of the object is stored to its place in the associated object data table in block A316. Calibration objects are classified as type 0 or normal. The program then returns to the block A300 where the image scan registers are incremented to scan the field for the next object.

Alternatively, if the key press was a 9 as tested for in block A328, this means either a calibration cell object was rejected or a current specimen cell object was rejected. Thus, in block A322 the rejected cell object is colored in a different color (white) than an accepted or classified cell object, and the program returns to the scanning routine entry at block A300 to find another object. Coloring the cell object alerts the operator that the object has been analyzed in this field, coloring the object another color differentiates the object from an accepted or classified cell objects.

If, however, the key press is a CTRL/F1 as tested for in block A336, then the operator desires to move the identifying box to the last previously measured object. The program will then interrogate the field array to find the last object pointer in block A346. This pointer is used to create the box around the previous cell object by transferring control to block A313 before getting another key press in block A314. By using a series of CTRL/F1 keys the operator may selectively move the identifying box from previously measured cell object to previously measured cell object in a reverse direction. If, after the box is placed around a particular cell object, the operator desires to reclassify that cell object, he then has the option of classifying it with the keys 0–5 in block A326.

The identifying box may be moved to the next unmeasured cell object by selecting the key CTRL/F2. The key is tested for in block A338 and if found, immediately returns the program control to the image scan entry in block A300. The effect of this operation is to allow the operator to skip the present cell object and move the identifying box to the next cell object without either rejecting or accepting the present cell. A series of CTRL/F2 presses will move the box forward through the cells without measuring them.

If all of the cell objects in a particular field appear normal as specimen cells, or as is generally the case with control cells they are acceptable, the operator may want to classify them all automatically. To accomplish this, an operator presses the key CTRL/F3. This key press is detected by block A339 and transfers control to block A341 where the automatic mode flag is set. The program then returns to the entry of the image scan in block A300. However, instead of going through the normal sequence of placing a box around the next object and waiting for a key press, the program will loop to automatically classify the rest of the cells of a field. The automatic mode flag being set is sensed in block A313 and the program automatically transfers control to block A316. Automatically classified cells are categorized as normal or type 0. Thus, a scan and labelling loop will be executed via blocks A300, A302, A306, A313, A316, A318, and A320 until the scan of the entire field has been completed as sensed in block A304.

Another option that the operator can select is the cell cutting function which is entered by pressing the key CTRL/F4. This key is detected in block A342 and transfers control to the cell cutting function operation in block A352. When the CTRL and F4 keys are pressed, the user enters the cell cutting mode. While in this mode, the user is permitted to make cut lines inside the indentifier box. The operator cannot make a cut line over a pixel that belongs to a measured or a rejected cell. A measured cell is a cell that has been classified as type 0, 1, 2, 3, 4, or 5. Numeric lock must be activated in order to perform a cell cutting operation. A cross hair is located where the cut is to take place. The following table lists the cell cutting operations that can be performed plus the key that must be pressed in order to select the desired operation. The function allows the splitting of overlapping cells by artificially making a perimeter between two areas, a cut. Thus, the labelling routine will only label one area as a cell object.

| (KEY) | (ACTION) |
|-------|----------|
| 0 | Turn splitting on and off |
| 1 | Go down and left one step |
| 2 | Go down one step |
| 3 | Go down and right one step |
| 4 | Go left one step |
| 5 | Go to the center of the box |
| 6 | Go right one step |
| 7 | Go up and left one step |
| 8 | Go up one step |
| 9 | Go up and right one step |
| ENTER | Re-do last step (up to 100 pixels) |
| ESC | Exit cell splitting mode |

A step is three pixels. When beginning a new cut, the first pixel will not be cut. For operation 5, the cross hair will not move if the center pixel belongs to a measured or rejected cell.

After the cell cutting is performed in block A352, the scanner registers are set to the entry point of the particular object cut. The program then returns to the scan entry in block A300. Because the cell object has the same entry point but a different perimeter, the labelling routine (block A306) will label the cell object as now cut.

Another option that the operator has is the ability to select any object within a field. The selection of this mode is accomplished by pressing the CTRL/F5 key which is sensed in block A340. An affirmative branch from block A340 transfers control to block A348 where the select object mode is entered.

When the CTRL and F5 keys are pressed, the user enters the selection mode. Numeric lock must be activated in order to perform a selection operation. A cross hair will appear at the current selection point. The following table lists the selection operations that can be performed plus the key that must be pressed in order to select the desired operation.

| (KEY) | (ACTION) |
|-------|----------|
| 0 | Select cross hair movement step size [5 or 15] |
| 1 | Go down and left one step |
| 2 | Go down one step |
| 3 | Go down and right one step |
| 4 | Go left one step |
| 5 | Go to the center of the image |
| 6 | Go right one step |
| 7 | Go up and left one step |
| 8 | Go up one step |
| 9 | Go up and right one step |
| ESC | Exit selection mode |

When the selection mode is exited, the box will move to the first unmeasured cell after the selection point. If there are no cells after the cross hair, the box will go to the next unclassified cell.

After the object is selected by the above described technique, the scanner registers are set to the entry point of that particular object in block A348 and the program returns to the scan entry in block A300. This creates the identifier box around the object using its X, Y limits and provides the operator with the option of then pressing another key and performing other measurements and classifications on that selected object.

Another function is provided by key CTRL/F6 which is tested for in block A330. This feature provides an operator with the ability to move the indentifier box forward by reading the next cell object pointed in block A324 and then drawing around the box the chosen object in block A313. The key CTRL/F1, CTRL/F2 thereby allows an operator to quickly revise pervious cell classification by stepping forward and backwards, respectively, through the pointers of the previously measured cells.

When the enter key is sensed, in block A332, control of the program is transferred to block A310. In that block, the cell object array (FIG. 24B) is updated with the present field array to store all of the data collected for the particular objects in the field. Alternatively, the sensing of the escape key returns the program immediately to the place in the software where it was called.

It will be appreciated that the illustrated control 22 has been programmed to do the cell classification and optical density analysis. Such classification and analysis is similar to that outlined in U.S. Pat. No. 4,453,266 for the classification or red blood cells and the present invention can be particularly useful in the analysis of red blood cells wherein the optical density of the hemoglobin content is measured rather than the DNA content as above described. As common in red blood cell analysis, the red blood cells need not be stained for image enhancement so that the staining calibration step may be eliminated for red blood cells when using the specific wave length of light specified in the aforementioned Bacus patents.

A further use of the present invention is to provide a precise measurement of hemoglobin in actual picograms for calibrating other instruments such as a Coulter counter. In such a process, the control blood cells 40 will have a known predetermined hemoglobin value and the specimen blood cells 12 of unknown hemoglobin value will be placed on the specimen area 61. Then the apparatus will be calibrated to show the histogram for the hemoglobin content of the specimen cells 12.

It will also be appreciated that the various calibration steps may be eliminated or combined and done simultaneously rather than done in the order and in the sequence and in the manner described for the preferred embodiment of the invention in making a DNA analysis. The use of the present invention for antigen analysis may include the steps of binding of monoclonal antibodies to the specimen and control cell objects. Later the monoclonal antibodies may be conjugated with an enzyme stain. Also, the monoclonal antibodies may be conjugated with a fluorescent material. Thereafter, the fluorescent stain may be excited at a wave length which excites the fluorescence and the specimen objects observed at another wave length at which fluorescent emission occurs. When the antigen is made for a particular virus, the control cell specimen objects may be treated with a nucleic acid probe specific for the genome of the virus.

While a preferred embodiment of the invention has been illustrated, it will be obvious to those skilled in the art that various modifications and changes may be made thereto without departing from the spirit and scope of the invention as defined in the appended claims.

A software program for the system control 22 is provided in the attached listings pages 1a-199a which follow. The listings are of a preferred embodiment of the invention useful for DNA analysis of cell objects.

```
CC
CC                CELL ANALYSIS SYSTEMS, INC.
CC                   (C) COPYRIGHT 1986
CC****************************************************************
CC
CC      :PROGRAM NAME
CC      :SAQQ01
CC
CC      :SUBROUTINES
CC      :SAQQ02
CC
CC      :CALLING SEQUENCE
CC      :NONE
CC
CC      :PARAMETERS
CC      :NONE
CC
CC      :DESCRIPTION
CC      :SAQQ01 SERVES AS THE MAINLINE PROGRAM FOR THE PLOIDY SOFTWARE
CC      :PACKAGE.
CC
CC****************************************************************
CC########
        PROGRAM SAQQ01
        INTEGER*2 I$RETURN,I
        CHARACTER*9 READ$INPUT$VALUE
C
        INCLUDE 'IMAGE.FIN'
        INCLUDE 'IMAGED.FIN'
        INCLUDE 'SCREEN.FIN'
C
C       **************** INITIALIZE VARIABLES ****************
C
        READ$INPUT$VALUE = ' '
C
        CALL SYCHEN('SAMENU  ',I$RETURN)
C
C       ************* INITIALIZE THE SCREEN ******************
C
        CALL SCREEN(INITIAL$SCREEN,SCREEN$NAME,FIELD$NAME,
     *              DATA$AREA,SCERR)
        IF (SCERR .NE. NO$SCREEN$ERROR)
     *      CALL SYERR(INITIAL$SCREEN,SCREEN$NAME,FIELD$NAME,SCERR,
     *                 'INITIAL SCREEN')
C
C       ************* CLEAR THE SCREEN ******************
C
        CALL SCREEN(CLEAR$SCREEN,SCREEN$NAME,FIELD$NAME,
     *              DATA$AREA,SCERR)
        IF (SCERR .NE. NO$SCREEN$ERROR)
     *      CALL SYERR(CLEAR$SCREEN,SCREEN$NAME,FIELD$NAME,SCERR,
     *                 'CLEAR SCREEN')
C
C       ****************** GET THE SCREEN ******************
C
```

```
      SCREEN$NAME = 'QEN001'
      CALL SCREEN(GET$SCREEN,SCREEN$NAME,FIELD$NAME,
     *            DATA$AREA,SCERR)
      IF (SCERR .NE. NO$SCREEN$ERROR)
     *   CALL SYERR(GET$SCREEN,SCREEN$NAME,FIELD$NAME,SCERR,
     *              'GET SCREEN')
C
C     *************** KILL THE UNUSED FIELDS ****************
C
      DATA$AREA(1) = 3
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DATA$AREA(1) = 5
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DATA$AREA(1) = 10
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DATA$AREA(1) = 20
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DATA$AREA(1) = 21
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DATA$AREA(1) = 60
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DATA$AREA(1) = 61
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
      DO 100 I=69,80
        DATA$AREA(1) = I
        CALL SCREEN(GROUP$KILL$FIELD,SCREEN$NAME,FIELD$NAME,
     *              DATA$AREA,SCERR)
        IF (SCERR .NE. NO$SCREEN$ERROR)
     *     CALL SYERR(GROUP$KILL$FIELD,SCREEN$NAME,FIELD$NAME,SCERR,
     *                'GROUP KILL FIELD')
100   CONTINUE
      DATA$AREA(1) = 90
      CALL SCREEN(GROUP$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$KILL$FIELD,SCREEN$NAME,FIELD$NAME,SCERR,
     *              'GROUP KILL FIELD')
C
      FIELD$NAME = '0001'
      CALL SCREEN(KILL$FIELD,SCREEN$NAME,FIELD$NAME,
     *            DATA$AREA,SCERR)
      IF (SCERR .NE. NO$SCREEN$ERROR)
```

```
     *      CALL SYERR(KILL$FIELD,SCREEN$NAME,FIELD$NAME,SCERR,
     *                'KILL FIELD')
            FIELD$NAME = 'STUD'
            CALL SCREEN(KILL$FIELD,SCREEN$NAME,FIELD$NAME,
     *                DATA$AREA,SCERR)
            IF (SCERR .NE. NO$SCREEN$ERROR)
     *         CALL SYERR(KILL$FIELD,SCREEN$NAME,FIELD$NAME,SCERR,
     *                'KILL FIELD')
C***************************************************************
C
C         *************** SET CURSOR ****************
C
C***************************************************************
            FIELD$NAME = 'MS02'
            CALL SCREEN(SET$CURSOR,SCREEN$NAME,FIELD$NAME,
     *                DATA$AREA,SCERR)
            IF (SCERR .NE. NO$SCREEN$ERROR)
     *         CALL SYERR(SET$CURSOR,SCREEN$NAME,FIELD$NAME,SCERR,
     *                'SET CURSOR')
C***************************************************************
C
C         ************** READ INPUT *******************
C
C***************************************************************
            CALL SCREEN(READ$INPUT,SCREEN$NAME,FIELD$NAME,
     *                DATA$AREA,SCERR)
            IF (SCERR .EQ. SCREEN$ESCAPE .OR.
     *          SCERR .EQ. SCREEN$FUNCTION)
     *      THEN
              CONTINUE
            ELSE
              CALL SYERR(READ$INPUT,SCREEN$NAME,FIELD$NAME,SCERR,
     *                'READ INPUT')
            ENDIF
            CALL CNARST(9,DATA$AREA,READ$INPUT$VALUE)
            IF (SCERR .EQ. SCREEN$ESCAPE) READ$INPUT$VALUE = 'EXIT'
C
C       ************** KILL THE INITIAL FIELDS ***************
C
            DATA$AREA(1) = 1
            CALL SCREEN(GROUP$KILL$FIELD,SCREEN$NAME,FIELD$NAME,
     *                DATA$AREA,SCERR)
            IF (SCERR .NE. NO$SCREEN$ERROR)
     *         CALL SYERR(GROUP$KILL$FIELD,SCREEN$NAME,FIELD$NAME,SCERR,
     *                'GROUP KILL FIELD')
C
C       ************** UNKILL THE APPROPRIATE FIELDS ***************
C
            DATA$AREA(1) = 3
            CALL SCREEN(GROUP$UN$KILL$FIELD,SCREEN$NAME,FIELD$NAME,
     *                DATA$AREA,SCERR)
            IF (SCERR .NE. NO$SCREEN$ERROR)
     *         CALL SYERR(GROUP$UN$KILL$FIELD,SCREEN$NAME,FIELD$NAME,SCERR,
     *                'GROUP UNKILL FIELD')
            DATA$AREA(1) = 10
            CALL SCREEN(GROUP$UN$KILL$FIELD,SCREEN$NAME,FIELD$NAME,
     *                DATA$AREA,SCERR)
            IF (SCERR .NE. NO$SCREEN$ERROR)
     *         CALL SYERR(GROUP$UN$KILL$FIELD,SCREEN$NAME,FIELD$NAME,SCERR,
     *                'GROUP UNKILL FIELD')
C
C       ***************** CALL THE MAIN SUBROUTINE *******************
C
            CALL SAQQ02(SCREEN$NAME,READ$INPUT$VALUE)
            IF (I$RETURN .EQ. 0)
     *      THEN
              CALL EXIT
            ENDIF
            END
C
```

```
CC              CELL ANALYSIS SYSTEMS, INC.
CC                 (C) COPYRIGHT 1986
CC*******************************************************************
CC
CC      :PROGRAM NAME
CC      :SAQQ02
CC
CC      :SUBROUTINES
CC      :IMMAIN
CC      :SAQQ03
CC      :SAQQ04
CC      :SCREEN
CC
CC      :CALLING SEQUENCE
CC      :SAQQ02(SCRN$NAME,READ$INPUT$VALUE)
CC
CC      :PARAMETERS
CC      :SCRN$NAME - THE NAME OF THE CURRENT SCREEN
CC      :READ$INPUT$VALUE - THE FUNCTION THAT THE USER SELECTED
CC
CC      :DESCRIPTION
CC      :SAQQ02 HANDLES THE OPERATION OF THE MAIN SCREEN OF PLOIDY
CC
CC*******************************************************************
CC########
        SUBROUTINE SAQQ02(SCRN$NAME,READ$INPUT$VALUE)
        CHARACTER*1 ERR$MESSAGE
        CHARACTER*3 CONFIRM$ANSWER
        CHARACTER*4 CURSOR$POSITION
        CHARACTER*(*) SCRN$NAME
        CHARACTER*9 READ$INPUT$VALUE
        CHARACTER*32 ERR$ONE,ERR$TWO
        INTEGER*2 CAL$LIGHT$LEVEL,
     *            ANALYSIS$TOTAL,I,
     *            K,REDSAVE(128),GREENSAVE(128),
     *            BLUESAVE(128),XY$COUNTER,XY$COORDS(3,512),
     *            PICO$HIST(640)
        REAL*4 FIRST$PEAK$MASS,FIRST$PEAK$INDEX,FIRST$PEAK$AREA,
     *         SEC$PEAK$MASS,SEC$PEAK$INDEX,SEC$PEAK$AREA,
     *         DNA$CONV$VALUE
        LOGICAL*1 CONFIRM$EXIT,CONFIRM$FIELDS$KILLED,FATAL$ERROR,
     *            ANALYZE$FLAG,FIRST$TIME,FOCUS$ACTIVE,
     *            FOCUS$FLAG,XY$INIT,SET$LIGHT$FLAG
C
        INCLUDE 'SAQCCD.FIN'
        INCLUDE 'SAQCDT.FIN'
        INCLUDE 'IMAGED.FIN'
        INCLUDE 'SCREEN.FIN'
C
        DATA FIRST$TIME /.TRUE./,
     *       FOCUS$ACTIVE /.FALSE./,
     *       FOCUS$FLAG /.FALSE./,
     *       XY$INIT /.FALSE./
C
C       ***************** INITIALIZE VARIABLES *****************
C
        SCREEN$NAME = SCRN$NAME
        SET$LIGHT$FLAG = .FALSE.
        ERR$MESSAGE = ' '
        CURSOR$POSITION = 'MS02'
        ERR$ONE = ' '
        ERR$TWO = ' '
        CONFIRM$ANSWER = ' '
        CAL$LIGHT$LEVEL = 0
        ANALYSIS$TOTAL = 0
        XY$COUNTER = 0
        DNA$CONV$VALUE = 7.18
        FIRST$PEAK$MASS = 0.0
        FIRST$PEAK$INDEX = 0.0
        FIRST$PEAK$AREA = 0.0
        SEC$PEAK$MASS = 0.0
```

```
          SEC$PEAK$INDEX = 0.0
          SEC$PEAK$AREA = 0.0
          I = 0
          K = 0
          IO$STATUS = 0
          DO 23 I=1,512
           DO 24 J=1,3
              XY$COORDS(J,1) = 0
    24     CONTINUE
    23   CONTINUE
          DO 30 I=1,640
             PICO$HIST(I) = 0
    30   CONTINUE
          CONFIRM$EXIT = .FALSE.
          CONFIRM$FIELDS$KILLED = .TRUE.
          FATAL$ERROR = .FALSE.
          ANALYZE$FLAG = .FALSE.
C
C        ************* INITIALIZE COMMON BLOCK VARIABLES ***************
C
          CALL SAQQ28(SCREEN$NAME,FATAL$ERROR)
          IF (FATAL$ERROR)
       *  THEN
             ERR$ONE = 'DUE TO A PROGRAMMING PROBLEM,'
             ERR$TWO = 'YOU CAN ONLY USE HELP OR EXIT.'
             ERR$MESSAGE = 'W'
          ENDIF
C***************************************************************************
C
C        ************** ERROR MESSAGE ACTION ************
C
C ***************************************************************************
   100    IF (ERR$MESSAGE .EQ. 'C')
       *  THEN
             ERR$ONE = ' '
             ERR$TWO = ' '
          ENDIF
          IF (ERR$MESSAGE .EQ. 'C' .OR.
       *      ERR$MESSAGE .EQ. 'W')
       *  THEN
             FIELD$NAME = 'ERR1'
             CALL CNSTAR(32,ERR$ONE,DATA$AREA)
             CALL SCREEN(PUT$FIELD,SCREEN$NAME,FIELD$NAME,
       *                DATA$AREA,SCERR)
             IF (SCERR .NE. NO$SCREEN$ERROR)
       *        CALL SYERR(PUT$FIELD,SCREEN$NAME,FIELD$NAME,SCERR,
       *                   'PUT FIELD')
             FIELD$NAME = 'ERR2'
             CALL CNSTAR(32,ERR$TWO,DATA$AREA)
             CALL SCREEN(PUT$FIELD,SCREEN$NAME,FIELD$NAME,
       *                DATA$AREA,SCERR)
             IF (SCERR .NE. NO$SCREEN$ERROR)
       *        CALL SYERR(PUT$FIELD,SCREEN$NAME,FIELD$NAME,SCERR,
       *                   'PUT FIELD')
          ENDIF
          IF (ERR$MESSAGE .EQ. 'C') ERR$MESSAGE = ' '
          IF (ERR$MESSAGE .EQ. 'W') ERR$MESSAGE = 'C'
          IF (ERR$MESSAGE .NE. 'C') ERR$MESSAGE = ' '
C
C        ********** CHECK FOR A 'FATAL'(I.E. SERIOUS) ERROR **********
*
          IF (FATAL$ERROR)
       *  THEN
             IF (FIRST$TIME) FIRST$TIME = .FALSE.
             FIELD$NAME = 'MS02'
             CALL SCREEN(KILL$FIELD,SCREEN$NAME,FIELD$NAME,
       *                DATA$AREA,SCERR)
             IF (SCERR .NE. NO$SCREEN$ERROR)
       *        CALL SYERR(KILL$FIELD,SCREEN$NAME,FIELD$NAME,SCERR,
       *                   'KILL FIELD')
             FIELD$NAME = 'MS03'
```

```
              CALL SCREEN(KILL$FIELD,SCREEN$NAME,FIELD$NAME,
     *                   DATA$AREA,SCERR)
              IF (SCERR .NE. NO$SCREEN$ERROR)
     *          CALL SYERR(KILL$FIELD,SCREEN$NAME,FIELD$NAME,SCERR,
     *                     'KILL FIELD')
              FIELD$NAME = 'MS04'
              CALL SCREEN(KILL$FIELD,SCREEN$NAME,FIELD$NAME,
     *                   DATA$AREA,SCERR)
              IF (SCERR .NE. NO$SCREEN$ERROR)
     *          CALL SYERR(KILL$FIELD,SCREEN$NAME,FIELD$NAME,SCERR,
     *                     'KILL FIELD')
              CURSOR$POSITION = 'MS07'
            ENDIF
C
C       ******* CHECK TO SEE IF THE CONFIRM FIELDS HAVE TO BE KILLED ******
C
            IF (.NOT. CONFIRM$EXIT .AND. .NOT. CONFIRM$FIELDS$KILLED)
     *      THEN
              DATA$AREA(1) = 5
              CALL SCREEN(GROUP$KILL$FIELD,SCREEN$NAME,FIELD$NAME,
     *                   DATA$AREA,SCERR)
              IF (SCERR .NE. NO$SCREEN$ERROR)
     *          CALL SYERR(GROUP$KILL$FIELD,SCREEN$NAME,FIELD$NAME,SCERR,
     *                     'GROUP KILL FIELD')
              CONFIRM$FIELDS$KILLED = .TRUE.
            ENDIF
C
C       ************** CHECK FOR FIRST TIME ****************
C
            IF (FIRST$TIME)
     *      THEN
              FIRST$TIME = .FALSE.
              SCERR = SCREEN$FUNCTION
              GOTO 200
            ENDIF
C **************************************************************************
C
C       *************** SET CURSOR ****************
C
C **************************************************************************
            FIELD$NAME = CURSOR$POSITION
            CALL SCREEN(SET$CURSOR,SCREEN$NAME,FIELD$NAME,
     *                  DATA$AREA,SCERR)
            IF (SCERR .NE. NO$SCREEN$ERROR)
     *        CALL SYERR(SET$CURSOR,SCREEN$NAME,FIELD$NAME,SCERR,
     *                   'SET CURSOR')
C **************************************************************************
C
C       ************** READ INPUT ********************
C
C **************************************************************************
            CALL SCREEN(READ$INPUT,SCREEN$NAME,FIELD$NAME,
     *                  DATA$AREA,SCERR)
            IF (SCERR .EQ. SCREEN$ESCAPE .OR.
     *          SCERR .EQ. SCREEN$FUNCTION .OR.
     *          SCERR .EQ. SCREEN$DATA)
     *      THEN
              CONTINUE
            ELSE
              CALL SYERR(READ$INPUT,SCREEN$NAME,FIELD$NAME,SCERR,
     *                   'READ INPUT')
            ENDIF
            CALL CNARST(9,DATA$AREA,READ$INPUT$VALUE)
            IF (FATAL$ERROR .AND. (READ$INPUT$VALUE .EQ. 'EXIT' .OR.
     *          SCERR .EQ. SCREEN$ESCAPE)) RETURN
            IF (SCERR .EQ. SCREEN$ESCAPE)
     *      THEN
              IF (CONFIRM$EXIT)
     *        THEN
                CONFIRM$EXIT = .FALSE.
```

```
                    CURSOR$POSITION = 'MS07'
                    GOTO 100
                  ENDIF
                ENDIF
      C
      C         *************** IF EXITING, THEN CONFIRM IT ****************
      C
        200     IF ((READ$INPUT$VALUE .EQ. 'EXIT' .AND.
             *      SCERR .EQ. SCREEN$FUNCTION) .OR.
             *      SCERR .EQ. SCREEN$ESCAPE)
             * THEN
                  CONFIRM$EXIT = .TRUE.
                  DATA$AREA(1) = 5
                  CALL SCREEN(GROUP$UN$KILL$FIELD,SCREEN$NAME,FIELD$NAME,
             *               DATA$AREA,SCERR)
                  IF (SCERR .NE. NO$SCREEN$ERROR)
             *      CALL SYERR(GROUP$UN$KILL$FIELD,SCREEN$NAME,FIELD$NAME,SCERR,
             *                 'GROUP UNKILL FIELD')
                  CONFIRM$FIELDS$KILLED = .FALSE.
                  CURSOR$POSITION = 'MS28'
                  GOTO 100
                ENDIF
      C
      C         **************** CHECK EXIT CONFIRMATION *****************
      C
                IF (READ$INPUT$VALUE .EQ. 'NO ')
             * THEN
                  CONFIRM$EXIT = .FALSE.
                  CURSOR$POSITION = 'MS07'
                  GOTO 100
                ENDIF
                IF (READ$INPUT$VALUE .EQ. 'YES') RETURN
      C
      C         ******** CODE TO HANDLE THE FIRST PART OF THE LABEL FUNCTION ********
      C
                IF (READ$INPUT$VALUE .EQ. 'LABEL' .AND.
             *      SCERR .EQ. SCREEN$FUNCTION)
             * THEN
                  CURSOR$POSITION = 'LD04'
                  GOTO 100
                ENDIF
      C
      C         **** CODE TO HANDLE THE SECOND PART OF THE LABEL FUNCTION ****
      C
                IF (READ$INPUT$VALUE .EQ. 'LABEL' .AND.
             *      SCERR .EQ. SCREEN$DATA)
             * THEN
                  FIELD$NAME = 'LD04'
                  CALL SCREEN(GET$FIELD,SCREEN$NAME,FIELD$NAME,
             *               DATA$AREA,SCERR)
                  IF (SCERR .NE. NO$SCREEN$ERROR)
             *      CALL SYERR(GET$FIELD,SCREEN$NAME,FIELD$NAME,SCERR,
             *                 'GET FIELD')
                  FIELD$NAME = 'LD05'
                  CALL SCREEN(GET$FIELD,SCREEN$NAME,FIELD$NAME,
             *               DATA$AREA,SCERR)
                  IF (SCERR .NE. NO$SCREEN$ERROR)
             *      CALL SYERR(GET$FIELD,SCREEN$NAME,FIELD$NAME,SCERR,
             *                 'GET FIELD')
                  FIELD$NAME = 'LD06'
                  CALL SCREEN(GET$FIELD,SCREEN$NAME,FIELD$NAME,
             *               DATA$AREA,SCERR)
                  IF (SCERR .NE. NO$SCREEN$ERROR)
             *      CALL SYERR(GET$FIELD,SCREEN$NAME,FIELD$NAME,SCERR,
             *                 'GET FIELD')
                  DNA$CONV$VALUE = DATA$REAL
                  FIELD$NAME = 'LD06'
                  DATA$REAL = DNA$CONV$VALUE
                  CALL SCREEN(PUT$FIELD,SCREEN$NAME,FIELD$NAME,
             *               DATA$AREA,SCERR)
                  IF (SCERR .NE. NO$SCREEN$ERROR)
```

```
   *      CALL SYERR(PUT$FIELD,SCREEN$NAME,FIELD$NAME,SCERR,
   *              'PUT FIELD')
          CURSOR$POSITION = 'MS02'
          GOTO 100
        ENDIF
C
C
C           *********** CODE TO HANDLE THE CALIBRATE COMMAND ************
C
        IF (READ$INPUT$VALUE .EQ. 'CALIBRATE' .AND.
   *         SCERR .EQ. SCREEN$FUNCTION)
   *    THEN
          IF (ERR$MESSAGE .EQ. 'C')
   *      THEN
            ERR$ONE = ' '
            ERR$TWO = ' '
            FIELD$NAME = 'ERR1'
            CALL CNSTAR(32,ERR$ONE,DATA$AREA)
            CALL SCREEN(PUT$FIELD,SCREEN$NAME,FIELD$NAME,
   *              DATA$AREA,SCERR)
            IF (SCERR .NE. NO$SCREEN$ERROR)
   *          CALL SYERR(PUT$FIELD,SCREEN$NAME,FIELD$NAME,SCERR,
   *                'PUT FIELD')
            FIELD$NAME = 'ERR2'
            CALL CNSTAR(32,ERR$TWO,DATA$AREA)
            CALL SCREEN(PUT$FIELD,SCREEN$NAME,FIELD$NAME,
   *                DATA$AREA,SCERR)
            IF (SCERR .NE. NO$SCREEN$ERROR)
   *          CALL SYERR(PUT$FIELD,SCREEN$NAME,FIELD$NAME,SCERR,
   *                'PUT FIELD')
            ERR$MESSAGE = ' '
          ENDIF
C
C
C           *************** KILL THE MAIN SCREEN'S FIELDS **************
C
          DO 300 I=2,3
            DATA$AREA(1) = I
            CALL SCREEN(GROUP$KILL$FIELD,SCREEN$NAME,FIELD$NAME,
   *              DATA$AREA,SCERR)
            IF (SCERR .NE. NO$SCREEN$ERROR)
   *          CALL SYERR(GROUP$KILL$FIELD,SCREEN$NAME,FIELD$NAME,SCERR,
   *                'GROUP KILL FIELD')
300       CONTINUE
          DATA$AREA(1) = 30
          CALL SCREEN(GROUP$KILL$FIELD,SCREEN$NAME,FIELD$NAME,
   *            DATA$AREA,SCERR)
          IF (SCERR .NE. NO$SCREEN$ERROR)
   *        CALL SYERR(GROUP$KILL$FIELD,SCREEN$NAME,FIELD$NAME,SCERR,
   *              'GROUP KILL FIELD')
          IF (.NOT. CONFIRM$FIELDS$KILLED)
   *      THEN
            DATA$AREA(1) = 5
            CALL SCREEN(GROUP$KILL$FIELD,SCREEN$NAME,FIELD$NAME,
   *              DATA$AREA,SCERR)
            IF (SCERR .NE. NO$SCREEN$ERROR)
   *          CALL SYERR(GROUP$KILL$FIELD,SCREEN$NAME,FIELD$NAME,SCERR,
   *                'GROUP KILL FIELD')
            CONFIRM$FIELDS$KILLED = .TRUE.
          ENDIF
C
C
C           ****** CALL THE SUBROUTINE THAT HANDLES THE CALIBRATE SCREEN ****
C
          CALL SAQQ03(SCREEN$NAME,DNA$CONV$VALUE,CAL$LIGHT$LEVEL,
   *            ANALYZE$FLAG,FOCUS$ACTIVE,FOCUS$FLAG,
   *            XY$INIT,REDSAVE,GREENSAVE,BLUESAVE,
   *            ANALYSIS$TOTAL,FIRST$PEAK$MASS,FIRST$PEAK$INDEX,
   *            FIRST$PEAK$AREA,SEC$PEAK$MASS,SEC$PEAK$INDEX,
   *            FIRST$PEAK$AREA,XY$COUNTER,XY$COORDS,PICO$HIST,
   *            SET$LIGHT$FLAG,FATAL$ERROR)
C
C
C           ********* IF APPROPRIATE, UNKILL THE MAIN SCREEN'S FIELDS ********
```

```
              IF (FATAL$ERROR .OR. .NOT. ANALYZE$FLAG)
     *        THEN
                DO 400 I=2,3
                  DATA$AREA(1) = I
                  CALL SCREEN(GROUP$UN$KILL$FIELD,SCREEN$NAME,FIELD$NAME,
     *                        DATA$AREA,SCERR)
                  IF (SCERR .NE. NO$SCREEN$ERROR)
     *              CALL SYERR(GROUP$UN$KILL$FIELD,SCREEN$NAME,FIELD$NAME,
     *                         SCERR,'GROUP UNKILL FIELD')
400             CONTINUE
                DATA$AREA(1) = 30
                CALL SCREEN(GROUP$UN$KILL$FIELD,SCREEN$NAME,FIELD$NAME,
     *                      DATA$AREA,SCERR)
                IF (SCERR .NE. NO$SCREEN$ERROR)
     *            CALL SYERR(GROUP$UN$KILL$FIELD,SCREEN$NAME,FIELD$NAME,
     *                       SCERR,'GROUP UNKILL FIELD')
              ENDIF
              IF (FATAL$ERROR)
     *        THEN
                ERR$ONE = 'DUE TO A PROGRAMMING PROBLEM,'
                ERR$TWO = 'YOU CAN ONLY USE HELP OR EXIT.'
                ERR$MESSAGE = 'W'
                GOTO 100
              ENDIF
              IF (.NOT. ANALYZE$FLAG)
     *        THEN
C
C             ********** UPDATE THE MAIN SCREEN'S STATUS FIELDS **********
C
                CALL SAQQ29(SCREEN$NAME,CAL$LIGHT$LEVEL,ANALYSIS$TOTAL,
     *                      FIRST$PEAK$MASS,FIRST$PEAK$INDEX,
     *                      SEC$PEAK$MASS,SEC$PEAK$INDEX)
                CURSOR$POSITION = 'MS03'
              ELSE
C
C             ******* CALL THE SUBROUTINE THAT HANDLES THE ANALYZE SCREEN *****
C
                CALL SAQQ04(SCREEN$NAME,DNA$CONV$VALUE,CAL$LIGHT$LEVEL,
     *                      ANALYSIS$TOTAL,FIRST$PEAK$MASS,
     *                      FIRST$PEAK$INDEX,FIRST$PEAK$AREA,SEC$PEAK$MASS,
     *                      SEC$PEAK$INDEX,SEC$PEAK$AREA,REDSAVE,GREENSAVE,
     *                      BLUESAVE,XY$COUNTER,XY$COORDS,PICO$HIST,
     *                      FOCUS$FLAG,FATAL$ERROR)
C
C             ********** UNKILL THE MAIN SCREEN'S FIELDS ************
C
                DO 500 I=2,3
                  DATA$AREA(1) = I
                  CALL SCREEN(GROUP$UN$KILL$FIELD,SCREEN$NAME,FIELD$NAME,
     *                        DATA$AREA,SCERR)
                  IF (SCERR .NE. NO$SCREEN$ERROR)
     *              CALL SYERR(GROUP$UN$KILL$FIELD,SCREEN$NAME,FIELD$NAME,
     *                         SCERR,'GROUP UNKILL FIELD')
500             CONTINUE
                DATA$AREA(1) = 30
                CALL SCREEN(GROUP$UN$KILL$FIELD,SCREEN$NAME,FIELD$NAME,
     *                      DATA$AREA,SCERR)
                IF (SCERR .NE. NO$SCREEN$ERROR)
     *            CALL SYERR(GROUP$UN$KILL$FIELD,SCREEN$NAME,FIELD$NAME,
     *                       SCERR,'GROUP UNKILL FIELD')

*********** CHECK FOR A 'FATAL' ERROR ************

IF (FATAL$ERROR)
     *          THEN
                  ERR$ONE = 'DUE TO A PROGRAMMING PROBLEM,'
                  ERR$TWO = 'YOU CAN ONLY USE HELP OR EXIT.'
                  ERR$MESSAGE = 'W'
                  GOTO 100
                ENDIF
```

```
********** UPDATE THE MAIN SCREEN'S STATUS FIELDS **********
      CALL SAQQ29(SCREEN$NAME,CAL$LIGHT$LEVEL,ANALYSIS$TOTAL,
     *            FIRST$PEAK$MASS,FIRST$PEAK$INDEX,
     *            SEC$PEAK$MASS,SEC$PEAK$INDEX)
      CURSOR$POSITION = 'MS04'
    ENDIF
    GOTO 100
  ENDIF

********** CODE TO HANDLE THE ANALYZE COMMAND **********

IF (READ$INPUT$VALUE .EQ. 'ANALYZE' .AND.
     *    SCERR .EQ. SCREEN$FUNCTION)
     * THEN
    IF (ERR$MESSAGE .EQ. 'C')
     *    THEN
      ERR$ONE = ' '
      ERR$TWO = ' '
      FIELD$NAME = 'ERR1'
      CALL CNSTAR(32,ERR$ONE,DATA$AREA)
      CALL SCREEN(PUT$FIELD,SCREEN$NAME,FIELD$NAME,
     *            DATA$AREA,SCERR)
      IF (SCERR .NE. NO$SCREEN$ERROR)
     *    CALL SYERR(PUT$FIELD,SCREEN$NAME,FIELD$NAME,SCERR,
     *               'PUT FIELD')
      FIELD$NAME = 'ERR2'
      CALL CNSTAR(32,ERR$TWO,DATA$AREA)
      CALL SCREEN(PUT$FIELD,SCREEN$NAME,FIELD$NAME,
     *            DATA$AREA,SCERR)
      IF (SCERR .NE. NO$SCREEN$ERROR)
     *   CALL SYERR(PUT$FIELD,SCREEN$NAME,FIELD$NAME,SCERR,
     *              'PUT FIELD')
      ERR$MESSAGE = ' '
    ENDIF

***** CHECK TO SEE IF THE PEAK LIGHT LEVEL IS IN RANGE ******

IF (.NOT. SET$LIGHT$FLAG)
     *  THEN
     *            ANALYSIS$TOTAL,FIRST$PEAK$MASS,FIRST$PEAK$INDEX,
     *            FIRST$PEAK$AREA,SEC$PEAK$MASS,SEC$PEAK$INDEX,
     *            SEC$PEAK$AREA,REDSAVE,GREENSAVE,BLUESAVE,
     *            XY$COUNTER,XY$COORDS,PICO$HIST,
     *            FOCUS$FLAG,FATAL$ERROR)
C
C    ********** UNKILL THE MAIN SCREEN'S FIELDS ************
C
    DO 700 I=2,3
      DATA$AREA(1) = I
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *    CALL SYERR(GROUP$UN$KILL$FIELD,SCREEN$NAME,FIELD$NAME,
     *               SCERR,'GROUP UNKILL FIELD')
700 CONTINUE
    DATA$AREA(1) = 30
    CALL SCREEN(GROUP$UN$KILL$FIELD,SCREEN$NAME,FIELD$NAME,
     *          DATA$AREA,SCERR)
    IF (SCERR .NE. NO$SCREEN$ERROR)
     *  CALL SYERR(GROUP$UN$KILL$FIELD,SCREEN$NAME,FIELD$NAME,
     *             SCERR,'GROUP UNKILL FIELD')
C
C    *********** CHECK FOR A 'FATAL' ERROR ************
C
    IF (FATAL$ERROR)
     *  THEN
      ERR$ONE = 'DUE TO A PROGRAMMING PROBLEM,'
      ERR$TWO = 'YOU CAN ONLY USE HELP OR EXIT.'
      ERR$MESSAGE = 'W'
```

```
              GOTO 100
            · ENDIF
C
C           ********** UPDATE THE MAIN SCREEN'S STATUS FIELDS **********
C
            CALL SAQQ29(SCREEN$NAME,CAL$LIGHT$LEVEL,ANALYSIS$TOTAL,
     *                  FIRST$PEAK$MASS,FIRST$PEAK$INDEX,
     *                  SEC$PEAK$MASS,SEC$PEAK$INDEX)
            CURSOR$POSITION = 'MS04'
            GOTO 100
          ENDIF
C*****************************************************************
C         ********* CODE TO HANDLE THE SWITCH COMMAND **********
C*****************************************************************
          IF (READ$INPUT$VALUE .EQ. 'SWITCH' .AND.
     *        SCERR .EQ. SCREEN$FUNCTION)
     *    THEN
C
C           ****** CALL THE SUBROUTINE THAT HANDLES THE SWITCH SCREEN ****
C
            CALL SAQQ27()
C
C           ****************** GET THE SCREEN ******************
C
            SCREEN$NAME = 'QEN001'
            CALL SCREEN(GET$SCREEN,SCREEN$NAME,FIELD$NAME,
     *                  DATA$AREA,SCERR)
            IF (SCERR .NE. NO$SCREEN$ERROR)
     *        CALL SYERR(GET$SCREEN,SCREEN$NAME,FIELD$NAME,SCERR,
     *                   'GET SCREEN')
C
C           *************** KILL THE UNUSED FIELDS ***************
C
            DATA$AREA(1) = 5
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            DATA$AREA(1) = 1
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            DATA$AREA(1) = 20
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            DATA$AREA(1) = 21
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            DATA$AREA(1) = 60
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            DATA$AREA(1) = 61
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            DO 800 I=69,80
              DATA$AREA(1) = I
```

```
              CALL SCREEN(GROUP$KILL$FIELD,SCREEN$NAME,FIELD$NAME,
     *                   DATA$AREA,SCERR)
              IF (SCERR .NE. NO$SCREEN$ERROR)
     *          CALL SYERR(GROUP$KILL$FIELD,SCREEN$NAME,FIELD$NAME,SCERR,
     *                     'GROUP KILL FIELD')
800           CONTINUE
              DATA$AREA(1) = 90
              CALL SCREEN(GROUP$KILL$FIELD,SCREEN$NAME,FIELD$NAME,
     *                   DATA$AREA,SCERR)
              IF (SCERR .NE. NO$SCREEN$ERROR)
     *          CALL SYERR(GROUP$KILL$FIELD,SCREEN$NAME,FIELD$NAME,SCERR,
     *                     'GROUP KILL FIELD')
              FIELD$NAME = '0001'
              CALL SCREEN(KILL$FIELD,SCREEN$NAME,FIELD$NAME,
     *                   DATA$AREA,SCERR)
              IF (SCERR .NE. NO$SCREEN$ERROR)
     *          CALL SYERR(KILL$FIELD,SCREEN$NAME,FIELD$NAME,SCERR,
     *                     'KILL FIELD')
              FIELD$NAME = 'STUD'
              CALL SCREEN(KILL$FIELD,SCREEN$NAME,FIELD$NAME,
     *                   DATA$AREA,SCERR)
              IF (SCERR .NE. NO$SCREEN$ERROR)
     *          CALL SYERR(KILL$FIELD,SCREEN$NAME,FIELD$NAME,SCERR,
     *                     'KILL FIELD')
C
C             ********** UPDATE THE MAIN SCREEN'S STATUS FIELDS **********
C
              CALL SAQQ29(SCREEN$NAME,CAL$LIGHT$LEVEL,ANALYSIS$TOTAL,
     *                    FIRST$PEAK$MASS,FIRST$PEAK$INDEX,
     *                    SEC$PEAK$MASS,SEC$PEAK$INDEX)
              CURSOR$POSITION = 'ZZZZ'
              GOTO 100
            ENDIF
            END
CC
CC              CELL ANALYSIS SYSTEMS, INC.
CC                  (C) COPYRIGHT 1986
CC**************************************************************
CC
CC      :PROGRAM NAME
CC      :SAQQ03
CC
CC      :SUBROUTINES
CC      :SAQQ06
CC      :SAQQ11
CC      :SAQQ12
CC      :SAQQ13
CC
CC      :CALLING SEQUENCE
CC      :SAQQ03(SCRN$NAME,DNA$CONV$VALUE,CAL$LIGHT$LEVEL,ANALYZE$FLAG,
CC              FOCUS$ACTIVE,FOCUS$FLAG,XY$INIT,REDSAVE,GREENSAVE,BLUESAVE,
CC              SET$LIGHT$FLAG,FATAL$ERROR)
CC
CC      :PARAMETERS
CC      :SCRN$NAME - THE NAME OF THE CURRENT SCREEN
CC      :DNA$CONV$VALUE - THE DNA CONVERSION VALUE
CC      :CAL$LIGHT$LEVEL - THE PEAK LIGHT LEVEL
CC      :ANALYZE$FLAG - FLAG THAT SPECIFIES IF THE USER SELECTED THE ANALYZE
CC                     FUNCTION WHILE IN THE CALIBRATION SCREEN
CC      :FOCUS$ACTIVE - A FLAG THAT SPECIFIES IF THE FOCUS FUNCTION CAN BE
CC                     USED
CC      :FOCUS$FLAG - A FLAG THAT SPECIFIES IF THE FOCUS IMAGE IS ON
CC      :XY$INIT - A FLAG THAT SPECIFIES IF THE FOCUS FUNCTION CAN BE USED
CC      :REDSAVE - AN ARRAY CONTAINING THE ORIGINAL (RED,2) TABLE VALUES
CC      :GREENSAVE - AN ARRAY CONTAINING THE ORIGINAL (GREEN,2) TABLE VALUES
CC      :BLUESAVE - AN ARRAY CONTAINING THE ORIGINAL (BLUE,2) TABLE VALUES
CC      :SET$LIGHT$FLAG - A LOGICAL VARIABLE THAT SPECIFIES IF THE SET-LIGHT
CC                       FUNCTION IN THE CALIBRATE SCREEN WAS DONE
CC                       SUCCESSFULLY ONCE
CC      :FATAL$ERROR - A FLAG THAT SPECIFIES IF A 'FATAL'(I.E. SERIOUS) ERROR
CC                    OCCURRED WHILE INSIDE SA0003
```

```
CC
CC    :DESCRIPTION
CC    :SAQQ03 IS THE MAIN SUBROUTINE THAT HANDLES THE CALIBRATION SCREEN.
CC
CC***************************************************************************
CC#########
      SUBROUTINE SAQQ03(SCRN$NAME,DNA$CONV$VALUE,CAL$LIGHT$LEVEL,
     *                  ANALYZE$FLAG,FOCUS$ACTIVE,FOCUS$FLAG,
     *                  XY$INIT,REDSAVE,GREENSAVE,BLUESAVE,
     *                  ANALYSIS$TOTAL,FIRST$PEAK$MASS,
     *                  FIRST$PEAK$INDEX,FIRST$PEAK$AREA,
     *                  SEC$PEAK$MASS,SEC$PEAK$INDEX,SEC$PEAK$AREA,
     *                  XY$COUNTER,XY$COORDS,PICO$HIST,
     *                  SET$LIGHT$FLAG,FATAL$ERROR)
      CHARACTER*1 ERR$MESSAGE
      CHARACTER*2 VARIABLE$ENDING(32),VARIABLE$ENDING2(11)
      CHARACTER*3 CONFIRM$ANSWER
      CHARACTER*4 CURSOR$POSITION
      CHARACTER*(*) SCRN$NAME
      CHARACTER*6 XCHAR,YCHAR
      CHARACTER*9 READ$INPUT$VALUE
      CHARACTER*20 CURR$XY$STRING
      CHARACTER*32 ERR$ONE,ERR$TWO
      INTEGER*2 CAL$LIGHT$LEVEL,I,PTR,CELL$COUNT,X,Y,J,K,
     *          REDSAVE(*),GREENSAVE(*),BLUESAVE(*),COUNT,
     *          ANALYSIS$TOTAL,XY$COUNTER,XY$COORDS(3,512),
     *          PICO$HIST(*)
      INTEGER*4 MASS(513),AREA(513)
      REAL*4 FIRST$PEAK$MASS,FIRST$PEAK$INDEX,FIRST$PEAK$AREA,
     *       SEC$PEAK$MASS,SEC$PEAK$INDEX,SEC$PEAK$AREA
      LOGICAL*1 FATAL$ERROR,CONFIRM$CLEAR,
     *          CONFIRM$FIELDS$KILLED,XY$INIT,
     *          FOCUS$ACTIVE,FOCUS$FLAG,ANALYZE$FLAG,
     *          CELL$REJECTED(513),SAVE$DATA$FLAG,
     *          MEASURE$FIELDS$KILLED,SET$LIGHT$FLAG
C
      INCLUDE 'SAQCCD.FIN'
      INCLUDE 'SAQCDT.FIN'
      INCLUDE 'IMAGED.FIN'
      INCLUDE 'SCREEN.FIN'
C
      DATA VARIABLE$ENDING
     *     /'32','33','34','35','36','37','38','39','40','41',
     *      '42','43','44','45','46','47','48','49','50','51',
     *      '52','53','54','55','56','57','58','59','60','61',
     *      '62','63'/,
     *     VARIABLE$ENDING2
     *     /'20','21','22','23','24','25',
     *      '26','27','28','29','30'/
C
C     ********** INITIALIZE THE APPROPRIATE VARIABLES **********
C
      SCREEN$NAME = SCRN$NAME
      ERR$MESSAGE = ' '
      CONFIRM$ANSWER = ' '
      CURSOR$POSITION = 'CS02'
      XCHAR = ' '
      YCHAR = ' '
      READ$INPUT$VALUE = ' '
      CURR$XY$STRING = ' '
      ERR$ONE = ' '
      ERR$TWO = ' '
      I = 0
      J = 0
      PTR = 0
      CELL$COUNT = 0
      COUNT = 0
      X = 0
      Y = 0
      FATAL$ERROR = .FALSE.
```

```
      CONFIRM$FIELDS$KILLED = .FALSE.
      ANALYZE$FLAG = .FALSE.
      SAVE$DATA$FLAG = .FALSE.
      DO 10 I=1,513
        CELL$REJECTED(I) = .TRUE.
 10   CONTINUE
C
C     ************ UNKILL THE NECESSARY FIELDS ************
C
      DATA$AREA(1) = 20
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
      DATA$AREA(1) = 21
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
      DATA$AREA(1) = 60
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
      DATA$AREA(1) = 61
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
      MEASURE$FIELDS$KILLED = .FALSE.
C
C     ************ KILL HISTOGRAM NUMBER FIELDS ***************
C
      IF (PCCD$CELLCNT .EQ. 0)
     * THEN
         DO 25 I=1,11
           FIELD$NAME = 'CS'//VARIABLE$ENDING2(I)
           CALL SCREEN(KILL$FIELD,SCREEN$NAME,FIELD$NAME,
     *                 DATA$AREA,SCERR)
           IF (SCERR .NE. NO$SCREEN$ERROR)
     *       CALL SYERR(KILL$FIELD,SCREEN$NAME,FIELD$NAME,SCERR,
     *                  'KILL FIELD')
 25      CONTINUE
      ENDIF
      FIELD$NAME = 'CS13'
      DATA$AREA(1) = CAL$LIGHT$LEVEL
      CALL SCREEN(PUT$FIELD,SCREEN$NAME,FIELD$NAME,
     *            DATA$AREA,SCERR)
      IF (SCERR .NE. NO$SCREEN$ERROR)
     *   CALL SYERR(PUT$FIELD,SCREEN$NAME,FIELD$NAME,SCERR,
     *              'PUT FIELD')
C
C     *********** CALL THE HISTOGRAM SUBROUTINE *************
C
      CALL SAQQ12(SCREEN$NAME,PCCD$CELLCNT,PCCD$CELLDATA)
C
C     ************ CHECK FOR A 'FATAL' ERROR ************
C
      IF (FATAL$ERROR) GOTO 100
C
C     ************** CALL THE STATISTICS SUBROUTINE ***************
C
      CALL SAQQ13(SCREEN$NAME,FATAL$ERROR)
C
C     ************ CODE TO HANDLE ERROR MESSAGES ************
C
```

```
   *  THEN
        ERR$ONE = ' '
        ERR$TWO = ' '
      ENDIF
      IF (ERR$MESSAGE .EQ. 'C' .OR.
   *      ERR$MESSAGE .EQ. 'W')
   *  THEN
        FIELD$NAME = 'ERR1'
        CALL CNSTAR(32,ERR$ONE,DATA$AREA)
        CALL SCREEN(PUT$FIELD,SCREEN$NAME,FIELD$NAME,
   *                DATA$AREA,SCERR)
        IF (SCERR .NE. NO$SCREEN$ERROR)
   *        CALL SYERR(PUT$FIELD,SCREEN$NAME,FIELD$NAME,SCERR,
   *                   'PUT FIELD')
        FIELD$NAME = 'ERR2'
        CALL CNSTAR(32,ERR$TWO,DATA$AREA)
        CALL SCREEN(PUT$FIELD,SCREEN$NAME,FIELD$NAME,
   *                DATA$AREA,SCERR)
        IF (SCERR .NE. NO$SCREEN$ERROR)
   *      CALL SYERR(PUT$FIELD,SCREEN$NAME,FIELD$NAME,SCERR,
   *                 'PUT FIELD')
      ENDIF
      IF (ERR$MESSAGE .EQ. 'C') ERR$MESSAGE = ' '
      IF (ERR$MESSAGE .EQ. 'W') ERR$MESSAGE = 'C'
      IF (ERR$MESSAGE .NE. 'C') ERR$MESSAGE = ' '
C
C     ************** CHECK FOR A 'FATAL' ERROR ***************
C
      IF (FATAL$ERROR)
   *  THEN
        DATA$AREA(1) = 20
        CALL SCREEN(GROUP$KILL$FIELD,SCREEN$NAME,FIELD$NAME,
   *                DATA$AREA,SCERR)
        IF (SCERR .NE. NO$SCREEN$ERROR)
   *      CALL SYERR(GROUP$KILL$FIELD,SCREEN$NAME,FIELD$NAME,SCERR,
   *                 'GROUP KILL FIELD')
        DATA$AREA(1) = 21
        CALL SCREEN(GROUP$KILL$FIELD,SCREEN$NAME,FIELD$NAME,
   *                DATA$AREA,SCERR)
        IF (SCERR .NE. NO$SCREEN$ERROR)
   *      CALL SYERR(GROUP$KILL$FIELD,SCREEN$NAME,FIELD$NAME,SCERR,
   *                 'GROUP KILL FIELD')
        DATA$AREA(1) = 60
        CALL SCREEN(GROUP$KILL$FIELD,SCREEN$NAME,FIELD$NAME,
   *                DATA$AREA,SCERR)
        IF (SCERR .NE. NO$SCREEN$ERROR)
   *      CALL SYERR(GROUP$KILL$FIELD,SCREEN$NAME,FIELD$NAME,SCERR,
   *                 'GROUP KILL FIELD')
        DATA$AREA(1) = 61
        CALL SCREEN(GROUP$KILL$FIELD,SCREEN$NAME,FIELD$NAME,
   *                DATA$AREA,SCERR)
        IF (SCERR .NE. NO$SCREEN$ERROR)
   *      CALL SYERR(GROUP$KILL$FIELD,SCREEN$NAME,FIELD$NAME,SCERR,
   *                 'GROUP KILL FIELD')
        RETURN
      ENDIF
C
C     **** CHECK TO SEE IF THE CONFIRM FIELDS HAVE TO BE KILLED ****
C
      IF (.NOT. CONFIRM$CLEAR .AND.
   *      .NOT. CONFIRM$FIELDS$KILLED)
   *  THEN
        DATA$AREA(1) = 5
        CALL SCREEN(GROUP$KILL$FIELD,SCREEN$NAME,FIELD$NAME,
   *                DATA$AREA,SCERR)
        IF (SCERR .NE. NO$SCREEN$ERROR)
   *      CALL SYERR(GROUP$KILL$FIELD,SCREEN$NAME,FIELD$NAME,SCERR,
   *                 'GROUP KILL FIELD')
        CONFIRM$FIELDS$KILLED = .TRUE.
      ENDIF
```

```
C          **** CHECK TO SEE IF THE CONFIRM FIELDS HAVE TO BE KILLED ****
C
           IF (.NOT. CONFIRM$CLEAR .AND.
      *        MEASURE$FIELDS$KILLED)
      *    THEN
             DATA$AREA(1) = 61
            ·CALL SCREEN(GROUP$UN$KILL$FIELD,SCREEN$NAME,FIELD$NAME,
      *              DATA$AREA,SCERR)
             IF (SCERR .NE. NO$SCREEN$ERROR)
      *        CALL SYERR(GROUP$UN$KILL$FIELD,SCREEN$NAME,FIELD$NAME,
      *                   SCERR,'GROUP UNKILL FIELD')
             MEASURE$FIELDS$KILLED = .FALSE.
           ENDIF
C
C          ************ SET THE CURSOR POSITION **************
C
           FIELD$NAME = CURSOR$POSITION
           CALL SCREEN(SET$CURSOR,SCREEN$NAME,FIELD$NAME,
      *               DATA$AREA,SCERR)
           IF (SCERR .NE. NO$SCREEN$ERROR)
      *      CALL SYERR(SET$CURSOR,SCREEN$NAME,FIELD$NAME,SCERR,
      *                 'SET CURSOR')
C
C          ************ READ THE INPUT SELECTION *************
C
           CALL SCREEN(READ$INPUT,SCREEN$NAME,FIELD$NAME,
      *               DATA$AREA,SCERR)
           IF (SCERR .EQ. SCREEN$ESCAPE .OR.
      *        SCERR .EQ. SCREEN$FUNCTION .OR.
      *        SCERR .EQ. SCREEN$DATA)
      *    THEN
             CONTINUE
           ELSE
             CALL SYERR(READ$INPUT,SCREEN$NAME,FIELD$NAME,SCERR,
      *                 'READ INPUT')
           ENDIF
           CALL CNARST(9,DATA$AREA,READ$INPUT$VALUE)
           IF (SCERR .EQ. SCREEN$ESCAPE)
      *    THEN
             IF (CONFIRM$CLEAR)
      *      THEN
               CONFIRM$CLEAR = .FALSE.
               CURSOR$POSITION = 'CS06'
               GOTO 100
             ENDIF
             READ$INPUT$VALUE = 'MAIN'
             SCERR = SCREEN$FUNCTION
           ENDIF
C
           IF (SCERR .EQ. SCREEN$FUNCTION) CONFIRM$CLEAR = .FALSE.
C***************************************************************
C
C                CODE TO HANDLE THE SET-LIGHT COMMAND
C
C***************************************************************
           IF (READ$INPUT$VALUE .EQ. 'SET-LIGHT' .AND.
      *        SCERR .EQ. SCREEN$FUNCTION)
      *    THEN
             CAL$LIGHT$LEVEL = 0
C
C          ************* SELECT THE FIRST TABLES *************
C
           IM$TABLE$NUM = 1
           DO 200 I=1,4
             IM$GROUP$NUM = I
             CALL IMMAIN(IMAGE$SELECT$TABLE,IMERR)
             IF (IMERR .NE. ' ')
      *      THEN
               FATAL$ERROR = .TRUE.
               GOTO 100
             ENDIF
```

```
200     CONTINUE
C
C       ************* START IMAGE ACQUISITION **************
C
        CALL IMMAIN(IMAGE$START$ACQ,IMERR)
        IF (IMERR .NE. ' ')
     *  THEN
          FATAL$ERROR = .TRUE.
          GOTO 100
        ENDIF
C
C       ************* GET AN AVERAGED IMAGE **************
C
        CALL IMMAIN(IMAGE$GET$AVERAGE,IMERR)
        IF (IMERR .NE. ' ')
     *  THEN
          FATAL$ERROR = .TRUE.
          GOTO 100
        ENDIF
C
C       ************* GET THE HISTOGRAM **************
C
        IM$HIST$SAMPLE = 1
        CALL IMMAIN(IMAGE$HISTOGRAM,IMERR)
        IF (IMERR .NE. ' ')
     *  THEN
          FATAL$ERROR = .TRUE.
          GOTO 100
        ENDIF
C
C       ******* CHECK TO MAKE SURE THAT THE IMAGE IS BLANK *********
C
        IM$SMOOTH$LOW$LIM = 0
        IM$SMOOTH$HIGH$LIM = 255
        IM$PKS$WANTED = 4
        CALL IMMAIN(IMAGE$SMOOTH$HIST,IMERR)
        IF (IMERR .NE. ' ')
     *  THEN
          FATAL$ERROR = .TRUE.
          GOTO 100
        ENDIF
C
C       ********* PUT OUT THE PEAK LIGHT LEVEL VALUE **********
C
        I = IM$PKS$FOUND*2
        CAL$LIGHT$LEVEL = IM$VALLS$PKS(I)-1
        FIELD$NAME = 'CS13'
        DATA$AREA(1) = CAL$LIGHT$LEVEL
        CALL SCREEN(PUT$FIELD,SCREEN$NAME,FIELD$NAME,
     *              DATA$AREA,SCERR)
        IF (SCERR .NE. NO$SCREEN$ERROR)
     *    CALL SYERR(PUT$FIELD,SCREEN$NAME,FIELD$NAME,SCERR,
     *               'PUT FIELD')
C
C       ***** CHECK TO SEE IF THE PEAK LIGHT LEVEL IS OUT OF RANGE ****
C
        IF (CAL$LIGHT$LEVEL .LT. 129 .OR. CAL$LIGHT$LEVEL .GT. 131)
     *  THEN
          CALL IMMAIN(IMAGE$START$ACQ,IMERR)
          IF (IMERR .NE. ' ')
     *    THEN
            FATAL$ERROR = .TRUE.
            GOTO 100
          ENDIF
          IF (SET$LIGHT$FLAG)
     *    THEN
            IM$TABLE$NUM = 2
            DO 250 I=1,4
              IM$GROUP$NUM = I
              CALL IMMAIN(IMAGE$SELECT$TABLE,IMERR)
```

```
                    IF (IMERR .NE. ' ')
     *            THEN
                     FATAL$ERROR = .TRUE.
                     GOTO 100
                  ENDIF
250           CONTINUE
           ENDIF
           ERR$ONE = 'THE PEAK LIGHT LEVEL'
           ERR$TWO = 'IS NOT IN RANGE(129 TO 131).'
           ERR$MESSAGE = 'W'
           CURSOR$POSITION = 'CS02'
           GOTO 100
        ENDIF
C
C       ********* CHECK FOR A BLANK FIELD ***************
C
        J = 0
        DO 225 I=1,IM$PKS$FOUND
           K = IM$VALLS$PKS(2*I)
           IF (IM$HISTOGRAM(K) .GT. 35) J=J+1
225     CONTINUE
        IF (J .GE. 2)
     *  THEN
           CALL IMMAIN(IMAGE$START$ACQ,IMERR)
           IF (IMERR .NE. ' ')
     *     THEN
              FATAL$ERROR = .TRUE.
              GOTO 100
           ENDIF
           IF (SET$LIGHT$FLAG)
     *     THEN
              IM$TABLE$NUM = 2
              DO 275 I=1,4
                 IM$GROUP$NUM = I
                 CALL IMMAIN(IMAGE$SELECT$TABLE,IMERR)
                 IF (IMERR .NE. ' ')
     *           THEN
                    FATAL$ERROR = .TRUE.
                    GOTO 100
                 ENDIF
275           CONTINUE
           ENDIF
           ERR$ONE = 'YOU ARE NOT ON A BLANK FIELD.'
           ERR$TWO = ' '
           ERR$MESSAGE = 'W'
           CURSOR$POSITION = 'CS02'
           GOTO 100
        ENDIF
C
C       ********** CALIBRATE THE SECOND OUTPUT TABLES ********
C
        IF (.NOT. SET$LIGHT$FLAG)
     *  THEN
           CALL IMMAIN(IMAGE$OUT$TABLES$SEQ,IMERR)
           IF (IMERR .NE. ' ')
     *     THEN
              FATAL$ERROR = .TRUE.
              GOTO 100
           ENDIF
        ENDIF
C
C       ************** SUBTRACT NOISE ****************
C
        IF (.NOT. FOCUS$ACTIVE) FOCUS$ACTIVE = .TRUE.
        IF (.NOT. SET$LIGHT$FLAG) SET$LIGHT$FLAG = .TRUE.
        CALL IMMAIN(IMAGE$SUBTRACT$SAVE,IMERR)
        IF (IMERR .NE. ' ')
     *  THEN
           FATAL$ERROR = .TRUE.
           GOTO 100
        ENDIF
```

```
C
C              ************** SELECT THE SECOND TABLES **************
C
               IM$TABLE$NUM = 2
               DO 300 I=1,4
                  IM$GROUP$NUM = I
                  CALL IMMAIN(IMAGE$SELECT$TABLE,IMERR)
                  IF (IMERR .NE. ' ')
     *            THEN
                     FATAL$ERROR = .TRUE.
                     GOTO 100
                  ENDIF
    300        CONTINUE
C
C              ************* START IMAGE ACQUISITION **************
C
               CALL IMMAIN(IMAGE$START$ACQ,IMERR)
               IF (IMERR .NE. ' ')
     *         THEN
                  FATAL$ERROR = .TRUE.
                  GOTO 100
               ENDIF
               FOCUS$ACTIVE = .TRUE.
               CURSOR$POSITION = 'CS02'
               GOTO 100
            ENDIF
C*******************************************************************
C
C              CODE TO HANDLE THE SET-XY COMMAND
C
C*******************************************************************
            IF (READ$INPUT$VALUE .EQ. 'SET-XY' .AND.
     *          SCERR .EQ. SCREEN$FUNCTION)
     *      THEN
C
C           ********* CHECK TO SEE IF A CELL HAS BEEN CLASSIFIED *********
C
               IF (PCCD$CELLCNT .GT. 0)
     *         THEN
                  ERR$ONE = 'WHEN THE CELL COUNT IS NOT EQUAL'
                  ERR$TWO = 'TO ZERO, YOU CANNOT USE SET-XY.'
                  ERR$MESSAGE = 'W'
                  CURSOR$POSITION = 'CS03'
                  GOTO 100
               ENDIF
               DO 400 I=1,10
C
C              ************ RESET CHANNELS *********
C
                  CALL IMMAIN(IMAGE$CHANNELS$RESET,IMERR)
                  IF (IMERR .NE. ' ')
     *            THEN
                     FATAL$ERROR = .TRUE.
                     GOTO 100
                  ENDIF
C
C              ************ READ CHANNEL VALUES ************
C
                  CALL IMMAIN(IMAGE$CHANNELS,IMERR)
                  IF (IMERR .NE. ' ')
     *            THEN
                     FATAL$ERROR = .TRUE.
                     GOTO 100
                  ENDIF
C
C              ****** CHECK TO SEE IF THE CHANNELS HAVE BEEN RESET ******
C
                  IF (IM$CHANNEL$ONE .LT. 2.0 .AND. IM$CHANNEL$ONE .GT. -2.0
     *                .AND.
     *                IM$CHANNEL$TWO .LT. 2.0 .AND. IM$CHANNEL$TWO .GT. -2.0)
     *              GOTO 500
```

```
      400     CONTINUE
              ERR$ONE = 'THE XY SETTINGS COULD NOT BE'
              ERR$TWO = 'INITIALIZED.'
              ERR$MESSAGE = 'W'
              CURSOR$POSITION = 'CS03'
              GOTO 100
      500     ERR$ONE = 'THE X AND Y COORDINATES'
              ERR$TWO = 'ARE SET TO (0,0).'
              ERR$MESSAGE = 'W'
              CURSOR$POSITION = 'CS03'
              XY$INIT = .TRUE.
              GOTO 100
            ENDIF
C*********************************************************************
C
C             CODE TO HANDLE THE XY COMMAND
C
C*********************************************************************
          IF (READ$INPUT$VALUE .EQ. 'XY' .AND.
     *        SCERR .EQ. SCREEN$FUNCTION)
     *    THEN
            IF (.NOT. XY$INIT)
     *      THEN
              ERR$ONE = 'XY CANNOT BE USED,'
              ERR$TWO = 'BECAUSE X Y MUST BE INITIALIZED.'
              ERR$MESSAGE = 'W'
              CURSOR$POSITION = 'CS05'
              GOTO 100
            ENDIF
C
C           ********** READ CHANNEL VALUES **********
C
      600   CALL IMMAIN(IMAGE$CHANNELS,IMERR)
            IF (IMERR .NE. ' ')
     *      THEN
              FATAL$ERROR = .TRUE.
              GOTO 100
            ENDIF
C
C           ********** CONVERT CHANNEL VALUES TO INTEGER **********
C
            X = INT((IM$CHANNEL$ONE*0.125)+0.5)
            Y = INT((IM$CHANNEL$TWO*0.125)+0.5)
            WRITE(XCHAR,700)X
            WRITE(YCHAR,700)Y
      700   FORMAT(I6)
            CURR$XY$STRING = 'X='//XCHAR//'     '//'Y='//YCHAR
C
C           ******* PUT OUT THE X AND Y VALUES *******
C
            FIELD$NAME = 'ERR1'
            CALL CNSTAR(32,CURR$XY$STRING//'            ',
     *                  DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            ERR$MESSAGE = 'C'
C
C           **** CHECK TO SEE IF THE USER WANTS ANOTHER CHANNEL READING ****
C
            CALL SCREEN(READ$KEYBOARD,SCREEN$NAME,FIELD$NAME,
     *                  DATA$AREA,SCERR)
            IF (SCERR .EQ. READ$KEYBOARD) GOTO 600
            CURSOR$POSITION = 'CS05'
            GOTO 100
          ENDIF
C*********************************************************************
C
C             CODE TO HANDLE THE FIRST PART OF THE CLEAR COMMAND
```

```
C
C*******************************************************************
        IF (READ$INPUT$VALUE .EQ. 'CLEAR' .AND.
     *      SCERR .EQ. SCREEN$FUNCTION)
     *  THEN
C
C       ******* CHECK TO SEE IF THERE IS DATA TO CLEAR ******
C
          IF (PCCD$CELLCNT .LE. 0)
     *    THEN
            ERR$ONE = 'YOU CANNOT USE CLEAR BECAUSE'
            ERR$TWO = 'THERE IS NO DATA TO CLEAR.'
            ERR$MESSAGE = 'W'
            CURSOR$POSITION = 'CS06'
            GOTO 100
          ENDIF
C
C       ****************** CONFIRM CLEAR ******************
C
          CONFIRM$CLEAR = .TRUE.
C
C       ************ KILL MEASURE FIELDS ************
C
          DATA$AREA(1) = 61
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$KILL$FIELD,SCREEN$NAME,FIELD$NAME,SCERR,
     *                'GROUP KILL FIELD')
          MEASURE$FIELDS$KILLED = .TRUE.
C
C       ************ UNKILL CONFIRM FIELDS ************
C
          DATA$AREA(1) = 5
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$UN$KILL$FIELD,SCREEN$NAME,FIELD$NAME,SCERR,
     *                'GROUP UNKILL FIELD')
          CONFIRM$FIELDS$KILLED = .FALSE.
          CURSOR$POSITION = 'MS28'
          GOTO 100
        ENDIF
C*******************************************************************
C
C       CODE TO HANDLE THE NO COMMAND
C
C*******************************************************************
        IF (READ$INPUT$VALUE .EQ. 'NO ')
     *  THEN
          CONFIRM$CLEAR = .FALSE.
          CURSOR$POSITION = 'CS06'
          GOTO 100
        ENDIF
C*******************************************************************
C
C       CODE TO HANDLE THE YES COMMAND
C
C*******************************************************************
        IF (READ$INPUT$VALUE .EQ. 'YES')
     *  THEN
          CONFIRM$CLEAR = .FALSE.
          PCCD$CELLCNT = 0
          PCCD$MEAN = 0
          FIELD$NAME = 'CS15'
          DATA$AREA(1) = 0
          CALL SCREEN(PUT$FIELD,SCREEN$NAME,FIELD$NAME,
     *                DATA$AREA,SCERR)
          IF (SCERR .NE. NO$SCREEN$ERROR)
     *      CALL SYERR(PUT$FIELD,SCREEN$NAME,FIELD$NAME,SCERR,
     *                'PUT FIELD')
```

```
                  FIELD$NAME = 'CS17'
                  DATA$INTEGER$4 = 0
         *        CALL SCREEN(PUT$FIELD,SCREEN$NAME,FIELD$NAME,
         *                    DATA$AREA,SCERR)
                  IF (SCERR .NE. NO$SCREEN$ERROR)
         *          CALL SYERR(PUT$FIELD,SCREEN$NAME,FIELD$NAME,SCERR,
         *                     'PUT FIELD')
                  DO 800 I=1,32
                     FIELD$NAME = 'CS'//VARIABLE$ENDING(I)
                     CALL CNSTAR(32,' '
         *                       DATA$AREA)
                     CALL SCREEN(PUT$FIELD,SCREEN$NAME,FIELD$NAME,
         *                       DATA$AREA,SCERR)
                     IF (SCERR .NE. NO$SCREEN$ERROR)
         *             CALL SYERR(PUT$FIELD,SCREEN$NAME,FIELD$NAME,SCERR,
         *                        'PUT FIELD')
         800      CONTINUE
                  DO 900 I=1,512
                     PCCD$CELLDATA(I) = JFIX(0)
                     PCCD$AREA(I) = JFIX(0)
         900      CONTINUE
                  DO 905 I=1,513
                     MASS(I) = JFIX(0)
                     AREA(I) = JFIX(0)
         905      CONTINUE
C
C
C            ************ KILL HISTOGRAM NUMBER FIELDS ***************
C
                  DO 925 I=1,11
                     FIELD$NAME = 'CS'//VARIABLE$ENDING2(I)
                     CALL SCREEN(KILL$FIELD,SCREEN$NAME,FIELD$NAME,
         *                       DATA$AREA,SCERR)
                     IF (SCERR .NE. NO$SCREEN$ERROR)
         *             CALL SYERR(KILL$FIELD,SCREEN$NAME,FIELD$NAME,SCERR,
         *                        'KILL FIELD')
         925      CONTINUE
                  ANALYSIS$TOTAL = 0
                  FIRST$PEAK$MASS = 0.0
                  FIRST$PEAK$INDEX = 0.0
                  FIRST$PEAK$AREA = 0.0
                  SEC$PEAK$MASS = 0.0
                  SEC$PEAK$INDEX = 0.0
                  SEC$PEAK$AREA = 0.0
                  XY$COUNTER = 0
                  DO 930 I = 1,512
                     XY$COORDS(1,I) = 0
                     XY$COORDS(2,I) = 0
                     XY$COORDS(3,I) = 0
         930      CONTINUE
                  DO 935 I=1,640
                     PICO$HIST(I) = 0
         935      CONTINUE
                  DO 940 I=1,6
                     PCDT$COUNT(I) = 0
                     PCDT$OFF$SCALE(I) = 0
         940      CONTINUE
                  DO 945 I=1,2000
                     PCDT$MASS(I) = 0
                     PCDT$AREA(I) = 0
                     PCDT$CLASS(I) = -1
                     PCDT$640(I) = 0
         945      CONTINUE
                  CURSOR$POSITION = 'CS06'
                  GOTO 100
               ENDIF
C*****************************************************************
C
C
C            CODE TO HANDLE THE FOCUS COMMAND
C
C*****************************************************************
```

```
        IF (READ$INPUT$VALUE .EQ. 'FOCUS' .AND.
     *      SCERR .EQ. SCREEN$FUNCTION)
     *  THEN
           IF (.NOT. FOCUS$ACTIVE)
     *     THEN
              ERR$ONE = 'THE PEAK LIGHT LEVEL IS OUT OF'
              ERR$TWO = 'RANGE, YOU CANNOT USE FOCUS.'
              ERR$MESSAGE = 'W'
              CURSOR$POSITION = 'CS07'
              GOTO 100
           ENDIF
C
C         ************ CALL FOCUS SUBROUTINE *************
C
C
        CALL SAQQ06(REDSAVE,GREENSAVE,BLUESAVE,FOCUS$FLAG,
     *              FATAL$ERROR)
        IF (FATAL$ERROR) GOTO 100
        CURSOR$POSITION = 'CS07'
        GOTO 100
      ENDIF
C***************************************************************
C
C       CODE TO HANDLE THE ANALYZE COMMAND
C
C***************************************************************
        IF (READ$INPUT$VALUE .EQ. 'ANALYZE' .AND.
     *      SCERR .EQ. SCREEN$FUNCTION)
     *  THEN
C
C       ******* CHECK TO SEE IF THE PEAK LIGHT LEVEL IS IN RANGE *******
C
           IF (.NOT. SET$LIGHT$FLAG)
     *     THEN
              ERR$ONE = 'THE PEAK LIGHT LEVEL IS OUT OF'
              ERR$TWO = 'RANGE, YOU CANNOT USE ANALYZE.'
              ERR$MESSAGE = 'W'
              CURSOR$POSITION = 'CS08'
              GOTO 100
           ENDIF
C
C       ********* CHECK TO SEE IF THE CELL COUNT IS IN RANGE *********
C
           IF (PCCD$CELLCNT .LT. 50 .OR. PCCD$CELLCNT .GT. 512)
     *     THEN
              ERR$ONE = 'THE CELL COUNT MUST BE BETWEEN'
              ERR$TWO = '50 AND 512 TO USE ANALYZE.'
              ERR$MESSAGE = 'W'
              CURSOR$POSITION = 'CS08'
              GOTO 100
           ENDIF
C
C       ******** CHECK TO MAKE SURE THAT THE DNA **********
C       ******** CONVERSION VALUE IS IN RANGE    **********
C
           IF (DNA$CONV$VALUE .LT. 1.0 .OR. DNA$CONV$VALUE .GT. 99.99)
     *     THEN
              ERR$ONE = 'THE DNA CONVERSION VALUE IS OUT'
              ERR$TWO = 'OF RANGE,YOU CANNOT USE ANALYZE.'
              ERR$MESSAGE = 'W'
              CURSOR$POSITION = 'CS08'
              GOTO 100
           ENDIF
C
        ANALYZE$FLAG = .TRUE.
        IF (PCCD$CELLCNT .GT. 0)
     *  THEN
           PCCD$PICOMASS = DBLE(PCCD$MEAN)/
     *                     PCCD$CALIB$CELL$DNA
        ELSE
           PCCD$PICOMASS = 1.0
```

```
          ENDIF
C
C         ********** KILL THE CALIBRATION SCREEN'S FIELDS **********
C
          DATA$AREA(1) = 20
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$KILL$FIELD,SCREEN$NAME,FIELD$NAME,SCERR,
     *                'GROUP KILL FIELD')
          DATA$AREA(1) = 21
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$KILL$FIELD,SCREEN$NAME,FIELD$NAME,SCERR,
     *                'GROUP KILL FIELD')
          DATA$AREA(1) = 60
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$KILL$FIELD,SCREEN$NAME,FIELD$NAME,SCERR,
     *                'GROUP KILL FIELD')
          DATA$AREA(1) = 61
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$KILL$FIELD,SCREEN$NAME,FIELD$NAME,SCERR,
     *                'GROUP KILL FIELD')
C
C         ********* CLEAR AWAY ANY EXISTING ERROR MESSAGES *********
C
          IF (ERR$MESSAGE .EQ. 'C')
     *    THEN
            ERR$ONE = ' '
            FIELD$NAME = 'ERR1'
            CALL CNSTAR(32,'                              ',
     *                  DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                  'PUT FIELD')
            FIELD$NAME = 'ERR2'
            CALL CNSTAR(32,'                              ',
     *                  DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                  'PUT FIELD')
          ENDIF
          RETURN
        ENDIF
C*****************************************************************
C
C         CODE TO HANDLE THE MAIN COMMAND
C
C*****************************************************************
        IF (READ$INPUT$VALUE .EQ. 'MAIN' .AND.
     *      SCERR .EQ. SCREEN$FUNCTION)
     *  THEN
          IF (PCCD$CELLCNT .GT. 0)
     *    THEN
            PCCD$PICOMASS = DBLE(PCCD$MEAN)/
     *                      PCCD$CALIB$CELL$DNA
          ELSE
            PCCD$PICOMASS = 1.0
          ENDIF
C
C         ********** KILL THE CALIBRATION SCREEN'S FIELDS **********
```

```
C
            DATA$AREA(1) = 20
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *         CALL SYERR(GROUP$KILL$FIELD,SCREEN$NAME,FIELD$NAME,SCERR,
     *                    'GROUP KILL FIELD')
            DATA$AREA(1) = 21
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *         CALL SYERR(GROUP$KILL$FIELD,SCREEN$NAME,FIELD$NAME,SCERR,
     *                    'GROUP KILL FIELD')
            DATA$AREA(1) = 60
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *         CALL SYERR(GROUP$KILL$FIELD,SCREEN$NAME,FIELD$NAME,SCERR,
     *                    'GROUP KILL FIELD')
            DATA$AREA(1) = 61
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *         CALL SYERR(GROUP$KILL$FIELD,SCREEN$NAME,FIELD$NAME,SCERR,
     *                    'GROUP KILL FIELD')
C
C           ******** CLEAR AWAY ANY EXISTING ERROR MESSAGES ********
C
            IF (ERR$MESSAGE .EQ. 'C')
     *      THEN
               ERR$ONE = ' '
               FIELD$NAME = 'ERR1'
               CALL CNSTAR(32,'                                        ',
     *                     DATA$AREA)
               CALL SCREEN(PUT$FIELD,SCREEN$NAME,FIELD$NAME,
     *                     DATA$AREA,SCERR)
               IF (SCERR .NE. NO$SCREEN$ERROR)
     *            CALL SYERR(PUT$FIELD,SCREEN$NAME,FIELD$NAME,SCERR,
     *                       'PUT FIELD')
               FIELD$NAME = 'ERR2'
               CALL CNSTAR(32,'                                        ',
     *                     DATA$AREA)
               CALL SCREEN(PUT$FIELD,SCREEN$NAME,FIELD$NAME,
     *                     DATA$AREA,SCERR)
               IF (SCERR .NE. NO$SCREEN$ERROR)
     *            CALL SYERR(PUT$FIELD,SCREEN$NAME,FIELD$NAME,SCERR,
     *                       'PUT FIELD')
            ENDIF
            RETURN
         ENDIF
C***********************************************************************
C
C              CODE TO HANDLE THE MEASURE COMMAND
C
C***********************************************************************
         IF (READ$INPUT$VALUE .EQ. 'MEASURE' .AND.
     *       SCERR .EQ. SCREEN$FUNCTION)
     *   THEN
C
C        ******* CHECK TO SEE IF THE PEAK LIGHT LEVEL IS IN RANGE *******
C
            IF (.NOT. SET$LIGHT$FLAG)
     *      THEN
               ERR$ONE = 'THE PEAK LIGHT LEVEL IS OUT OF'
               ERR$TWO = 'RANGE, YOU CANNOT USE MEASURE.'
               ERR$MESSAGE = 'W'
               CURSOR$POSITION = 'CS04'
               GOTO 100
            ENDIF
```

```
C
C       ***** CHECK TO SEE IF THIS IS ROOM TO CLASSIFY MORE CELLS *****
C
        IF (PCCD$CELLCNT .GE. 512)
     *  THEN
          ERR$ONE = 'MAXIMUM CONTROL CELL COUNT'
          ERR$TWO = 'HAS BEEN REACHED.'
          ERR$MESSAGE = 'W'
          CURSOR$POSITION = 'CS04'
          GOTO 100
        ENDIF
C
C       ********* IF FOCUS IS ON, THEN DEACTIVATE IT **********
C
        IF (FOCUS$FLAG)
     *  THEN
          CALL SAQQ06(REDSAVE,GREENSAVE,BLUESAVE,FOCUS$FLAG,
     *                FATAL$ERROR)
          IF (FATAL$ERROR) GOTO 100
        ENDIF
C
C       ************ CALL THE MEASURE SUBROUTINE ************
C
        CALL SAQQ11(SCREEN$NAME,LAST$OBJECT,CELL$COUNT,MASS,AREA,
     *              CELL$REJECTED,SAVE$DATA$FLAG,FATAL$ERROR)
C
C       ************ CHECK FOR A 'FATAL' ERROR ************
C
        IF (FATAL$ERROR) GOTO 100
C
        IF (.NOT. SAVE$DATA$FLAG)
     *  THEN
          CURSOR$POSITION = 'CS04'
          GOTO 100
        ENDIF
        PTR = PCCD$CELLCNT+1
        COUNT = 0
        DO 1000 I=1,LAST$OBJECT
          IF (.NOT. CELL$REJECTED(I))
     *    THEN
            PCCD$CELLDATA(PTR) = MASS(I)
            PCCD$AREA(PTR) = AREA(I)
            COUNT = COUNT+1
            PTR = PTR+1
            IF (PTR .GT. 512)
     *      THEN
              ERR$ONE = 'MAXIMUM CONTROL CELL COUNT'
              ERR$TWO = 'HAS BEEN REACHED.'
              ERR$MESSAGE = 'W'
              GOTO 1025
            ENDIF
1000    CONTINUE
        COUNT = CELL$COUNT
1025    IF (CELL$COUNT .GT. 0)
     *  THEN
          PCCD$CELLCNT = PCCD$CELLCNT+COUNT
        ENDIF
C
C       *********** CALL THE HISTOGRAM SUBROUTINE *************
C
        CALL SAQQ12(SCREEN$NAME,PCCD$CELLCNT,PCCD$CELLDATA)
C
C       ************ CHECK FOR A 'FATAL' ERROR ************
C
        IF (FATAL$ERROR) GOTO 100
```

```
C
C          ************* CALL THE STATISTICS SUBROUTINE **************
C
           CALL SAQQ13(SCREEN$NAME,FATAL$ERROR)
C
C          ************ CHECK FOR A 'FATAL' ERROR ************
C
           IF (FATAL$ERROR) GOTO 100
           CURSOR$POSITION = 'CS04'
           GOTO 100
         ENDIF
         END
CC
CC                CELL ANALYSIS SYSTEMS, INC.
CC                    (C) COPYRIGHT 1986
CC*****************************************************************
CC
CC       :PROGRAM NAME
CC       :SAQQ04
CC
CC       :SUBROUTINES
CC
CC       :CALLING SEQUENCE
CC       :SAQQ04(SCRN$NAME,DNA$CONV$VALUE,CAL$LIGHT$LEVEL,FIRST$PEAK$MASS,
CC               FIRST$PEAK$INDEX,FIRST$PEAK$AREA,SEC$PEAK$MASS,SEC$PEAK$INDEX,
CC               SEC$PEAK$AREA,REDSAVE,GREENSAVE,BLUESAVE,XY$COUNTER,
CC               XY$COORDS,PICO$HIST,FOCUS$FLAG,FATAL$ERROR)
CC
CC       :PARAMETERS
CC       :SCRN$NAME - THE NAME OF THE CURRENT SCREEN
CC       :DNA$CONV$VALUE - THE DNA CONVERSION VALUE
CC       :CAL$LIGHT$LEVEL - THE PEAK LIGHT LEVEL
CC       :FIRST$PEAK$MASS - MASS OF THE FIRST PEAK
CC       :FIRST$PEAK$INDEX - INDEX OF THE FIRST PEAK
CC       :FIRST$PEAK$AREA - AREA OF THE FIRST PEAK
CC       :SEC$PEAK$MASS - MASS OF THE SECOND PEAK
CC       :SEC$PEAK$INDEX - INDEX OF THE SECOND PEAK
CC       :SEC$PEAK$AREA - AREA OF THE SECOND PEAK
CC       :REDSAVE - AN ARRAY CONTAINING THE ORIGINAL (RED,2) TABLE VALUES
CC       :GREENSAVE - AN ARRAY CONTAINING THE ORIGINAL (GREEN,2) TABLE VALUES
CC       :BLUESAVE - AN ARRAY CONTAINING THE ORIGINAL (BLUE,2) TABLE VALUES
CC       :XY$COUNTER - A VARIABLES THAT CONTAINS THE NUMBER OF XY COORDINATES
CC       :XY$COORDS - A 2-D ARRAY THAT CONTAINS THE XY COORDINATE DATA
CC       :PICO$HIST - AN ARRAY THAT CONTAINS THE RAW HISTOGRAM OF THE
CC                    CELL MASS DATA
CC       :FOCUS$FLAG - A FLAG THAT SPECIFIES IF THE FOCUS IMAGE IS ON
CC       :FATAL$ERROR - A FLAG THAT SPECIFIES IF A 'FATAL'(I.E. SERIOUS) ERROR
CC                      OCCURRED WHILE INSIDE SAQQ04
CC
CC       :DESCRIPTION
CC       :SAQQ04 IS THE MAIN SUBROUTINE THAT HANDLES THE ANALYSIS SCREEN.
CC
CC*****************************************************************
CC#########
         SUBROUTINE SAQQ04(SCRN$NAME,DNA$CONV$VALUE,CAL$LIGHT$LEVEL,
       *                   ANALYSIS$TOTAL,FIRST$PEAK$MASS,
       *                   FIRST$PEAK$INDEX,FIRST$PEAK$AREA,
       *                   SEC$PEAK$MASS,SEC$PEAK$INDEX,SEC$PEAK$AREA,
       *                   REDSAVE,GREENSAVE,BLUESAVE,XY$COUNTER,
       *                   XY$COORDS,PICO$HIST,FOCUS$FLAG,FATAL$ERROR)
         CHARACTER*1 ERR$MESSAGE,CHAR$VALUE,LEFT$ARROW,RIGHT$ARROW,
       *             UP$ARROW,LT$SYMBOL,GT$SYMBOL,FB$SYMBOL,HB$SYMBOL
         CHARACTER*2 VAR$ENDING1(39),VAR$ENDING2(5),VAR$ENDING3(32),
       *             TEMP
         CHARACTER*3 CONFIRM$ANSWER
         CHARACTER*4 CURSOR$POSITION,FIELD1,FIELD2,FIELD3
         CHARACTER*(*) SCRN$NAME
         CHARACTER*6 SELECTED$STRING,TYPE$STRING,
       *             TYPE$LETTERS,XCHAR,YCHAR
```

```
      CHARACTER*10 BIN$STRING,READ$INPUT$VALUE
      CHARACTER*20 CURR$XY$STRING
      CHARACTER*32 ERR$ONE,ERR$TWO,HIST$STRING
      INTEGER*2 I,ANALYSIS$TOTAL,CAL$LIGHT$LEVEL,LOW$THRES,
     *          HIGH$THRES,XSCALE$NUM,XSCALE$INCREMENT,LAST$OBJECT,
     *          CELL$COUNT,PTR,COUNT,CELL$TYPE(151),REDSAVE(*),
     *          GREENSAVE(*),BLUESAVE(*),TYPE$VALUE,X$SCALE(5),
     *          CURRENT$BIN,BIN,WIDTH,BUCKET,IEND,XY(2),XY$COUNTER,
     *          XY$COORDS(3,512),PICO$HIST(*),START,
     *          END,HALF$WIDTH,MAX,MAX$VALUE,DIFF,J,X,Y,
     *          AREAS$STATUS(32),TEMP$AREAS(32),AREA1$COUNT,
     *          AREA2$COUNT
      INTEGER*4 DATA$VECTOR(32),MASS(151),AREA(151)
      REAL*4 FIRST$PEAK$MASS,FIRST$PEAK$INDEX,FIRST$PEAK$AREA,
     *       SEC$PEAK$MASS,SEC$PEAK$INDEX,SEC$PEAK$AREA,LOW,HIGH,
     *       DNA$CONV$VALUE
      REAL*8 ASUM,AREA$CONV
      LOGICAL*1 AUTO$SCALE,TYPE$SELECTED(6),FATAL$ERROR,
     *          CONFIRM$CLEAR,CONFIRM$FIELDS$KILLED,
     *          AN$FIELDS$KILLED,PREV$SELECTED(6),CHANGE$FLAG,
     *          CELL$REJECTED(151),SAVE$DATA$FLAG,FOCUS$FLAG,
     *          CONFIRM$MEASURE,ARROWS$EXIST,BIN$EXISTS,
     *          AREA$FIELDS$KILLED,AREA1$FLAG,AREA2$FLAG,
     *          SPLIT$FLAG,END$FLAG
C
      INCLUDE 'SAQCCD.FIN'
      INCLUDE 'SAQCDT.FIN'
      INCLUDE 'IMAGED.FIN'
      INCLUDE 'SCREEN.FIN'
C
      DATA VAR$ENDING1
     *    /'25','26','27','28','29','30','31','32','33','34',
     *     '35','36','37','38','39','40','41','42','43','44',
     *     '45','46','47','48','49','50','51','52','53','54',
     *     '55','56','57','58','59','60','61','62','63'/,
     *    VAR$ENDING2
     *    /'36','37','38','39','40'/,
     *    VAR$ENDING3
     *    /'01','02','03','04','05','06','07','08','09','10',
     *     '11','12','13','14','15','16','17','18','19','20',
     *     '21','22','23','24','25','26','27','28','29','30',
     *     '31','32'/,
     *    LEFT$ARROW /Z'11'/,
     *    RIGHT$ARROW /Z'10'/,
     *    UP$ARROW/Z'5E'/,
     *    LT$SYMBOL/Z'3C'/,
     *    GT$SYMBOL/Z'3E'/,
     *    FB$SYMBOL/Z'DB'/,
     *    HB$SYMBOL/Z'DC'/,
     *    TYPE$LETTERS /'N1234L'/

********** INITIALIZE THE APPROPRIATE VARIABLES **********

ERR$MESSAGE = ' '
      CHAR$VALUE = ' '
      CURSOR$POSITION = 'AS03'
      SCREEN$NAME = SCRN$NAME
      SELECTED$STRING = ' '
      TYPE$STRING = ' '
      READ$INPUT$VALUE = ' '
      ERR$ONE = ' '
      ERR$TWO = ' '
      CONFIRM$ANSWER = ' '
      BIN$STRING = ' '
      XCHAR = ' '
      YCHAR = ' '
      CURR$XY$STRING = ' '
      FIELD1 = ' '
      FIELD2 = ' '
      FIELD3 = ' '
      HIST$STRING = ' '
```

```
      X = 0
      Y = 0
      I = 0
      J = 0
      AREA1$COUNT = 0
      AREA2$COUNT = 0
      ANALYSIS$TOTAL = 0
      LOW$THRES = PCSG$LO$THRES
      HIGH$THRES = PCSG$HI$THRES
      XSCALE$NUM = 0
      XSCALE$INCREMENT = 0
      LAST$OBJECT = 0
      CELL$COUNT = 0
      PTR = 0
      COUNT = 0
      CURRENT$BIN = 0
      BIN = 0
      BUCKET = 0
      WIDTH = INT(0.1*PCCD$PICOMASS)
      XY(1) = 0
      XY(2) = 0
      HIGH = 0
      LOW = 0
      START = 0
      DATA$AREA(1) = 0
      CALL SCREEN(PUT$FIELD,SCREEN$NAME,FIELD$NAME,
     *            DATA$AREA,SCERR)
      IF (SCERR .NE. NO$SCREEN$ERROR)
     *   CALL SYERR(PUT$FIELD,SCREEN$NAME,FIELD$NAME,SCERR,
     *              'PUT FIELD')
C
C     ************ RESET ALL TYPE TO TRUE *************
C
      DO 100 I=1,6
        TYPE$SELECTED(I) = .TRUE.
100   CONTINUE
C
C     *************** CALCULATE THE TOTAL COUNT ****************
C
      DO 200 I=1,6
        ANALYSIS$TOTAL = ANALYSIS$TOTAL+PCDT$COUNT(I)
200   CONTINUE
      FIELD$NAME = 'AS31'
      DATA$AREA(1) = ANALYSIS$TOTAL
      CALL SCREEN(PUT$FIELD,SCREEN$NAME,FIELD$NAME,
     *            DATA$AREA,SCERR)
      IF (SCERR .NE. NO$SCREEN$ERROR)
     *   CALL SYERR(PUT$FIELD,SCREEN$NAME,FIELD$NAME,SCERR,
     *              'PUT FIELD')
C
C     ************* UNKILL THE APPROPRIATE FIELDS *************
C
      DATA$AREA(1) = 20
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
      DATA$AREA(1) = 70
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
      DATA$AREA(1) = 71
      CALL SCREEN(GROUP$UN$KILL$FIELD,SCREEN$NAME,FIELD$NAME,
     *            DATA$AREA,SCERR)
      IF (SCERR .NE. NO$SCREEN$ERROR)
     *   CALL SYERR(GROUP$UN$KILL$FIELD,SCREEN$NAME,FIELD$NAME,SCERR,
     *              'GROUP UNKILL FIELD')
```

```
            DATA$AREA(1) = 73
            CALL SCREEN(GROUP$UN$KILL$FIELD,SCREEN$NAME,FIELD$NAME,
          *             DATA$AREA,SCERR)
            IF (SCERR .NE. NO$SCREEN$ERROR)
          *    CALL SYERR(GROUP$UN$KILL$FIELD,SCREEN$NAME,FIELD$NAME,SCERR,
          *               'GROUP UNKILL FIELD')
    C
    C       ************ DISPLAY THE APPROPRIATE VERTICAL FIELDS *************
    C
            CALL SAQQ26(SCREEN$NAME,CURRENT$BIN,HIST$STRING,AREAS$STATUS,
          *             AREA1$COUNT,AREA2$COUNT)
    C
    C       **************** CALCULATE THE X SCALE VALUES ***************
    C
            XSCALE$NUM = 64
            X$SCALE(1) = 0
            DO 500 I=1,4
               X$SCALE(I+1) = I*16
      500   CONTINUE
    C
    C       **************** PUT UP THE HISTOGRAM ***************
    C
            CALL SAQQ14(SCREEN$NAME,PICO$HIST,TYPE$SELECTED,AUTO$SCALE,
          *             X$SCALE,DATA$VECTOR,XSCALE$NUM,SHOWN$COUNT)
    C
    C       ************* PUT UP THE ANALYSIS DATA ****************
    C
            CALL SAQQ15(SCREEN$NAME,DNA$CONV$VALUE,ANALYSIS$TOTAL,
          *             PICO$HIST,TYPE$SELECTED,FIRST$PEAK$MASS,
          *             FIRST$PEAK$INDEX,FIRST$PEAK$AREA,FATAL$ERROR)
            IF (FATAL$ERROR) GOTO 600
            SELECTED$STRING = 'N1234L'
            FIELD$NAME = 'AS44'
            CALL CNSTAR(6,SELECTED$STRING,DATA$AREA)
            CALL SCREEN(PUT$FIELD,SCREEN$NAME,FIELD$NAME,
          *             DATA$AREA,SCERR)
            IF (SCERR .NE. NO$SCREEN$ERROR)
          *    CALL SYERR(PUT$FIELD,SCREEN$NAME,FIELD$NAME,SCERR,
          *               'PUT FIELD')
    C
    C       ********* IF APPROPRIATE, KILL THE HISTOGRAM NUMBER FIELDS **********
    C
            IF (ANALYSIS$TOTAL .EQ. 0)
          *    THEN
               DO 300 I=1,5
                 FIELD$NAME = 'AS'//VAR$ENDING2(I)
                 CALL SCREEN(KILL$FIELD,SCREEN$NAME,FIELD$NAME,
          *                  DATA$AREA,SCERR)
                 IF (SCERR .NE. NO$SCREEN$ERROR)
          *         CALL SYERR(KILL$FIELD,SCREEN$NAME,FIELD$NAME,SCERR,
          *                    'KILL FIELD')
      300      CONTINUE
               DO 400 I=1,6
                 FIELD$NAME = 'CS'//VAR$ENDING1(I)
                 CALL SCREEN(KILL$FIELD,SCREEN$NAME,FIELD$NAME,
          *                  DATA$AREA,SCERR)
                 IF (SCERR .NE. NO$SCREEN$ERROR)
          *         CALL SYERR(KILL$FIELD,SCREEN$NAME,FIELD$NAME,SCERR,
          *                    'KILL FIELD')
      400      CONTINUE
            ENDIF
    C
    C       ************ CODE TO HANDLE ERROR MESSAGES ************
    C
      600   IF (ERR$MESSAGE .EQ. 'C')
          *    THEN
               ERR$ONE = ' '
               ERR$TWO = ' '
            ENDIF
```

```
          IF (ERR$MESSAGE .EQ. 'C' .OR.
    *         ERR$MESSAGE .EQ. 'W')
    *   THEN
            FIELD$NAME = 'ERR1'
            CALL CNSTAR(32,ERR$ONE,DATA$AREA)
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                     'PUT FIELD')
            FIELD$NAME = 'ERR2'
            CALL CNSTAR(32,ERR$TWO,DATA$AREA)
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                     'PUT FIELD')
          ENDIF
          IF (ERR$MESSAGE .EQ. 'C') ERR$MESSAGE = ' '
          IF (ERR$MESSAGE .EQ. 'W') ERR$MESSAGE = 'C'
          IF (ERR$MESSAGE .NE. 'C') ERR$MESSAGE = ' '
C
C         ************** CHECK FOR A 'FATAL' ERROR **************
C
          IF (FATAL$ERROR)
    *   THEN
            DATA$AREA(1) = 20
            CALL SCREEN(GROUP$KILL$FIELD,SCREEN$NAME,FIELD$NAME,
    *                  DATA$AREA,SCERR)
            IF (SCERR .NE. NO$SCREEN$ERROR)
    *         CALL SYERR(GROUP$KILL$FIELD,SCREEN$NAME,FIELD$NAME,SCERR,
    *                    'GROUP KILL FIELD')
            DO 605 I=69,80
              DATA$AREA(1) = I
              CALL SCREEN(GROUP$KILL$FIELD,SCREEN$NAME,FIELD$NAME,
    *                    DATA$AREA,SCERR)
              IF (SCERR .NE. NO$SCREEN$ERROR)
    *           CALL SYERR(GROUP$KILL$FIELD,SCREEN$NAME,FIELD$NAME,
    *                      SCERR,'GROUP KILL FIELD')
  605       CONTINUE
            RETURN
          ENDIF
C
C         **** CHECK TO SEE IF THE CONFIRM FIELDS HAVE TO BE KILLED ****
C
          IF (.NOT. CONFIRM$CLEAR .AND. .NOT. CONFIRM$MEASURE .AND.
    *         .NOT. CONFIRM$FIELDS$KILLED)
    *   THEN
            DATA$AREA(1) = 5
            CALL SCREEN(GROUP$KILL$FIELD,SCREEN$NAME,FIELD$NAME,
    *                  DATA$AREA,SCERR)
            IF (SCERR .NE. NO$SCREEN$ERROR)
    *         CALL SYERR(GROUP$KILL$FIELD,SCREEN$NAME,FIELD$NAME,SCERR,
    *                    'GROUP KILL FIELD')
            DATA$AREA(1) = 72
            CALL SCREEN(GROUP$KILL$FIELD,SCREEN$NAME,FIELD$NAME,
    *                  DATA$AREA,SCERR)
            IF (SCERR .NE. NO$SCREEN$ERROR)
    *         CALL SYERR(GROUP$KILL$FIELD,SCREEN$NAME,FIELD$NAME,SCERR,
    *                    'GROUP KILL FIELD')
            DATA$AREA(1) = 71
            CALL SCREEN(GROUP$UN$KILL$FIELD,SCREEN$NAME,FIELD$NAME,
    *                  DATA$AREA,SCERR)
            IF (SCERR .NE. NO$SCREEN$ERROR)
    *         CALL SYERR(GROUP$UN$KILL$FIELD,SCREEN$NAME,FIELD$NAME,
```

```
                          SCERR,'GROUP UNKILL FIELD')
          DATA$AREA(1) = 73
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *       CALL SYERR(GROUP$UN$KILL$FIELD,SCREEN$NAME,FIELD$NAME,
     *                  SCERR,'GROUP UNKILL FIELD')
          CONFIRM$FIELDS$KILLED = .TRUE.
        ENDIF
        IF (.NOT.AREA$FIELDS$KILLED.AND.READ$INPUT$VALUE.NE.'AREA 1-2')
     *  THEN
          DATA$AREA(1) = 79
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *       CALL SYERR(GROUP$KILL$FIELD,SCREEN$NAME,FIELD$NAME,
     *                  SCERR,'GROUP KILL FIELD')
          AREA$FIELDS$KILLED = .TRUE.
          FIELD$NAME = 'AS79'
          CALL SCREEN(UN$KILL$FIELD,SCREEN$NAME,FIELD$NAME,
     *                DATA$AREA,SCERR)
          IF (SCERR .NE. NO$SCREEN$ERROR)
     *       CALL SYERR(UN$KILL$FIELD,SCREEN$NAME,FIELD$NAME,
     *                  SCERR,'UNKILL FIELD')
          FIELD$NAME = 'AS79'
          CALL CNSTAR(32,HIST$STRING,DATA$AREA)
          CALL SCREEN(PUT$FIELD,SCREEN$NAME,FIELD$NAME,
     *                DATA$AREA,SCERR)
          IF (SCERR .NE. NO$SCREEN$ERROR)
     *       CALL SYERR(PUT$FIELD,SCREEN$NAME,FIELD$NAME,SCERR,
     *                  'PUT FIELD')
        ENDIF
C
C
C       ************ SET THE CURSOR POSITION **************
C
        FIELD$NAME = CURSOR$POSITION
        CALL SCREEN(SET$CURSOR,SCREEN$NAME,FIELD$NAME,
     *              DATA$AREA,SCERR)
        IF (SCERR .NE. NO$SCREEN$ERROR)
     *     CALL SYERR(SET$CURSOR,SCREEN$NAME,FIELD$NAME,SCERR,
     *                'SET CURSOR')
C
C
C       ************ READ THE INPUT SELECTION **************
C
        CALL SCREEN(READ$INPUT,SCREEN$NAME,FIELD$NAME,
     *              DATA$AREA,SCERR)
        IF (SCERR .EQ. SCREEN$ESCAPE .OR.
     *      SCERR .EQ. SCREEN$FUNCTION .OR.
     *      SCERR .EQ. SCREEN$DATA)
     *  THEN
          CONTINUE
        ELSE
          CALL SYERR(READ$INPUT,SCREEN$NAME,FIELD$NAME,SCERR,
     *               'READ INPUT')
        ENDIF
        CALL CNARST(10,DATA$AREA,READ$INPUT$VALUE)
        IF (SCERR .EQ. SCREEN$ESCAPE .AND. ARROWS$EXIST)
     *  THEN
          DATA$AREA(1) = 74
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *       CALL SYERR(GROUP$KILL$FIELD,SCREEN$NAME,FIELD$NAME,
     *                  SCERR,'GROUP KILL FIELD')
          ARROWS$EXIST = .FALSE.
          FIELD$NAME = 'AA'//VAR$ENDING3(CURRENT$BIN)
          CALL SCREEN(KILL$FIELD,SCREEN$NAME,FIELD$NAME,
     *                DATA$AREA,SCERR)
          IF (SCERR .NE. NO$SCREEN$ERROR)
```

```
*         CALL SYERR(KILL$FIELD,SCREEN$NAME,FIELD$NAME,
*                    SCERR,'KILL FIELD')
          IF (AREAS$STATUS(CURRENT$BIN) .EQ. 0)
*         THEN
             FIELD$NAME = 'CS'//VAR$ENDING1(CURRENT$BIN+7)
          ELSEIF (AREAS$STATUS(CURRENT$BIN) .EQ. 1)
*         THEN
             FIELD$NAME = 'AB'//VAR$ENDING3(CURRENT$BIN)
          ELSE
             FIELD$NAME = 'AC'//VAR$ENDING3(CURRENT$BIN)
          ENDIF
          CALL SCREEN(UN$KILL$FIELD,SCREEN$NAME,FIELD$NAME,
*                     DATA$AREA,SCERR)
          IF (SCERR .NE. NO$SCREEN$ERROR)
*            CALL SYERR(UN$KILL$FIELD,SCREEN$NAME,FIELD$NAME,
*                       SCERR,'UNKILL FIELD')
          CURSOR$POSITION = 'AS66'
          GOTO 600
       ENDIF
       IF (SCERR .EQ. SCREEN$ESCAPE)
*      THEN
          IF (CONFIRM$CLEAR)
*         .THEN
             CONFIRM$CLEAR = .FALSE.
             CURSOR$POSITION = 'AS05'
             GOTO 600
          ELSEIF (CONFIRM$MEASURE)
*         THEN
             CONFIRM$MEASURE = .FALSE.
             CURSOR$POSITION = 'AS03'
             GOTO 600
          ENDIF
          READ$INPUT$VALUE = 'MAIN'
          SCERR = SCREEN$FUNCTION
       ENDIF
C
C***************************************************************
C
C         CODE TO HANDLE THE CK-LIGHT COMMAND
C
C***************************************************************
       IF (READ$INPUT$VALUE .EQ. 'CK-LIGHT' .AND.
*          SCERR .EQ. SCREEN$FUNCTION)
*      THEN
          CALL SAQQ25(SCREEN$NAME,CAL$LIGHT$LEVEL,FATAL$ERROR)
          IF (FATAL$ERROR) GOTO 600
C
C         ***** CHECK TO SEE IF THE PEAK LIGHT LEVEL IS OUT OF RANGE ****
C
          IF (CAL$LIGHT$LEVEL .LT. 129 .OR. CAL$LIGHT$LEVEL .GT. 131)
*         THEN
             ERR$ONE = 'THE PEAK LIGHT LEVEL'
             ERR$TWO = 'IS NOT IN RANGE(129 TO 131).'
             ERR$MESSAGE = 'W'
          ENDIF
          CURSOR$POSITION = 'AS02'
          GOTO 600
       ENDIF
C***************************************************************
C
C         CODE TO HANDLE THE FIRST PART OF THE CLEAR COMMAND
C
C***************************************************************
       IF (READ$INPUT$VALUE .EQ. 'CLEAR' .AND.
*          SCERR .EQ. SCREEN$FUNCTION)
*      THEN
C
C         ******* CHECK TO SEE IF THERE IS DATA TO CLEAR *******
```

```fortran
C
            IF (ANALYSIS$TOTAL .LE. 0)
     *      THEN
              ERR$ONE = 'YOU CANNOT USE CLEAR BECAUSE'
              ERR$TWO = 'THERE IS NO DATA TO CLEAR.'
              ERR$MESSAGE = 'W'
              CURSOR$POSITION = 'AS05'
              GOTO 600
            ENDIF
C
C           *********** KILL MEASURE FIELDS *************
C
            DATA$AREA(1) = 71
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
C
C           ************ UNKILL CONFIRM FIELDS *************
C
            DATA$AREA(1) = 5
            CALL SCREEN(GROUP$UN$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$UN$KILL$FIELD,SCREEN$NAME,FIELD$NAME,SCERR,
     *                   'GROUP UNKILL FIELD')
            CONFIRM$CLEAR = .TRUE.
            CONFIRM$FIELDS$KILLED = .FALSE.
            CURSOR$POSITION = 'MS28'
            GOTO 600
          ENDIF
C***********************************************************************
C
C         CODE TO HANDLE THE NO-CLEAR COMMAND
C
C***********************************************************************
        IF (CONFIRM$CLEAR .AND. READ$INPUT$VALUE .EQ. 'NO ')
     *  THEN
            CONFIRM$CLEAR = .FALSE.
            CURSOR$POSITION = 'AS05'
            GOTO 600
          ENDIF
C***********************************************************************
C
C         CODE TO HANDLE THE YES-CLEAR COMMAND
C
C***********************************************************************
        IF (CONFIRM$CLEAR .AND. READ$INPUT$VALUE .EQ. 'YES')
     *  THEN
            CONFIRM$CLEAR = .FALSE.
            FIRST$PEAK$MASS = 0.0
            FIRST$PEAK$INDEX = 0.0
            FIRST$PEAK$AREA = 0.0
            SEC$PEAK$MASS = 0.0
            SEC$PEAK$INDEX = 0.0
            SEC$PEAK$AREA = 0.0
            DO 900 I=1,6
              PCDT$COUNT(I) = 0
              PCDT$OFF$SCALE(I) = 0
 900        CONTINUE
            XY$COUNTER = 0
            DO 925 I=1,512
              XY$COORDS(1,I) = 0
              XY$COORDS(2,I) = 0
              XY$COORDS(3,I) = 0
 925        CONTINUE
            ANALYSIS$TOTAL = 0
            SHOWN$COUNT = 0
            DO 950 I=1,640
              PICO$HIST(I) = 0
```

```
 950       CONTINUE
           DO 1000 I=1,2000
             PCDT$MASS(I) = 0
             PCDT$AREA(I) = 0
             PCDT$CLASS(I) = -1
             PCDT$640(I) = 0
1000       CONTINUE
           DO 960 I=1,32
             AREAS$STATUS(I) = 0
 960       CONTINUE
           CURRENT$BIN = 0
C
C          ********* CALL THE SUBROUTINE THAT CLEARS AWAY *********
C          ********* THE AREA 1 AND AREA 2 DATA          *********
C
           CALL SAQQ26(SCREEN$NAME,CURRENT$BIN,HIST$STRING,
     *                 AREAS$STATUS,AREA1$COUNT,AREA2$COUNT)
           DO 1200 I=1,6
             DATA$REAL = 0.0
             FIELD$NAME = 'AS'//VAR$ENDING1(I)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,SCERR,
     *                    'PUT FIELD')
1200       CONTINUE
           DO 1300 I=1,3
             DATA$AREA(1) = 0
             FIELD$NAME = 'AS'//VAR$ENDING1(I+6)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,SCERR,
     *                    'PUT FIELD')
1300       CONTINUE
           DO 1400 I=1,32
             FIELD$NAME = 'CS'//VAR$ENDING1(I+7)
             CALL CNSTAR(10,'          ',DATA$AREA)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,SCERR,
     *                    'PUT FIELD')
             FIELD$NAME = 'AA'//VAR$ENDING3(I)
             CALL CNSTAR(10,'          ',DATA$AREA)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,SCERR,
     *                    'PUT FIELD')
             FIELD$NAME = 'AB'//VAR$ENDING3(I)
             CALL CNSTAR(10,'          ',DATA$AREA)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,SCERR,
     *                    'PUT FIELD')
             FIELD$NAME = 'AC'//VAR$ENDING3(I)
             CALL CNSTAR(10,'          ',DATA$AREA)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,SCERR,
     *                    'PUT FIELD')
1400       CONTINUE
C
C          ************ KILL HISTOGRAM NUMBER FIELDS ****************
```

```
            DO 1500 I=1,5
              FIELD$NAME = 'AS'//VAR$ENDING2(I)
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,SCERR,
     *                    'KILL FIELD')
 1500       CONTINUE
            DO 1600 I=1,6
              FIELD$NAME = 'CS'//VAR$ENDING1(I)
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,SCERR,
     *                    'KILL FIELD')
 1600       CONTINUE
            CURSOR$POSITION = 'AS05'
            GOTO 600
          ENDIF
C***********************************************************************
C
C             CODE TO HANDLE THE BOUNDARY COMMAND
C
C***********************************************************************
          IF (READ$INPUT$VALUE .EQ. 'BOUNDARY' .AND.
     *        SCERR .EQ. SCREEN$FUNCTION)
     *    THEN
C
C           *********** IF SCREEN ACQUISITION IS ACTIVE, ************
C           *********** THEN TEMPORARILY STOP IT         ************
C
            CALL IMMAIN(IMAGE$ACQ$STATUS,IMERR)
            IF (IMERR .NE. ' ')
     *      THEN
              FATAL$ERROR = .TRUE.
              GOTO 600
            ENDIF
            IF (IM$ACQ$STATUS .NE. 0)
     *      THEN
              CALL IMMAIN(IMAGE$STOP$ACQ,IMERR)
              IF (IMERR .NE. ' ')
     *        THEN
                FATAL$ERROR = .TRUE.
                GOTO 600
              ENDIF
            ENDIF
C
C           ********* CLEAR AWAY ANY EXISTING ERROR MESSAGES *********
C
            IF (ERR$MESSAGE .EQ. 'C')
     *      THEN
              ERR$ONE = ' '
              FIELD$NAME = 'ERR1'
              CALL CNSTAR(32,'                              ',
     *                    DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                    'PUT FIELD')
              FIELD$NAME = 'ERR2'
              CALL CNSTAR(32,'                              ',
     *                    DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                    'PUT FIELD')
            ENDIF
```

```
C
C         *************** KILL THE ANALYSIS SCREEN'S FIELDS **************
C
          DATA$AREA(1) = 20
          CALL SCREEN(GROUP$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$KILL$FIELD,SCREEN$NAME,FIELD$NAME,SCERR,
     *                'GROUP KILL FIELD')
          DO 620 I=69,80
            DATA$AREA(1) = I
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$KILL$FIELD,SCREEN$NAME,FIELD$NAME,SCERR,
     *                  'GROUP KILL FIELD')
 620      CONTINUE
C
C         ****** CALL THE SUBROUTINE THAT HANDLES THE BOUNDARY SCREEN ******
C
          CALL SAQQ05(SCREEN$NAME,LOW$THRES,FATAL$ERROR)
          IF (FATAL$ERROR) GOTO 600
          PCSG$LO$THRES = LOW$THRES
C
C         *********** UNKILL THE ANALYSIS SCREEN'S FIELDS ***********
C
          DATA$AREA(1) = 20
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$UN$KILL$FIELD,SCREEN$NAME,FIELD$NAME,SCERR,
     *                'GROUP UNKILL FIELD')
          DATA$AREA(1) = 70
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$UN$KILL$FIELD,SCREEN$NAME,FIELD$NAME,SCERR,
     *                'GROUP UNKILL FIELD')
          DATA$AREA(1) = 71
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$UN$KILL$FIELD,SCREEN$NAME,FIELD$NAME,SCERR,
     *                'GROUP UNKILL FIELD')
          DATA$AREA(1) = 73
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *      CALL SYERR(GROUP$UN$KILL$FIELD,SCREEN$NAME,FIELD$NAME,SCERR,
     *                'GROUP UNKILL FIELD')
          CALL SAQQ24(SCREEN$NAME,AREAS$STATUS)
          IF (ANALYSIS$TOTAL .EQ. 0)
     *    THEN
            DO 625 I=1,5
              FIELD$NAME = 'AS'//VAR$ENDING2(I)
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,SCERR,
     *                    'KILL FIELD')
 625        CONTINUE
            DO 650 I=1,6
              FIELD$NAME = 'CS'//VAR$ENDING1(I)
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,SCERR,
     *                    'KILL FIELD')
 650        CONTINUE
          ENDIF
```

```
C
C
C        ******* IF NECESSARY, ACTIVATE SCREEN ACQUISITION **********
         IF (IM$ACQ$STATUS .NE. 0)
       *  THEN
            CALL IMMAIN(IMAGE$START$ACQ,IMERR)
            IF (IMERR .NE. ' ')
       *     THEN
              FATAL$ERROR = .TRUE.
              GOTO 600
            ENDIF
         ENDIF
         CURSOR$POSITION = 'AS09'
         GOTO 600
       ENDIF
C***************************************************************************
C
C
C             CODE TO HANDLE THE FOCUS COMMAND
C
C***************************************************************************
       IF (READ$INPUT$VALUE .EQ. 'FOCUS' .AND.
      *    SCERR .EQ. SCREEN$FUNCTION)
      *  THEN
          CALL SAQQ06(REDSAVE,GREENSAVE,BLUESAVE,FOCUS$FLAG,
      *               FATAL$ERROR)
          CURSOR$POSITION = 'AS06'
          GOTO 600
       ENDIF
C***************************************************************************
C
C
C             CODE TO HANDLE THE SCALE COMMAND
C
C***************************************************************************
       IF (READ$INPUT$VALUE .EQ. 'SCALE' .AND.
      *    SCERR .EQ. SCREEN$FUNCTION)
      *  THEN
C
C
C        ******* CLEAR SECOND PEAK DATA, IF IT EXISTS **********
C
         IF (CURRENT$BIN .NE. 0)
       *  THEN
            CURRENT$BIN = 0
            SEC$PEAK$MASS = 0.0
            SEC$PEAK$INDEX = 0.0
            SEC$PEAK$AREA = 0.0
            FIELD$NAME = 'AS28'
            DATA$REAL = 0.0
            CALL SCREEN(PUT$FIELD,SCREEN$NAME,FIELD$NAME,
       *                DATA$AREA,SCERR)
            IF (SCERR .NE. NO$SCREEN$ERROR)
       *      CALL SYERR(PUT$FIELD,SCREEN$NAME,FIELD$NAME,SCERR,
       *                 'PUT FIELD')
            FIELD$NAME = 'AS29'
            DATA$REAL = 0.0
            CALL SCREEN(PUT$FIELD,SCREEN$NAME,FIELD$NAME,
       *                DATA$AREA,SCERR)
            IF (SCERR .NE. NO$SCREEN$ERROR)
       *      CALL SYERR(PUT$FIELD,SCREEN$NAME,FIELD$NAME,SCERR,
       *                 'PUT FIELD')
            FIELD$NAME = 'AS30'
            DATA$REAL = 0.0
            CALL SCREEN(PUT$FIELD,SCREEN$NAME,FIELD$NAME,
       *                DATA$AREA,SCERR)
            IF (SCERR .NE. NO$SCREEN$ERROR)
       *      CALL SYERR(PUT$FIELD,SCREEN$NAME,FIELD$NAME,SCERR,
```

```
   *                 'PUT FIELD')
               ENDIF
C
C      ******** CALL THE SUBROUTINE THAT CLEARS AWAY *********
C      ******** THE AREA 1 AND AREA 2 DATA           *********
C
               CALL SAQQ26(SCREEN$NAME,CURRENT$BIN,HIST$STRING,
   *                       AREAS$STATUS,AREA1$COUNT,AREA2$COUNT)
               IF (XSCALE$NUM .EQ. 16)
   *           THEN
                  XSCALE$NUM = 32
                  XSCALE$INCREMENT = 8
               ELSEIF (XSCALE$NUM .EQ. 32)
   *           THEN
                  XSCALE$NUM = 64
                  XSCALE$INCREMENT = 16
               ELSE
                  XSCALE$NUM = 16
                  XSCALE$INCREMENT = 4
               ENDIF
               X$SCALE(1) = 0
               DO 1700 I=2,5
                  X$SCALE(I) = X$SCALE(I-1)+XSCALE$INCREMENT
 1700          CONTINUE
               AUTO$SCALE = .FALSE.
C
C          ************ PUT OUT THE NEW HISTOGRAM *************
C
               CALL SAQQ14(SCREEN$NAME,PICO$HIST,TYPE$SELECTED,AUTO$SCALE,
   *                       X$SCALE,DATA$VECTOR,XSCALE$NUM,SHOWN$COUNT)
               AUTO$SCALE = .TRUE.
               CURSOR$POSITION = 'AS08'
               GOTO 600
            ENDIF
C***************************************************************************
C
C               CODE TO HANDLE THE REPORT COMMAND
C
C***************************************************************************
            IF (READ$INPUT$VALUE .EQ. 'REPORT' .AND.
   *            SCERR .EQ. SCREEN$DATA)
   *        THEN
               DO 1800 I=1,6
                  PREV$SELECTED(I) = TYPE$SELECTED(I)
                  TYPE$SELECTED(I) = .FALSE.
 1800          CONTINUE
               FIELD$NAME = 'AS44'
               CALL SCREEN(GET$FIELD,SCREEN$NAME,FIELD$NAME,
   *                      DATA$AREA,SCERR)
               IF (SCERR .NE. NO$SCREEN$ERROR)
   *              CALL SYERR(GET$FIELD,SCREEN$NAME,FIELD$NAME,SCERR,
   *                         'GET FIELD')
               CALL CNARST(6,DATA$AREA,TYPE$STRING)
               DO 1900 I=1,6
                  CHAR$VALUE = TYPE$STRING(I:I)
                  IF ((CHAR$VALUE .EQ. 'N' .OR. CHAR$VALUE .EQ. 'n' .OR.
   *                  CHAR$VALUE .EQ. '0') .AND. .NOT. TYPE$SELECTED(1))
   *              THEN
                     TYPE$SELECTED(1) = .TRUE.
                  ELSEIF (CHAR$VALUE .EQ. '1' .AND. .NOT. TYPE$SELECTED(2))
   *              THEN
                     TYPE$SELECTED(2) = .TRUE.
                  ELSEIF (CHAR$VALUE .EQ. '2' .AND. .NOT. TYPE$SELECTED(3))
   *              THEN
                     TYPE$SELECTED(3) = .TRUE.
                  ELSEIF (CHAR$VALUE .EQ. '3' .AND. .NOT. TYPE$SELECTED(4))
   *              THEN
                     TYPE$SELECTED(4) = .TRUE.
                  ELSEIF (CHAR$VALUE .EQ. '4' .AND. .NOT. TYPE$SELECTED(5))
```

```
          *       THEN
                    TYPE$SELECTED(5) = .TRUE.
                  ELSEIF ((CHAR$VALUE .EQ. 'L' .OR. CHAR$VALUE .EQ. '1' .OR.
          *          CHAR$VALUE .EQ. '5') .AND. .NOT. TYPE$SELECTED(6))
          *       THEN
                    TYPE$SELECTED(6) = .TRUE.
                  ENDIF
      1900    CONTINUE
                CHANGE$FLAG = .FALSE.
                DO 2000 I=1,6
                  IF (TYPE$SELECTED(I) .NEQV. PREV$SELECTED(I))
          *         CHANGE$FLAG = .TRUE.
      2000    CONTINUE
                IF (.NOT. CHANGE$FLAG)
          *     THEN
                  ERR$ONE = 'THE TYPES HAVE NOT'
                  ERR$TWO = 'BEEN CHANGED.'
                  ERR$MESSAGE = 'W'
                  CURSOR$POSITION = 'AS07'
                  GOTO 600
                ENDIF
      C
      C         .******** CLEAR SECOND PEAK DATA, IF IT EXISTS **********
      C
                IF (CURRENT$BIN .NE. 0)
          *     THEN
                  CURRENT$BIN = 0
                  SEC$PEAK$MASS = 0.0
                  SEC$PEAK$INDEX = 0.0
                  SEC$PEAK$AREA = 0.0
                  FIELD$NAME = 'AS28'
                  DATA$REAL = 0.0
                  CALL SCREEN(PUT$FIELD,SCREEN$NAME,FIELD$NAME,
          *                   DATA$AREA,SCERR)
                  IF (SCERR .NE. NO$SCREEN$ERROR)
          *         CALL SYERR(PUT$FIELD,SCREEN$NAME,FIELD$NAME,SCERR,
          *                    'PUT FIELD')
                  FIELD$NAME = 'AS29'
                  DATA$REAL = 0.0
                  CALL SCREEN(PUT$FIELD,SCREEN$NAME,FIELD$NAME,
          *                   DATA$AREA,SCERR)
                  IF (SCERR .NE. NO$SCREEN$ERROR)
          *         CALL SYERR(PUT$FIELD,SCREEN$NAME,FIELD$NAME,SCERR,
          *                    'PUT FIELD')
                  FIELD$NAME = 'AS30'
                  DATA$REAL = 0.0
                  CALL SCREEN(PUT$FIELD,SCREEN$NAME,FIELD$NAME,
          *                   DATA$AREA,SCERR)
                  IF (SCERR .NE. NO$SCREEN$ERROR)
          *         CALL SYERR(PUT$FIELD,SCREEN$NAME,FIELD$NAME,SCERR,
          *                    'PUT FIELD')
                ENDIF
      C
      C         ********* CALL THE SUBROUTINE THAT CLEARS AWAY *********
      C         ********* THE AREA 1 AND AREA 2 DATA          *********
      C
                CALL SAQQ26(SCREEN$NAME,CURRENT$BIN,HIST$STRING,
          *                 AREAS$STATUS,AREA1$COUNT,AREA2$COUNT)
                SELECTED$STRING = ' '
                J = 1
                DO 2050 I=1,6
                  IF (TYPE$SELECTED(I))
          *       THEN
                    SELECTED$STRING(J:J) = TYPE$LETTERS(I:I)
                    J = J+1
                  ENDIF
      2050    CONTINUE
      C
      C         *************** CALCULATE THE X SCALE VALUES **************
      C
                XSCALE$NUM = 64
```

```
              X$SCALE(1) = 0
              DO 2075 I=1,4
                X$SCALE(I+1) = I*16
 2075         CONTINUE
C
C             ************* CALCULATE THE CELL MASS HISTOGRAM *********
C
              DO 2080 I=1,640
                PICO$HIST(I) = 0
 2080         CONTINUE
              DO 2090 I=1,ANALYSIS$TOTAL
                J = PCDT$CLASS(I)+1
                IF (.NOT. TYPE$SELECTED(J)) GOTO 2090
                BUCKET = PCDT$640(I)
                IF (BUCKET .LT. 1 .OR. BUCKET .GT. 640)
     *          THEN
                  CONTINUE
                ELSE
                  PICO$HIST(BUCKET) = PICO$HIST(BUCKET)+1
                ENDIF
 2090         CONTINUE
C
C             **************** PUT UP THE HISTOGRAM **************
C
              AUTO$SCALE = .TRUE.
              CALL SAQQ14(SCREEN$NAME,PICO$HIST,TYPE$SELECTED,AUTO$SCALE,
     *                    X$SCALE,DATA$VECTOR,XSCALE$NUM,SHOWN$COUNT)
C
C             ************* PUT UP THE ANALYSIS DATA ***************
C
              CALL SAQQ15(SCREEN$NAME,DNA$CONV$VALUE,ANALYSIS$TOTAL,
     *                    PICO$HIST,TYPE$SELECTED,FIRST$PEAK$MASS,
     *                    FIRST$PEAK$INDEX,FIRST$PEAK$AREA,FATAL$ERROR)
              IF (FATAL$ERROR) GOTO 600
              FIELD$NAME = 'AS44'
              CALL CNSTAR(6,SELECTED$STRING,DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                    'PUT FIELD')
C
              CURSOR$POSITION = 'AS07'
              GOTO 600
            ENDIF
C***************************************************************************
C
C             CODE TO HANDLE THE MAIN COMMAND
C
C***************************************************************************
            IF (READ$INPUT$VALUE .EQ. 'MAIN' .AND.
     *          SCERR .EQ. SCREEN$FUNCTION)
     *      THEN
C
C             ********** KILL THE CALIBRATION SCREEN'S FIELDS **********
C
              DATA$AREA(1) = 20
              CALL SCREEN(GROUP$KILL$FIELD,SCREEN$NAME,FIELD$NAME,
     *                    DATA$AREA,SCERR)
              IF (SCERR .NE. NO$SCREEN$ERROR)
     *          CALL SYERR(GROUP$KILL$FIELD,SCREEN$NAME,FIELD$NAME,SCERR,
     *                    'GROUP KILL FIELD')
              DO 2098 I=69,80
                DATA$AREA(1) = I
                CALL SCREEN(GROUP$KILL$FIELD,SCREEN$NAME,FIELD$NAME,
     *                      DATA$AREA,SCERR)
                IF (SCERR .NE. NO$SCREEN$ERROR)
     *            CALL SYERR(GROUP$KILL$FIELD,SCREEN$NAME,FIELD$NAME,SCERR,
     *                      'GROUP KILL FIELD')
```

```
2098        CONTINUE
            IF (CURRENT$BIN .NE. 0)
      *     .THEN
              IF (HIST$STRING(CURRENT$BIN:CURRENT$BIN) .EQ. UP$ARROW)
      *       THEN
                HIST$STRING(CURRENT$BIN:CURRENT$BIN) = ' '
              ELSEIF (HIST$STRING(CURRENT$BIN:CURRENT$BIN) .EQ.
      *              LT$SYMBOL)
      *       THEN
                HIST$STRING(CURRENT$BIN:CURRENT$BIN) = '1'
              ELSE
                HIST$STRING(CURRENT$BIN:CURRENT$BIN) = '2'
              ENDIF
            ENDIF
C
C
C         ********* CLEAR AWAY ANY EXISTING ERROR MESSAGES *********
            IF (ERR$MESSAGE .EQ. 'C')
      *     THEN
              ERR$ONE = '  '
              FIELD$NAME = 'ERR1'
              CALL CNSTAR(32,'
      *                       DATA$AREA)                            ',
              CALL SCREEN(PUT$FIELD,SCREEN$NAME,FIELD$NAME,
      *                   DATA$AREA,SCERR)
              IF (SCERR .NE. NO$SCREEN$ERROR)
      *         CALL SYERR(PUT$FIELD,SCREEN$NAME,FIELD$NAME,SCERR,
      *                    'PUT FIELD')
              FIELD$NAME = 'ERR2'
              CALL CNSTAR(32,'
      *                       DATA$AREA)                            ',
              CALL SCREEN(PUT$FIELD,SCREEN$NAME,FIELD$NAME,
      *                   DATA$AREA,SCERR)
              IF (SCERR .NE. NO$SCREEN$ERROR)
      *         CALL SYERR(PUT$FIELD,SCREEN$NAME,FIELD$NAME,SCERR,
      *                    'PUT FIELD')
            ENDIF
            RETURN
          ENDIF
C*****************************************************************
C
C
C         CODE TO HANDLE THE FIRST PART OF THE CLASSIFY COMMAND
C
C*****************************************************************
          IF (READ$INPUT$VALUE .EQ. 'CLASSIFY' .AND.
      *       SCERR .EQ. SCREEN$FUNCTION)
      *   THEN
C
C         ***** CHECK TO SEE IF THIS IS ROOM TO CLASSIFY MORE CELLS *****
C
            IF (ANALYSIS$TOTAL .GE. 2000)
      *     THEN
              ERR$ONE = 'MAXIMUM CLASSIFICATION CELL'
              ERR$TWO = 'COUNT HAS BEEN REACHED.'
              ERR$MESSAGE = 'W'
              CURSOR$POSITION = 'AS03'
              GOTO 600
            ENDIF
C
C
C         ************* KILL MEASURE FIELDS *************
C
            DATA$AREA(1) = 71
            CALL SCREEN(GROUP$KILL$FIELD,SCREEN$NAME,FIELD$NAME,
      *                 DATA$AREA,SCERR)
            IF (SCERR .NE. NO$SCREEN$ERROR)
      *       CALL SYERR(GROUP$KILL$FIELD,SCREEN$NAME,FIELD$NAME,SCERR,
      *                  'GROUP KILL FIELD')
            DATA$AREA(1) = 73
            CALL SCREEN(GROUP$KILL$FIELD,SCREEN$NAME,FIELD$NAME,
      *                 DATA$AREA,SCERR)
            IF (SCERR .NE. NO$SCREEN$ERROR)
```

```
     *      CALL SYERR(GROUP$KILL$FIELD,SCREEN$NAME,FIELD$NAME,SCERR,
     *                 'GROUP KILL FIELD')
C
C       *********** UNKILL CONFIRM AND MEASURE FIELDS ************
C
            DATA$AREA(1) = 5
            CALL SCREEN(GROUP$UN$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$UN$KILL$FIELD,SCREEN$NAME,FIELD$NAME,SCERR,
     *                   'GROUP UNKILL FIELD')
            DATA$AREA(1) = 72
            CALL SCREEN(GROUP$UN$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$UN$KILL$FIELD,SCREEN$NAME,FIELD$NAME,SCERR,
     *                   'GROUP UNKILL FIELD')
            CONFIRM$MEASURE = .TRUE.
            CONFIRM$FIELDS$KILLED = .FALSE.
            CURSOR$POSITION = 'MS27'
            GOTO 600
          ENDIF
C*****************************************************************
C
C         CODE TO HANDLE THE NO-CLASSIFY COMMAND
C
C*****************************************************************
          IF (CONFIRM$MEASURE .AND. READ$INPUT$VALUE .EQ. 'NO ')
     *    THEN
            CONFIRM$MEASURE = .FALSE.
            CURSOR$POSITION = 'AS03'
            GOTO 600
          ENDIF
C*****************************************************************
C
C         CODE TO HANDLE THE YES-CLASSIFY COMMAND
C
C*****************************************************************
          IF (CONFIRM$MEASURE .AND. READ$INPUT$VALUE .EQ. 'YES')
     *    THEN
            CONFIRM$MEASURE = .FALSE.
            IF (FOCUS$FLAG)
     *      THEN
              CALL SAQQ06(REDSAVE,GREENSAVE,BLUESAVE,FOCUS$FLAG,
     *                    FATAL$ERROR)
              IF (FATAL$ERROR) GOTO 600
            ENDIF
            CALL SAQQ16.(SCRN$NAME,LAST$OBJECT,CELL$COUNT,MASS,AREA,XY,
     *                   CELL$TYPE,CELL$REJECTED,SAVE$DATA$FLAG,FATAL$ERROR)
            IF (FATAL$ERROR) GOTO 600
            IF (.NOT. SAVE$DATA$FLAG)
     *      .THEN
              CURSOR$POSITION = 'AS03'
              GOTO 600
            ENDIF
            DO 2095 I=1,640
              PICO$HIST(I) = 0
 2095       CONTINUE
            DO 2096 I=1,ANALYSIS$TOTAL
              BUCKET = PCDT$640(I)
              IF (BUCKET .LT. 1 .OR. BUCKET .GT. 640)
     *        THEN
                CONTINUE
              ELSE
                PICO$HIST(BUCKET) = PICO$HIST(BUCKET)+1
              ENDIF
 2096       CONTINUE
            IF (XY$COUNTER .LT. 512)
```

```
              *    THEN
                      XY$COUNTER = XY$COUNTER+1
                      XY$COORDS(1,XY$COUNTER) = XY$COUNTER
                      XY$COORDS(2,XY$COUNTER) = XY(1)
                      XY$COORDS(3,XY$COUNTER) = XY(2)
                   ELSE
                      ERR$ONE = 'THE XY COORDINATES COORDINATES'
                      ERR$TWO = 'OF THE IMAGE WERE NOT SAVED.'
                      ERR$MESSAGE = 'W'
                   ENDIF
                   START = ANALYSIS$TOTAL+1
                   DO 2100 I=1,LAST$OBJECT
                   IF (CELL$REJECTED(I)) GOTO 2100
                   TYPE$VALUE = CELL$TYPE(I)
                   IF (TYPE$VALUE .LT. 0 .OR. TYPE$VALUE .GT. 5) GOTO 2100
                   TYPE$VALUE = TYPE$VALUE+1
                   IF (ANALYSIS$TOTAL .GE. 2000)
              *    THEN
                      ERR$ONE = 'MAXIMUM CLASSIFICATION CELL'
                      ERR$TWO = 'COUNT HAS BEEN REACHED.'
                      ERR$MESSAGE = 'W'
                   ELSE
                      PCDT$COUNT(TYPE$VALUE) = PCDT$COUNT(TYPE$VALUE)+1
                      ANALYSIS$TOTAL = ANALYSIS$TOTAL+1
                      PCDT$MASS(ANALYSIS$TOTAL) = MASS(I)
                      PCDT$AREA(ANALYSIS$TOTAL) = AREA(I)
                      PCDT$CLASS(ANALYSIS$TOTAL) = TYPE$VALUE-1
                   ENDIF
        2100    CONTINUE
        C
        C
        C        ************ RESET ALL TYPE TO TRUE *************
        C
                   DO 2300 I=1,6
                      TYPE$SELECTED(I) = .TRUE.
        2300    CONTINUE
                   SELECTED$STRING = 'N1234L'
        C
        C
        C        ***************** CALCULATE THE X SCALE VALUES ****************
        C
                   XSCALE$NUM = 64
                   X$SCALE(1) = 0
                   DO 2400 I=1,4
                      X$SCALE(I+1) = I*16
        2400    .CONTINUE
        C
                   FIELD$NAME = 'AS44'
                   CALL CNSTAR(6,SELECTED$STRING,DATA$AREA)
                   CALL SCREEN(PUT$FIELD,SCREEN$NAME,FIELD$NAME,
              *                DATA$AREA,SCERR)
                   IF (SCERR .NE. NO$SCREEN$ERROR)
              *       CALL SYERR(PUT$FIELD,SCREEN$NAME,FIELD$NAME,SCERR,
              *                  'PUT FIELD')
        C
                   FIELD$NAME = 'AS31'
                   DATA$AREA(1) = ANALYSIS$TOTAL
                   CALL SCREEN(PUT$FIELD,SCREEN$NAME,FIELD$NAME,
              *                DATA$AREA,SCERR)
                   IF (SCERR .NE. NO$SCREEN$ERROR)
              *       CALL SYERR(PUT$FIELD,SCREEN$NAME,FIELD$NAME,SCERR,
              *                  'PUT FIELD')
        C
        C
        C        ********* CALL THE SUBROUTINE THAT CLEARS AWAY *********
        C        ********* THE AREA 1 AND AREA 2 DATA           *********
        C
                   CALL SAQQ26(SCREEN$NAME,CURRENT$BIN,HIST$STRING,
              *                AREAS$STATUS,AREA1$COUNT,AREA2$COUNT)
```

```
C
C          ************ CALCULATE THE CELL MASS HISTOGRAM *********
C
           END = ANALYSIS$TOTAL
           DO 2425 I=START,END
             IF (PCDT$MASS(I) .LT. 1) GOTO 2425
             BUCKET = INT((PCDT$MASS(I)-HALF$WIDTH)/WIDTH)+1
             PCDT$640(I) = BUCKET
             IF (BUCKET .LT. 1 .OR. BUCKET .GT. 640)
      *      THEN
               J = PCDT$CLASS(I)+1
               PCDT$OFF$SCALE(J) = PCDT$OFF$SCALE(J)+1
             ELSE
               PICO$HIST(BUCKET) = PICO$HIST(BUCKET)+1
             ENDIF
 2425      CONTINUE
C
C          **************** PUT UP THE HISTOGRAM **************
C
           AUTO$SCALE = .TRUE.
           CALL SAQQ14(SCREEN$NAME,PICO$HIST,TYPE$SELECTED,AUTO$SCALE,
      *                X$SCALE,DATA$VECTOR,XSCALE$NUM,SHOWN$COUNT)
C
C          ************* PUT UP THE ANALYSIS DATA ***************
C
           CALL SAQQ15(SCREEN$NAME,DNA$CONV$VALUE,ANALYSIS$TOTAL,
      *                PICO$HIST,TYPE$SELECTED,FIRST$PEAK$MASS,
      *                FIRST$PEAK$INDEX,FIRST$PEAK$AREA,FATAL$ERROR)
           IF (FATAL$ERROR) GOTO 600
           IF (CURRENT$BIN .EQ. 0)
      *    THEN
             CURSOR$POSITION = 'AS03'
             GOTO 600
           ENDIF
C
C          ************ UPDATE SECOND PEAK VALUES ************
C
           CALL SAQQ23(SCREEN$NAME,DNA$CONV$VALUE,ANALYSIS$TOTAL,
      *                PICO$HIST,TYPE$SELECTED,XSCALE$NUM,CURRENT$BIN,
      *                FIRST$PEAK$MASS,SEC$PEAK$MASS,
      *                SEC$PEAK$INDEX,SEC$PEAK$AREA)
           CURSOR$POSITION = 'AS03'
           GOTO 600
         ENDIF
C*******************************************************************
C
C          CODE TO SELECT THE SECOND PEAK
C
C*******************************************************************
       IF (READ$INPUT$VALUE .EQ. 'SELECT-2ND')
      * THEN
C
C          ****** IF SHOWN COUNT EQUALS ZERO, PRINT OUT MESSAGE ******
C
           IF (SHOWN$COUNT .EQ. 0)
      *    THEN
             ERR$ONE = 'SELECT-2ND CANNOT BE USED WHEN'
             ERR$TWO = 'SHOWN COUNT EQUALS ZERO.'
             ERR$MESSAGE = 'W'
             CURSOR$POSITION = 'AS66'
             GOTO 600
           ENDIF
           BIN$EXISTS = .FALSE.
C
C          ****** IF NO SECOND PEAK EXISTS, FIND A STARTING POINT ******
C
```

```
              IF (CURRENT$BIN .EQ. 0)
     *        THEN
                DO 2500 I=32,1,-1
                  IF (DATA$VECTOR(I) .NE. 0)
     *            THEN
                    IF (I .NE. CURRENT$BIN) CURRENT$BIN = I
                    BIN$EXISTS = .TRUE.
                    GOTO 2600
                  ENDIF
2500            CONTINUE
              ELSE
                BIN$EXISTS = .TRUE.
              ENDIF
2600          IF (.NOT. BIN$EXISTS)
     *        THEN
                ERR$ONE = 'THERE IS NO PEAK TO SELECT.'
                ERR$TWO = ' '
                ERR$MESSAGE = 'W'
                CURSOR$POSITION = 'AS66'
                GOTO 600
              ENDIF
C .
C            *********** KILL AND UNKILL THE APPROPRIATE FIELDS *********
C
              DATA$AREA(1) = 74
              CALL SCREEN(GROUP$UN$KILL$FIELD,SCREEN$NAME,FIELD$NAME,
     *              DATA$AREA,SCERR)
              IF (SCERR .NE. NO$SCREEN$ERROR)
     *          CALL SYERR(GROUP$UN$KILL$FIELD,SCREEN$NAME,FIELD$NAME,
     *                     SCERR,'GROUP UNKILL FIELD')
              ARROWS$EXIST = .TRUE.
             .IF (AREAS$STATUS(CURRENT$BIN) .EQ. 0)
     * .        THEN
                FIELD$NAME = 'CS'//VAR$ENDING1(CURRENT$BIN+7)
              ELSEIF (AREAS$STATUS(CURRENT$BIN) .EQ. 1)
     *        THEN
                FIELD$NAME = 'AB'//VAR$ENDING3(CURRENT$BIN)
              ELSE
                FIELD$NAME = 'AC'//VAR$ENDING3(CURRENT$BIN)
              ENDIF
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,
     *                     SCERR,'KILL FIELD')
              FIELD$NAME = 'AA'//VAR$ENDING3(CURRENT$BIN)
              CALL SCREEN(UN$KILL$FIELD,SCREEN$NAME,FIELD$NAME,
     *                    DATA$AREA,SCERR)
              IF (SCERR .NE. NO$SCREEN$ERROR)
     *          CALL SYERR(UN$KILL$FIELD,SCREEN$NAME,FIELD$NAME,
     *                     SCERR,'UNKILL FIELD')
              IF (AREAS$STATUS(CURRENT$BIN) .EQ. 0)
     *        THEN
                HIST$STRING(CURRENT$BIN:CURRENT$BIN) = UP$ARROW
              ELSEIF (AREAS$STATUS(CURRENT$BIN) .EQ. 1)
     *        THEN
                HIST$STRING(CURRENT$BIN:CURRENT$BIN) = LT$SYMBOL
              ELSE
                HIST$STRING(CURRENT$BIN:CURRENT$BIN) = GT$SYMBOL
              ENDIF
              FIELD$NAME = 'AS79'
              CALL CNSTAR(32,HIST$STRING,DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,
     *                     SCERR,'PUT FIELD')
```

```
C
C            ************* UPDATE SECOND PEAK VALUES ************
C
             CALL SAQQ23(SCREEN$NAME,DNA$CONV$VALUE,ANALYSIS$TOTAL,
     *                   PICO$HIST,TYPE$SELECTED,XSCALE$NUM,CURRENT$BIN,
     *                   FIRST$PEAK$MASS,SEC$PEAK$MASS,
     *                   SEC$PEAK$INDEX,SEC$PEAK$AREA)
             CURSOR$POSITION = 'AS67'
             GOTO 600
           ENDIF
C*******************************************************************
C
C            CODE TO HANDLE THE BIN SELECTION
C
C*******************************************************************
           IF (READ$INPUT$VALUE .EQ. LEFT$ARROW .OR.
     *         READ$INPUT$VALUE .EQ. RIGHT$ARROW)
     *     THEN
C
C            ************* KILL AND UNKILL THE APPROPRIATE FIELDS *************
C
             FIELD$NAME = 'AA'//VAR$ENDING3(CURRENT$BIN)
             CALL SCREEN(KILL$FIELD,SCREEN$NAME,FIELD$NAME,
     *                   DATA$AREA,SCERR)
             IF (SCERR .NE. NO$SCREEN$ERROR)
     *         CALL SYERR(KILL$FIELD,SCREEN$NAME,FIELD$NAME,
     *                    SCERR,'KILL FIELD')
             IF (AREAS$STATUS(CURRENT$BIN) .EQ. 0)
     *       THEN
                FIELD$NAME = 'CS'//VAR$ENDING1(CURRENT$BIN+7)
             ELSEIF (AREAS$STATUS(CURRENT$BIN) .EQ. 1)
     *       THEN
                FIELD$NAME = 'AB'//VAR$ENDING3(CURRENT$BIN)
             ELSE
                FIELD$NAME = 'AC'//VAR$ENDING3(CURRENT$BIN)
             ENDIF
             CALL SCREEN(UN$KILL$FIELD,SCREEN$NAME,FIELD$NAME,
     *                   DATA$AREA,SCERR)
             IF (SCERR .NE. NO$SCREEN$ERROR)
     *         CALL SYERR(UN$KILL$FIELD,SCREEN$NAME,FIELD$NAME,
     *                    SCERR,'UNKILL FIELD')
             IF (AREAS$STATUS(CURRENT$BIN) .EQ. 0)
     *       THEN
                HIST$STRING(CURRENT$BIN:CURRENT$BIN) = ' '
             ELSEIF (AREAS$STATUS(CURRENT$BIN) .EQ. 1)
     *       THEN
                HIST$STRING(CURRENT$BIN:CURRENT$BIN) = '1'
             ELSE
                HIST$STRING(CURRENT$BIN:CURRENT$BIN) = '2'
             ENDIF
C
C            ************* PUT OUT THE HISTOGRAM'S SYMBOL STRING *************
C
             FIELD$NAME = 'AS79'
             CALL CNSTAR(32,HIST$STRING,DATA$AREA)
             CALL SCREEN(PUT$FIELD,SCREEN$NAME,FIELD$NAME,
     *                   DATA$AREA,SCERR)
             IF (SCERR .NE. NO$SCREEN$ERROR)
     *         CALL SYERR(PUT$FIELD,SCREEN$NAME,FIELD$NAME,
     *                    SCERR,'PUT FIELD')
C
C            ************* FIND THE NEXT BIN *************
C
             BIN = CURRENT$BIN
 2700        IF (READ$INPUT$VALUE .EQ. LEFT$ARROW)
     *       THEN
               IF (BIN .EQ. 1)
     *         THEN
                  BIN = 32
               ELSE
                  BIN = BIN-1
               ENDIF
```

```
              ELSE
                IF (BIN .EQ. 32)
     *          THEN
                  BIN = 1
                ELSE
                  BIN = BIN+1
                ENDIF
              ENDIF
              IF (DATA$VECTOR(BIN) .NE. 0) GOTO 2800
              IF (BIN .EQ. CURRENT$BIN)
     *        THEN
                IF (READ$INPUT$VALUE .EQ. LEFT$ARROW)
     *          THEN
                  CURSOR$POSITION = 'AS67'
                ELSE
                  CURSOR$POSITION = 'AS68'
                ENDIF
                GOTO 600
              ENDIF
              GOTO 2700
 2800         CURRENT$BIN = BIN
C
C             *********** KILL AND UNKILL THE APPROPRIATE FIELDS **************
C
              I = AREAS$STATUS(CURRENT$BIN)
              IF (I .EQ. 0)
     *        THEN
                TEMP = VAR$ENDING1(CURRENT$BIN+7)
                FIELD$NAME = 'CS'//TEMP
              ELSEIF (I .EQ. 1)
     *        THEN
                TEMP = VAR$ENDING3(CURRENT$BIN)
                FIELD$NAME = 'AB'//TEMP
              ELSE
                TEMP = VAR$ENDING3(CURRENT$BIN)
                FIELD$NAME = 'AC'//TEMP
              ENDIF
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,
     *                     SCERR,'KILL FIELD')
              FIELD$NAME = 'AA'//VAR$ENDING3(CURRENT$BIN)
              CALL SCREEN(UN$KILL$FIELD,SCREEN$NAME,FIELD$NAME,
     *                    DATA$AREA,SCERR)
              IF (SCERR .NE. NO$SCREEN$ERROR)
     *          CALL SYERR(UN$KILL$FIELD,SCREEN$NAME,FIELD$NAME,
     *                     SCERR,'UNKILL FIELD')
              IF (AREAS$STATUS(CURRENT$BIN) .EQ. 0)
     *        THEN
                HIST$STRING(CURRENT$BIN:CURRENT$BIN) = UP$ARROW
              ELSEIF (AREAS$STATUS(CURRENT$BIN) .EQ. 1)
     *        THEN
                HIST$STRING(CURRENT$BIN:CURRENT$BIN) = LT$SYMBOL
              ELSE
                HIST$STRING(CURRENT$BIN:CURRENT$BIN) = GT$SYMBOL
              ENDIF
              FIELD$NAME = 'AS79'
              CALL CNSTAR(32,HIST$STRING,DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,
     *                     SCERR,'PUT FIELD')
C
C
C             ************ UPDATE SECOND PEAK VALUES ************
C
              CALL SAQQ23.(SCREEN$NAME,DNA$CONV$VALUE,ANALYSIS$TOTAL,
     *                     PICO$HIST,TYPE$SELECTED,XSCALE$NUM,CURRENT$BIN,
     *                     FIRST$PEAK$MASS,SEC$PEAK$MASS,
```

```
      *                 SEC$PEAK$INDEX,SEC$PEAK$AREA)
              .IF (READ$INPUT$VALUE .EQ. LEFT$ARROW)
      *       THEN
                 CURSOR$POSITION = 'AS67'
              ELSE
                 CURSOR$POSITION = 'AS68'
              ENDIF
              GOTO 600
           ENDIF
C****************************************************************
C
C          CODE TO HANDLE THE DISPLAY-XY SELECTION
C
C****************************************************************
           IF (READ$INPUT$VALUE .EQ. 'DISPLAY-XY')
      *    THEN
C
C          ********** CHECK TO MAKE SURE THAT THERE EXISTS **********
C          ********** XY COORDINATES                       **********
C
           IF (XY$COUNTER .EQ. 0)
      *    THEN
              ERR$ONE = 'DISPLAY-XY CAN''T BE USED BECAUSE'
              ERR$TWO = 'THERE ARE NO XY COORDINATES.'
              ERR$MESSAGE = 'W'
              CURSOR$POSITION = 'AS04'
              GOTO 600
           ENDIF
C
C          ************* KILL THE ANALYSIS SCREEN'S FIELDS *************
C
           DATA$AREA(1) = 10
           CALL SCREEN(GROUP$KILL$FIELD,SCREEN$NAME,FIELD$NAME,
      *               DATA$AREA,SCERR)
           IF (SCERR .NE. NO$SCREEN$ERROR)
      *       CALL SYERR(GROUP$KILL$FIELD,SCREEN$NAME,FIELD$NAME,SCERR,
      *                  'GROUP KILL FIELD')
           DATA$AREA(1) = 20
           CALL SCREEN(GROUP$KILL$FIELD,SCREEN$NAME,FIELD$NAME,
      *               DATA$AREA,SCERR)
           IF (SCERR .NE. NO$SCREEN$ERROR)
      *       CALL SYERR(GROUP$KILL$FIELD,SCREEN$NAME,FIELD$NAME,SCERR,
      *                  'GROUP KILL FIELD')
           DO 2920 I=69,80
              DATA$AREA(1) = I
              CALL SCREEN(GROUP$KILL$FIELD,SCREEN$NAME,FIELD$NAME,
      *                  DATA$AREA,SCERR)
              IF (SCERR .NE. NO$SCREEN$ERROR)
      *          CALL SYERR(GROUP$KILL$FIELD,SCREEN$NAME,FIELD$NAME,
      *                     SCERR,'GROUP KILL FIELD')
 2920      CONTINUE
C
C          ************* UNKILL THE XY SCREEN'S FIELDS **********
C
           DATA$AREA(1) = 90
           CALL SCREEN(GROUP$UN$KILL$FIELD,SCREEN$NAME,FIELD$NAME,
      *               DATA$AREA,SCERR)
           IF (SCERR .NE. NO$SCREEN$ERROR)
      *       CALL SYERR(GROUP$UN$KILL$FIELD,SCREEN$NAME,FIELD$NAME,
      *                  SCERR,'GROUP UNKILL FIELD')
C
C          .******** CALL THE SUBROUTINE THAT HANDLES THE XY SCREEN ********
C
           CALL SAQQ22(SCREEN$NAME,XY$COUNTER,XY$COORDS,FATAL$ERROR)
           IF (FATAL$ERROR) GOTO 600
C
C          ************** UNKILL THE ANALYSIS SCREEN'S FIELDS **************
C
           DATA$AREA(1) = 10
           CALL SCREEN(GROUP$UN$KILL$FIELD,SCREEN$NAME,FIELD$NAME,
      *               DATA$AREA,SCERR)
```

```fortran
              IF (SCERR .NE. NO$SCREEN$ERROR)
     *          CALL SYERR(GROUP$UN$KILL$FIELD,SCREEN$NAME,FIELD$NAME,SCERR,
     *                     'GROUP UNKILL FIELD')
              DATA$AREA(1) = 20
              CALL SCREEN(GROUP$UN$KILL$FIELD,SCREEN$NAME,FIELD$NAME,
     *                    DATA$AREA,SCERR)
              IF (SCERR .NE. NO$SCREEN$ERROR)
     *          CALL SYERR(GROUP$UN$KILL$FIELD,SCREEN$NAME,FIELD$NAME,SCERR,
     *                     'GROUP UNKILL FIELD')
              DATA$AREA(1) = 70
              CALL SCREEN(GROUP$UN$KILL$FIELD,SCREEN$NAME,FIELD$NAME,
     *                    DATA$AREA,SCERR)
              IF (SCERR .NE. NO$SCREEN$ERROR)
     *          CALL SYERR(GROUP$UN$KILL$FIELD,SCREEN$NAME,FIELD$NAME,SCERR,
     *                     'GROUP UNKILL FIELD')
              DATA$AREA(1) = 71
              CALL SCREEN(GROUP$UN$KILL$FIELD,SCREEN$NAME,FIELD$NAME,
     *                    DATA$AREA,SCERR)
              IF (SCERR .NE. NO$SCREEN$ERROR)
     *          CALL SYERR(GROUP$UN$KILL$FIELD,SCREEN$NAME,FIELD$NAME,SCERR,
     *                     'GROUP UNKILL FIELD')
              DATA$AREA(1) = 73
              CALL SCREEN(GROUP$UN$KILL$FIELD,SCREEN$NAME,FIELD$NAME,
     *                    DATA$AREA,SCERR)
              IF (SCERR .NE. NO$SCREEN$ERROR)
     *          CALL SYERR(GROUP$UN$KILL$FIELD,SCREEN$NAME,FIELD$NAME,SCERR,
     *                     'GROUP UNKILL FIELD')
C
              CALL SAQQ24(SCREEN$NAME,AREAS$STATUS)
C
C
C            ************ KILL THE XY SCREEN'S FIELDS **********
C
              DATA$AREA(1) = 90
              CALL SCREEN(GROUP$KILL$FIELD,SCREEN$NAME,FIELD$NAME,
     *                    DATA$AREA,SCERR)
              IF (SCERR .NE. NO$SCREEN$ERROR)
     *          CALL SYERR(GROUP$KILL$FIELD,SCREEN$NAME,FIELD$NAME,
     *                     SCERR,'GROUP KILL FIELD')
              CURSOR$POSITION = 'AS04'
              GOTO 600
           ENDIF
C*********************************************************************
C
C
C            CODE TO HANDLE THE XY COMMAND
C
C*********************************************************************
           IF (READ$INPUT$VALUE .EQ. 'XY')
     *     THEN
C
C            ********** READ CHANNEL VALUES *********
C
 2900         CALL IMMAIN(IMAGE$CHANNELS,IMERR)
              IF (IMERR .NE. ' ')
     *        THEN
                FATAL$ERROR = .TRUE.
                GOTO 600
              ENDIF
C
C            ********** CONVERT CHANNEL VALUES TO INTEGER **********
C
              X = INT((IM$CHANNEL$ONE*0.125)+0.5)
              Y = INT((IM$CHANNEL$TWO*0.125)+0.5)
              WRITE(XCHAR,3000)X
              WRITE(YCHAR,3000)Y
 3000         FORMAT(I6)
              CURR$XY$STRING = 'X='//XCHAR//'    '//'Y='//YCHAR
C
C            ******* PUT OUT THE X AND Y VALUES ********
C
              FIELD$NAME = 'ERR1'
```

```
     *                    DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                     'PUT FIELD')
              ERR$MESSAGE = 'C'
C
C            **** CHECK TO SEE IF THE USER WANTS ANOTHER CHANNEL READING ****
C
              CALL SCREEN(READ$KEYBOARD,SCREEN$NAME,FIELD$NAME,
     *                    DATA$AREA,SCERR)
              IF (SCERR .EQ. READ$KEYBOARD) GOTO 2900
              CURSOR$POSITION = 'AS69'
              GOTO 600
            ENDIF
C***************************************************************************
C
C            CODE TO HANDLE THE FIRST PART OF THE AREA 1-2 COMMAND
C
C***************************************************************************
          IF (READ$INPUT$VALUE .EQ. 'AREA 1-2' .AND.
     *        SCERR .EQ. SCREEN$FUNCTION)
     *    THEN
C
C            ****** IF SHOWN COUNT EQUALS ZERO, PRINT OUT MESSAGE ******
C
            IF (SHOWN$COUNT .EQ. 0)
     *      THEN
              ERR$ONE = 'AREA 1-2 CANNOT BE USED WHEN'
              ERR$TWO = 'SHOWN COUNT EQUALS ZERO.'
              ERR$MESSAGE = 'W'
              CURSOR$POSITION = 'AS78'
              GOTO 600
            ENDIF
C
C            ********** KILL AND UNKILL THE APPROPRIATE FIELDS **********
C
            FIELD$NAME = 'AS79'
            CALL SCREEN(KILL$FIELD,SCREEN$NAME,FIELD$NAME,
     *                  DATA$AREA,SCERR)
            IF (SCERR .NE. NO$SCREEN$ERROR)
     *        CALL SYERR(KILL$FIELD,SCREEN$NAME,FIELD$NAME,
     *                   SCERR,'KILL FIELD')
            DATA$AREA(1) = 79
            CALL SCREEN(GROUP$UN$KILL$FIELD,SCREEN$NAME,FIELD$NAME,
     *                  DATA$AREA,SCERR)
            IF (SCERR .NE. NO$SCREEN$ERROR)
     *        CALL SYERR(GROUP$UN$KILL$FIELD,SCREEN$NAME,FIELD$NAME,
     *                   SCERR,'GROUP UNKILL FIELD')
            DO 3150 I=1,32
              FIELD$NAME = 'AR'//VAR$ENDING3(I)
              DATA$AREA(1) = AREAS$STATUS(I)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                     'PUT FIELD')
 3150       CONTINUE
            AREA$FIELDS$KILLED = .FALSE.
            CURSOR$POSITION = 'AR01'
            GOTO 600
          ENDIF
C***************************************************************************
C
C            CODE TO HANDLE THE SECOND PART OF THE AREA 1-2 COMMAND
C
C***************************************************************************
```

```
              IF (READ$INPUT$VALUE .EQ. 'AREA 1-2' .AND.
     *           SCERR .EQ. SCREEN$DATA)
     *        THEN
                 DO 3100 I=1,32
                   FIELD$NAME = 'AR'//VAR$ENDING3(I)
                   CALL SCREEN(GET$FIELD,SCREEN$NAME,FIELD$NAME,
     *                         DATA$AREA,SCERR)
                   IF (SCERR .NE. NO$SCREEN$ERROR)
     *               CALL SYERR(GET$FIELD,SCREEN$NAME,FIELD$NAME,
     *                          SCERR,'GET FIELD')
                   TEMP$AREAS(I) = DATA$AREA(1)
3100           CONTINUE
               DO 3200 I=1,32
                 IF (TEMP$AREAS(I) .LT. 0 .OR. TEMP$AREAS(I) .GT. 2)
     *           THEN
                   ERR$ONE = 'ALL VALUES MUST BE'
                   ERR$TWO = 'IN THE RANGE, 0 TO 2.'
                   ERR$MESSAGE = 'W'
                   CURSOR$POSITION = 'AS78'
                   GOTO 600
                 ENDIF
3200           CONTINUE
               AREA1$FLAG = .FALSE.
               AREA2$FLAG = .FALSE.
               SPLIT$FLAG = .FALSE.
               END$FLAG = .FALSE.
               DO 3300 I=1,32
                 IF (TEMP$AREAS(I) .EQ. 1)
     *           THEN
                   IF (.NOT. AREA1$FLAG) AREA1$FLAG = .TRUE.
                   IF (SPLIT$FLAG)
     *             THEN
                     ERR$ONE = 'AREA 1 MUST BE CONTINUOUS.'
                     ERR$TWO = ' '
                     ERR$MESSAGE = 'W'
                     CURSOR$POSITION = 'AS78'
                     GOTO 600
                   ENDIF
                 ELSEIF (TEMP$AREAS(I) .EQ. 2)
     *           THEN
                   IF (.NOT. SPLIT$FLAG) SPLIT$FLAG = .TRUE.
                   IF (.NOT. AREA2$FLAG) AREA2$FLAG = .TRUE.
                   IF (.NOT. AREA1$FLAG)
     *             THEN
                     ERR$ONE = 'AREA 2 CANNOT BE SPECIFIED'
                     ERR$TWO = 'FIRST.'
                     ERR$MESSAGE = 'W'
                     CURSOR$POSITION = 'AS78'
                     GOTO 600
                   ELSEIF (END$FLAG)
     *             THEN
                     ERR$ONE = 'AREA 2 MUST BE CONTINUOUS.'
                     ERR$TWO = ' '
                     ERR$MESSAGE = 'W'
                     CURSOR$POSITION = 'AS78'
                     GOTO 600
                   ENDIF
                 ELSE
                   IF (AREA1$FLAG .AND. .NOT. SPLIT$FLAG) SPLIT$FLAG=.TRUE.
                   IF (AREA2$FLAG .AND. .NOT. END$FLAG) END$FLAG=.TRUE.
                 ENDIF
3300           CONTINUE
               DO 3400 I=1,32
                 AREAS$STATUS(I) = TEMP$AREAS(I)
3400           CONTINUE
               AREA1$COUNT = 0
               AREA2$COUNT = 0
               DO 3500 I=1,32
                 IF (AREAS$STATUS(I) .EQ. 1)
     *           THEN
```

```
              AREA1$COUNT = AREA1$COUNT+DATA$VECTOR(I)
          ELSEIF (AREAS$STATUS(I) .EQ. 2)
          THEN
              AREA2$COUNT = AREA2$COUNT+DATA$VECTOR(I)
          ENDIF
3500    CONTINUE
        FIELD$NAME = 'AS76'
        DATA$AREA(1) = AREA1$COUNT
        CALL SCREEN(PUT$FIELD,SCREEN$NAME,FIELD$NAME,
                    DATA$AREA,SCERR)
        IF (SCERR .NE. NO$SCREEN$ERROR)
          CALL SYERR(PUT$FIELD,SCREEN$NAME,FIELD$NAME,SCERR,
                     'PUT FIELD')
        FIELD$NAME = 'AS77'
        DATA$AREA(1) = AREA2$COUNT
        CALL SCREEN(PUT$FIELD,SCREEN$NAME,FIELD$NAME,
                    DATA$AREA,SCERR)
        IF (SCERR .NE. NO$SCREEN$ERROR)
          CALL SYERR(PUT$FIELD,SCREEN$NAME,FIELD$NAME,SCERR,
                     'PUT FIELD')
        CALL SAQQ24(SCREEN$NAME,AREAS$STATUS)
        DO 3700 I=1,32
          IF (AREAS$STATUS(I) .EQ. 0)
          THEN
              HIST$STRING(I:I) = ' '
          ELSEIF (AREAS$STATUS(I) .EQ. 1)
          THEN
              HIST$STRING(I:I) = '1'
          ELSE
              HIST$STRING(I:I) = '2'
          ENDIF
3700    CONTINUE
        IF (CURRENT$BIN .NE. 0)
        THEN
          IF (AREAS$STATUS(CURRENT$BIN) .EQ. 0)
          THEN
              HIST$STRING(CURRENT$BIN:CURRENT$BIN) = UP$ARROW
          ELSEIF (AREAS$STATUS(CURRENT$BIN) .EQ. 1)
          THEN
              HIST$STRING(CURRENT$BIN:CURRENT$BIN) = LT$SYMBOL
          ELSE
              HIST$STRING(CURRENT$BIN:CURRENT$BIN) = GT$SYMBOL
          ENDIF
        ENDIF
        DATA$AREA(1) = 79
        CALL SCREEN(GROUP$KILL$FIELD,SCREEN$NAME,FIELD$NAME,
                    DATA$AREA,SCERR)
        IF (SCERR .NE. NO$SCREEN$ERROR)
          CALL SYERR(GROUP$KILL$FIELD,SCREEN$NAME,FIELD$NAME,
                     SCERR,'GROUP KILL FIELD')
        FIELD$NAME = 'AS79'
        CALL SCREEN(UN$KILL$FIELD,SCREEN$NAME,FIELD$NAME,
                    DATA$AREA,SCERR)
        IF (SCERR .NE. NO$SCREEN$ERROR)
          CALL SYERR(UN$KILL$FIELD,SCREEN$NAME,FIELD$NAME,
                     SCERR,'UNKILL FIELD')
        FIELD$NAME = 'AS79'
        CALL CNSTAR(32,HIST$STRING,DATA$AREA)
        CALL SCREEN(PUT$FIELD,SCREEN$NAME,FIELD$NAME,
                    DATA$AREA,SCERR)
        IF (SCERR .NE. NO$SCREEN$ERROR)
          CALL SYERR(PUT$FIELD,SCREEN$NAME,FIELD$NAME,
                     SCERR,'PUT FIELD')
        CURSOR$POSITION = 'AS78'
        GOTO 600
      ENDIF
      END
CC              CELL ANALYSIS SYSTEMS, INC.
CC              (C) COPYRIGHT 1986
CC
```

```
CC****************************************************************
CC
CC        :PROGRAM NAME
CC        :SAQQ05
CC
CC        :SUBROUTINES
CC        :CNARST
CC        :CNSTAR
CC        :IMMAIN
CC        :IMOVB
CC        :SCREEN
CC        :6YERR
CC
CC        :CALLING SEQUENCE
CC        :SAQQ05(SCRN$NAME,THRESHOLD,FATAL$ERROR)
CC
CC        :PARAMETERS
CC        :SCRN$NAME - SCREEN NAME OF THE CURRENT SCREEN
CC        :THRESHOLD - GREY LEVEL VALUE OF THE FIRST THRESHOLD
CC        :FATAL$ERROR - A FLAG THAT SPECIFIES IF A 'FATAL'(I.E. SERIOUS)
CC                      ERROR OCCURRED INSIDE THIS SUBROUTINE
CC
CC        :DESCRIPTION
CC        :ALLOWS THE USER TO ADJUST THE LOW THRESHOLD ON THE FIRST OUTPUT
CC        :TABLES.
CC
CC****************************************************************
CC########
        SUBROUTINE SAQQ05(SCRN$NAME,THRESHOLD,FATAL$ERROR)
        CHARACTER*1 ERR$MESSAGE,UP1,DOWN1
        CHARACTER*4 CURSOR$POSITION
        CHARACTER*(*) SCRN$NAME
        CHARACTER*13 READ$INPUT$VALUE
        CHARACTER*32 ERR$ONE,ERR$TWO
        INTEGER*2 STUDY$TYPE,THRESHOLD,
     *            LEVEL1,STEP$SIZE,RED$TABLE(128),
     *            GREEN$TABLE(128),BLUE$TABLE(128),VALUES$255(128),
     *            COUNT,VALUES$0(128),I,
     *            PREV$LEVEL1,BLUE$COUNT,WHITE$COUNT,
     *            INDEX1,SAVED$RED1(128),
     *            SAVED$GREEN1(128),SAVED$BLUE1(128)
        LOGICAL*1 LGCL$RED$TABLE(0:255),
     *            LGCL$GREEN$TABLE(0:255),LGCL$BLUE$TABLE(0:255),
     *            FATAL$ERROR
C
        EQUIVALENCE (RED$TABLE(1),LGCL$RED$TABLE(0)),
     *              (GREEN$TABLE(1),LGCL$GREEN$TABLE(0)),
     *              (BLUE$TABLE(1),LGCL$BLUE$TABLE(0))
C
        INCLUDE 'IMAGED.FIN'
        INCLUDE 'SCREEN.FIN'
        DATA VALUES$255 /128*Z'FFFF'/,
     *       VALUES$0 /128*Z'0000'/,
     *       UP1 /Z'18'/,
     *       DOWN1 /Z'19'/
C
C       ************ INITIALIZE THE APPROPRIATE VARIABLES **************
C
        SCREEN$NAME = SCRN$NAME
        ERR$ONE = ' '
        ERR$TWO = ' '
        ERR$MESSAGE = ' '
        CURSOR$POSITION = 'BS06'
        READ$INPUT$VALUE = ' '
        LEVEL1 = THRESHOLD
        STEP$SIZE = 1
        COUNT = 0
        INDEX1 = 0
        PREV$LEVEL1 = 0
        BLUE$COUNT = 0
        WHITE$COUNT = 0
```

```
          I = 0
          FATAL$ERROR = .FALSE.
C
C         ********** INITIALIZE STEP SIZE FIELD *************
C
          FIELD$NAME = 'BS10'
          DATA$AREA(1) = STEP$SIZE
          CALL SCREEN(PUT$FIELD,SCREEN$NAME,FIELD$NAME,
     *                DATA$AREA,SCERR)
          IF (SCERR .NE. NO$SCREEN$ERROR)
     *       CALL SYERR(PUT$FIELD,SCREEN$NAME,FIELD$NAME,SCERR,
     *                  'PUT FIELD')
C
C         ********* UNKILL THE CURRENT SCREEN'S FIELDS ********
C
          DATA$AREA(1) = 80
          CALL SCREEN(GROUP$UN$KILL$FIELD,SCREEN$NAME,FIELD$NAME,
     *                DATA$AREA,SCERR)
          IF (SCERR .NE. NO$SCREEN$ERROR)
     *       CALL SYERR(GROUP$UN$KILL$FIELD,SCREEN$NAME,FIELD$NAME,SCERR,
     *                  'GROUP UNKILL FIELD')
C*********************************************************************
C
C              SAVE THE FIRST OUTPUT TABLES
C
C*********************************************************************
          IM$TABLE$NUM = 1
          IM$GROUP$NUM = 1
          CALL IMMAIN(IMAGE$GET$TABLE,IMERR)
          IF (IMERR .NE. ' ')
     *    THEN
             FATAL$ERROR = .TRUE.
             GOTO 700
          ENDIF
          DO 100 I=1,128
             SAVED$RED1(I) = IM$TABLE(I)
  100     CONTINUE
          IM$GROUP$NUM = 2
          CALL IMMAIN(IMAGE$GET$TABLE,IMERR)
          IF (IMERR .NE. ' ')
     *    THEN
             FATAL$ERROR = .TRUE.
             GOTO 700
          ENDIF
          DO 200 I=1,128
             SAVED$GREEN1(I) = IM$TABLE(I)
  200     CONTINUE
          IM$GROUP$NUM = 3
          CALL IMMAIN(IMAGE$GET$TABLE,IMERR)
          IF (IMERR .NE. ' ')
     *    THEN
             FATAL$ERROR = .TRUE.
             GOTO 700
          ENDIF
          DO 300 I=1,128
             SAVED$BLUE1(I) = IM$TABLE(I)
  300     CONTINUE
C*********************************************************************
C
C         MAKE THE APPROPRIATE CHANGES TO THE
C              FIRST OUTPUT TABLES
C
C*********************************************************************
          BLUE$COUNT = LEVEL1+1
          INDEX1 = LEVEL1+1
          WHITE$COUNT = 255-LEVEL1
          CALL IMOVB(256,VALUES$255(1),LGCL$BLUE$TABLE(0))
          CALL IMOVB(BLUE$COUNT,VALUES$0(1),LGCL$GREEN$TABLE(0))
          CALL IMOVB(WHITE$COUNT,VALUES$255(1),
     *               LGCL$GREEN$TABLE(INDEX1))
          CALL IMOVB(BLUE$COUNT,VALUES$0(1),LGCL$RED$TABLE(0))
```

```fortran
      CALL IMOVB(WHITE$COUNT,VALUES$255(1),
     *              LGCL$RED$TABLE(INDEX1))
C***************************************************************
C
C         WRITE OUT THE CHANGES OF THE FIRST OUTPUT
C         TABLES TO THE IMAGE BOARD
C
C***************************************************************
      IM$TABLE$NUM = 1
      IM$GROUP$NUM = 1
      DO 400 I=1,128
         IM$TABLE(I) = RED$TABLE(I)
  400 CONTINUE
      CALL IMMAIN(IMAGE$PUT$TABLE,IMERR)
      IF (IMERR .NE. ' ')
     *  THEN
         FATAL$ERROR = .TRUE.
         GOTO 700
      ENDIF
      IM$GROUP$NUM = 2
      DO 500 I=1,128
         IM$TABLE(I) = GREEN$TABLE(I)
  500 CONTINUE
      CALL IMMAIN(IMAGE$PUT$TABLE,IMERR)
      IF (IMERR .NE. ' ')
     *  THEN
         FATAL$ERROR = .TRUE.
         GOTO 700
      ENDIF
      IM$GROUP$NUM = 3
      DO 600 I=1,128
         IM$TABLE(I) = BLUE$TABLE(I)
  600 CONTINUE
      CALL IMMAIN(IMAGE$PUT$TABLE,IMERR)
      IF (IMERR .NE. ' ')
     *  THEN
         FATAL$ERROR = .TRUE.
         GOTO 700
      ENDIF
C***************************************************************
C
C           ERROR MESSAGE HANDLING CODE
C
C***************************************************************
  700 IF (ERR$MESSAGE .EQ. 'C')
     *  THEN
         ERR$ONE = ' '
         ERR$TWO = ' '
      ENDIF
      IF (ERR$MESSAGE .EQ. 'C' .OR.
     *    ERR$MESSAGE .EQ. 'W')
     *  THEN
         FIELD$NAME = 'ERR1'
         CALL CNSTAR(32,ERR$ONE,DATA$AREA)
         CALL SCREEN(PUT$FIELD,SCREEN$NAME,FIELD$NAME,
     *               DATA$AREA,SCERR)
         IF (SCERR .NE. NO$SCREEN$ERROR)
     *     CALL SYERR(PUT$FIELD,SCREEN$NAME,FIELD$NAME,SCERR,
     *                'PUT FIELD')
         FIELD$NAME = 'ERR2'
         CALL CNSTAR(32,ERR$TWO,DATA$AREA)
         CALL SCREEN(PUT$FIELD,SCREEN$NAME,FIELD$NAME,
     *               DATA$AREA,SCERR)
         IF (SCERR .NE. NO$SCREEN$ERROR)
     *     CALL SYERR(PUT$FIELD,SCREEN$NAME,FIELD$NAME,SCERR,
     *                'PUT FIELD')
      ENDIF
      IF (ERR$MESSAGE .EQ. 'C') ERR$MESSAGE = ' '
      IF (ERR$MESSAGE .EQ. 'W') ERR$MESSAGE = 'C'
      IF (ERR$MESSAGE .NE. 'C') ERR$MESSAGE = ' '
C
```

```
C         ******** IF A 'FATAL' ERROR OCCURRED THEN EXIT THE SUBROUTINE ********
C
          IF (FATAL$ERROR)
     *    THEN
C
C         ********* KILL THE CURRENT SCREEN'S FIELDS ********
C
             DATA$AREA(1) = 80
             CALL SCREEN(GROUP$KILL$FIELD,SCREEN$NAME,FIELD$NAME,
     *                   DATA$AREA,SCERR)
             IF (SCERR .NE. NO$SCREEN$ERROR)
     *         CALL SYERR(GROUP$KILL$FIELD,SCREEN$NAME,FIELD$NAME,SCERR,
     *                    'GROUP KILL FIELD')

RETURN
          ENDIF
C
C         ************ SET CURSOR ****************
C
          FIELD$NAME = CURSOR$POSITION
          CALL SCREEN(SET$CURSOR,SCREEN$NAME,FIELD$NAME,
     *                DATA$AREA,SCERR)
          IF (SCERR .NE. NO$SCREEN$ERROR)
     *      CALL SYERR(SET$CURSOR,SCREEN$NAME,FIELD$NAME,SCERR,
     *                 'SET CURSOR')
C
C         *************** READ INPUT ****************
C
          CALL SCREEN(READ$INPUT,SCREEN$NAME,FIELD$NAME,
     *                DATA$AREA,SCERR)
          IF (SCERR .EQ. SCREEN$ESCAPE .OR.
     *        SCERR .EQ. SCREEN$FUNCTION .OR.
     *        SCERR .EQ. SCREEN$DATA)
     *    THEN
            CONTINUE
          ELSE
            CALL SYERR(READ$INPUT,SCREEN$NAME,FIELD$NAME,SCERR,
     *                 'READ INPUT')
          ENDIF
          CALL CHARST(13,DATA$AREA,READ$INPUT$VALUE)
          IF (SCERR .EQ. SCREEN$ESCAPE) READ$INPUT$VALUE = 'EXIT'
C
C         ******* IF EXITING FROM THE ADJUST CELL FINDINGS SCREEN, *******
C         ******* CLEAR ANY LEFTOVER ERROR MESSAGES, RESET THE     *******
C         ******* FIRST OUTPUT TABLES TO THEIR ORIGINAL VALUES,    *******
C         ******* SWITCH BACK TO THE SECOND OUTPUT TABLES, AND     *******
C         ******* KILL THE CURRENT SCREEN'S FIELDS
C
          IF (READ$INPUT$VALUE .EQ. 'EXIT')
     *    THEN
C
C            ********** IF NECESSARY, ERASE ANY ERROR MESSAGES **********
C
             IF (ERR$MESSAGE .EQ. 'C')
     *       THEN
                ERR$ONE = ' '
                ERR$TWO = ' '
                FIELD$NAME = 'ERR1'
                CALL CNSTAR(32,ERR$ONE,DATA$AREA)
                CALL SCREEN(PUT$FIELD,SCREEN$NAME,FIELD$NAME,
     *                      DATA$AREA,SCERR)
                IF (SCERR .NE. NO$SCREEN$ERROR)
     *            CALL SYERR(PUT$FIELD,SCREEN$NAME,FIELD$NAME,SCERR,
     *                       'PUT FIELD')
                FIELD$NAME = 'ERR2'
                CALL CNSTAR(32,ERR$TWO,DATA$AREA)
                CALL SCREEN(PUT$FIELD,SCREEN$NAME,FIELD$NAME,
     *                      DATA$AREA,SCERR)
                IF (SCERR .NE. NO$SCREEN$ERROR)
     *            CALL SYERR(PUT$FIELD,SCREEN$NAME,FIELD$NAME,SCERR,
     *                       'PUT FIELD')
             ENDIF
```

```
C
C         *** RESTORE THE FIRST OUTPUT TABLES TO THEIR ORIGINAL VALUES ***
C
          IM$TABLE$NUM = 1
          IM$GROUP$NUM = 1
          DO 800 I=1,128
            IM$TABLE(I) = SAVED$RED1(I)
  800     CONTINUE
          CALL IMMAIN(IMAGE$PUT$TABLE,IMERR)
          IF (IMERR .NE. ' ')
      *   THEN
            FATAL$ERROR = .TRUE.
            GOTO 700
          ENDIF
          IM$GROUP$NUM = 2
          DO 900 I=1,128
            IM$TABLE(I) = SAVED$GREEN1(I)
  900     CONTINUE
          CALL IMMAIN(IMAGE$PUT$TABLE,IMERR)
          IF (IMERR .NE. ' ')
      *   THEN
            FATAL$ERROR = .TRUE.
            GOTO 700
          ENDIF
          IM$GROUP$NUM = 3
          DO 1000 I=1,128
            IM$TABLE(I) = SAVED$BLUE1(I)
 1000     CONTINUE
          CALL IMMAIN(IMAGE$PUT$TABLE,IMERR)
          IF (IMERR .NE. ' ')
      *   THEN
            FATAL$ERROR = .TRUE.
            GOTO 700
          ENDIF
C
C         ********** SELECT THE SECOND OUTPUT TABLES ************
C
          IM$TABLE$NUM = 2
          DO 1100 I=1,3
            IM$GROUP$NUM = I
            CALL IMMAIN(IMAGE$SELECT$TABLE,IMERR)
            IF (IMERR .NE. ' ')
      *     THEN
              FATAL$ERROR = .TRUE.
              GOTO 700
            ENDIF
 1100     CONTINUE
          THRESHOLD = LEVEL1
C
C         ********* KILL THE CURRENT SCREEN'S FIELDS ********
C
          DATA$AREA(1) = 80
          CALL SCREEN(GROUP$KILL$FIELD,SCREEN$NAME,FIELD$NAME,
      *               DATA$AREA,SCERR)
          IF (SCERR .NE. NO$SCREEN$ERROR)
      *     CALL SYERR(GROUP$KILL$FIELD,SCREEN$NAME,FIELD$NAME,SCERR,
      *                'GROUP KILL FIELD')
          RETURN
        ENDIF
C****************************************************************
C
C         CODE TO GET THE STEP SIZE VALUE
C
C****************************************************************
        IF (READ$INPUT$VALUE .EQ. 'SET STEP SIZE' .AND.
      *     SCERR .EQ. SCREEN$DATA)
      * THEN
          FIELD$NAME = 'BS10'
          CALL SCREEN(GET$FIELD,SCREEN$NAME,FIELD$NAME,
      *               DATA$AREA,SCERR)
          IF (SCERR .NE. NO$SCREEN$ERROR)
```

```
      *     CALL SYERR(GET$FIELD,SCREEN$NAME,FIELD$NAME,SCERR,
      *                'GET FIELD')
            STEP$SIZE = DATA$AREA(1)
            CURSOR$POSITION = 'BS06'
            GOTO 700
          ENDIF
C***********************************************************************
C
C         CODE TO HANDLE A CHANGE IN THE THRESHOLD
C
C***********************************************************************
          IF (READ$INPUT$VALUE .EQ. UP1 .OR.
      *       READ$INPUT$VALUE .EQ. DOWN1)
      *   THEN
C
C              ***** SET CURSOR POSITION *****
C
             IF (READ$INPUT$VALUE .EQ. UP1)
      *      THEN
                CURSOR$POSITION = 'BS03'
             ELSEIF (READ$INPUT$VALUE .EQ. DOWN1)
      *      THEN
                CURSOR$POSITION = 'BS04'
             ENDIF
C
C              ****** CHECK TO SEE IF THE STEP SIZE IS ZERO ******
C
             IF (STEP$SIZE .EQ. 0) GOTO 700
C
C              ******* CHECK TO SEE IF THE STEP SIZE IS IN RANGE ********
C
             IF (STEP$SIZE .LT. 0 .OR. STEP$SIZE .GT. 128)
      *      THEN
                ERR$ONE = 'THE STEP SIZE VALUE IS NOT'
                ERR$TWO = 'IN RANGE (0 TO 128).'
                ERR$MESSAGE = 'W'
                GOTO 700
             ENDIF
C
C              ***** CHECK FOR AN INCREASE IN THE THRESHOLD ******
C
             IF (READ$INPUT$VALUE .EQ. UP1)
      *      THEN
                IF ((LEVEL1+STEP$SIZE) .GT. 255)
      *         THEN
                   ERR$ONE = 'YOU CANNOT MAKE THE'
                   ERR$TWO = 'THRESHOLD MORE THAN 255.'
                   ERR$MESSAGE = 'W'
                   GOTO 700
                ENDIF
                PREV$LEVEL1 = LEVEL1
                LEVEL1 = LEVEL1+STEP$SIZE
C
C              ***** CHECK FOR A DECREASE IN THE THRESHOLD ******
C
             ELSEIF (READ$INPUT$VALUE .EQ. DOWN1)
      *      THEN
                IF ((LEVEL1-STEP$SIZE) .LT. 0)
      *         THEN
                   ERR$ONE = 'YOU CANNOT MAKE THE'
                   ERR$TWO = 'THRESHOLD LESS THAN ZERO.'
                   ERR$MESSAGE = 'W'
                   GOTO 700
                ENDIF
                PREV$LEVEL1 = LEVEL1
                LEVEL1 = LEVEL1-STEP$SIZE
             ENDIF
C***********************************************************************
C
C         MAKE THE APPROPRIATE CHANGES TO THE
C         FIRST OUTPUT TABLES
C
```

```
C
C***************************************************************
        BLUE$COUNT = LEVEL1+1
        INDEX1 = LEVEL1+1
        WHITE$COUNT = 255-LEVEL1
        CALL IMOVB(256,VALUES$255(1),LGCL$BLUE$TABLE(0))
        CALL IMOVB(BLUE$COUNT,VALUES$0(1),LGCL$GREEN$TABLE(0))
        CALL IMOVB(WHITE$COUNT,VALUES$255(1),
    *            LGCL$GREEN$TABLE(INDEX1))
        CALL IMOVB(BLUE$COUNT,VALUES$0(1),LGCL$RED$TABLE(0))
        CALL IMOVB(WHITE$COUNT,VALUES$255(1),
    *            LGCL$RED$TABLE(INDEX1))
C***************************************************************
C
C       WRITE OUT THE CHANGES OF THE FIRST OUTPUT
C       TABLES TO THE IMAGE BOARD
C
C***************************************************************
        IM$TABLE$NUM = 1
        IM$GROUP$NUM = 1
        DO 1200 I=1,128
          IM$TABLE(I) = RED$TABLE(I)
1200    CONTINUE
        CALL IMMAIN(IMAGE$PUT$TABLE,IMERR)
        IF (IMERR .NE. ' ')
    *   THEN
          FATAL$ERROR = .TRUE.
          GOTO 700
        ENDIF
        IM$GROUP$NUM = 2
        DO 1300 I=1,128
          IM$TABLE(I) = GREEN$TABLE(I)
1300    CONTINUE
        CALL IMMAIN(IMAGE$PUT$TABLE,IMERR)
        IF (IMERR .NE. ' ')
    *   THEN
          FATAL$ERROR = .TRUE.
          GOTO 700
        ENDIF
        IM$GROUP$NUM = 3
        DO 1400 I=1,128
          IM$TABLE(I) = BLUE$TABLE(I)
1400    CONTINUE
        CALL IMMAIN(IMAGE$PUT$TABLE,IMERR)
        IF (IMERR .NE. ' ')
    *   THEN
          FATAL$ERROR = .TRUE.
          GOTO 700
        ENDIF
        GOTO 700
      ENDIF
      END
CC
CC            CELL ANALYSIS SYSTEMS, INC.
CC              (C) COPYRIGHT 1986
CC*****************************************************************
CC
CC    :PROGRAM NAME
CC    :SAQQ06
CC
CC    :SUBROUTINES
CC    :NONE
CC
CC    :CALLING SEQUENCE
CC    :SAQQ06(RED$SAVE,GREEN$SAVE,BLUE$SAVE,FOCUS$FLAG,FATAL$ERROR)
CC
CC    :PARAMETERS
CC    :RED$SAVE - AN ARRAY CONTAINING THE ORIGINAL (RED,2) TABLE VALUES
CC    :GREEN$SAVE - AN ARRAY CONTAINING THE ORIGINAL (GREEN,2) TABLE VALUES
CC    :BLUE$SAVE - AN ARRAY CONTAINING THE ORIGINAL (BLUE,2) TABLE VALUES
CC    :FOCUS$FLAG - A FLAG THAT SPECIFIES IF THE FOCUS IMAGE IS ON
```

```
CC      :FATAL$ERROR - A FLAG THAT SPECIFIES IF A 'FATAL'(I.E SERIOUS) ERROR
CC                    OCCURRED WHILE INSIDE SAQQ06
CC
CC      :DESCRIPTION
CC      :IF FOCUS$FLAG IS SET TO FALSE, THEN SAQQ06 WILL CHANGE THE TABLES
CC      :SO THAT THE FOCUS SCREEN IS ON. IF FOCUS$FLAG IS .TRUE., SAQQ06 WILL
CC      :RESTORE THE TABLES TO THEIR ORIGINAL VALUES, SO THAT THE FOCUS
CC      :SCREEN IS OFF
CC
CC*********************************************************************
CC########
        SUBROUTINE SAQQ06(RED$SAVE,GREEN$SAVE,BLUE$SAVE,
     *                    FOCUS$FLAG,FATAL$ERROR)
        INTEGER*2 RED$SAVE(*),GREEN$SAVE(*),BLUE$SAVE(*)
        INTEGER*2 RED(128),GREEN(128),BLUE(128)
        LOGICAL*1 FOCUS$FLAG,FATAL$ERROR
C
        INCLUDE 'IMAGED.FIN'
        INCLUDE 'SCREEN.FIN'
C
        DATA RED /17*0,
     *            Z'1830',Z'475F',Z'778F',Z'A6BE',
     *            Z'B6AE',Z'A59D',Z'958D',Z'857D',
     *            Z'756D',Z'655D',Z'554C',Z'443C',
     *            Z'342C',Z'242F',Z'3A45',Z'505B',
     *            Z'6671',Z'7C87',Z'929C',Z'A7B2',
     *            Z'BDC8',Z'D3DE',Z'E9F4',Z'FFF8',
     *            Z'F1E9',Z'E2DB',Z'D4CC',Z'C5BE',
     *            Z'BCAF',Z'A8A1',Z'9A92',Z'8B84',
     *            Z'7D75',Z'6E67',Z'6058',Z'5157',
     *            Z'5D63',Z'696F',Z'757B',Z'8187',
     *            Z'8D93',Z'999F',Z'A5AB',Z'B1B7',
     *            Z'BDC3',Z'B9B0',Z'A69D',Z'938A',
     *            Z'8076',Z'6D63',Z'5A50',Z'473D',
     *            Z'5064',Z'778B',Z'9EB1',Z'C5D8',
     *            Z'ECFF',54*0/
        DATA GREEN /5*0,
     *            Z'000D',Z'1B28',Z'3643',Z'515E',
     *            Z'6C79',Z'8794',Z'A2AF',Z'BDCA',
     *            Z'D8E5',Z'DCD2',Z'C9BF',Z'B6AD',
     *            Z'A39A',Z'9087',Z'7D74',Z'6B61',
     *            Z'584E',Z'454D',Z'545C',Z'646B',
     *            Z'737A',Z'826A',Z'9199',Z'A1A8',
     *            Z'B0B7',Z'BFC7',Z'CED6',Z'CABE',
     *            Z'B2A6',Z'9A8E',Z'8277',Z'6B5F',
     *            Z'5347',Z'3B2F',Z'2328',Z'2D32',
     *            Z'383D',Z'4247',Z'4C51',Z'565C',
     *            Z'6166',Z'6B70',Z'757B',Z'8085',
     *            Z'8A8F',Z'9499',Z'9FA4',Z'A9AE',
     *            Z'A69F',Z'9790',Z'8881',Z'7971',
     *            Z'6A62',Z'5B53',Z'4C44',Z'3D35',
     *            Z'2D26',Z'1E17',Z'0F08',15*0,
     *            Z'1429',Z'3D4F',Z'6072',Z'8495',
     *            Z'A7B8',Z'CADC',Z'EDFF',42*0/
        DATA BLUE /Z'0B16',Z'212C',Z'3743',Z'4E59',
     *            Z'646F',Z'7A85',Z'909B',Z'A6B1',
     *            Z'BCC8',Z'D3DE',Z'E9F4',Z'FFF4',
     *            Z'EADF',Z'D5CA',Z'BFB5',Z'AA9F',
     *            Z'958A',Z'8075',Z'6A60',Z'554A',
     *            Z'4035',Z'2B20',Z'150B',25*0,
     *            Z'1123',Z'3446',Z'5768',Z'7A8B',
     *            Z'9DAE',Z'A69F',Z'9790',Z'8881',
     *            Z'7971',Z'6A62',Z'5B53',Z'4C44',
     *            Z'3D35',Z'2D26',Z'1E17',Z'0F08',
     *            5*0,
     *            Z'0016',Z'2B41',Z'576C',Z'8298',
     *            Z'ADC3',Z'B9B0',Z'A69D',Z'938A',
     *            Z'8076',Z'6D63',Z'5A50',Z'473D',
     *            Z'5368',Z'7E93',Z'A9BE',Z'D4E9',
     *            Z'FFFF',42*0/
C
```

```
C          ********* INITIALIZE VARIABLE ************
C
           FATAL$ERROR = .FALSE.
C
C          *********** IF FOCUS$FLAG IS TRUE, THEN RESTORE TABLES **********
C          *********** TO THEIR ORIGINAL VALUES                  **********
C
           IF (FOCUS$FLAG)
     *     THEN
              CALL IMOVB(256,RED$SAVE(1),IM$TABLE(1))
              IM$TABLE$NUM = 2
              IM$GROUP$NUM = 1
              CALL IMMAIN(IMAGE$PUT$TABLE,IMERR)
              IF (IMERR .NE. ' ')
     *        THEN
                 FATAL$ERROR = .TRUE.
                 RETURN
              ENDIF
              CALL IMOVB(256,GREEN$SAVE(1),IM$TABLE(1))
              IM$TABLE$NUM = 2
              IM$GROUP$NUM = 2
              CALL IMMAIN(IMAGE$PUT$TABLE,IMERR)
              IF (IMERR .NE. ' ')
     *        THEN
                 FATAL$ERROR = .TRUE.
                 RETURN
              ENDIF
              CALL IMOVB(256,BLUE$SAVE(1),IM$TABLE(1))
              IM$TABLE$NUM = 2
              IM$GROUP$NUM = 3
              CALL IMMAIN(IMAGE$PUT$TABLE,IMERR)
              IF (IMERR .NE. ' ')
     *        THEN
                 FATAL$ERROR = .TRUE.
                 RETURN
              ENDIF
              FOCUS$FLAG = .FALSE.
C
C          ******* IF FOCUS$FLAG IS FALSE, THEN SAVE THE TABLE VALUES ******
C          ******* AND THEN CHANGE THE TABLES TO PUT UP A FOCUS IMAGE ******
C
           ELSE
              IM$TABLE$NUM = 2
              IM$GROUP$NUM = 1
              CALL IMMAIN(IMAGE$GET$TABLE,IMERR)
              IF (IMERR .NE. ' ')
     *        THEN
                 FATAL$ERROR = .TRUE.
                 RETURN
              ENDIF
              CALL IMOVB(256,IM$TABLE(1),RED$SAVE(1))
              CALL IMOVB(256,RED(1),IM$TABLE(1))
              CALL IMMAIN(IMAGE$PUT$TABLE,IMERR)
              IF (IMERR .NE. ' ')
     *        THEN
                 FATAL$ERROR = .TRUE.
                 RETURN
              ENDIF
              IM$TABLE$NUM = 2
              IM$GROUP$NUM = 2
              CALL IMMAIN(IMAGE$GET$TABLE,IMERR)
              IF (IMERR .NE. ' ')
     *        THEN
                 FATAL$ERROR = .TRUE.
                 RETURN
              ENDIF
              CALL IMOVB(256,IM$TABLE(1),GREEN$SAVE(1))
              CALL IMOVB(256,GREEN(1),IM$TABLE(1))
              CALL IMMAIN(IMAGE$PUT$TABLE,IMERR)
              IF (IMERR .NE. ' ')
     *        THEN
```

```
              FATAL$ERROR = .TRUE.
              RETURN
          ENDIF
          IM$TABLE$NUM = 2
          IM$GROUP$NUM = 3
          CALL IMMAIN(IMAGE$GET$TABLE,IMERR)
          IF (IMERR .NE. ' ')
    *        THEN
              FATAL$ERROR = .TRUE.
              RETURN
          ENDIF
          CALL IMOVB(256,IM$TABLE(1),BLUE$SAVE(1))
          CALL IMOVB(256,BLUE(1),IM$TABLE(1))
          CALL IMMAIN(IMAGE$PUT$TABLE,IMERR)
          IF (IMERR .NE. ' ')
    *        THEN
              FATAL$ERROR = .TRUE.
              RETURN
          ENDIF
          FOCUS$FLAG = .TRUE.
       ENDIF
       ENDCC
CC             CELL ANALYSIS SYSTEMS, INC.
CC             (C) COPYRIGHT 1986
CC***************************************************************
CC
CC    :PROGRAM NAME
CC    :SAQQ07(XMIN,XMAX,YMIN,YMAX,FATAL$ERROR)
CC
CC    :SUBROUTINES
CC    :IMMAIN
CC    :IMOVB$
CC    :IMOVBH
CC
CC    :CALLING SEQUENCE
CC    :SAQQ07(XMIN,XMAX,YMIN,YMAX,BOX$LEFT$POS,BOX$RIGHT$POS,
CC            BOX$TOP$POS,BOX$BOTTOM$POS,FATAL$ERROR)
CC
CC    :PARAMETERS
CC    :XMIN - MINIMUM X VALUE OF THE BOX
CC    :XMAX - MAXIMUM X VALUE OF THE BOX
CC    :YMIN - MINIMUM Y VALUE OF THE BOX
CC    :YMAX - MINIMUM Y VALUE OF THE BOX
CC    :BOX$LEFT$POS - THE LEFT POSITION OF THE BOX
CC    :BOX$RIGHT$POS - THE RIGHT POSITION OF THE BOX
CC    :BOX$TOP$POS - THE TOP POSITION OF THE BOX
CC    :BOX$BOTTOM$POS - THE BOTTOM POSITION OF THE BOX
CC    :FATAL$ERROR - A FLAG THAT SPECIFIES IF A 'FATAL'(I.E. SERIOUS) ERROR
CC                   OCCURRED WHILE IN SAQQ07
CC
CC    :DESCRIPTION
CC    :SAQQ07 PUT AT BOX AT THE SPECIFIED LOCATION
CC
CC***************************************************************
CC##########
          SUBROUTINE SAQQ07(XMIN,XMAX,YMIN,YMAX,BOX$LEFT$POS,
    *                      BOX$RIGHT$POS,BOX$TOP$POS,BOX$BOTTOM$POS,
    *                      FATAL$ERROR)
          INTEGER*2 XMIN,XMAX,YMIN,YMAX,HORIZ$BOX$LENGTH,
    *              VERT$BOX$LENGTH,BOX$TOP$POS,BOX$BOTTOM$POS,
    *              BOX$LEFT$POS,BOX$RIGHT$POS,VALUES$254(128)
          LOGICAL*1 FATAL$ERROR
C
          INCLUDE 'IMAGED.FIN'
          INCLUDE 'IMAGEL.FIN'
          INCLUDE 'SCREEN.FIN'
C
          DATA VALUES$254 /128*Z'FEFE'/
C
C             ************* INITIALIZE VARIABLE ************
C
```

```
      FATAL$ERROR = .FALSE.
      HORIZ$BOX$LENGTH = 0
      VERT$BOX$LENGTH = 0
      BOX$TOP$POS = 0
      BOX$BOTTOM$POS = 0
      BOX$LEFT$POS = 0
      BOX$RIGHT$POS = 0
C
C
C   ************ CALCULATE ACTUALLY BOX COORDINATES **************
C
      IF (XMIN .EQ. 1 .OR. XMAX .EQ. 254)
    * THEN
        BOX$LEFT$POS = XMIN-1
        BOX$RIGHT$POS = XMAX+1
      ELSE
        BOX$LEFT$POS = XMIN-2
        BOX$RIGHT$POS = XMAX+2
      ENDIF
      HORIZ$BOX$LENGTH = (BOX$RIGHT$POS-BOX$LEFT$POS)+1
      IF (YMIN .EQ. 1 .OR. YMAX .EQ. 254)
    * THEN
        BOX$TOP$POS = YMIN-1
        BOX$BOTTOM$POS = YMAX+1
      ELSE
        BOX$TOP$POS = YMIN-2
        BOX$BOTTOM$POS = YMAX+2
      ENDIF
      VERT$BOX$LENGTH = (BOX$BOTTOM$POS-BOX$TOP$POS)+1
C
C
C   *********** PLACE A BOX AROUND THE OBJECT **************
C
      CALL IMOVB$(HORIZ$BOX$LENGTH,VALUES$254(1),
    *             IMAGEL(BOX$LEFT$POS,BOX$TOP$POS))
      CALL IMOVB$(HORIZ$BOX$LENGTH,VALUES$254(1),
    *             IMAGEL(BOX$LEFT$POS,BOX$BOTTOM$POS))
      CALL IMOVBH(VERT$BOX$LENGTH,VALUES$254(1),
    *             IMAGEL(BOX$LEFT$POS,BOX$TOP$POS))
      CALL IMOVBH(VERT$BOX$LENGTH,VALUES$254(1),
    *             IMAGEL(BOX$RIGHT$POS,BOX$TOP$POS))
C
C
C   ************ PUT OUT THE BOX ****************
C
      CALL IMMAIN(IMAGE$PUT,IMERR)
      IF (IMERR .NE. ' ')
    * THEN
        FATAL$ERROR = .TRUE.
        RETURN
      ENDIF
C
C
C   ******* COPY IMAGE BUFFER 2 TO IMAGE BUFFER 1 *******
C
      CALL IMMAIN(IMAGE$COPY$2$1,IMERR)
      IF (IMERR .NE. ' ')
    * THEN
        FATAL$ERROR = .TRUE.
        RETURN
      ENDIF
      ENDCC
CC           CELL ANALYSIS SYSTEMS, INC.
CC               (C) COPYRIGHT 1986
CC*********************************************************************
CC
CC      :PROGRAM NAME
CC      :SAQQ09
CC
CC      :SUBROUTINES
CC      :IMMAIN
CC      :IMOVBI
CC
```

```
CC            XMIN,XMAX,YMIN,YMAX,END$FLAG,FATAL$ERROR)
CC
CC      :PARAMETERS
CC      :LOW$THRES - THE LOW THRESHOLD VALUE
CC      :HIGH$THRES - THE HIGH THRESHOLD VALUE
CC      :X$STEP - THE PIXEL STEP IN THE X DIRECTION
CC      :Y$STEP - THE PIXEL STEP IN THE Y DIRECTION
CC      :X$POS - THE X COORDINATE OF THE LOCATION OF THE NEXT OBJECT
CC      :Y$POS - THE Y COORDINATE OF THE LOCATION OF THE NEXT OBJECT
CC      :ADDR - THE OFFSET OF THE NEXT OBJECT
CC      :XMIN - THE MINIMUM X POSITION OF THE NEXT OBJECT
CC      :XMAX - THE MAXIMUM X POSITION OF THE NEXT OBJECT
CC      :YMIN - THE MINIMUM Y POSITION OF THE NEXT OBJECT
CC      :YMAX - THE MAXIMUM Y POSITION OF THE NEXT OBJECT
CC      :END$FLAG - A FLAG THAT SPECIFIES IF NO MORE OBJECTS WERE FOUND
CC                  IN THE CURRENT IMAGE
CC      :FATAL$ERROR - A FLAG THAT SPECIFIES IF A "FATAL'(I.E. SERIOUS)
CC                  ERROR OCCURRED WHILE IN SAQQ09
CC
CC      :DESCRIPTION
CC      :SAQQ09 FINDS THE NEXT OBJECT IN THE IMAGE, IF ANY.
CC
CC***********************************************************************
CC########
        SUBROUTINE SAQQ09(LOW$THRES,HIGH$THRES,X$STEP,Y$STEP,
     *                   X$POS,Y$POS,ADDR,XMIN,XMAX,YMIN,YMAX,
     *                   END$FLAG,FATAL$ERROR)
C
        INTEGER*2 LOW$THRES,HIGH$THRES,X$STEP,Y$STEP,X$POS,Y$POS,
     *            ADDR,XMIN,XMAX,YMIN,YMAX,I,IMG$LINE(256),VALUE,
     *            XLEN,YLEN
C
        LOGICAL*1 END$FLAG,FATAL$ERROR
C
        INCLUDE 'SAQCCD.FIN'
        INCLUDE 'IMAGED.FIN'
        INCLUDE 'IMAGEL.FIN'
        INCLUDE 'SCREEN.FIN'
C
C       ************ INITIALIZE THE APPROPRIATE VARIABLES *************
C
        ADDR = 0
        YMIN = 0
        XMAX = 0
        YMIN = 0
        YMAX = 0
        I = 0
        VALUE = 0
        XLEN = 0
        YLEN = 0
        END$FLAG = .FALSE.
        FATAL$ERROR = .FALSE.
C
C       ********** FIND THE NEXT OBJECT IN THE CURRENT IMAGE **********
C
 100    CALL IMOVBI(256,IMAGEL(0,Y$POS),IMG$LINE(0))
        DO 200 I=X$POS,255,X$STEP
          X$POS = I
          VALUE = IMG$LINE(I)
          IF (VALUE .GE. LOW$THRES .AND. VALUE .LE. HIGH$THRES)
     *    THEN
            ADDR = Y$POS*256+X$POS
            GOTO 300
          ENDIF
 200    CONTINUE
        X$POS = 2
        Y$POS = Y$POS+Y$STEP
        IF (Y$POS .GT. 255)
     *  THEN
          END$FLAG = .TRUE.
          RETURN
```

```
        ELSE
          GOTO 100
        ENDIF
C
C
C       ********** RELABEL THE OBJECT TO SEE IF IT'S THE RIGHT *********
C       ********** SIZE AND IT'S NOT TOUCHING A BOUNDARY       *********
C
 300    IM$X$DIM = 256
        IM$Y$DIM = 256
        IM$LINEAR$OFFSET = ADDR
        IM$LOW$LIMIT = LOW$THRES
        IM$HIGH$LIMIT = HIGH$THRES
        IM$REPLACE$VALUE = 248
        IM$LABEL$TRACE = 0
C
C
C       *************** RELABEL THE OBJECT ****************
C
        CALL IMMAIN(IMAGE$RELABEL,IMERR)
        IF (IMERR .NE. ' ')
     *  THEN
C
C
C         ********** CHECK FOR STACK OVERFLOW ERROR **********
C
          IF (IMERR .EQ. 'R1')
     *    THEN
            CALL IMMAIN(IMAGE$COPY$1$2,IMERR)
            IF (IMERR .NE. ' ')
     *      THEN
              FATAL$ERROR = .TRUE.
              RETURN
            ENDIF
            X$POS = X$POS+X$STEP
            GOTO 100
          ENDIF
          FATAL$ERROR = .TRUE.
          RETURN
        ENDIF
C
C
C       ********** CHECK SIZE AND BOUNDARY CRITERIA ***********]
C
        YMIN = IM$LABEL$BOUNDARY(1)
        XMIN = IM$LABEL$BOUNDARY(2)
        YMAX = IM$LABEL$BOUNDARY(3)
        XMAX = IM$LABEL$BOUNDARY(4)
        XLEN = (XMAX-XMIN)+1
        YLEN = (YMAX-YMIN)+1
        IF ((IM$EDGE$CODE .NE. 0) .OR.
     *      (IM$PIXEL$SUM .LT. 9000) .OR.
     *      (IM$PIXEL$SUM .GT. 17000) .OR.
     *      (IM$PIXEL$COUNT .LT. 75) .OR.
     *      (IM$PIXEL$COUNT .GT. 300) .OR.
     *      (XLEN .LT. PCCSG$XDIM$MIN) .OR.
     *      (YLEN .LT. PCCSG$YDIM$MIN) .OR.
     *      (XLEN .GT. PCCSG$XDIM$MAX) .OR.
     *      (YLEN .GT. PCCSG$YDIM$MAX) .OR.
     *      (2*XLEN+YLEN .LT. PCCSG$DIAM$SUM$MIN) .OR.
     *      (2*XLEN+YLEN .GT. PCCSG$DIAM$SUM$MAX))
     *  THEN
          CALL IMMAIN(IMAGE$COPY$1$2,IMERR)
          IF (IMERR .NE. ' ')
     *    THEN
            FATAL$ERROR = .TRUE.
            RETURN
          ENDIF
          X$POS = X$POS+X$STEP
          GOTO 100
        ENDIF
C
C
C       ********** COPY IMAGE BUFFER 2 TO IMAGE BUFFER 1 **********
```

```
          IF (IMERR .NE. ' ')
     *    THEN
             FATAL$ERROR = .TRUE.
             RETURN
          ENDIF
C
C         **************** PUT OUT THE IMAGE *****************
C
          CALL IMMAIN(IMAGE$PUT,IMERR)
          IF (IMERR .NE. ' ')
     *    THEN
             FATAL$ERROR = .TRUE.
             RETURN
          ENDIF
          ENDCC
CC              CELL ANALYSIS SYSTEMS, INC.
CC                 (C) COPYRIGHT 1986
CC*********************************************************************
CC
CC        :PROGRAM NAME
CC        :SAQQ10
CC
CC        :SUBROUTINES
CC        :IMMAIN
CC        :SAQQ20
CC        :SAQQ21
CC
CC        :CALLING SEQUENCE
CC        :SAQQ10(LOW$THRES,HIGH$THRES,X$STEP,Y$STEP,X$POS,Y$POS,
CC                MASS,AREA,CELL$ADDR,CELL$REJECTED,CURRENT$OBJECT,
CC                LAST$OBJECT,CELL$COUNT,FATAL$ERROR)
CC
CC        :PARAMETERS
CC        :LOW$THRES - LOW THRESHOLD VALUE
CC        :HIGH$THRES - HIGH THRESHOLD VALUE
CC        :X$STEP - X DIRECTION INCREMENT
CC        :Y$STEP - Y DIRECTION INCREMENT
CC        :X$POS - X COORDINATE OF THE CURRENT POSITION
CC        :Y$POS - Y COORDINATE OF THE CURRENT POSITION
CC        :MASS - ARRAY CONTAINING MASSES OF OBJECTS
CC        :AREA - ARRAY CONTAINING AREAS OF OBJECTS
CC        :CELL$ADDR - ARRAY CONTAINING THE OBJECT ADDRESSES
CC        :CELL$REJECTED - A LOGICAL ARRAY THAT SPECIFIES IF AN OBJECT
CC                         WAS REJECTED
CC        :CURRENT$OBJECT - INDEX OF THE CURRENT OBJECT
CC        :LAST$OBJECT - INDEX OF THE LAST OBJECT
CC        :CELL$COUNT - CELL COUNT
CC        :FATAL$ERROR - A FLAG THAT SPECIFIES IF A 'FATAL'(I.E. SERIOUS) ERROR
CC                       OCCURRED WHILE IN SAQQ10
CC
CC        :DESCRIPTION
CC        :SAQQ10 PERFORMS THE AUTOMATIC OPERATION
CC
CC*********************************************************************
CC########
          SUBROUTINE SAQQ10(LOW$THRES,HIGH$THRES,X$STEP,Y$STEP,
     *                      X$POS,Y$POS,MASS,AREA,
     *                      CELL$ADDR,CELL$REJECTED,CURRENT$OBJECT,
     *                      LAST$OBJECT,CELL$COUNT,FATAL$ERROR)
C
          INTEGER*2 LOW$THRES,HIGH$THRES,X$STEP,Y$STEP,X$POS,Y$POS,
     *              CURRENT$OBJECT,LAST$OBJECT,CELL$ADDR(*),
     *              CELL$COUNT,XMIN,XMAX,YMIN,
     *              YMAX,ADDR
          INTEGER*4 MASS(*),AREA(*)
          LOGICAL*1 CELL$REJECTED(*),FATAL$ERROR,END$FLAG
C
          INCLUDE 'SAQCCD.FIN'
          INCLUDE 'IMAGED.FIN'
          INCLUDE 'SCREEN.FIN'
```

```
C
C          ************** INITIALIZE VARIABLES *****************
C
           FATAL$ERROR = .FALSE.
           END$FLAG = .FALSE.
           XMIN = 0
           XMAX = 0
           YMIN = 0
           YMAX = 0
           ADDR = 0
C
C          *************** FIND THE NEXT OBJECT ****************
C
   100     IF (LAST$OBJECT .GT. 512) RETURN
           IM$X$DIM = 256
           IM$Y$DIM = 256
           IM$LINEAR$OFFSET = CELL$ADDR(CURRENT$OBJECT)
           IM$LOW$LIMIT = LOW$THRES
           IM$HIGH$LIMIT = HIGH$THRES
           IM$REPLACE$VALUE = 252
           IM$LABEL$TRACE = 0
           CALL IMMAIN(IMAGE$RELABEL,IMERR)
           IF (IMERR .NE. ' ')
     *     THEN
              FATAL$ERROR = .TRUE.
              RETURN
           ENDIF
           CELL$COUNT = CELL$COUNT+1
           CELL$REJECTED(CURRENT$OBJECT) = .FALSE.
C
C          ************ COPY IMAGE BUFFER 1 TO IMAGE BUFFER 2 ************
C
           CALL IMMAIN(IMAGE$COPY$1$2,IMERR)
           IF (IMERR .NE. ' ')
     *     THEN
              FATAL$ERROR = .TRUE.
              RETURN
           ENDIF
C
C          **************** PUT OUT THE IMAGE ****************
C
           CALL IMMAIN(IMAGE$PUT,IMERR)
           IF (IMERR .NE. ' ')
     *     THEN
              FATAL$ERROR = .TRUE.
              RETURN
           ENDIF
C
C          ****** CALL THE SUBROUTINE WHICH SEARCHES FOR THE NEXT OBJECT ******
C
           CALL SAQQ21(LOW$THRES,HIGH$THRES,X$STEP,Y$STEP,X$POS,Y$POS,
     *                 ADDR,XMIN,XMAX,YMIN,YMAX,END$FLAG,FATAL$ERROR)
           IF (FATAL$ERROR) RETURN
           IF (END$FLAG) RETURN
           CURRENT$OBJECT = CURRENT$OBJECT+1
           LAST$OBJECT = CURRENT$OBJECT
           CELL$ADDR(CURRENT$OBJECT) = ADDR
           CELL$REJECTED(CURRENT$OBJECT) = .TRUE.
           MASS(CURRENT$OBJECT) = IM$PIXEL$SUM+
     *                            TMP$CAL$OFFSET
           AREA(CURRENT$OBJECT) = IM$PIXEL$COUNT
           GOTO 100
           ENDCC
CC            CELL ANALYSIS SYSTEMS, INC.
CC                (C) COPYRIGHT 1986
CC*******************************************************************************
CC
CC     :PROGRAM NAME
CC     :SAQQ11
```

```
CC      :IMMAIN
CC      :SAQQ07
CC      :SAQQ08
CC      :SAQQ09
CC      :SAQQ10
CC      :SCREEN
CC
CC      :CALLING SEQUENCE
CC      :SAQQ11(SCRN$NAME,LAST$OBJECT,CELL$COUNT,MASS,AREA,CELL$REJECTED,
CC               SAVE$DATA$FLAG,FATAL$ERROR)
CC
CC      :PARAMETERS
CC      :SCRN$NAME - THE NAME OF THE CURRENT SCREEN
CC      :LAST$OBJECT - INDEX INTO THE MASS AND AREA ARRAYS, OF THE LAST OBJECT
CC      :CELL$COUNT - NUMBER OF CELLS THAT WERE ACCEPTED
CC      :MASS - AN ARRAY THAT CONTAINS THE MASSES OF THE OBJECTS
CC      :AREA - AN ARRAY THAT CONTAINS THE AREA OF THE OBJECTS
CC      :CELL$REJECTED - A LOGICAL ARRAY THAT SPECIFIES IF AN OBJECT WAS
CC                       ACCEPTED OR REJECTED
CC      :SAVE$DATA$FLAG - A FLAG THAT SPECIFIES IF THE DATA, THAT WAS MEASURED,
CC                       WILL BE SAVED
CC      :FATAL$ERROR - A FLAG THAT SPECIFIES IF A 'FATAL'(I.E SERIOUS) ERROR
CC                    OCCURRED WHILE IN SAQQ11
CC
CC      :DESCRIPTION
CC      :SAQQ11 HANDLES THE MEASURE COMMAND THAT IS IN THE CALIBRATION SCREEN
CC
CC*******************************************************************
CC#########
        SUBROUTINE SAQQ11(SCRN$NAME,LAST$OBJECT,CELL$COUNT,MASS,AREA,
     *                   CELL$REJECTED,SAVE$DATA$FLAG,FATAL$ERROR)
C
        CHARACTER*1 ERR$MESSAGE
        CHARACTER*3 NUM$STRING,KEY$TYPE
        CHARACTER*(*) SCRN$NAME
        CHARACTER*7 STRNG
        CHARACTER*8 READ$INPUT$VALUE
        CHARACTER*9 SELECTED$FUNCTION
        CHARACTER*32 ERR$ONE,ERR$TWO
        INTEGER*2 I,LOW$THRES,HIGH$THRES,X$POS,Y$POS,ADDR,X$STEP,
     *            Y$STEP,XMIN,XMAX,YMIN,YMAX,CURRENT$OBJECT,
     *            LAST$OBJECT,OBJECT$BOUNDARY(4,513),
     *            NUM$VALUE,CELL$ADDR(513),
     *            CELL$COUNT,XLEN,YLEN,NUM$PAD$VALUE,
     *            BOX$TOP$POS,BOX$BOTTOM$POS,BOX$LEFT$POS,
     *            BOX$RIGHT$POS
        INTEGER*4 MASS(*),AREA(*),VALUE$64K
        LOGICAL*1 FATAL$ERROR,END$FLAG,CELL$REJECTED(*),
     *            SAVE$DATA$FLAG

INCLUDE 'SAQCCD.FIN'
        INCLUDE 'IMAGED.FIN'
        INCLUDE 'SCREEN.FIN'

DATA VALUE$64K /65536/

*********** INITALIZE THE APPROPRIATE VARIABLES ***********

SCREEN$NAME = SCRN$NAME
        ERR$MESSAGE = ' '
        NUM$STRING = ' '
        KEY$TYPE = ' '
        READ$INPUT$VALUE = ' '
        STRNG = ' '
        ERR$ONE = ' '
        ERR$TWO = ' '
        SELECTED$FUNCTION = ' '
        I = 0
        LOW$THRES = PCCSG$LO$THRES
```

```
            YLEN = 0
            X$POS = 0
            Y$POS = 0
            ADDR = 771
            X$STEP = PCCSG$X$STEP
            Y$STEP = PCCSG$Y$STEP
            XMIN = 0
            XMAX = 0
            YMIN = 0
            YMAX = 0
            NUM$VALUE = 0
            CELL$COUNT = 0
            NUM$PAD$VALUE = 0
            BOX$TOP$POS = 0
            BOX$BOTTOM$POS = 0
            BOX$LEFT$POS = 0
            BOX$RIGHT$POS = 0
            CURRENT$OBJECT = 0
            LAST$OBJECT = 0
            SAVE$DATA$FLAG = .FALSE.
C
C
C       *************** GET THE SUBTRACTED IMAGE ***************
            CALL IMMAIN(IMAGE$SUBTRACT$GET,IMERR)
            IF (IMERR .NE. ' ')
        *   THEN
              FATAL$ERROR = .TRUE.
              GOTO 600
            ENDIF
C
C
C       ******** COPY IMAGE BUFFER 1 TO IMAGE BUFFER 2 **********
            CALL IMMAIN(IMAGE$COPY$1$2,IMERR)
            IF (IMERR .NE. ' ')
        *   THEN
              FATAL$ERROR = .TRUE.
              GOTO 600
            ENDIF
C
C
C       ********** PUT THE IMAGE TO THE DISPLAY ***********
            CALL IMMAIN(IMAGE$PUT,IMERR)
            IF (IMERR .NE. ' ')
        *   THEN
              FATAL$ERROR = .TRUE.
              GOTO 600
            ENDIF
C
C
C       *************** FIND THE FIRST OBJECT ***************
            X$POS = MOD(ADDR,256)
            Y$POS = INT(ADDR/256.)
            CALL SAQQ09(LOW$THRES,HIGH$THRES,X$STEP,Y$STEP,X$POS,Y$POS,
        *               ADDR,XMIN,XMAX,YMIN,YMAX,END$FLAG,FATAL$ERROR)
            IF (FATAL$ERROR) GOTO 600
            IF (END$FLAG)
        *   THEN
              CALL IMMAIN(IMAGE$START$ACQ,IMERR)
              IF (IMERR .NE. ' ')
        *     THEN
                FATAL$ERROR = .TRUE.
                GOTO 600
              ENDIF
              RETURN
            ENDIF
C
C
C       *************** ENABLE FUNCTION KEYS ***************
            CALL SCREEN(ENABLE$FUNCTION$KEYS,SCREEN$NAME,FIELD$NAME,
```

```
      *  CALL SYERR(ENABLE$FUNCTION$KEYS,SCREEN$NAME,FIELD$NAME,SCERR,
      *              'ENABLE FUNCTION KEYS')
C
C     *************** UPDATE VARIABLES *****************
C
         CURRENT$OBJECT = 1
         LAST$OBJECT = 1
         OBJECT$BOUNDARY(1,CURRENT$OBJECT) = YMIN
         OBJECT$BOUNDARY(2,CURRENT$OBJECT) = XMIN
         OBJECT$BOUNDARY(3,CURRENT$OBJECT) = YMAX
         OBJECT$BOUNDARY(4,CURRENT$OBJECT) = XMAX
         CELL$ADDR(CURRENT$OBJECT) = ADDR
         CELL$REJECTED(CURRENT$OBJECT) = .TRUE.
         MASS(CURRENT$OBJECT) = IM$PIXEL$SUM+
      *                         TMP$CAL$OFFSET
         AREA(CURRENT$OBJECT) = IM$PIXEL$COUNT
C
C     *************** PUT A BOX AROUND THE OBJECT ***************
C
         CALL SAQQ07(XMIN,XMAX,YMIN,YMAX,
      *               BOX$LEFT$POS,BOX$RIGHT$POS,BOX$TOP$POS,
      *               BOX$BOTTOM$POS,FATAL$ERROR)
C
C     ************** ERROR MESSAGE HANDLING CODE ****************
C
  600    IF (ERR$MESSAGE .EQ. 'C')
      *  THEN
            ERR$ONE = ' '
            ERR$TWO = ' '
         ENDIF
         IF (ERR$MESSAGE .EQ. 'C' .OR.
      *       ERR$MESSAGE .EQ. 'W')
      *  THEN
            FIELD$NAME = 'ERR1'
            CALL CNSTAR(32,ERR$ONE,DATA$AREA)
            CALL SCREEN(PUT$FIELD,SCREEN$NAME,FIELD$NAME,
      *                  DATA$AREA,SCERR)
            IF (SCERR .NE. NO$SCREEN$ERROR)
      *         CALL SYERR(PUT$FIELD,SCREEN$NAME,FIELD$NAME,SCERR,
      *                     'PUT FIELD')
            FIELD$NAME = 'ERR2'
            CALL CNSTAR(32,ERR$TWO,DATA$AREA)
            CALL SCREEN(PUT$FIELD,SCREEN$NAME,FIELD$NAME,
      *                  DATA$AREA,SCERR)
            IF (SCERR .NE. NO$SCREEN$ERROR)
      *         CALL SYERR(PUT$FIELD,SCREEN$NAME,FIELD$NAME,SCERR,
      *                     'PUT FIELD')
         ENDIF
         IF (ERR$MESSAGE .EQ. 'C') ERR$MESSAGE = ' '
         IF (ERR$MESSAGE .EQ. 'W') ERR$MESSAGE = 'C'
         IF (ERR$MESSAGE .NE. 'C') ERR$MESSAGE = ' '
C
C     ********** CHECK FOR A 'FATAL'(I.E. SERIOUS) ERROR **********
C
         IF (FATAL$ERROR)
      *  THEN
C
C     *************** DISABLE FUNCTION KEYS *****************
C
            CALL SCREEN(DISABLE$FUNCTION$KEYS,SCREEN$NAME,FIELD$NAME,
      *                  DATA$AREA,SCERR)
            IF (SCERR .NE. NO$SCREEN$ERROR)
      *         CALL SYERR(DISABLE$FUNCTION$KEYS,SCREEN$NAME,FIELD$NAME,
      *                     SCERR,'DISABLE FUNCTION KEYS')
            RETURN
         ENDIF
C
C     ********** SET THE CURSOR TO THE APPROPRIATE FIELD **********
C
         FIELD$NAME = 'CS67'
         CALL SCREEN(SET$CURSOR,SCREEN$NAME,FIELD$NAME,
```

```
      *              DATA$AREA,SCERR)
             IF (SCERR .NE. NO$SCREEN$ERROR)
      *         CALL SYERR(SET$CURSOR,SCREEN$NAME,FIELD$NAME,SCERR,
      *                    'SET CURSOR')
C
C
C    ************* ACTIVATE NUMERIC PAD ****************

CALL SCREEN(NUMERIC$PAD,SCREEN$NAME,FIELD$NAME,
      *                  DATA$AREA,SCERR)
             IF (SCERR .EQ. SCREEN$ESCAPE .OR.
      *          SCERR .EQ. NO$SCREEN$ERROR .OR.
      *          SCERR .EQ. SCREEN$FUNCT$KEY)
      *       THEN
               CONTINUE
             ELSE
               ERR$ONE = 'YOU HAVE TYPED IN'
               ERR$TWO = 'AN INVALID CHARACTER.'
               ERR$MESSAGE = 'W'
               GOTO 600
             ENDIF
             CALL CNARST(8,DATA$AREA,READ$INPUT$VALUE)
C
C
C    *********** IF EXITING TAKE THE APPROPRIATE ACTION ********

IF (SCERR .EQ. SCREEN$ESCAPE)
      *       THEN
C
C
C    *************** DISABLE FUNCTION KEYS ***************

CALL SCREEN(DISABLE$FUNCTION$KEYS,SCREEN$NAME,FIELD$NAME,
      *                  DATA$AREA,SCERR)
             IF (SCERR .NE. NO$SCREEN$ERROR)
      *         CALL SYERR(DISABLE$FUNCTION$KEYS,SCREEN$NAME,FIELD$NAME,
      *                    SCERR,'DISABLE FUNCTION KEYS')
C
C
C    *********** CLEAR AWAY ANY EXISITING ERROR MESSAGE ***********

IF (ERR$MESSAGE .EQ. 'C')
      *       THEN
               ERR$ONE = ' '
               ERR$TWO = ' '
               FIELD$NAME = 'ERR1'
               CALL CNSTAR(32,ERR$ONE,DATA$AREA)
               CALL SCREEN(PUT$FIELD,SCREEN$NAME,FIELD$NAME,
      *                    DATA$AREA,SCERR)
               IF (SCERR .NE. NO$SCREEN$ERROR)
      *           CALL SYERR(PUT$FIELD,SCREEN$NAME,FIELD$NAME,SCERR,
      *                      'PUT FIELD')
               FIELD$NAME = 'ERR2'
               CALL CNSTAR(32,ERR$TWO,DATA$AREA)
               CALL SCREEN(PUT$FIELD,SCREEN$NAME,FIELD$NAME,
      *                    DATA$AREA,SCERR)
               IF (SCERR .NE. NO$SCREEN$ERROR)
      *           CALL SYERR(PUT$FIELD,SCREEN$NAME,FIELD$NAME,SCERR,
      *                      'PUT FIELD')
             ENDIF
C
C
C    *************** START IMAGE ACQUISITION ***************

CALL IMMAIN(IMAGE$START$ACQ,IMERR)
             IF (IMERR .NE. ' ') FATAL$ERROR = .TRUE.
             RETURN
           ENDIF
C
C
C    ************ DETERMINE THE USER'S SELECTION ************

SELECTED$FUNCTION = ' '
           IF (SCERR .EQ. SCREEN$FUNCT$KEY)
      *     THEN
             KEY$TYPE = READ$INPUT$VALUE(1:3)
```

```
          IF (KEY$TYPE .NE. 'CTL')
     *    THEN
            ERR$ONE = 'YOU CANNOT USE THE '//KEY$TYPE//' KEY.'
            ERR$TWO = ' '
            ERR$MESSAGE = 'W'
            GOTO 600
          ENDIF
          NUM$STRING = READ$INPUT$VALUE(5:7)
          IF (NUM$STRING .EQ. 'F1')
     *    THEN
            SELECTED$FUNCTION = 'BACKUP'
          ELSEIF (NUM$STRING .EQ. 'F2')
     *    THEN
            SELECTED$FUNCTION = 'NEXT'
          ELSEIF (NUM$STRING .EQ. 'F3')
     *    THEN
            SELECTED$FUNCTION = 'AUTOMATIC'
          ELSEIF (NUM$STRING .EQ. 'F6')
     *    THEN
            SELECTED$FUNCTION = 'SKIP'
          ELSE
            ERR$ONE = 'YOU CAN ONLY USE THE'
            ERR$TWO = 'F1, F2, AND F3 KEYS.'
            ERR$MESSAGE = 'W'
            GOTO 600
          ENDIF
        ELSEIF (SCERR .EQ. ' ')
     *  THEN
          NUM$PAD$VALUE = DATA$AREA(1)
          IF (NUM$PAD$VALUE .EQ. 12)
     *    THEN
            $AVE$DATA$FLAG = .TRUE.
C
C         *************** DISABLE FUNCTION KEYS ***************
C
          CALL SCREEN(DISABLE$FUNCTION$KEYS,SCREEN$NAME,FIELD$NAME,
     *                DATA$AREA,SCERR)
          IF (SCERR .NE. NO$SCREEN$ERROR)
     *      CALL SYERR(DISABLE$FUNCTION$KEYS,SCREEN$NAME,FIELD$NAME,
     *                 SCERR,'DISABLE FUNCTION KEYS')
C
C         ********** CLEAR AWAY ANY EXISITING ERROR MESSAGE ***********
C
          IF (ERR$MESSAGE .EQ. 'C')
     *    THEN
            ERR$ONE = ' '
            ERR$TWO = ' '
            FIELD$NAME = 'ERR1'
            CALL CNSTAR(32,ERR$ONE,DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            FIELD$NAME = 'ERR2'
            CALL CNSTAR(32,ERR$TWO,DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
          ENDIF
C
C         *************** START IMAGE ACQUISITION **************
C
          CALL IMMAIN(IMAGE$START$ACQ,IMERR)
          IF (IMERR .NE. ' ') FATAL$ERROR = .TRUE.
          RETURN
        ELSEIF (NUM$PAD$VALUE .EQ. 0)
     *  THEN
```

```
              SELECTED$FUNCTION = 'ACCEPT'
          ELSEIF (NUM$PAD$VALUE .EQ. 9)
        *   THEN
              SELECTED$FUNCTION = 'REJECT'
          ELSE
            ERR$ONE = '0 AND 9 ARE THE ONLY VALID'
            ERR$TWO = 'NUMBERS.'
            ERR$MESSAGE = 'W'
            GOTO 600
          ENDIF
        ELSE
          ERR$ONE = 'YOU HAVE ENTERED AN INVALID'
          ERR$TWO = 'RESPONSE, PLEASE RESELECT.'
          ERR$MESSAGE = 'W'
          GOTO 600
        ENDIF
C***************************************************************
C
C
C              CODE TO SKIP OVER AN OBJECT
C
C***************************************************************
        IF (SELECTED$FUNCTION .EQ. 'SKIP')
      *   THEN
          IF (CURRENT$OBJECT .EQ. LAST$OBJECT)
      *     THEN
            ERR$ONE = 'YOU CANNOT USE SKIP WHEN'
            ERR$TWO = 'THE BOX IS AT THE END.'
            ERR$MESSAGE = 'W'
            GOTO 600
          ENDIF
C
C
C          *********** MOVE BOX TO THE NEXT OBJECT **************

CURRENT$OBJECT = CURRENT$OBJECT+1
          YMIN = OBJECT$BOUNDARY(1,CURRENT$OBJECT)
          XMIN = OBJECT$BOUNDARY(2,CURRENT$OBJECT)
          YMAX = OBJECT$BOUNDARY(3,CURRENT$OBJECT)
          XMAX = OBJECT$BOUNDARY(4,CURRENT$OBJECT)
          ADDR = CELL$ADDR(CURRENT$OBJECT)
          CALL SAQQ07(XMIN,XMAX,YMIN,YMAX,
      *               BOX$LEFT$POS,BOX$RIGHT$POS,BOX$TOP$POS,
      *               BOX$BOTTOM$POS,FATAL$ERROR)
          GOTO 600
        ENDIF
C***************************************************************
C
C
C              CODE TO REJECT AN OBJECT
C
C***************************************************************
        IF (SELECTED$FUNCTION .EQ. 'REJECT')
      *   THEN
C
C
C         ********* CHECK TO SEE IF THE USER IS REJECTING ***********
C         ********* AN ALREADY MEASURED OBJECT            ***********

IF (CURRENT$OBJECT .LT. LAST$OBJECT)
      *     THEN
C
C
C           **** CHECK TO SEE IF THE OBJECT HAS ALREADY BEEN REJECTED ****

IF (CELL$REJECTED(CURRENT$OBJECT))
      *       THEN
              ERR$ONE = 'YOU CANNOT REJECT A'
              ERR$TWO = 'REJECTED CELL.'
              ERR$MESSAGE = 'W'
              GOTO 600
            ENDIF
C
C           ************* REJECT THE CEJECT ************
```

```
         IM$X$DIM = 256
         IM$Y$DIM = 256
         IM$LINEAR$OFFSET = CELL$ADDR(CURRENT$OBJECT)
         IM$LOW$LIMIT = 252
         IM$HIGH$LIMIT = 252
         IM$REPLACE$VALUE = 248
         IM$LABEL$TRACE = 0
         CALL IMMAIN(IMAGE$RELABEL,IMERR)
         IF (IMERR .NE. ' ')
   *     THEN
            FATAL$ERROR = .TRUE.
            GOTO 600
         ENDIF
         CELL$REJECTED(CURRENT$OBJECT) = .TRUE.
         CELL$COUNT = CELL$COUNT-1
         CALL IMMAIN(IMAGE$COPY$1$2,IMERR)
         IF (IMERR .NE. ' ')
   *     THEN
            FATAL$ERROR = .TRUE.
            GOTO 600
         ENDIF
C
C  ************ MOVE BOX TO THE NEXT OBJECT ***************
C
         CURRENT$OBJECT = CURRENT$OBJECT+1
         YMIN = OBJECT$BOUNDARY(1,CURRENT$OBJECT)
         XMIN = OBJECT$BOUNDARY(2,CURRENT$OBJECT)
         YMAX = OBJECT$BOUNDARY(3,CURRENT$OBJECT)
         XMAX = OBJECT$BOUNDARY(4,CURRENT$OBJECT)
         ADDR = CELL$ADDR(CURRENT$OBJECT)
         CALL SAQQ07(XMIN,XMAX,YMIN,YMAX,
   *               BOX$LEFT$POS,BOX$RIGHT$POS,BOX$TOP$POS,
   *               BOX$BOTTOM$POS,FATAL$ERROR)
         GOTO 600
C
C  ********** CODE TO HANDLE THE REJECTION OF AN OBJECT **********
C  ********** THAT HAS NOT BEEN MEASURED YET           **********
C
      ELSE
C
C  ************ CHECK TO SEE IF THERE IS ROOM IN THE ARRAYS *********
C  ************ TO ACCEPT ANOTHER OBJECT                    *********
C
         IF (LAST$OBJECT .GT. 512)
   *     THEN
            ERR$ONE = 'YOU CANNOT CLASSIFY MORE'
            ERR$TWO = 'THAN 512 CELLS IN THE IMAGE.'
            ERR$MESSAGE = 'W'
            GOTO 600
         ENDIF
C
C  ************ REJECT THE OBJECT *************
C
         IM$X$DIM = 256
         IM$Y$DIM = 256
         IM$LINEAR$OFFSET = ADDR
         IM$LOW$LIMIT = LOW$THRES
         IM$HIGH$LIMIT = HIGH$THRES
         IM$REPLACE$VALUE = 248
         IM$LABEL$TRACE = 0
         CALL IMMAIN(IMAGE$RELABEL,IMERR)
         IF (IMERR .NE. ' ')
   *     THEN
            IF (IMERR .EQ. 'R1')
   *        THEN
               X$POS = X$POS+X$STEP
            ELSE
               FATAL$ERROR = .TRUE.
               GOTO 600
            ENDIF
         ENDIF
```

```
              CALL IMMAIN(IMAGE$RELABEL,IMERR)
              IF (IMERR .NE. ' ')
    *         THEN
                IF (IMERR .EQ. 'R1')
    *           THEN
                  X$POS = X$POS+X$STEP
                ELSE
                  FATAL$ERROR = .TRUE.
                  GOTO 600
                ENDIF
              ENDIF
              CELL$REJECTED(CURRENT$OBJECT) = .TRUE.
              CALL IMMAIN(IMAGE$COPY$1$2,IMERR)
              IF (IMERR .NE. ' ')
    *         THEN
                FATAL$ERROR = .TRUE.
                GOTO 600
              ENDIF
              CALL IMMAIN(IMAGE$PUT,IMERR)
              IF (IMERR .NE. ' ')
    *         THEN
                FATAL$ERROR = .TRUE.
                GOTO 600
              ENDIF
 C
 C
 C           *********** SEARCH FOR THE NEXT OBJECT ************

CALL SAQQ09(LOW$THRES,HIGH$THRES,X$STEP,Y$STEP,X$POS,
    *                    Y$POS,ADDR,XMIN,XMAX,YMIN,YMAX,END$FLAG,
    *                    FATAL$ERROR)
              IF (FATAL$ERROR) GOTO 600
 C
 C
 C           ********** CHECK TO SEE IF NO MORE OBJECTS WERE FOUND **********

IF (END$FLAG)
    *         THEN
                SAVE$DATA$FLAG = .TRUE.
 C
 C
 C           ************* DISABLE FUNCTION KEYS *************

CALL SCREEN(DISABLE$FUNCTION$KEYS,SCREEN$NAME,FIELD$NAME,
    *                     DATA$AREA,SCERR)
              IF (SCERR .NE. NO$SCREEN$ERROR)
    *           CALL SYERR(DISABLE$FUNCTION$KEYS,SCREEN$NAME,FIELD$NAME,
    *                      SCERR,'DISABLE FUNCTION KEYS')
 C
 C
 C           *********** CLEAR AWAY ANY EXISTING ERROR MESSAGE ************

IF (ERR$MESSAGE .EQ. 'C')
    *         THEN
                ERR$ONE = ' '
                ERR$TWO = ' '
                FIELD$NAME = 'ERR1'
                CALL CNSTAR(32,ERR$ONE,DATA$AREA)
                CALL SCREEN(PUT$FIELD,SCREEN$NAME,FIELD$NAME,
    *                      DATA$AREA,SCERR)
    *           IF (SCERR .NE. NO$SCREEN$ERROR)
    *             CALL SYERR(PUT$FIELD,SCREEN$NAME,FIELD$NAME,SCERR,
                             'PUT FIELD')
                FIELD$NAME = 'ERR2'
                CALL CNSTAR(32,ERR$TWO,DATA$AREA)
                CALL SCREEN(PUT$FIELD,SCREEN$NAME,FIELD$NAME,
    *                      DATA$AREA,SCERR)
                IF (SCERR .NE. NO$SCREEN$ERROR)
    *             CALL SYERR(PUT$FIELD,SCREEN$NAME,FIELD$NAME,SCERR,
                             'PUT FIELD')
              ENDIF
 C
 C
 C           *************** START IMAGE ACQUISITION **************
```

```
      CALL IMMAIN(IMAGE$START$ACQ,IMERR)
      IF (IMERR .NE. ' ') FATAL$ERROR = .TRUE.
      RETURN
   ENDIF
   CURRENT$OBJECT = CURRENT$OBJECT+1
   LAST$OBJECT = CURRENT$OBJECT
   OBJECT$BOUNDARY(1,CURRENT$OBJECT) = YMIN
   OBJECT$BOUNDARY(2,CURRENT$OBJECT) = XMIN
   OBJECT$BOUNDARY(3,CURRENT$OBJECT) = YMAX
   OBJECT$BOUNDARY(4,CURRENT$OBJECT) = XMAX
   CELL$REJECTED(CURRENT$OBJECT) = .TRUE.
   CELL$ADDR(CURRENT$OBJECT) = ADDR
   MASS(CURRENT$OBJECT) = IM$PIXEL$SUM+
*                          TMP$CAL$OFFSET

************ SAVE MASS AND AREA VALUES **************

AREA(CURRENT$OBJECT) = IM$PIXEL$COUNT

************* PUT A BOX AROUND THE OBJECT *************

CALL SAQQ07(XMIN,XMAX,YMIN,YMAX,
*              BOX$LEFT$POS,BOX$RIGHT$POS,BOX$TOP$POS,
*              BOX$BOTTOM$POS,FATAL$ERROR)
   GOTO 600
  ENDIF
 ENDIF
****************************************************************

CODE TO HANDLE THE BACKUP COMMAND

****************************************************************
   IF (SELECTED$FUNCTION .EQ. 'BACKUP')
*  THEN

***** CHECK TO SEE IF THERE IS AN OBJECT TO BACKUP TO ******

IF (CURRENT$OBJECT .LE. 1)
*     THEN
         ERR$ONE = 'YOU CANNOT BACKUP BECAUSE'
         ERR$TWO = 'THERE IS NO OBJECT TO BACKUP TO.'
         ERR$MESSAGE = 'W'
         GOTO 600
      ENDIF
      CURRENT$OBJECT = CURRENT$OBJECT-1
      ADDR = CELL$ADDR(CURRENT$OBJECT)
      YMIN = OBJECT$BOUNDARY(1,CURRENT$OBJECT)
      XMIN = OBJECT$BOUNDARY(2,CURRENT$OBJECT)
      YMAX = OBJECT$BOUNDARY(3,CURRENT$OBJECT)
      XMAX = OBJECT$BOUNDARY(4,CURRENT$OBJECT)

************* PUT A BOX AROUND THE OBJECT ***************

CALL SAQQ07(XMIN,XMAX,YMIN,YMAX,
*                 BOX$LEFT$POS,BOX$RIGHT$POS,BOX$TOP$POS,
*                 BOX$BOTTOM$POS,FATAL$ERROR)
      GOTO 600
   ENDIF
****************************************************************

CODE TO HANDLE THE NEXT COMMAND

****************************************************************
   IF (SELECTED$FUNCTION .EQ. 'NEXT')
*  THEN

***** CHECK TO SEE IF THE CURRENT OBJECT IS THE NEXT OBJECT *****

IF (CURRENT$OBJECT .EQ. LAST$OBJECT)
*     THEN
         ERR$ONE =. 'THIS IS THE NEXT OBJECT.'
```

```
              ERR$TWO = ' '
              ERR$MESSAGE = 'W'
              GOTO 600
            ENDIF
            CURRENT$OBJECT = LAST$OBJECT
            ADDR = CELL$ADDR(CURRENT$OBJECT)
            YMIN = OBJECT$BOUNDARY(1,CURRENT$OBJECT)
            XMIN = OBJECT$BOUNDARY(2,CURRENT$OBJECT)
            YMAX = OBJECT$BOUNDARY(3,CURRENT$OBJECT)
            XMAX = OBJECT$BOUNDARY(4,CURRENT$OBJECT)
  C
  C
  C           ********** PUT A BOX AROUND THE OBJECT *************
            CALL SAQQ07(XMIN,XMAX,YMIN,YMAX,
       *                BOX$LEFT$POS,BOX$RIGHT$POS,BOX$TOP$POS,
       *                BOX$BOTTOM$POS,FATAL$ERROR)
            GOTO 600
          ENDIF
  C************************************************************************
  C
  C
  C                 CODE TO HANDLE THE ACCEPT COMMAND
  C
  C************************************************************************
          IF (SELECTED$FUNCTION .EQ. 'ACCEPT')
       *  THEN
  C
  C         ***** CHECK TO SEE IF THERE IS ROOM IN THE ARRAYS *****
  C         ***** TO ACCEPT ANOTHER OBJECT                    *****
  C
            IF (LAST$OBJECT .GT. 512)
       *    THEN
              ERR$ONE = 'YOU CANNOT CLASSIFY MORE'
              ERR$TWO = 'THAN 512 CELLS IN THE IMAGE.'
              ERR$MESSAGE = 'W'
              GOTO 600
            ENDIF
  C
  C
  C         ********** CHECK TO SEE IF THE USER IS ACCEPTING ************
  C         ********** AN ALREADY MEASURED OBJECT             ************
  C
            IF (CURRENT$OBJECT .LT. LAST$OBJECT)
       *    THEN
  C
  C
  C           ********* CHECK TO SEE IF THE USER IS TRYING TO *********
  C           ********* ACCEPT AN ALREADY ACCEPTED OBJECT     *********
  C
              IF (.NOT. CELL$REJECTED(CURRENT$OBJECT))
       *      THEN
                ERR$ONE = 'THE OBJECT HAS ALREADY'
                ERR$TWO = 'BEEN ACCEPTED.'
                ERR$MESSAGE = 'W'
                GOTO 600
              ENDIF
  C
  C
  C           ********** RELABEL THE REJECT OBJECT RED ************
              IM$X$DIM = 256
              IM$Y$DIM = 256
              IM$LINEAR$OFFSET = CELL$ADDR(CURRENT$OBJECT)
              IM$LOW$LIMIT = 248
              IM$HIGH$LIMIT = 248
              IM$REPLACE$VALUE = 252
              IM$LABEL$TRACE = 0
              CALL IMMAIN(IMAGE$RELABEL,IMERR)
              IF (IMERR .NE. ' ')
       *      THEN
                FATAL$ERROR = .TRUE.
                RETURN
              ENDIF
              CELL$REJECTED(CURRENT$OBJECT) = .FALSE.
              CELL$COUNT = CELL$COUNT+1
              CURRENT$OBJECT = CURRENT$OBJECT+1
```

```
C
C        ******* COPY IMAGE BUFFER 1 TO IMAGE BUFFER 2 *********
C
         CALL IMMAIN(IMAGE$COPY$1$2,IMERR)
         IF (IMERR .NE. ' ')
     *   THEN
            FATAL$ERROR = .TRUE.
            GOTO 600
         ENDIF
         ADDR = CELL$ADDR(CURRENT$OBJECT)
         YMIN = OBJECT$BOUNDARY(1,CURRENT$OBJECT)
         XMIN = OBJECT$BOUNDARY(2,CURRENT$OBJECT)
         YMAX = OBJECT$BOUNDARY(3,CURRENT$OBJECT)
         XMAX = OBJECT$BOUNDARY(4,CURRENT$OBJECT)
C
C        ************ PUT A BOX AROUND THE OBJECT ***************
C
         CALL SAQQ07(XMIN,XMAX,YMIN,YMAX,
     *               BOX$LEFT$POS,BOX$RIGHT$POS,BOX$TOP$POS,
     *               BOX$BOTTOM$POS,FATAL$ERROR)
         GOTO 600
      ENDIF
C
C        ********** CODE TO ACCEPT AN UNMEASURED OBJECT **********
C
      IM$X$DIM = 256
      IM$Y$DIM = 256
      IM$LINEAR$OFFSET = CELL$ADDR(CURRENT$OBJECT)
      IM$LOW$LIMIT = LOW$THRES
      IM$HIGH$LIMIT = HIGH$THRES
      IM$REPLACE$VALUE = 252
      IM$LABEL$TRACE = 0
      CALL IMMAIN(IMAGE$RELABEL,IMERR)
      IF (IMERR .NE. ' ')
     *  THEN
         FATAL$ERROR = .TRUE.
         GOTO 600
      ENDIF
      XLEN = (IM$LABEL$BOUNDARY(4)-IM$LABEL$BOUNDARY(2))+1
      YLEN = (IM$LABEL$BOUNDARY(3)-IM$LABEL$BOUNDARY(1))+1
      IF ((IM$EDGE$CODE .NE. 0) .OR.
     *    (XLEN .LT. PCCSG$XDIM$MIN) .OR.
     *    (YLEN .LT. PCCSG$YDIM$MIN) .OR.
     *    (XLEN .GT. PCCSG$XDIM$MAX) .OR.
     *    (YLEN .GT. PCCSG$YDIM$MAX) .OR.
     *    (2*XLEN+YLEN .LT. PCCSG$DIAM$SUM$MIN) .OR.
     *    (2*XLEN+YLEN .GT. PCCSG$DIAM$SUM$MAX))
     *  THEN
         FATAL$ERROR = .TRUE.
         GOTO 600
      ENDIF
      CELL$REJECTED(CURRENT$OBJECT) = .FALSE.
      CELL$COUNT = CELL$COUNT+1
C
C        ************ COPY IMAGE BUFFER 1 TO IMAGE BUFFER 2 *********
C
      CALL IMMAIN(IMAGE$COPY$1$2,IMERR)
      IF (IMERR .NE. ' ')
     *  THEN
         FATAL$ERROR = .TRUE.
         GOTO 600
      ENDIF
C
C        *************** FIND THE NEXT OBJECT ****************
C
      CALL SAQQ09(LOW$THRES,HIGH$THRES,X$STEP,Y$STEP,X$POS,Y$POS,
     *            ADDR,XMIN,XMAX,YMIN,YMAX,END$FLAG,FATAL$ERROR)
      IF (FATAL$ERROR) GOTO 600

C     ******* CHECK TO SEE IF NO MORE OBJECT WERE FOUND IN THE IMAGE *****
```

```
            IF (END$FLAG)
      *     THEN
              SAVE$DATA$FLAG = .TRUE.
C
C
C               *************** DISABLE FUNCTION KEYS ***************
            CALL SCREEN(DISABLE$FUNCTION$KEYS,SCREEN$NAME,FIELD$NAME,
      *                 DATA$AREA,SCERR)
            IF (SCERR .NE. NO$SCREEN$ERROR)
      *       CALL SYERR(DISABLE$FUNCTION$KEYS,SCREEN$NAME,FIELD$NAME,
      *                  SCERR,'DISABLE FUNCTION KEYS')
C
C
C            ********** CLEAR AWAY ANY EXISITING ERROR MESSAGE ***********

IF (ERR$MESSAGE .EQ. 'C')
      *     THEN
              ERR$ONE = ' '
              ERR$TWO = ' '
              FIELD$NAME = 'ERR1'
              CALL CNSTAR(32,ERR$ONE,DATA$AREA)
              CALL SCREEN(PUT$FIELD,SCREEN$NAME,FIELD$NAME,
      *                   DATA$AREA,SCERR)
              IF (SCERR .NE. NO$SCREEN$ERROR)
      *         CALL SYERR(PUT$FIELD,SCREEN$NAME,FIELD$NAME,SCERR,
      *                    'PUT FIELD')
              FIELD$NAME = 'ERR2'
              CALL CNSTAR(32,ERR$TWO,DATA$AREA)
              CALL SCREEN(PUT$FIELD,SCREEN$NAME,FIELD$NAME,
      *                   DATA$AREA,SCERR)
              IF (SCERR .NE. NO$SCREEN$ERROR)
      *         CALL SYERR(PUT$FIELD,SCREEN$NAME,FIELD$NAME,SCERR,
      *                    'PUT FIELD')
            ENDIF
C
C
C               ***************** START IMAGE ACQUISITION ***************

CALL IMMAIN(IMAGE$START$ACQ,IMERR)
            IF (IMERR .NE. ' ') FATAL$ERROR = .TRUE.
            RETURN
          ENDIF
          CURRENT$OBJECT = CURRENT$OBJECT+1
          LAST$OBJECT = CURRENT$OBJECT
          OBJECT$BOUNDARY(1,CURRENT$OBJECT) = YMIN
          OBJECT$BOUNDARY(2,CURRENT$OBJECT) = XMIN
          OBJECT$BOUNDARY(3,CURRENT$OBJECT) = YMAX
          OBJECT$BOUNDARY(4,CURRENT$OBJECT) = XMAX
          CELL$ADDR(CURRENT$OBJECT) = ADDR
          CELL$REJECTED(CURRENT$OBJECT) = .TRUE.
          MASS(CURRENT$OBJECT) = IM$PIXEL$SUM+
      *                          TMP$CAL$OFFSET
          AREA(CURRENT$OBJECT) = IM$PIXEL$COUNT
C
C
C               *************** PUT A BOX AROUND THE OBJECT ***************

CALL SAQQ07(XMIN,XMAX,YMIN,YMAX,
      *               BOX$LEFT$POS,BOX$RIGHT$POS,BOX$TOP$POS,
      *               BOX$BOTTOM$POS,FATAL$ERROR)
          GOTO 600
        ENDIF
C************************************************************************
C
C
C             CODE TO HANDLE THE AUTOMATIC COMMAND
C
C************************************************************************
        IF (SELECTED$FUNCTION .EQ. 'AUTOMATIC')
      *   THEN
C
C
C          ****** CHECK TO SEE IF THE USER WANTS TO DO AN          *****
C          ****** AUTOMATIC WHEN THE BOX IS NOT AT THE NEXT OBJECT *****
```

```
              IF (CURRENT$OBJECT .NE. LAST$OBJECT)
      *     THEN
                ERR$ONE = 'AUTOMATIC CANNOT BE USED WHEN'
                ERR$TWO = 'THE BOX ISN''T AT THE NEXT OBJECT'
                ERR$MESSAGE = 'W'
                GOTO 600
              ENDIF
C     ***** CHECK TO SEE IF THERE IS ROOM IN THE ARRAYS *****
C     ***** TO ACCEPT ANOTHER OBJECT                    *****
C
              IF (LAST$OBJECT .GT. 512)
      *     THEN
                ERR$ONE = 'YOU CANNOT CLASSIFY MORE'
                ERR$TWO = 'THAN 512 CELLS IN THE IMAGE.'
                ERR$MESSAGE = 'W'
                GOTO 600
              ENDIF
C
C     **************** DO AUTOMATIC *****************
C
              CALL SAQQ10(LOW$THRES,HIGH$THRES,X$STEP,Y$STEP,
      *                  X$POS,Y$POS,MASS,AREA,
      *                  CELL$ADDR,CELL$REJECTED,CURRENT$OBJECT,
      *                  LAST$OBJECT,CELL$COUNT,FATAL$ERROR)
              IF (FATAL$ERROR) GOTO 600
              SAVE$DATA$FLAG = .TRUE.
C
C     *************** DISABLE FUNCTION KEYS ***************
C
              CALL SCREEN(DISABLE$FUNCTION$KEYS,SCREEN$NAME,FIELD$NAME,
      *                  DATA$AREA,SCERR)
              IF (SCERR .NE. NO$SCREEN$ERROR)
      *         CALL SYERR(DISABLE$FUNCTION$KEYS,SCREEN$NAME,FIELD$NAME,
      *                  SCERR,'DISABLE FUNCTION KEYS')
C
C     *********** CLEAR AWAY ANY EXISITING ERROR MESSAGE ***********
C
              IF (ERR$MESSAGE .EQ. 'C')
      *     THEN
                ERR$ONE = ' '
                ERR$TWO = ' '
                FIELD$NAME = 'ERR1'
                CALL CNSTAR(32,ERR$ONE,DATA$AREA)
                CALL SCREEN(PUT$FIELD,SCREEN$NAME,FIELD$NAME,
      *                    DATA$AREA,SCERR)
                IF (SCERR .NE. NO$SCREEN$ERROR)
      *           CALL SYERR(PUT$FIELD,SCREEN$NAME,FIELD$NAME,SCERR,
      *                    'PUT FIELD')
                FIELD$NAME = 'ERR2'
                CALL CNSTAR(32,ERR$TWO,DATA$AREA)
                CALL SCREEN(PUT$FIELD,SCREEN$NAME,FIELD$NAME,
      *                    DATA$AREA,SCERR)
                IF (SCERR .NE. NO$SCREEN$ERROR)
      *           CALL SYERR(PUT$FIELD,SCREEN$NAME,FIELD$NAME,SCERR,
      *                    'PUT FIELD')
              ENDIF
C
C     **************** START IMAGE ACQUISITION ***************
C
              CALL IMMAIN(IMAGE$START$ACQ,IMERR)
              IF (IMERR .NE. ' ') FATAL$ERROR = .TRUE.
              RETURN
            ENDIF
          ENDCC
CC            CELL ANALYSIS SYSTEMS, INC.
CC               (C) COPYRIGHT 1986
CC*********************************************************************
CC
CC    :PROGRAM NAME
CC     :SAQQ12
```

```
CC      :SUBROUTINES
CC      :SCREEN
CC
CC      :CALLING SEQUENCE
CC      :SAQQ12(SCRN$NAME,TOTAL$COUNT,CELL$MASS)
CC
CC      :PARAMETERS
CC      :SCRN$NAME - NAME OF THE CURRENT SCREEN
CC      :TOTAL$COUNT - TOTAL NUMBER OF CONTROL CELLS THAT WERE CLASSIFIED
CC      :CELL$MASS - AN ARRAY CONTAINING THE MASSES OF THE ACCEPTED OBJECTS
CC
CC      :DESCRIPTION
CC      :SAQQ12 CREATES A HISTO    OF THE CONTROL CELL DATA
CC
CC*********************************************************************
CC#########
        SUBROUTINE SAQQ12(SCRN:      OTAL$COUNT,CELL$MASS)
        CHARACTER*1 HALF$BAR
        CHARACTER*2 VARIABLE$EN        )
        CHARACTER*(*) SCRN$NAME
        CHARACTER*10 WHOLE$BAR
        CHARACTER*10 HISTO$STRI:
        INTEGER*2 I,TOTAL$COUNT,      PTR,BAR$VALUE(32),END
        INTEGER*4 MAX$VALUE,CELL      *),X$SCALE(5),Y$SCALE(6),
     *              DATA$VECTOR(32
        REAL*4 SCALE$VALUE,INCRE
C
        INCLUDE 'SCREEN.FIN'
C
        DATA WHOLE$BAR /Z'DBDBDE       DBDBDBDB'/,
     *       HALF$BAR /Z'DC'/,
     *       VARIABLE$ENDING /'2       ','22','23','24','25','26',
     *                        '2       ','29','30','31','32','33',
     *                        '3       ','36','37','38','39','40',
     *                        '4       2','43','44','45','46','47',
     *                        '4       9','50','51','52','53','54',
     *                        '5       6','57','58','59','60','61',
     *                        '6       3'/
C
C       ********** INITIALIZE    APPROPRIATE VARIABLES ***********
C
        SCREEN$NAME = SCRN$NAME
        I = 0
        WIDTH = 0
        PTR = 0
        END = 0
        MAX$VALUE = 0
        SCALE$VALUE = 0.0
        INCREMENT = 0.0
        DO 50 I=1,32
          HISTO$STRING(I) = ' '
   50   CONTINUE
        IF (TOTAL$COUNT .EQ. 0) GOTO 1110
C
C       ************ FIND THE SCALE VALUES FOR THE X AXIS *************
C
        DO 100 I=1,TOTAL$COUNT
          MAX$VALUE = MAX0(MAX$VALUE,CELL$MASS(I))
  100   CONTINUE
        SCALE$VALUE = 32.0
        IF (SCALE$VALUE .GE. MAX$VALUE) GOTO 200
  300   CONTINUE
        SCALE$VALUE = (SCALE$VALUE/2.0)*3.0
        IF (SCALE$VALUE .GE. MAX$VALUE) GOTO 200
        SCALE$VALUE = (SCALE$VALUE/3.0)*4.0
        IF (SCALE$VALUE .GE. MAX$VALUE) GOTO 200
        SCALE$VALUE = (SCALE$VALUE/2.0)*3.0
        IF (SCALE$VALUE .GE. MAX$VALUE) GOTO 200
        SCALE$VALUE = (SCALE$VALUE/3.0)*5.0
        IF (SCALE$VALUE .GE. MAX$VALUE) GOTO 200
        SCALE$VALUE = (SCALE$VALUE/5.0)*7.0
```

```
          IF (SCALE$VALUE .GE. MAX$VALUE) GOTO 200
          SCALE$VALUE = (SCALE$VALUE/7.0)*10.0
          IF (SCALE$VALUE .GE. MAX$VALUE) GOTO 200
          GOTO 300
   200    CONTINUE
          DO 400 I=1,5
            X$SCALE(I) = (SCALE$VALUE/4.0)*(I-1)
   400    CONTINUE
     C
     C    ************** BUCKET THE CELL DATA ****************
     C
          DO 500 I=1,32
            DATA$VECTOR(I) = 0
   500    CONTINUE
          WIDTH = X$SCALE(5)/32
          DO 600 I=1,TOTAL$COUNT
            PTR = (CELL$MASS(I)/JFIX(WIDTH))+1
            IF (PTR .LT. 1 .OR. PTR .GT. 32) GOTO 600
            DATA$VECTOR(PTR) = DATA$VECTOR(PTR)+1
   600    CONTINUE
     C
     C    *********** DETERMINE THE SCALE VALUES FOR THE Y AXIS *************
     C
          MAX$VALUE = 0
          DO 700 I=1,32
            MAX$VALUE = MAX0(MAX$VALUE,DATA$VECTOR(I))
   700    CONTINUE
          SCALE$VALUE = 20.0
          IF (SCALE$VALUE .GE. MAX$VALUE) GOTO 800
          GOTO 900
  1000    CONTINUE
          SCALE$VALUE = (SCALE$VALUE/2.0)*3.0
          IF (SCALE$VALUE .GE. MAX$VALUE) GOTO 800
          SCALE$VALUE = (SCALE$VALUE/3.0)*4.0
          IF (SCALE$VALUE .GE. MAX$VALUE) GOTO 800
   900    CONTINUE
          SCALE$VALUE = (SCALE$VALUE/2.0)*3.0
          IF (SCALE$VALUE .GE. MAX$VALUE) GOTO 800
          SCALE$VALUE = (SCALE$VALUE/3.0)*5.0
          IF (SCALE$VALUE .GE. MAX$VALUE) GOTO 800
          SCALE$VALUE = (SCALE$VALUE/5.0)*7.0
          IF (SCALE$VALUE .GE. MAX$VALUE) GOTO 800
          SCALE$VALUE = (SCALE$VALUE/7.0)*10.0
          IF (SCALE$VALUE .GE. MAX$VALUE) GOTO 800
          GOTO 1000
   800    CONTINUE
          DO 1100 I=1,6
            Y$SCALE(I) = (SCALE$VALUE/5.0)*(I-1)
  1100    CONTINUE
     C
     C    *************** CALCULATE BAR VALUES ****************
     C
          MAX$VALUE = Y$SCALE(6)
          INCREMENT = REAL(MAX$VALUE)/20.0
          DO 1200 I=1,32
            BAR$VALUE(I) = INT((REAL(DATA$VECTOR(I))/INCREMENT)+0.5)
            IF (BAR$VALUE(I) .GT. 20) BAR$VALUE(I) = 20
  1200    CONTINUE
     C
     C    ************ CREATE HISTOGRAM STRINGS **************
     C
          DO 1300 I=1,32
            END = BAR$VALUE(I)/2
            IF (END .EQ. 0) GOTO 1400
            HISTO$STRING(I)(1:END) = WHOLE$BAR(1:END)
  1400    CONTINUE
          IF (BAR$VALUE(I) .NE. END*2)
        *   HISTO$STRING(I)(END+1:END+1) = HALF$BAR
          IF ((BAR$VALUE(I) .EQ. 0) .AND. (DATA$VECTOR(I) .NE. 0))
        *   HISTO$STRING(I)(1:1) = '.'
  1300    CONTINUE
```

```
C
C  ************** PUT OUT HISTOGRAM STRINGS ***************
   1110  DO 1500 I=1,32
            FIELD$NAME = 'CS'//VARIABLE$ENDING(I+12)
            CALL CNSTAR(10,HISTO$STRING(I),DATA$AREA)
   *        CALL SCREEN(PUT$FIELD,SCREEN$NAME,FIELD$NAME,
   *                    DATA$AREA,SCERR)
            IF (SCERR .NE. NO$SCREEN$ERROR)
   *           CALL SYERR(PUT$FIELD,SCREEN$NAME,FIELD$NAME,SCERR,
   *                      'PUT FIELD')
   1500  CONTINUE
         IF (TOTAL$COUNT .EQ. 0)
   *        THEN
            DO 1550 I=1,11
               FIELD$NAME = 'CS'//VARIABLE$ENDING(I)
   *           CALL SCREEN(KILL$FIELD,SCREEN$NAME,FIELD$NAME,
   *                       DATA$AREA,SCERR)
               IF (SCERR .NE. NO$SCREEN$ERROR)
   *              CALL SYERR(KILL$FIELD,SCREEN$NAME,FIELD$NAME,SCERR,
   *                         'KILL FIELD')
   1550     CONTINUE
            RETURN
         ENDIF
C
C
C  ************ PUT OUT X AXIS SCALE NUMBERS *************
         DO 1600 I=1,5
            FIELD$NAME = 'CS'//VARIABLE$ENDING(I)
   *        CALL SCREEN(UN$KILL$FIELD,SCREEN$NAME,FIELD$NAME,
   *                    DATA$AREA,SCERR)
            IF (SCERR .NE. NO$SCREEN$ERROR)
   *           CALL SYERR(UN$KILL$FIELD,SCREEN$NAME,FIELD$NAME,SCERR,
   *                      'UNKILL FIELD')
            FIELD$NAME = 'CS'//VARIABLE$ENDING(I)
            DATA$INTEGER$4 = X$SCALE(I)
   *        CALL SCREEN(PUT$FIELD,SCREEN$NAME,FIELD$NAME,
   *                    DATA$AREA,SCERR)
            IF (SCERR .NE. NO$SCREEN$ERROR)
   *           CALL SYERR(PUT$FIELD,SCREEN$NAME,FIELD$NAME,SCERR,
   *                      'PUT FIELD')
   1600  CONTINUE
C
C
C  ************ PUT OUT Y AXIS SCALE NUMBERS *************
         DO 1700 I=1,6
            FIELD$NAME = 'CS'//VARIABLE$ENDING(I+5)
   *        CALL SCREEN(UN$KILL$FIELD,SCREEN$NAME,FIELD$NAME,
   *                    DATA$AREA,SCERR)
            IF (SCERR .NE. NO$SCREEN$ERROR)
   *           CALL SYERR(UN$KILL$FIELD,SCREEN$NAME,FIELD$NAME,SCERR,
   *                      'UNKILL FIELD')
            FIELD$NAME = 'CS'//VARIABLE$ENDING(I+5)
            DATA$INTEGER$4 = Y$SCALE(I)
   *        CALL SCREEN(PUT$FIELD,SCREEN$NAME,FIELD$NAME,
   *                    DATA$AREA,SCERR)
            IF (SCERR .NE. NO$SCREEN$ERROR)
   *           CALL SYERR(PUT$FIELD,SCREEN$NAME,FIELD$NAME,SCERR,
   *                      'PUT FIELD')
   1700  CONTINUE
         ENDCC
CC
CC             CELL ANALYSIS SYSTEMS, INC.
CC                 (C) COPYRIGHT 1986
CC***************************************************************
CC
CC
CC     :PROGRAM NAME
CC     :SAQQ13
CC
CC     :SUBROUTINES
CC     :NONE
CC
CC     :CALLING SEQUENCE
```

```
CC          :SAQQ13(SCRN$NAME,FATAL$ERROR)
CC
CC          :PARAMETERS
CC          :SCRN$NAME - NAME OF THE CURRENT SCREEN
CC          :FATAL$ERROR - A FLAG THAT SPECIFIES IF A 'FATAL'(I.E. SERIOUS) ERROR
CC                        OCCURRED WHILE IN SAQQ13
CC
CC
CC          :DESCRIPTION
CC          :SAQQ13 CALCULATES THE STATISTICS FOR THE CALIBRATION SCREEN
CC
CC*****************************************************************************
CC#########
            SUBROUTINE SAQQ13(SCRN$NAME,FATAL$ERROR)
            CHARACTER*(*) SCRN$NAME
            INTEGER*2 MX$COUNT,BUCKET,MIN$OD$BUCKET,IEND,I,J,K
            REAL*4 STDDEV,PCV,AREA$STDDEV,AREA$PCV,WIDTH,HALF$WIDTH
            REAL*8 SUM,VARIANCE,MEAN,AREA$MEAN,COUNT,MODE
            LOGICAL*1 FATAL$ERROR
C
            INCLUDE 'SAQCCD.FIN'
            INCLUDE 'IMAGED.FIN'
            INCLUDE 'SCREEN.FIN'
C
C           ************* INITIALIZE APPROPRIATE VARIABLES ***************
C
            SCREEN$NAME = SCRN$NAME
            FATAL$ERROR = .FALSE.
            BUCKET = 0
            IEND = 0
            I = 0
            J = 0
            K = 0
            SUM = 0.0
            VARIANCE = 0.0
            MEAN = 0.0
            MODE = 0.0
            STDDEV = 0.0
            PCV = 0.0
            WIDTH = 200.0
            HALF$WIDTH = WIDTH/2.0
            MIN$OD$BUCKET = INT(2000./WIDTH)
            AREA$MEAN = 0.0
            AREA$STDDEV = 0.0
            AREA$PCV = 0.0
            MX$COUNT = 0
            COUNT = 0.0
            DO 100 I=1,256
              IM$HISTOGRAM(I) = 0
    100     CONTINUE

C
C           **** CHECK TO SEE IF THE CELL COUNT IS LESS THAN OR EQUAL TO 1 ****
C
            IF (PCCD$CELLCNT .LE. 1) GOTO 800
C
C           ***************** CALCULATE MEAN ********************
C
            IEND = PCCD$CELLCNT
            DO 200 I=1,IEND
              SUM = SUM+DBLE(PCCD$CELLDATA(I))
    200     CONTINUE
            MEAN = SUM/DBLE(PCCD$CELLCNT)
C
C           ***************** CALCULATE FREQUENCY ******************
C
            IEND = PCCD$CELLCNT
            DO 300 I=1,IEND
              BUCKET = 1+INT((PCCD$CELLDATA(I)-HALFWIDTH)/WIDTH)
              IF (BUCKET .GT. 256 .OR. BUCKET .LT. 1) GOTO 300
              IF (IM$HISTOGRAM(BUCKET)+100 .GT. 32767)
```

```
            THEN
               IM$HISTOGRAM(BUCKET) = 32767
            ELSE
               IM$HISTOGRAM(BUCKET) = IM$HISTOGRAM(BUCKET)+100
            ENDIF
  300    CONTINUE
C
C        *************** FIND MAXIMUM COUNT ****************
C
         DO 400 I=MIN$OD$BUCKET,256
            K = 256+MIN$OD$BUCKET-I
            IF (IM$HISTOGRAM(K) .GE. MX$COUNT)
       *    THEN
               J = K
               MX$COUNT = IM$HISTOGRAM(K)
            ENDIF
  400    CONTINUE
C
C        ****************** SMOOTH THE HISTOGRAM ******************
C
         IM$PKS$WANTED = 2
         IM$SMOOTH$LOW$LIM = MIN$OD$BUCKET
         IM$SMOOTH$HIGH$LIM = 255
         CALL IMMAIN(IMAGE$SMOOTH$HIST,IMERR)
         IF (IMERR .NE. ' ')
       * THEN
            FATAL$ERROR = .TRUE.
            RETURN
         ENDIF
         IF (IM$PKS$FOUND .EQ. 0 .OR. IM$VALLS$PKS(2) .EQ. 256)
       * THEN
            MODE = 0.
         ELSEIF (IM$PKS$FOUND .EQ. 1)
       * THEN
            MODE = INT(WIDTH+0.5)*IM$VALLS$PKS(2)
         ELSE
            I = ABS(IM$VALLS$PKS(2)-J)
            K = ABS(IM$VALLS$PKS(4)-J)
            IF (K .GT. I)
       *    THEN
               MODE = INT(WIDTH+0.5)*IM$VALLS$PKS(2)
            ELSE
               MODE = INT(WIDTH+0.5)*IM$VALLS$PKS(4)
            ENDIF
         ENDIF
C
C        *************** CALCULATE DNA VS. MODE INTERCEPT ****************
C
         IEND = PCCD$CELLCNT
         DO 500 I=1,IEND
            VARIANCE = VARIANCE+(DBLE(PCCD$CELLDATA(I))-MEAN)**2
  500    CONTINUE
         VARIANCE = VARIANCE/DBLE(PCCD$CELLCNT-1)
         STDDEV = SNGL(DSQRT(VARIANCE))
         PCV = STDDEV/SNGL(MEAN)*100.0
         SUM = 0.0
         IEND = PCCD$CELLCNT
         DO 600 I=1,IEND
            SUM = SUM+DBLE(PCCD$AREA(I))
  600    CONTINUE
         AREA$MEAN = SUM/DBLE(PCCD$CELLCNT)
         VARIANCE = 0.0
         DO 700 I=1,IEND
            VARIANCE = VARIANCE+(DBLE(PCCD$AREA(I))-AREA$MEAN)**2
  700    CONTINUE
         VARIANCE = VARIANCE/DBLE(PCCD$CELLCNT-1)
         AREA$STDDEV = SNGL(DSQRT(VARIANCE))
         AREA$PCV = AREA$STDDEV/SNGL(AREA$MEAN)*100.0
  800    CONTINUE
C
C        ******* PUT OUT STATISTICS TO THE CALIBRATION SCREEN *********
C
```

```
      FIELD$NAME = 'CS15'
      DATA$AREA(1) = PCCD$CELLCNT
      CALL SCREEN(PUT$FIELD,SCREEN$NAME,FIELD$NAME,
     *            DATA$AREA,SCERR)
      IF (SCERR .NE. NO$SCREEN$ERROR)
     *   CALL SYERR(PUT$FIELD,SCREEN$NAME,FIELD$NAME,SCERR,
     *              'PUT FIELD')
      MEAN = DBLE(MODE)
      FIELD$NAME = 'CS17'
      DATA$INTEGER$4 = JFIX(MEAN+0.5)
      CALL SCREEN(PUT$FIELD,SCREEN$NAME,FIELD$NAME,
     *            DATA$AREA,SCERR)
      IF (SCERR .NE. NO$SCREEN$ERROR)
     *   CALL SYERR(PUT$FIELD,SCREEN$NAME,FIELD$NAME,SCERR,
     *              'PUT FIELD')
C
C     *************** SET COMMON VARIABLES ***************
C
      PCCD$MEAN = SNGL(MEAN)
      ENDCC
CC              CELL ANALYSIS SYSTEMS, INC.
CC              (C) COPYRIGHT 1986
CC*******************************************************************
CC
CC
CC    :PROGRAM NAME
CC    :SAQQ14
CC
CC    :SUBROUTINES
CC    :SCREEN
CC
CC    :CALLING SEQUENCE
CC    :SAQQ14(SCRN$NAME,PICO$HIST,TYPE$SELECTED,AUTO$SCALE,X$SCALE,
CC            DATA$VECTOR,XSCALE$NUM,SHOWN$COUNT)
CC
CC    :PARAMETERS
CC    :SCRN$NAME - NAME OF THE CURRENT SCREEN
CC    :PICO$HIST - AN ARRAY THAT CONTAINS THE RAW HISTOGRAM OF THE
CC                 CELL MASS DATA
CC    :TYPE$SELECTED - A LOGICAL ARRAY THAT SPECIFIES WHICH TYPES
CC                    WERE SELECTED
CC    :AUTO$SCALE - A LOGICAL VARIABLE THAT SPECIFIES IF AUTO SCALING
CC                  IS ACTIVE
CC    :X$SCALE - AN ARRAY THAT CONTAINS THE X AXIS SCALING VALUES
CC    :DATA$VECTOR - AN ARRAY THAT CONTAINS THE HISTOGRAM COUNTS
CC    :XSCALE$NUM - LAST X SCALE FACTOR
CC    :SHOWN$COUNT - THE NUMBER OF CELLS DISPLAYED ON THE HISTOGRAM
CC
CC    :DESCRIPTION
CC    :SAQQ14 CREATES A HISTOGRAM OF THE CELL DATA
CC
CC*******************************************************************
CC#########
      SUBROUTINE SAQQ14(SCRN$NAME,PICO$HIST,TYPE$SELECTED,
     *                  AUTO$SCALE,X$SCALE,DATA$VECTOR,XSCALE$NUM,
     *                  SHOWN$COUNT)
      CHARACTER*1 HALF$BAR
      CHARACTER*2 VARIABLE$ENDING(39),VAR$ENDING2(32)
      CHARACTER*(*) SCRN$NAME
      CHARACTER*10 HISTO$STRING(32),WHOLE$BAR
      INTEGER*2 I,BAR$VALUE(32),END,OFF$SCALE,
     *          MAX$BUCKET,INCREMENT2,PICO$HIST(*),INCR,K,
     *          SHOWN$COUNT,X$SCALE(*),XSCALE$NUM
      INTEGER*4 Y$SCALE(6),DATA$VECTOR(*),MAX$VALUE
      REAL*4 SCALE$VALUE,INCREMENT
      LOGICAL*1 AUTO$SCALE,TYPE$SELECTED(*)
C
      INCLUDE 'SAQCCD.FIN'
      INCLUDE 'SAQCDT.FIN'
      INCLUDE 'SCREEN.FIN'
C
      DATA WHOLE$BAR /Z'DBDBDBDBDBDBDBDBDBDB'/,
```

```
    *         HALF$BAR /Z'DC'/,
    *         VARIABLE$ENDING
    *            /'25','26','27','28','29','30','31','32','33',
    *             '34','35','36','37','38','39','40',
    *             '41','42','43','44','45','46','47',
    *             '48','49','50','51','52','53','54',
    *             '55','56','57','58','59','60','61',
    *             '62','63'/,
    *         VAR$ENDING2
    *            /'01','02','03','04','05','06','07','08','09','10',
    *             '11','12','13','14','15','16','17','18','19','20',
    *             '21','22','23','24','25','26','27','28','29','30',
    *             '31','32'/
C
C
C         ************ INITIALIZE THE APPROPRIATE VARIABLES ************
C
          SCREEN$NAME = SCRN$NAME
          DO 50 I=1,32
             HISTO$STRING(I) = ' '
             BAR$VALUE(I) = 0
 50       CONTINUE
          I = 0
          END = 0
          K = 0
          INCR = 0
          OFF$SCALE = 0
          MAX$BUCKET = 0
          INCREMENT2 = 0
          MAX$VALUE = 0
          SHOWN$COUNT = 0
          SCALE$VALUE = 0.0
          INCREMENT = 0.0
          MAX$BUCKET = 0
          OFF$SCALE = 0
C
C         ***************** BUCKET THE DATA ******************
C
          DO 120 I=1,6
             IF (.NOT. TYPE$SELECTED(I)) GOTO 120
             OFF$SCALE = OFF$SCALE+PCDT$OFF$SCALE(I)
 120      CONTINUE
          DO 150 I=640,1,-1
             IF (PICO$HIST(I) .NE. 0)
    *        THEN
                MAX$BUCKET = I
                GOTO 160
             ENDIF
 150      CONTINUE
 160      IF (MAX$BUCKET .EQ. 0)
    *     THEN
             SHOWN$COUNT = 0
             GOTO 1525
          ENDIF
          IF (AUTO$SCALE .AND. X$SCALE(5) .EQ. 64)
    *     THEN
             IF (MAX$BUCKET .LE. 160)
    *        THEN
                XSCALE$NUM = 16
                INCREMENT2 = 4
             ELSEIF (MAX$BUCKET .LE. 320)
    *        THEN
                XSCALE$NUM = 32
                INCREMENT2 = 8
             ELSE
                GOTO 170
             ENDIF
             X$SCALE(1) = 0
             DO 180 I=2,5
                X$SCALE(I) = X$SCALE(I-1)+INCREMENT2
 180         CONTINUE
          ENDIF
```

```
      170   END = XSCALE$NUM*10
            DO 190 I=1,END
               SHOWN$COUNT = SHOWN$COUNT+PICO$HIST(I)
      190   CONTINUE
            DO 200 I=END+1,640
               OFF$SCALE = OFF$SCALE+PICO$HIST(I)
      200   CONTINUE
            IF (XSCALE$NUM .EQ. 16)
          * THEN
               INCR = 5
            ELSEIF (XSCALE$NUM .EQ. 32)
          * THEN
               INCR = 10
            ELSE
               INCR = 20
            ENDIF
            DO 300 I=1,32
               DATA$VECTOR(I) = 0
      300   CONTINUE
            DO 320 I=1,INCR-1
               DATA$VECTOR(1) = DATA$VECTOR(1)+PICO$HIST(I)
      320   CONTINUE
            DO 400 I=1,30
               DO 420 J=0,INCR-1
                  K = (I*INCR)+J
                  DATA$VECTOR(I+1) = DATA$VECTOR(I+1)+PICO$HIST(K)
      420      CONTINUE
      400   CONTINUE
            DO 440 I=0,INCR
               K = (31*INCR)+I
               DATA$VECTOR(32) = DATA$VECTOR(32)+PICO$HIST(K)
      440   CONTINUE
    C
    C     ********** DETERMINE THE SCALE VALUES FOR THE Y AXIS ***********
    C
      625   MAX$VALUE = 0
            DO 700 I=1,32
               MAX$VALUE = MAX0(MAX$VALUE,DATA$VECTOR(I))
      700   CONTINUE
            SCALE$VALUE = 20.0
            IF (SCALE$VALUE .GE. MAX$VALUE) GOTO 800
            GOTO 900
     1000   CONTINUE
            SCALE$VALUE = (SCALE$VALUE/2.0)*3.0
            IF (SCALE$VALUE .GE. MAX$VALUE) GOTO 800
            SCALE$VALUE = (SCALE$VALUE/3.0)*4.0
            IF (SCALE$VALUE .GE. MAX$VALUE) GOTO 800
      900   CONTINUE
            SCALE$VALUE = (SCALE$VALUE/2.0)*3.0
            IF (SCALE$VALUE .GE. MAX$VALUE) GOTO 800
            SCALE$VALUE = (SCALE$VALUE/3.0)*5.0
            IF (SCALE$VALUE .GE. MAX$VALUE) GOTO 800
            SCALE$VALUE = (SCALE$VALUE/5.0)*7.0
            IF (SCALE$VALUE .GE. MAX$VALUE) GOTO 800
            SCALE$VALUE = (SCALE$VALUE/7.0)*10.0
            IF (SCALE$VALUE .GE. MAX$VALUE) GOTO 800
            GOTO 1000
      800   CONTINUE
            DO 1100 I=1,6
               Y$SCALE(I) = (SCALE$VALUE/5.0)*(I-1)
     1100   CONTINUE
    C
    C     *************** CALCULATE BAR VALUES ****************
    C
            MAX$VALUE = Y$SCALE(6)
            INCREMENT = REAL(MAX$VALUE)/20.0
            DO 1200 I=1,32
               BAR$VALUE(I) = INT((REAL(DATA$VECTOR(I))/INCREMENT)+0.5)
               IF (BAR$VALUE(I) .GT. 20) BAR$VALUE(I) = 20
     1200   CONTINUE
    C
```

```
C         ************ CREATE HISTOGRAM STRINGS ***************
C
          DO 1300 I=1,32
            END = BAR$VALUE(I)/2
            IF (END .EQ. 0) GOTO 1400
            HISTO$STRING(I)(1:END) = WHOLE$BAR(1:END)
 1400     CONTINUE
          IF (BAR$VALUE(I) .NE. END*2)
     *      HISTO$STRING(I)(END+1:END+1) = HALF$BAR
          IF ((BAR$VALUE(I) .EQ. 0) .AND. (DATA$VECTOR(I) .NE. 0))
     *      HISTO$STRING(I)(1:1) = '.'
 1300     CONTINUE
C
C         *************** PUT OUT HISTOGRAM STRINGS ****************
C
 1525     DO 1500 I=1,32
            FIELD$NAME = 'CS'//VARIABLE$ENDING(I+7)
            CALL CNSTAR(10,HISTO$STRING(I),DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            FIELD$NAME = 'AA'//VAR$ENDING2(I)
            CALL CNSTAR(10,HISTO$STRING(I),DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            FIELD$NAME = 'AB'//VAR$ENDING2(I)
            CALL CNSTAR(10,HISTO$STRING(I),DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            FIELD$NAME = 'AC'//VAR$ENDING2(I)
            CALL CNSTAR(10,HISTO$STRING(I),DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
 1500     CONTINUE
C
C         ******** IF THE SHOWN$COUNT IS NOT EQUAL TO ZERO, *********
C         ******** THEN PUT OUT THE SCALE VALUES. OTHERWISE *********
C         ******** KILL THE SCALE VALUE FIELDS              *********
C
          IF (SHOWN$COUNT .EQ. 0)
     *    THEN
            DO 1550 I=1,5
              FIELD$NAME = 'AS'//VARIABLE$ENDING(I+11)
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,SCERR,
     *                     'KILL FIELD')
 1550       CONTINUE
            DO 1575 I=1,6
              FIELD$NAME = 'CS'//VARIABLE$ENDING(I)
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,SCERR,
     *                     'KILL FIELD')
```

```
            CALL SCREEN(UN$KILL$FIELD,SCREEN$NAME,FIELD$NAME,
  *                DATA$AREA,SCERR)
            IF (SCERR .NE. NO$SCREEN$ERROR)
  *           CALL SYERR(UN$KILL$FIELD,SCREEN$NAME,FIELD$NAME,SCERR,
  *                'UNKILL FIELD')
            FIELD$NAME = 'AS'//VARIABLE$ENDING(I+11)
            DATA$AREA(1) = X$SCALE(I)
            CALL SCREEN(PUT$FIELD,SCREEN$NAME,FIELD$NAME,
  *                DATA$AREA,SCERR)
            IF (SCERR .NE. NO$SCREEN$ERROR)
  *           CALL SYERR(PUT$FIELD,SCREEN$NAME,FIELD$NAME,SCERR,
  *                'PUT FIELD')
1600      CONTINUE
C
C         *********** PUT OUT Y AXIS SCALE NUMBERS ************
C
          DO 1700 I=1,6
            FIELD$NAME = 'CS'//VARIABLE$ENDING(I)
            CALL SCREEN(UN$KILL$FIELD,SCREEN$NAME,FIELD$NAME,
  *                DATA$AREA,SCERR)
            IF (SCERR .NE. NO$SCREEN$ERROR)
  *           CALL SYERR(UN$KILL$FIELD,SCREEN$NAME,FIELD$NAME,SCERR,
  *                'UNKILL FIELD')
            FIELD$NAME = 'CS'//VARIABLE$ENDING(I)
            DATA$INTEGER$4 = Y$SCALE(I)
            CALL SCREEN(PUT$FIELD,SCREEN$NAME,FIELD$NAME,
  *                DATA$AREA,SCERR)
            IF (SCERR .NE. NO$SCREEN$ERROR)
  *           CALL SYERR(PUT$FIELD,SCREEN$NAME,FIELD$NAME,SCERR,
  *                'PUT FIELD')
1700      CONTINUE
          ENDIF
          FIELD$NAME = 'AS32'
          DATA$AREA(1) = SHOWN$COUNT
          CALL SCREEN(PUT$FIELD,SCREEN$NAME,FIELD$NAME,
  *                DATA$AREA,SCERR)
          IF (SCERR .NE. NO$SCREEN$ERROR)
  *         CALL SYERR(PUT$FIELD,SCREEN$NAME,FIELD$NAME,SCERR,
  *                'PUT FIELD')
          FIELD$NAME = 'AS33'
          DATA$AREA(1) = OFF$SCALE
          CALL SCREEN(PUT$FIELD,SCREEN$NAME,FIELD$NAME,
  *                DATA$AREA,SCERR)
          IF (SCERR .NE. NO$SCREEN$ERROR)
  *         CALL SYERR(PUT$FIELD,SCREEN$NAME,FIELD$NAME,SCERR,
  *                'PUT FIELD')
          ENDCC
CC             CELL ANALYSIS SYSTEMS, INC.
CC                 (C) COPYRIGHT 1986
CC****************************************************************
CC
CC     :PROGRAM NAME
CC     :SAQQ15
CC
CC     :SUBROUTINES
CC     :IMMAIN
CC     :SCREEN
CC
CC     :CALLING SEQUENCE
CC     :SAQQ15(SCRN$NAME,DNA$CONV$VALUE,ANALYSIS$TOTAL,PICO$HIST,TYPE$SELECTED,
CC            FIRST$PEAK$MASS,FIRST$PEAK$INDEX,FIRST$PEAK$AREA,FATAL$ERROR)
CC
CC     :PARAMETERS
CC     :SCRN$NAME - NAME OF THE CURRENT SCREEN
CC     :DNA$CONV$VALUE - THE DNA CONVERSION VALUE
CC     :ANALYSIS$TOTAL - THE NUMBER OF CELLS THAT HAVE BEEN MEASURED
CC     :PICO$HIST - AN ARRAY THAT CONTAINS THE RAW HISTOGRAM OF THE
CC                  CELL MASS DATA
CC     :TYPE$SELECTED - A LOGICAL ARRAY THAT SPECIFIES WHICH TYPES
CC                     WERE SELECTED
CC     :FIRST$PEAK$MASS - MASS OF FIRST PEAK
```

```
CC           :FIRST$PEAK$INDEX - INDEX OF THE FIRST PEAK
CC           :FIRST$PEAK$AREA - AREA OF THE FIRST PEAK
CC           :FATAL$ERROR - A FLAG THAT SPECIFIES IF A 'FATAL'(I.E. SERIOUS)
CC                         ERROR OCCURRED WHILE IN SAQQ15
CC
CC           :DESCRIPTION
CC           :SAQQ15 CALCULATES THE STATISTICS FOR THE ANALYSIS SCREEN
CC***********************************************************************
CC#######
         SUBROUTINE SAQQ15(SCRN$NAME,DNA$CONV$VALUE,
        *                  ANALYSIS$TOTAL,PICO$HIST,TYPE$SELECTED,
        *                  FIRST$PEAK$MASS,FIRST$PEAK$INDEX,
        *                  FIRST$PEAK$AREA,FATAL$ERROR)
         CHARACTER*(*) SCRN$NAME
         INTEGER*2 I,J,IEND,WIDTH,BUCKET,PICOMASS,MAX,MAX$VALUE,
        *           MODE,HALF$WIDTH,PICO$HIST(*),VALUE(21),INDX,INDX1,
        *           INDX2,DIFF,DIFF1,DIFF2,ANALYSIS$TOTAL,AREA$VALUE1,
        *           TIE$VALUES(15),TIE$COUNTER
         INTEGER*4 AREA$VALUE2
         REAL*4 MODE2,AMODE2,FIRST$PEAK$MASS,
        *        FIRST$PEAK$INDEX,FIRST$PEAK$AREA,TEMP,
        *        DNA$CONV$VALUE
         REAL*8 COUNT,ASUM,AREA$CONV
         LOGICAL*1 TYPE$SELECTED(*),FATAL$ERROR
C
         EQUIVALENCE (AREA$VALUE2,AREA$VALUE1)
C
         INCLUDE 'SAQCCD.FIN'
         INCLUDE 'SAQCDT.FIN'
         INCLUDE 'IMAGED.FIN'
         INCLUDE 'SCREEN.FIN'
C
C
C            ************* INITIALIZE APPROPRIATE VARIABLES *************
         SCREEN$NAME = SCRN$NAME
         MODE = 0
         AREA$VALUE1 = 0
         AREA$VALUE2 = 0
         TIE$COUNTER = 0
         ASUM = 0.0
         COUNT = 0.0
         I = 0
         J = 0
         DIFF = 0
         DIFF1 = 0
         DIFF2 = 0
         INDX = 0
         INDX1 = 0
         INDX2 = 0
         IEND = 0
         BUCKET = 0
         MAX = 0
         MAX$VALUE = 0
         HALF$WIDTH = 0
         FIRST$PEAK$MASS = 0.0
         FIRST$PEAK$INDEX = 0.0
         FIRST$PEAK$AREA = 0.0
         TEMP = 0.0
         FATAL$ERROR = .FALSE.
C
         MODE2 = 0.0
         AMODE2 = 0.0
         IF (ANALYSIS$TOTAL .EQ. 0) GOTO 700
         AREA$CONV = 31.8*((40.0/100.0)**2)
         PICOMASS = INT(PCCD$PICOMASS)
         WIDTH = 0.1*PICOMASS
         HALF$WIDTH = WIDTH/2
         DO 800 J=1,256
            IM$HISTOGRAM(J) = 0
800      CONTINUE
```

```
         CALL IMOVB(510,PICO$HIST(1),IM$HISTOGRAM(2))
         IM$HISTOGRAM(1) = 0
         DO 810 I=1,256
            IM$HISTOGRAM(I) = IM$HISTOGRAM(I)*15
810      CONTINUE
         MAX = 0
         MAX$VALUE = 0
         IM$SMOOTH$LOW$LIM = 15
         IM$SMOOTH$HIGH$LIM = 255
         IM$PKS$WANTED = 4
         CALL IMMAIN(IMAGE$SMOOTH$HIST,IMERR)
         IF (IMERR .NE. ' ')
     *   THEN
            FATAL$ERROR = .TRUE.
            RETURN
         ENDIF
         IF (IM$PKS$FOUND .EQ. 4)
     *   THEN
            CONTINUE
         ELSEIF (IM$PKS$FOUND .EQ. 3)
     *   THEN
            IM$VALLS$PKS(8) = -1
         ELSEIF (IM$PKS$FOUND .EQ. 2)
     *   THEN
            IM$VALLS$PKS(6) = -1
            IM$VALLS$PKS(8) = -1
         ELSEIF (IM$PKS$FOUND .EQ. 1 .AND. IM$VALLS$PKS(2) .NE. 256)
     *   THEN
            MODE = IM$VALLS$PKS(2)-1
            GOTO 990
         ENDIF
         IF (IM$VALLS$PKS(2) .EQ. 256 .OR. IM$PKS$FOUND .EQ. 0)
     *   THEN
            AMODE2 = 0
            MODE2 = 0
            GOTO 705
         ENDIF
         MAX$VALUE = 0
         DO 965 I=2,8
            INDX = IM$VALLS$PKS(I)
            IF (IM$HISTOGRAM(INDX) .GT. MAX$VALUE)
     *      THEN
               MODE = IM$VALLS$PKS(I)-1
               MAX$VALUE = IM$HISTOGRAM(INDX)
            ENDIF
965      CONTINUE
990      IF (MODE-7 .LT. 1)
     *   THEN
            VALUE(1) = -1
         ELSE
            VALUE(1) = PICO$HIST(MODE-7)
         ENDIF
         IF (MODE-6 .LT. 1)
     *   THEN
            VALUE(2) = -1
         ELSE
            VALUE(2) = PICO$HIST(MODE-6)
         ENDIF
         IF (MODE-5 .LT. 1)
     *   THEN
            VALUE(3) = -1
         ELSE
            VALUE(3) = PICO$HIST(MODE-5)
         ENDIF
         IF (MODE-4 .LT. 1)
     *   THEN
            VALUE(4) = -1
         ELSE
            VALUE(4) = PICO$HIST(MODE-4)
         ENDIF
         IF (MODE-3 .LT. 1)
```

```
    *    THEN
           VALUE(5) = -1
         ELSE
           VALUE(5) = PICO$HIST(MODE-3)
         ENDIF
         IF (MODE-2 .LT. 1)
    *    THEN
           VALUE(6) = -1
         ELSE
           VALUE(6) = PICO$HIST(MODE-2)
         ENDIF
         IF (MODE-1 .LT. 1)
    *    THEN
           VALUE(7) = -1
         ELSE
           VALUE(7) = PICO$HIST(MODE-1)
         ENDIF
         VALUE(8) = PICO$HIST(MODE)
         IF (MODE+1 .GT. 256)
    *    THEN
           VALUE(9) = -1
         ELSE
           VALUE(9) = PICO$HIST(MODE+1)
         ENDIF
         IF (MODE+2 .GT. 256)
    *    THEN
           VALUE(10) = -1
         ELSE
           VALUE(10) = PICO$HIST(MODE+2)
         ENDIF
         IF (MODE+3 .GT. 256)
    *    THEN
           VALUE(11) = -1
         ELSE
           VALUE(11) = PICO$HIST(MODE+3)
         ENDIF
         IF (MODE+4 .GT. 256)
    *    THEN
           VALUE(12) = -1
         ELSE
           VALUE(12) = PICO$HIST(MODE+4)
         ENDIF
         IF (MODE+5 .GT. 256)
    *    THEN
           VALUE(13) = -1
         ELSE
           VALUE(13) = PICO$HIST(MODE+5)
         ENDIF
         IF (MODE+6 .GT. 256)
    *    THEN
           VALUE(14) = -1
         ELSE
           VALUE(14) = PICO$HIST(MODE+6)
         ENDIF
         IF (MODE+7 .GT. 256)
    *    THEN
           VALUE(15) = -1
         ELSE
           VALUE(15) = PICO$HIST(MODE+7)
         ENDIF
         TIE$COUNTER = 1
         MAX$VALUE = 0
         DO 975 I=1,15
           J = (MODE-7)+(I-1)
           IF (VALUE(I) .GT. MAX$VALUE)
    *      THEN
             MAX$VALUE = VALUE(I)
             INDX = J
             DIFF = ABS(8-I)
```

```
          ELSEIF (VALUE(I) .EQ. MAX$VALUE .AND. MAX$VALUE .NE. 0)
      *     THEN
              TIE$COUNTER = TIE$COUNTER+1
              TIE$VALUES(TIE$COUNTER) = J
              IF (ABS(8-I) .LT. DIFF)
      *         THEN
                  INDX = J
                  DIFF = ABS(8-I)
              ENDIF
          ENDIF
 975    CONTINUE
          IF (MAX$VALUE .EQ. 0)
      *     THEN
              AMODE2 = 0
              MODE2 = 0
              GOTO 700
          ENDIF
          IF (TIE$COUNTER .EQ. 3)
      *     THEN
              INDX = TIE$VALUES(2)
          ELSEIF (TIE$COUNTER .EQ. 5)
      *     THEN
              INDX = TIE$VALUES(3)
          ELSEIF (TIE$COUNTER .EQ. 7)
      *     THEN
              INDX = TIE$VALUES(4)
          ELSEIF (TIE$COUNTER .EQ. 9)
      *     THEN
              INDX = TIE$VALUES(5)
          ELSEIF (TIE$COUNTER .EQ. 11)
      *     THEN
              INDX = TIE$VALUES(6)
          ELSEIF (TIE$COUNTER .EQ. 13)
      *     THEN
              INDX = TIE$VALUES(7)
          ELSEIF (TIE$COUNTER .EQ. 15)
      *     THEN
              INDX = TIE$VALUES(8)
          ENDIF
          MAX = INDX
          MODE2 = 0.1*INDX
          DO 1200 I=1,ANALYSIS$TOTAL
            J = PCDT$CLASS(I)+1
            IF (.NOT. TYPE$SELECTED(J)) GOTO 1200
            IF (PCDT$640(I) .LT. (MAX-3) .OR.
      *         PCDT$640(I) .GT. (MAX+3)) GOTO 1200
            AREA$VALUE1 = PCDT$AREA(I)
            ASUM = ASUM+DBLE(AREA$VALUE2)
            COUNT = COUNT+1.0
 1200   CONTINUE
          AMODE2 = SNGL(ASUM/COUNT)
          AMODE2 = AMODE2/AREA$CONV
 700    CONTINUE
          IF (ANALYSIS$TOTAL .NE. 0)
      *     THEN
              FIRST$PEAK$MASS = MODE2
              TEMP = MODE2/DNA$CONV$VALUE
              FIRST$PEAK$INDEX = TEMP+0.005
              FIRST$PEAK$AREA = AMODE2
          ENDIF
C
C       *************** PUT OUT VALUES ****************
C
 705    FIELD$NAME = 'AS25'
        DATA$REAL = FIRST$PEAK$MASS
        CALL SCREEN(PUT$FIELD,SCREEN$NAME,FIELD$NAME,
      *             DATA$AREA,SCERR)
        IF (SCERR .NE. NO$SCREEN$ERROR)
      *   CALL SYERR(PUT$FIELD,SCREEN$NAME,FIELD$NAME,SCERR,
      *              'PUT FIELD')
        FIELD$NAME = 'AS26'
```

```
              DATA$REAL = FIRST$PEAK$INDEX
              CALL SCREEN(PUT$FIELD,SCREEN$NAME,FIELD$NAME,
         *                DATA$AREA,SCERR)
              IF (SCERR .NE. NO$SCREEN$ERROR)
         *      CALL SYERR(PUT$FIELD,SCREEN$NAME,FIELD$NAME,SCERR,
         *                 'PUT FIELD')
              FIELD$NAME = 'AS27'
              DATA$REAL = FIRST$PEAK$AREA
              CALL SCREEN(PUT$FIELD,SCREEN$NAME,FIELD$NAME,
         *                DATA$AREA,SCERR)
              IF (SCERR .NE. NO$SCREEN$ERROR)
         *      CALL SYERR(PUT$FIELD,SCREEN$NAME,FIELD$NAME,SCERR,
         *                 'PUT FIELD')
              END
CC
CC
CC                CELL ANALYSIS SYSTEMS, INC.
CC                   (C) COPYRIGHT 1986
CC***************************************************************************
CC
CC       :PROGRAM NAME
CC       :SAQQ16
CC
CC       :SUBROUTINES
CC       :IMMAIN
CC       :SAQQ07
CC       :SAQQ08
CC       :SAQQ19
CC       :SAQQ17
CC       :SCREEN
CC
CC       :CALLING SEQUENCE
CC       :SAQQ16(SCRN$NAME,LAST$OBJECT,CELL$COUNT,MASS,AREA,CELL$TYPE,CELL$REJECT
CC               SAVE$DATA$FLAG,FATAL$ERROR)
CC
CC       :PARAMETERS
CC       :SCRN$NAME - THE NAME OF THE CURRENT SCREEN
CC       :LAST$OBJECT - INDEX INTO THE MASS AND AREA ARRAYS, OF THE LAST OBJECT
CC       :CELL$COUNT - NUMBER OF CELLS THAT WERE ACCEPTED
CC       :MASS - AN ARRAY THAT CONTAINS THE MASSES OF THE OBJECTS
CC       :AREA - AN ARRAY THAT CONTAINS THE AREA OF THE OBJECTS
CC       :CELL$TYPE - AN ARRAY THAT CONTAINS THE TYPE OF THE OBJECTS
CC       :CELL$REJECTED - A LOGICAL ARRAY THAT SPECIFIES IF AN OBJECT WAS
CC                       ACCEPTED OR REJECTED
CC       :SAVE$DATA$FLAG - A FLAG THAT SPECIFIES IF THE DATA, THAT WAS MEASURED,
CC                       WILL BE SAVED
CC       :FATAL$ERROR - A FLAG THAT SPECIFIES IF A 'FATAL'(I.E SERIOUS) ERROR
CC                     OCCURRED WHILE IN SAQQ11
CC
CC       :DESCRIPTION
CC       :SAQQ16 HANDLES THE MEASURE COMMAND THAT IS IN THE ANALYSIS SCREEN
CC
CC***************************************************************************
CC########
          SUBROUTINE SAQQ16(SCRN$NAME,LAST$OBJECT,CELL$COUNT,MASS,AREA,
         *                  XY,CELL$TYPE,CELL$REJECTED,SAVE$DATA$FLAG,
         *                  FATAL$ERROR)
C
          CHARACTER*1 ERR$MESSAGE
          CHARACTER*3 NUM$STRING,KEY$TYPE
          CHARACTER*(*) SCRN$NAME
          CHARACTER*7 STRNG
          CHARACTER*9 READ$INPUT$VALUE
          CHARACTER*9 SELECTED$FUNCTION
          CHARACTER*32 ERR$ONE,ERR$TWO
          INTEGER*2 I,LOW$THRES,HIGH$THRES,X$POS,Y$POS,ADDR,X$STEP,
         *           Y$STEP,XMIN,XMAX,YMIN,YMAX,CURRENT$OBJECT,
         *           LAST$OBJECT,OBJECT$BOUNDARY(4,151),
         *           NUM$VALUE,CELL$ADDR(151),
         *           CELL$COUNT,XLEN,YLEN,NUM$PAD$VALUE,
         *           STACK(3,100),J,X$DIR$CHANGE(9),Y$DIR$CHANGE(9),
```

```
     *          BOX$BOTTOM$POS,STACK$PTR,X$CENTER,Y$CENTER,
     *          CURSOR$X$POS,CURSOR$Y$POS,L$VALUE,NEW$CURSOR$X$POS,
     *          NEW$CURSOR$Y$POS,STEP$SIZE,X$LOC,Y$LOC,CELL$TYPE(*),
     *          TYPE$VALUE,TYPE$COLOR(6),CURSOR$STEP,TEMP$TYPE,
     *          HORIZ$LENGTH,VERT$LENGTH,VALUES$254(128),
     *          SAVED$LEFT(128),SAVED$RIGHT(128),SAVED$TOP(128),
     *          SAVED$BOTTOM(128),XY(2)
       INTEGER*4 MASS(*),AREA(*),VALUE$64K,ADDR$4
       LOGICAL*1 FATAL$ERROR,END$FLAG,CELL$REJECTED(*),
     *          SAVE$DATA$FLAG,PEN$DOWN,CENTER$INVALID,
     *          LGCL$VALUE
C
       EQUIVALENCE (LGCL$VALUE,L$VALUE),(ADDR$4,ADDR)
C
       INCLUDE 'SAQCDT.FIN'
       INCLUDE 'SAQCCD.FIN'
       INCLUDE 'IMAGED.FIN'
       INCLUDE 'IMAGEL.FIN'
       INCLUDE 'SCREEN.FIN'
C
       DATA VALUE$64K /65536/,
     *      VALUES$254/128*Z'FEFE'/,
     *      TYPE$COLOR /249,251,252,253,254,255/,
     *      X$DIR$CHANGE /-1,0,1,-1,9,1,-1,0,1/,
     *      Y$DIR$CHANGE /1,1,1,0,9,0,-1,-1,-1/
C
C      *********** INITALIZE THE APPROPRIATE VARIABLES ************
C
       SCREEN$NAME = SCRN$NAME
       ERR$MESSAGE = ' '
       NUM$STRING = ' '
       KEY$TYPE = ' '
       READ$INPUT$VALUE = ' '
       STRNG = ' '
       ERR$ONE = ' '
       ERR$TWO = ' '
       SELECTED$FUNCTION = ' '
       I = 0
       LOW$THRES = PCSG$LO$THRES
       HIGH$THRES = PCSG$HI$THRES
       XLEN = 0
       YLEN = 0
       X$POS = 0
       Y$POS = 0
       ADDR = 771
       X$STEP = PCSG$X$STEP
       Y$STEP = PCSG$Y$STEP
       TEMP$TYPE = 0
       XY(1) = 0
       XY(2) = 0
       XMIN = 0
       XMAX = 0
       YMIN = 0
       YMAX = 0
       CURSOR$STEP = 0
       NUM$VALUE = 0
       CELL$COUNT = 0
       NUM$PAD$VALUE = 0
       TYPE$VALUE = 0
       J = 0
       BOX$LEFT$POS = 0
       BOX$RIGHT$POS = 0
       BOX$TOP$POS = 0
       BOX$BOTTOM$POS = 0
       START = 0
       START$PTR = 0
       X$CENTER = 0
       Y$CENTER = 0
       CURSOR$X$POS = 0
       CURSOR$Y$POS = 0
```

```
        NEW$CURSOR$X$POS = 0
        NEW$CURSOR$Y$POS = 0
        STEP$SIZE = 0
        X$LOC = 0
        Y$LOC = 0
        PEN$DOWN = .FALSE.
        CENTER$INVALID = .FALSE.
        DO 10 I=1,151
           CELL$TYPE(I) = -1
           CELL$REJECTED(I) = .TRUE.
           MASS(I) = 0
           AREA(I) = 0
10      CONTINUE
        CURRENT$OBJECT = 0
        LAST$OBJECT = 0
        SAVE$DATA$FLAG = .FALSE.
C
C       *************** GET THE SUBTRACTED IMAGE ***************
C
        CALL IMMAIN(IMAGE$SUBTRACT$GET,IMERR)
        IF (IMERR .NE. ' ')
     *  THEN
           FATAL$ERROR = .TRUE.
           GOTO 600
        ENDIF
        XY(1) = INT((IM$CHANNEL$ONE*0.125)+0.5)
        XY(2) = INT((IM$CHANNEL$TWO*0.125)+0.5)
C
C       ********* COPY IMAGE BUFFER 1 TO IMAGE BUFFER 2 *********
C
        CALL IMMAIN(IMAGE$COPY$1$2,IMERR)
        IF (IMERR .NE. ' ')
     *  THEN
           FATAL$ERROR = .TRUE.
           GOTO 600
        ENDIF
C
C       ********** PUT THE IMAGE TO THE DISPLAY **********
C
        CALL IMMAIN(IMAGE$PUT,IMERR)
        IF (IMERR .NE. ' ')
     *  THEN
           FATAL$ERROR = .TRUE.
           GOTO 600
        ENDIF
C
C       **************** FIND THE FIRST OBJECT ****************
C
        X$POS = MOD(ADDR$4,256)
        Y$POS = INT(ADDR$4/256.)
        CALL SAQQ19(LOW$THRES,HIGH$THRES,X$STEP,Y$STEP,X$POS,Y$POS,
     *              ADDR,XMIN,XMAX,YMIN,YMAX,END$FLAG,FATAL$ERROR)
        IF (FATAL$ERROR) GOTO 600
        IF (END$FLAG)
     *  THEN
           CALL IMMAIN(IMAGE$START$ACQ,IMERR)
           IF (IMERR .NE. ' ')
     *     THEN
              FATAL$ERROR = .TRUE.
              GOTO 600
           ENDIF
           RETURN
        ENDIF
C
C       **************** ENABLE FUNCTION KEYS ****************
C
        CALL SCREEN(ENABLE$FUNCTION$KEYS,SCREEN$NAME,FIELD$NAME,
     *              DATA$AREA,SCERR)
        IF (SCERR .NE. NO$SCREEN$ERROR)
     *    CALL SYERR(ENABLE$FUNCTION$KEYS,SCREEN$NAME,FIELD$NAME,SCERR,
     *               'ENABLE FUNCTION KEYS')
```

```
C
C               *************** UPDATE VARIABLES ******************
C
        CURRENT$OBJECT = 1
        LAST$OBJECT = 1
        OBJECT$BOUNDARY(1,CURRENT$OBJECT) = YMIN
        OBJECT$BOUNDARY(2,CURRENT$OBJECT) = XMIN
        OBJECT$BOUNDARY(3,CURRENT$OBJECT) = YMAX
        OBJECT$BOUNDARY(4,CURRENT$OBJECT) = XMAX
        CELL$ADDR(CURRENT$OBJECT) = ADDR
        CELL$REJECTED(CURRENT$OBJECT) = .TRUE.
        MASS(CURRENT$OBJECT) = IM$PIXEL$SUM+
     *                         TMP$AN$OFFSET
        AREA(CURRENT$OBJECT) = IM$PIXEL$COUNT
C
C               *************** PUT A BOX AROUND THE OBJECT ***************
C
        CALL SAQQ07(XMIN,XMAX,YMIN,YMAX,
     *              BOX$LEFT$POS,BOX$RIGHT$POS,BOX$TOP$POS,
     *              BOX$BOTTOM$POS,FATAL$ERROR)
C
C               *************** ERROR MESSAGE HANDLING CODE ***************
C
  600   IF (ERR$MESSAGE .EQ. 'C')
     *  THEN
          ERR$ONE = ' '
          ERR$TWO = ' '
        ENDIF
        IF (ERR$MESSAGE .EQ. 'C' .OR.
     *      ERR$MESSAGE .EQ. 'W')
     *  THEN
          FIELD$NAME = 'ERR1'
          CALL CNSTAR(12,ERR$ONE,DATA$AREA)
          CALL SCREEN(PUT$FIELD,SCREEN$NAME,FIELD$NAME,
     *                DATA$AREA,SCERR)
          IF (SCERR .NE. NO$SCREEN$ERROR)
     *       CALL SYERR(PUT$FIELD,SCREEN$NAME,FIELD$NAME,SCERR,
     *                  'PUT FIELD')
          FIELD$NAME = 'ERR2'
          CALL CNSTAR(32,ERR$TWO,DATA$AREA)
          CALL SCREEN(PUT$FIELD,SCREEN$NAME,FIELD$NAME,
     *                DATA$AREA,SCERR)
          IF (SCERR .NE. NO$SCREEN$ERROR)
     *       CALL SYERR(PUT$FIELD,SCREEN$NAME,FIELD$NAME,SCERR,
     *                  'PUT FIELD')
        ENDIF
        IF (ERR$MESSAGE .EQ. 'C') ERR$MESSAGE = ' '
        IF (ERR$MESSAGE .EQ. 'W') ERR$MESSAGE = 'C'
        IF (ERR$MESSAGE .NE. 'C') ERR$MESSAGE = ' '
C
C               *********** CHECK FOR A 'FATAL'(I.E. SERIOUS) ERROR **********
C
        IF (FATAL$ERROR)
     *  THEN
C
C               *************** DISABLE FUNCTION KEYS ***************
C
        CALL SCREEN(DISABLE$FUNCTION$KEYS,SCREEN$NAME,FIELD$NAME,
     *              DATA$AREA,SCERR)
        IF (SCERR .NE. NO$SCREEN$ERROR)
     *    CALL SYERR(DISABLE$FUNCTION$KEYS,SCREEN$NAME,FIELD$NAME,
     *               SCERR,'DISABLE FUNCTION KEYS')
        DATA$AREA(1) = 76
        CALL SCREEN(GROUP$KILL$FIELD,SCREEN$NAME,FIELD$NAME,
     *              DATA$AREA,SCERR)
        IF (SCERR .NE. NO$SCREEN$ERROR)
     *    CALL SYERR(GROUP$KILL$FIELD,SCREEN$NAME,FIELD$NAME,SCERR,
     *               'GROUP KILL FIELD')
        DATA$AREA(1) = 77
        CALL SCREEN(GROUP$KILL$FIELD,SCREEN$NAME,FIELD$NAME,
     *              DATA$AREA,SCERR)
```

```
            IF (SCERR .NE. NO$SCREEN$ERROR)
     *        CALL SYERR(GROUP$KILL$FIELD,SCREEN$NAME,FIELD$NAME,SCERR,
     *                   'GROUP KILL FIELD')
            RETURN
          ENDIF
C
C
C         ********** SET THE CURSOR TO THE APPROPRIATE FIELD **********

FIELD$NAME = 'AS46'
          CALL SCREEN(SET$CURSOR,SCREEN$NAME,FIELD$NAME,
     *                DATA$AREA,SCERR)
          IF (SCERR .NE. NO$SCREEN$ERROR)
     *      CALL SYERR(SET$CURSOR,SCREEN$NAME,FIELD$NAME,SCERR,
     *                 'SET CURSOR')
C
C         ************* ACTIVATE NUMERIC PAD ****************
C
          CALL SCREEN(NUMERIC$PAD,SCREEN$NAME,FIELD$NAME,
     *                DATA$AREA,SCERR)
          IF (SCERR .EQ. SCREEN$ESCAPE .OR.
     *        SCERR .EQ. NO$SCREEN$ERROR .OR.
     *        SCERR .EQ. SCREEN$FUNCT$KEY)
     *    THEN
            CONTINUE
          ELSE
            ERR$ONE = 'YOU HAVE TYPED IN'
            ERR$TWO = 'AN INVALID CHARACTER.'
            ERR$MESSAGE = 'W'
            GOTO 600
          ENDIF
          CALL CNARST(8,DATA$AREA,READ$INPUT$VALUE)
C
C         ************ IF EXITING TAKE THE APPROPRIATE ACTION ************
C
          IF (SCERR .EQ. SCREEN$ESCAPE)
     *    THEN
C
C           ************* DISABLE FUNCTION KEYS *************
C
            CALL SCREEN(DISABLE$FUNCTION$KEYS,SCREEN$NAME,FIELD$NAME,
     *                  DATA$AREA,SCERR)
            IF (SCERR .NE. NO$SCREEN$ERROR)
     *        CALL SYERR(DISABLE$FUNCTION$KEYS,SCREEN$NAME,FIELD$NAME,
     *                   SCERR,'DISABLE FUNCTION KEYS')
C
C           ********** CLEAR AWAY ANY EXISITING ERROR MESSAGE **********
C
            IF (ERR$MESSAGE .EQ. 'C')
     *      THEN
              ERR$ONE = ' '
              ERR$TWO = ' '
              FIELD$NAME = 'ERR1'
              CALL CNSTAR(32,ERR$ONE,DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                     'PUT FIELD')
              FIELD$NAME = 'ERR2'
              CALL CNSTAR(32,ERR$TWO,DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *          CALL SYERR(PUT$FIELD,SCREEN$NAME,FIELD$NAME,SCERR,
     *                     'PUT FIELD')
            ENDIF
C
C           **************** START IMAGE ACQUISITION ***************
C
            CALL IMMAIN(IMAGE$START$ACQ,IMERR)
            IF (IMERR .NE. ' ') FATAL$ERROR = .TRUE.
```

```
        RETURN
     ENDIF
C
C    ************* DETERMINE THE USER'S SELECTION **************
C
     SELECTED$FUNCTION = ' '
     IF (SCERR .EQ. SCREEN$FUNCT$KEY)
   * THEN
        KEY$TYPE = READ$INPUT$VALUE(1:3)
        IF (KEY$TYPE .NE. 'CTL')
   *    THEN
           ERR$ONE = 'YOU CANNOT USE THE '//KEY$TYPE//' KEY.'
           ERR$TWO = ' '
           ERR$MESSAGE = 'W'
           GOTO 600
        ENDIF
        NUM$STRING = READ$INPUT$VALUE(5:7)
        IF (NUM$STRING .EQ. 'F1')
   *    THEN
           SELECTED$FUNCTION = 'BACKUP'
        ELSEIF (NUM$STRING .EQ. 'F2')
   *    THEN
           SELECTED$FUNCTION = 'NEXT'
        ELSEIF (NUM$STRING .EQ. 'F3')
   *    THEN
           SELECTED$FUNCTION = 'AUTOMATIC'
        ELSEIF (NUM$STRING .EQ. 'F4')
   *    THEN
           SELECTED$FUNCTION = 'CUT'
        ELSEIF (NUM$STRING .EQ. 'F5')
   *    THEN
           SELECTED$FUNCTION = 'POINT'
        ELSEIF (NUM$STRING .EQ. 'F6')
   *    THEN
           SELECTED$FUNCTION = 'SKIP'
        ELSE
           ERR$ONE = 'YOU CAN ONLY USE THE'
           ERR$TWO = 'F1,F2,F3,F4, AND F5 KEYS.'
           ERR$MESSAGE = 'W'
           GOTO 600
        ENDIF
     ELSEIF (SCERR .EQ. ' ')
   * THEN
        NUM$PAD$VALUE = DATA$AREA(1)
        IF (NUM$PAD$VALUE .EQ. 12)
   *    THEN
           SAVE$DATA$FLAG = .TRUE.
C
C    **************** DISABLE FUNCTION KEYS ****************
C
        CALL SCREEN(DISABLE$FUNCTION$KEYS,SCREEN$NAME,FIELD$NAME,
   *                DATA$AREA,SCERR)
        IF (SCERR .NE. NO$SCREEN$ERROR)
   *       CALL SYERR(DISABLE$FUNCTION$KEYS,SCREEN$NAME,FIELD$NAME,
   *                  SCERR,'DISABLE FUNCTION KEYS')
C
C    ********** CLEAR AWAY ANY EXISITING ERROR MESSAGE ************
C
        IF (ERR$MESSAGE .EQ. 'C')
   *    THEN
           ERR$ONE = ' '
           ERR$TWO = ' '
           FIELD$NAME = 'ERR1'
           CALL CNSTAR(32,ERR$ONE,DATA$AREA)
           CALL SCREEN(PUT$FIELD,SCREEN$NAME,FIELD$NAME,
   *                   DATA$AREA,SCERR)
           IF (SCERR .NE. NO$SCREEN$ERROR)
   *          CALL SYERR(PUT$FIELD,SCREEN$NAME,FIELD$NAME,SCERR,
   *                     'PUT FIELD')
           FIELD$NAME = 'ERR2'
           CALL CNSTAR(32,ERR$TWO,DATA$AREA)
```

```
*          CALL SCREEN(PUT$FIELD,SCREEN$NAME,FIELD$NAME,
                  DATA$AREA,SCERR)
*          IF (SCERR .NE. NO$SCREEN$ERROR)
*            CALL SYERR(PUT$FIELD,SCREEN$NAME,FIELD$NAME,SCERR,
                  'PUT FIELD')
           ENDIF
C
C
C          *************** START IMAGE ACQUISITION **************
           CALL IMMAIN(IMAGE$START$ACQ,IMERR)
           IF (IMERR .NE. ' ') FATAL$ERROR = .TRUE.
           RETURN
*        ELSEIF (NUM$PAD$VALUE .EQ. 0)
         THEN
           SELECTED$FUNCTION = 'ACCEPT'
           TYPE$VALUE = 0
*        ELSEIF (NUM$PAD$VALUE .EQ. 1)
         THEN
           SELECTED$FUNCTION = 'ACCEPT'
           TYPE$VALUE = 1
*        ELSEIF (NUM$PAD$VALUE .EQ. 2)
         THEN
           SELECTED$FUNCTION = 'ACCEPT'
           TYPE$VALUE = 2
*        ELSEIF (NUM$PAD$VALUE .EQ. 3)
         THEN
           SELECTED$FUNCTION = 'ACCEPT'
           TYPE$VALUE = 3
*        ELSEIF (NUM$PAD$VALUE .EQ. 4)
         THEN
           SELECTED$FUNCTION = 'ACCEPT'
           TYPE$VALUE = 4
*        ELSEIF (NUM$PAD$VALUE .EQ. 5)
         THEN
           SELECTED$FUNCTION = 'ACCEPT'
           TYPE$VALUE = 5
*        ELSEIF (NUM$PAD$VALUE .EQ. 9)
         THEN
           SELECTED$FUNCTION = 'REJECT'
         ELSE
           ERR$ONE = '0,1,2,3,4,5,AND 9 ARE THE'
           ERR$TWO = 'ONLY VALID NUMBERS.'
           ERR$MESSAGE = 'W'
           GOTO 600
         ENDIF
       ELSE
         ERR$ONE = 'YOU HAVE ENTERED AN INVALID'
         ERR$TWO = 'RESPONSE, PLEASE RESELECT.'
         ERR$MESSAGE = 'W'
         GOTO 600
       ENDIF
C*************************************************************
C
C          CODE TO SKIP OVER AN OBJECT
C
C*************************************************************
       IF (SELECTED$FUNCTION .EQ. 'SKIP')
*      THEN
         IF (CURRENT$OBJECT .EQ. LAST$OBJECT)
*        THEN
           ERR$ONE = 'YOU CANNOT USE SKIP WHEN'
           ERR$TWO = 'THE BOX IS AT THE END.'
           ERR$MESSAGE = 'W'
           GOTO 600
         ENDIF
C
C
C          ************ MOVE BOX TO THE NEXT OBJECT **************
         CURRENT$OBJECT = CURRENT$OBJECT+1
         YMIN = OBJECT$BOUNDARY(1,CURRENT$OBJECT)
         XMIN = OBJECT$BOUNDARY(2,CURRENT$OBJECT)
```

```
            YMAX = OBJECT$BOUNDARY(3,CURRENT$OBJECT)
            XMAX = OBJECT$BOUNDARY(4,CURRENT$OBJECT)
            ADDR = CELL$ADDR(CURRENT$OBJECT)
            X$POS = MOD(ADDR$4,256)
            Y$POS = INT(ADDR$4/256.)
            CALL SAQQ07(XMIN,XMAX,YMIN,YMAX,
      *                 BOX$LEFT$POS,BOX$RIGHT$POS,BOX$TOP$POS,
      *                 BOX$BOTTOM$POS,FATAL$ERROR)
            GOTO 600
         ENDIF
C***********************************************************************
C
C                CODE TO REJECT AN OBJECT
C
C***********************************************************************
         IF (SELECTED$FUNCTION .EQ. 'REJECT')
      *  THEN
C
C           ********** CHECK TO SEE IF THE USER IS REJECTING ************
C           ********** AN ALREADY MEASURED OBJECT            ************
C
            IF (CURRENT$OBJECT .LT. LAST$OBJECT)
      *     THEN
C
C              **** CHECK TO SEE IF THE OBJECT HAS ALREADY BEEN REJECTED *****
C
               IF (CELL$REJECTED(CURRENT$OBJECT))
      *        THEN
                  ERR$ONE = 'YOU CANNOT REJECT A'
                  ERR$TWO = 'REJECTED CELL.'
                  ERR$MESSAGE = 'W'
                  GOTO 600
               ENDIF
C
C              ************* REJECT THE OBJECT *************
C
               IM$X$DIM = 256
               IM$Y$DIM = 256
               IM$LINEAR$OFFSET = CELL$ADDR(CURRENT$OBJECT)
               IM$LOW$LIMIT = 249
               IM$HIGH$LIMIT = 255
               IM$REPLACE$VALUE = 248
               IM$LABEL$TRACE = 0
               CALL IMMAIN(IMAGE$RELABEL,IMERR)
               IF (IMERR .NE. ' ')
      *        THEN
                  FATAL$ERROR = .TRUE.
                  GOTO 600
               ENDIF
               CELL$TYPE(CURRENT$OBJECT) = -1
               CELL$REJECTED(CURRENT$OBJECT) = .TRUE.
               CELL$COUNT = CELL$COUNT-1
               CALL IMMAIN(IMAGE$COPY$1$2,IMERR)
               IF (IMERR .NE. ' ')
      *        THEN
                  FATAL$ERROR = .TRUE.
                  GOTO 600
               ENDIF
C
C              ************* MOVE BOX TO THE NEXT OBJECT **************
C
               CURRENT$OBJECT = CURRENT$OBJECT+1
               YMIN = OBJECT$BOUNDARY(1,CURRENT$OBJECT)
               XMIN = OBJECT$BOUNDARY(2,CURRENT$OBJECT)
               YMAX = OBJECT$BOUNDARY(3,CURRENT$OBJECT)
               XMAX = OBJECT$BOUNDARY(4,CURRENT$OBJECT)
               ADDR = CELL$ADDR(CURRENT$OBJECT)
               X$POS = MOD(ADDR$4,256)
               Y$POS = INT(ADDR$4/256.)
               CALL SAQQ07(XMIN,XMAX,YMIN,YMAX,
      *                    BOX$LEFT$POS,BOX$RIGHT$POS,BOX$TOP$POS,
```

```
                    BOX$BOTTOM$POS,FATAL$ERROR)
          GOTO 600

C  ********* CODE TO HANDLE THE REJECTION OF AN OBJECT **********
C  ********* THAT HAS NOT BEEN MEASURED YET                **********
C
      ELSE

C  *********** CHECK TO SEE IF THERE IS ROOM IN THE ARRAYS *********
C  *********** TO ACCEPT ANOTHER OBJECT
C
          IF (LAST$OBJECT .GT. 150)
          THEN
             ERR$ONE = 'YOU CANNOT CLASSIFY MORE'
             ERR$TWO = 'THAN 150 CELLS IN THE IMAGE.'
             ERR$MESSAGE = 'W'
             GOTO 600
          ENDIF

C  *********** REJECT THE OBJECT *************
C
          IM$X$DIM = 256
          IM$Y$DIM = 256
          IM$LINEAR$OFFSET = ADDR
          IM$LOW$LIMIT = LOW$THRES
          IM$HIGH$LIMIT = HIGH$THRES
          IM$REPLACE$VALUE = 248
          IM$LABEL$TRACE = 0
          CALL IMMAIN(IMAGE$RELABEL,IMERR)
          IF (IMERR .NE. ' ')
          THEN
             IF (IMERR .EQ. 'R1')
             THEN
                X$POS = X$POS+X$STEP
             ELSE
                FATAL$ERROR = .TRUE.
                GOTO 600
             ENDIF
          ENDIF
          CELL$TYPE(CURRENT$OBJECT) = -1
          CELL$REJECTED(CURRENT$OBJECT) = .TRUE.
          CALL IMMAIN(IMAGE$COPY$1$2,IMERR)
          IF (IMERR .NE. ' ')
          THEN
             FATAL$ERROR = .TRUE.
             GOTO 600
          ENDIF
          CALL IMMAIN(IMAGE$PUT,IMERR)
          IF (IMERR .NE. ' ')
          THEN
             FATAL$ERROR = .TRUE.
             GOTO 600
          ENDIF

C  ************ SEARCH FOR THE NEXT OBJECT *************
C
          CALL SAQQ19(LOW$THRES,HIGH$THRES,X$STEP,Y$STEP,X$POS,
     *                Y$POS,ADDR,XMIN,XMAX,YMIN,YMAX,END$FLAG,
     *                FATAL$ERROR)
          IF (FATAL$ERROR) GOTO 600

C  *********** CHECK TO SEE IF NO MORE OBJECTS WERE FOUND ***********
C
          IF (END$FLAG)
          THEN
             SAVE$DATA$FLAG = .TRUE.

C  *************** DISABLE FUNCTION KEYS ****************
C
             CALL SCREEN(DISABLE$FUNCTION$KEYS,SCREEN$NAME,FIELD$NAME,
     *                   DATA$AREA,SCERR)
```

```
            IF (SCERR .NE. NO$SCREEN$ERROR)
     *        CALL SYERR(DISABLE$FUNCTION$KEYS,SCREEN$NAME,FIELD$NAME,
     *                   SCERR,'DISABLE FUNCTION KEYS')
C
C          ********** CLEAR AWAY ANY EXISTING ERROR MESSAGE ************
C
            IF (ERR$MESSAGE .EQ. 'C')
     *      THEN
               ERR$ONE = ' '
               ERR$TWO = ' '
               FIELD$NAME = 'ERR1'
               CALL CNSTAR(32,ERR$ONE,DATA$AREA)
               CALL SCREEN(PUT$FIELD,SCREEN$NAME,FIELD$NAME,
     *                     DATA$AREA,SCERR)
               IF (SCERR .NE. NO$SCREEN$ERROR)
     *            CALL SYERR(PUT$FIELD,SCREEN$NAME,FIELD$NAME,SCERR,
     *                       'PUT FIELD')
               FIELD$NAME = 'ERR2'
               CALL CNSTAR(32,ERR$TWO,DATA$AREA)
               CALL SCREEN(PUT$FIELD,SCREEN$NAME,FIELD$NAME,
     *                     DATA$AREA,SCERR)
               IF (SCERR .NE. NO$SCREEN$ERROR)
     *            CALL SYERR(PUT$FIELD,SCREEN$NAME,FIELD$NAME,SCERR,
     *                       'PUT FIELD')
            ENDIF
C
C          **************** START IMAGE ACQUISITION ***************
C
            CALL IMMAIN(IMAGE$START$ACQ,IMERR)
            IF (IMERR .NE. ' ') FATAL$ERROR = .TRUE.
            RETURN
         ENDIF
         CURRENT$OBJECT = CURRENT$OBJECT+1
         LAST$OBJECT = CURRENT$OBJECT
         OBJECT$BOUNDARY(1,CURRENT$OBJECT) = YMIN
         OBJECT$BOUNDARY(2,CURRENT$OBJECT) = XMIN
         OBJECT$BOUNDARY(3,CURRENT$OBJECT) = YMAX
         OBJECT$BOUNDARY(4,CURRENT$OBJECT) = XMAX
         CELL$TYPE(CURRENT$OBJECT) = -1
         CELL$REJECTED(CURRENT$OBJECT) = .TRUE.
         CELL$ADDR(CURRENT$OBJECT) = ADDR
         MASS(CURRENT$OBJECT) = IM$PIXEL$SUM+
     *                          TMP$AN$OFFSET
C
C          ************** SAVE MASS AND AREA VALUES **************
C
         AREA(CURRENT$OBJECT) = IM$PIXEL$COUNT
C
C          ************* PUT A BOX AROUND THE OBJECT *************
C
         CALL SAQQ07(XMIN,XMAX,YMIN,YMAX,
     *               BOX$LEFT$POS,BOX$RIGHT$POS,BOX$TOP$POS,
     *               BOX$BOTTOM$POS,FATAL$ERROR)
         GOTO 600
      ENDIF
   ENDIF
C*******************************************************************
C
C          CODE TO HANDLE THE BACKUP COMMAND
C
C*******************************************************************
   IF (SELECTED$FUNCTION .EQ. 'BACKUP')
     * THEN
C
C       ***** CHECK TO SEE IF THERE IS AN OBJECT TO BACKUP TO ******
C
      IF (CURRENT$OBJECT .LE. 1)
     *  THEN
         ERR$ONE = 'YOU CANNOT BACKUP BECAUSE'
         ERR$TWO = 'THERE IS NO OBJECT TO BACKUP TO.'
         ERR$MESSAGE = 'W'
```

```
              GOTO 600
            ENDIF
            CURRENT$OBJECT = CURRENT$OBJECT-1
            ADDR = CELL$ADDR(CURRENT$OBJECT)
            X$POS = MOD(ADDR$4,256)
            Y$POS = INT(ADDR$4/256.)
            YMIN = OBJECT$BOUNDARY(1,CURRENT$OBJECT)
            XMIN = OBJECT$BOUNDARY(2,CURRENT$OBJECT)
            YMAX = OBJECT$BOUNDARY(3,CURRENT$OBJECT)
            XMAX = OBJECT$BOUNDARY(4,CURRENT$OBJECT)
C
C           ********** PUT A BOX AROUND THE OBJECT *************
C
            CALL SAQQ07(XMIN,XMAX,YMIN,YMAX,
     *                  BOX$LEFT$POS,BOX$RIGHT$POS,BOX$TOP$POS,
     *                  BOX$BOTTOM$POS,FATAL$ERROR)
            GOTO 600
         ENDIF
C****************************************************************
C
C              CODE TO HANDLE THE NEXT COMMAND
C
C****************************************************************
         IF (SELECTED$FUNCTION .EQ. 'NEXT')
     *   THEN
C
C           ***** CHECK TO SEE IF THE CURRENT OBJECT IS THE NEXT OBJECT *****
C
            IF (CURRENT$OBJECT .EQ. LAST$OBJECT)
     *      THEN
              ERR$ONE = 'THIS IS THE NEXT OBJECT.'
              ERR$TWO = ' '
              ERR$MESSAGE = 'W'
              GOTO 600
            ENDIF
            CURRENT$OBJECT = LAST$OBJECT
            ADDR = CELL$ADDR(CURRENT$OBJECT)
            X$POS = MOD(ADDR$4,256)
            Y$POS = INT(ADDR$4/256.)
            YMIN = OBJECT$BOUNDARY(1,CURRENT$OBJECT)
            XMIN = OBJECT$BOUNDARY(2,CURRENT$OBJECT)
            YMAX = OBJECT$BOUNDARY(3,CURRENT$OBJECT)
            XMAX = OBJECT$BOUNDARY(4,CURRENT$OBJECT)
C
C           ********** PUT A BOX AROUND THE OBJECT *************
C
            CALL SAQQ07(XMIN,XMAX,YMIN,YMAX,
     *                  BOX$LEFT$POS,BOX$RIGHT$POS,BOX$TOP$POS,
     *                  BOX$BOTTOM$POS,FATAL$ERROR)
            GOTO 600
         ENDIF
C****************************************************************
C
C              CODE TO HANDLE THE ACCEPT COMMAND
C
C****************************************************************
         IF (SELECTED$FUNCTION .EQ. 'ACCEPT')
     *   THEN
C
C           ***** CHECK TO SEE IF THERE IS ROOM IN THE ARRAYS *****
C           ***** TO ACCEPT ANOTHER OBJECT                    *****
C
            IF (LAST$OBJECT .GT. 150)
     *      THEN
              ERR$ONE = 'YOU CANNOT CLASSIFY MORE'
              ERR$TWO = 'THAN 150 CELLS IN THE IMAGE.'
              ERR$MESSAGE = 'W'
              GOTO 600
            ENDIF
C
```

```
C          ********** AN ALREADY MEASURED OBJECT
C
           IF (CURRENT$OBJECT .LT. LAST$OBJECT)
     *     THEN
C
C             ********* CHECK TO SEE IF THE USER IS TRYING TO *********
C             ********* RECLASSIFY AN OBJECT TO THE SAME TYPE *********
C
              IF (TYPE$VALUE .EQ. CELL$TYPE(CURRENT$OBJECT))
     *        THEN
                 ERR$ONE = 'THE OBJECT HAS ALREADY BEEN'
                 ERR$TWO = 'CLASSIFIED THE SELECTED TYPE.'
                 ERR$MESSAGE = 'W'
                 GOTO 600
              ENDIF
C
C             ******** RELABEL THE REJECTED OBJECT THE PROPER COLOR **********
C
              IM$X$DIM = 256
              IM$Y$DIM = 256
              IM$LINEAR$OFFSET = CELL$ADDR(CURRENT$OBJECT)
              TEMP$TYPE = CELL$TYPE(CURRENT$OBJECT)
              IF (TEMP$TYPE .EQ. -1)
     *        THEN
                 IM$LOW$LIMIT = 248
                 IM$HIGH$LIMIT = 248
              ELSE
                 IM$LOW$LIMIT = TYPE$COLOR(TEMP$TYPE+1)
                 IM$HIGH$LIMIT = TYPE$COLOR(TEMP$TYPE+1)
              ENDIF
              IM$REPLACE$VALUE = TYPE$COLOR(TYPE$VALUE+1)
              IM$LABEL$TRACE = 0
              CALL IMMAIN(IMAGE$RELABEL,IMERR)
              IF (IMERR .NE. ' ')
     *        THEN
                 FATAL$ERROR = .TRUE.
                 RETURN
              ENDIF
              CELL$TYPE(CURRENT$OBJECT) = TYPE$VALUE
              CELL$REJECTED(CURRENT$OBJECT) = .FALSE.
              CELL$COUNT = CELL$COUNT+1
              CURRENT$OBJECT = CURRENT$OBJECT+1
C
C             ******** COPY IMAGE BUFFER 1 TO IMAGE BUFFER 2 *********
C
              CALL IMMAIN(IMAGE$COPY$1$2,IMERR)
              IF (IMERR .NE. ' ')
     *        THEN
                 FATAL$ERROR = .TRUE.
                 GOTO 600
              ENDIF
              ADDR = CELL$ADDR(CURRENT$OBJECT)
              X$POS = MOD(ADDR$4,256)
              Y$POS = INT(ADDR$4/256.)
              YMIN = OBJECT$BOUNDARY(1,CURRENT$OBJECT)
              XMIN = OBJECT$BOUNDARY(2,CURRENT$OBJECT)
              YMAX = OBJECT$BOUNDARY(3,CURRENT$OBJECT)
              XMAX = OBJECT$BOUNDARY(4,CURRENT$OBJECT)
C
C             ************ PUT A BOX AROUND THE OBJECT ****************
C
              CALL SAQQ07(XMIN,XMAX,YMIN,YMAX,
     *                    BOX$LEFT$POS,BOX$RIGHT$POS,BOX$TOP$POS,
     *                    BOX$BOTTOM$POS,FATAL$ERROR)
              GOTO 600
           ENDIF
C
C          ********** CODE TO ACCEPT AN UNMEASURED OBJECT **********
C
           IM$X$DIM = 256
           IM$Y$DIM = 256
           IM$LINEAR$OFFSET = CELL$ADDR(CURRENT$OBJECT)
```

```
          IM$LOW$LIMIT = LOW$THRES
          IM$HIGH$LIMIT = HIGH$THRES
          IM$REPLACE$VALUE = TYPE$COLOR(TYPE$VALUE+1)
          IM$LABEL$TRACE = 0
          CALL IMMAIN(IMAGE$RELABEL,IMERR)
          IF (IMERR .NE. ' ')
     *    THEN
            FATAL$ERROR = .TRUE.
            GOTO 600
          ENDIF
          XLEN = (IM$LABEL$BOUNDARY(4)-IM$LABEL$BOUNDARY(2))+1
          YLEN = (IM$LABEL$BOUNDARY(3)-IM$LABEL$BOUNDARY(1))+1
          IF ((IM$EDGE$CODE .NE. 0) .OR.
     *        (XLEN .LT. PCSG$XDIM$MIN) .OR.
     *        (YLEN .LT. PCSG$YDIM$MIN) .OR.
     *        (XLEN .GT. PCSG$XDIM$MAX) .OR.
     *        (YLEN .GT. PCSG$YDIM$MAX) .OR.
     *        (2*XLEN+YLEN .LT. PCSG$DIAM$SUM$MIN) .OR.
     *        (2*XLEN+YLEN .GT. PCSG$DIAM$SUM$MAX))
     *    THEN
            FATAL$ERROR = .TRUE.
            GOTO 600
          ENDIF
          CELL$TYPE(CURRENT$OBJECT) = TYPE$VALUE
          CELL$REJECTED(CURRENT$OBJECT) = .FALSE.
          CELL$COUNT = CELL$COUNT+1
C
C         *********** COPY IMAGE BUFFER 1 TO IMAGE BUFFER 2 *********
C
          CALL IMMAIN(IMAGE$COPY$1$2,IMERR)
          IF (IMERR .NE. ' ')
     *    THEN
            FATAL$ERROR = .TRUE.
            GOTO 600
          ENDIF
C
C         *************** FIND THE NEXT OBJECT ****************
C
          CALL SAQQ19(LOW$THRES,HIGH$THRES,X$STEP,Y$STEP,X$POS,Y$POS,
     *                ADDR,XMIN,XMAX,YMIN,YMAX,END$FLAG,FATAL$ERROR)
          IF (FATAL$ERROR) GOTO 600
C
C         ******* CHECK TO SEE IF NO MORE OBJECT WERE FOUND IN THE IMAGE ****
C
          IF (END$FLAG)
     *    THEN
            SAVE$DATA$FLAG = .TRUE.
C
C           ************** DISABLE FUNCTION KEYS ***************
C
            CALL SCREEN(DISABLE$FUNCTION$KEYS,SCREEN$NAME,FIELD$NAME,
     *                  DATA$AREA,SCERR)
            IF (SCERR .NE. NO$SCREEN$ERROR)
     *      CALL SYERR(DISABLE$FUNCTION$KEYS,SCREEN$NAME,FIELD$NAME,
     *                  SCERR,'DISABLE FUNCTION KEYS')
C
C           ********** CLEAR AWAY ANY EXISITING ERROR MESSAGE ***********
C
            IF (ERR$MESSAGE .EQ. 'C')
     *      THEN
              ERR$ONE = ' '
              ERR$TWO = ' '
              FIELD$NAME = 'ERR1'
              CALL CNSTAR(32,ERR$ONE,DATA$AREA)
              CALL SCREEN(PUT$FIELD,SCREEN$NAME,FIELD$NAME,
     *                    DATA$AREA,SCERR)
              IF (SCERR .NE. NO$SCREEN$ERROR)
     *        CALL SYERR(PUT$FIELD,SCREEN$NAME,FIELD$NAME,SCERR,
     *                    'PUT FIELD')
              FIELD$NAME = 'ERR2'
              CALL CNSTAR(32,ERR$TWO,DATA$AREA)
              CALL SCREEN(PUT$FIELD,SCREEN$NAME,FIELD$NAME,
     *                    DATA$AREA,SCERR)
```

```
              IF (SCERR .NE. NO$SCREEN$ERROR)
     *          CALL SYERR(PUT$FIELD,SCREEN$NAME,FIELD$NAME,SCERR,
     *                     'PUT FIELD')
              ENDIF
C
C             *************** START IMAGE ACQUISITION **************
C.
              CALL IMMAIN(IMAGE$START$ACQ,IMERR)
              IF (IMERR .NE. ' ') FATAL$ERROR = .TRUE.
              RETURN
            ENDIF
            CURRENT$OBJECT = CURRENT$OBJECT+1
            LAST$OBJECT = CURRENT$OBJECT
            OBJECT$BOUNDARY(1,CURRENT$OBJECT) = YMIN
            OBJECT$BOUNDARY(2,CURRENT$OBJECT) = XMIN
            OBJECT$BOUNDARY(3,CURRENT$OBJECT) = YMAX
            OBJECT$BOUNDARY(4,CURRENT$OBJECT) = XMAX
            CELL$ADDR(CURRENT$OBJECT) = ADDR
            CELL$TYPE(CURRENT$OBJECT) = -1
            CELL$REJECTED(CURRENT$OBJECT) = .TRUE.
            MASS(CURRENT$OBJECT) = IM$PIXEL$SUM+
     *                             TMP$AN$OFFSET
            AREA(CURRENT$OBJECT) = IM$PIXEL$COUNT
C
C           *************** PUT A BOX AROUND THE OBJECT **************
C
            CALL SAQQ07(XMIN,XMAX,YMIN,YMAX,
     *              BOX$LEFT$POS,BOX$RIGHT$POS,BOX$TOP$POS,
     *              BOX$BOTTOM$POS,FATAL$ERROR)
            GOTO 600
          ENDIF
C********************************************************************
C
C             CODE TO HANDLE THE AUTOMATIC COMMAND
C
C********************************************************************
          IF (SELECTED$FUNCTION .EQ. 'AUTOMATIC')
     *    THEN
C
C           ****** CHECK TO SEE IF THE USER WANTS TO DO AN         *****
C           ****** AUTOMATIC WHEN THE BOX IS NOT AT THE NEXT OBJECT *****
C
            IF (CURRENT$OBJECT .NE. LAST$OBJECT)
     *      THEN
              ERR$ONE = 'AUTOMATIC CANNOT BE USED WHEN'
              ERR$TWO = 'THE BOX ISN''T AT THE NEXT OBJECT'
              ERR$MESSAGE = 'W'
              GOTO 600
            ENDIF
C           ***** CHECK TO SEE IF THERE IS ROOM IN THE ARRAYS *****
C           ***** TO ACCEPT ANOTHER OBJECT                    *****
C
            IF (LAST$OBJECT .GT. 150)
     *      THEN
              ERR$ONE = 'YOU CANNOT CLASSIFY MORE'
              ERR$TWO = 'THAN 150 CELLS IN THE IMAGE.'
              ERR$MESSAGE = 'W'
              GOTO 600
            ENDIF
C
C           **************** DO AUTOMATIC *****************
C
            CALL SAQQ17(LOW$THRES,HIGH$THRES,X$STEP,Y$STEP,
     *              X$POS,Y$POS,MASS,AREA,CELL$TYPE,
     *              CELL$ADDR,CELL$REJECTED,CURRENT$OBJECT,
     *              LAST$OBJECT,CELL$COUNT,FATAL$ERROR)
            IF (FATAL$ERROR) GOTO 600
            SAVE$DATA$FLAG = .TRUE.
C
C           **************** DISABLE FUNCTION KEYS ***************
C
```

```
            CALL SCREEN(DISABLE$FUNCTION$KEYS,SCREEN$NAME,FIELD$NAME,
     *              .DATA$AREA,SCERR)
            IF (SCERR .NE. NO$SCREEN$ERROR)
     *        CALL SYERR(DISABLE$FUNCTION$KEYS,SCREEN$NAME,FIELD$NAME,
     *              SCERR,'DISABLE FUNCTION KEYS')
C
C
C           *********** CLEAR AWAY ANY EXISITING ERROR MESSAGE ************
            IF (ERR$MESSAGE .EQ. 'C')
     *      THEN
              ERR$ONE = ' '
              ERR$TWO = ' '
              FIELD$NAME = 'ERR1'
              CALL CNSTAR(32,ERR$ONE,DATA$AREA)
              CALL SCREEN(PUT$FIELD,SCREEN$NAME,FIELD$NAME,
     *              DATA$AREA,SCERR)
              IF (SCERR .NE. NO$SCREEN$ERROR)
     *          CALL SYERR(PUT$FIELD,SCREEN$NAME,FIELD$NAME,SCERR,
     *              'PUT FIELD')
              FIELD$NAME = 'ERR2'
              CALL CNSTAR(32,ERR$TWO,DATA$AREA)
              CALL SCREEN(PUT$FIELD,SCREEN$NAME,FIELD$NAME,
     *              DATA$AREA,SCERR)
              IF (SCERR .NE. NO$SCREEN$ERROR)
     *          CALL SYERR(PUT$FIELD,SCREEN$NAME,FIELD$NAME,SCERR,
     *              'PUT FIELD')
            ENDIF
C
C
C           **************** START IMAGE ACQUISITION **************
            CALL IMMAIN(IMAGE$START$ACQ,IMERR)
            IF (IMERR .NE. ' ') FATAL$ERROR = .TRUE.
            RETURN
          ENDIF
C***********************************************************************
C
C              CODE TO HANDLE THE CUT COMMAND
C
C***********************************************************************
          IF (SELECTED$FUNCTION .EQ. 'CUT')
     *    THEN
C
C             ****** CHECK TO SEE IF THE USER IS TRYING ******
C             ****** TO CUT A CLASSIFIED OBJECT         ******
C
            IF (CURRENT$OBJECT .LT. LAST$OBJECT)
     *      THEN
              ERR$ONE = 'CUT CANNOT BE USED ON'
              ERR$TWO = 'A CLASSIFIED OBJECT.'
              ERR$MESSAGE = 'W'
              GOTO 600
            ENDIF
C
            HORIZ$LENGTH = (BOX$RIGHT$POS-BOX$LEFT$POS)+1
            VERT$LENGTH = (BOX$BOTTOM$POS-BOX$TOP$POS)+1
            CALL IMOVB(HORIZ$LENGTH,IMAGEL(BOX$LEFT$POS,BOX$TOP$POS),
     *              SAVED$TOP(1))
            CALL IMOVB(HORIZ$LENGTH,IMAGEL(BOX$LEFT$POS,BOX$BOTTOM$POS),
     *              SAVED$BOTTOM(1))
            CALL IMOVBV(VERT$LENGTH,IMAGEL(BOX$LEFT$POS,BOX$TOP$POS),
     *              SAVED$LEFT(1))
            CALL IMOVBV(VERT$LENGTH,IMAGEL(BOX$RIGHT$POS,BOX$TOP$POS),
     *              SAVED$RIGHT(1))
            CALL IMOVB$(HORIZ$LENGTH,VALUES$254(1),
     *              IMAGEL(BOX$LEFT$POS,BOX$TOP$POS))
            CALL IMOVB$(HORIZ$LENGTH,VALUES$254(1),
     *              IMAGEL(BOX$LEFT$POS,BOX$BOTTOM$POS))
            CALL IMOVBH(VERT$LENGTH,VALUES$254(1),
     *              IMAGEL(BOX$LEFT$POS,BOX$TOP$POS))
            CALL IMOVBH(VERT$LENGTH,VALUES$254(1),
     *              IMAGEL(BOX$RIGHT$POS,BOX$TOP$POS))
```

```
              STACK$PTR = 0
              PEN$DOWN = .FALSE.
              CENTER$INVALID = .FALSE.
              X$CENTER = INT((XMIN+XMAX)/2)
              Y$CENTER = INT((YMIN+YMAX)/2)
              CURSOR$X$POS = X$CENTER
              CURSOR$Y$POS = Y$CENTER
C
C             ***** DETERMINE IF THE CENTER PIXEL HAS A VALUE ****
C             ***** THAT IS OUT OF RANGE
C
              L$VALUE = IMAGEL(CURSOR$X$POS,CURSOR$Y$POS)
              IF (L$VALUE .GT. 247)
       *      THEN
                 CURSOR$X$POS = X$POS
                 CURSOR$Y$POS = Y$POS
                 CENTER$INVALID = .TRUE.
              ENDIF
C
C             ************* CREATE THE CURSOR ***************
C
              CALL SAQQ18(CURSOR$X$POS,CURSOR$Y$POS)
              CALL IMMAIN(IMAGE$PUT,IMERR)
              IF (IMERR .NE. ' ')
       *      THEN
                 FATAL$ERROR = .TRUE.
                 GOTO 600
              ENDIF
              FIELD$NAME = 'AS45'
              CALL SCREEN(KILL$FIELD,SCREEN$NAME,FIELD$NAME,
       *                  DATA$AREA,SCERR)
              IF (SCERR .NE. NO$SCREEN$ERROR)
       *         CALL SYERR(KILL$FIELD,SCREEN$NAME,FIELD$NAME,SCERR,
       *                    'KILL FIELD')
              FIELD$NAME = 'AS46'
              CALL SCREEN(KILL$FIELD,SCREEN$NAME,FIELD$NAME,
       *                  DATA$AREA,SCERR)
              IF (SCERR .NE. NO$SCREEN$ERROR)
       *         CALL SYERR(KILL$FIELD,SCREEN$NAME,FIELD$NAME,SCERR,
       *                    'KILL FIELD')
              DATA$AREA(1) = 76
              CALL SCREEN(GROUP$UN$KILL$FIELD,SCREEN$NAME,FIELD$NAME,
       *                  DATA$AREA,SCERR)
              IF (SCERR .NE. NO$SCREEN$ERROR)
       *         CALL SYERR(GROUP$UN$KILL$FIELD,SCREEN$NAME,FIELD$NAME,
       *                    SCERR,'GROUP UNKILL FIELD')
              FIELD$NAME = 'AS71'
              CALL SCREEN(SET$CURSOR,SCREEN$NAME,FIELD$NAME,
       *                  DATA$AREA,SCERR)
              IF (SCERR .NE. NO$SCREEN$ERROR)
       *         CALL SYERR(SET$CURSOR,SCREEN$NAME,FIELD$NAME,SCERR,
       *                    'SET CURSOR')
C
C             ******** PUT OUT STATUS MESSAGE **********
C
  700         IF (PEN$DOWN)
       *      THEN
                 ERR$ONE = 'CURSOR WILL MOVE AND CUT'
              ELSE
                 ERR$ONE = 'CURSOR WILL MOVE AND NOT CUT'
              ENDIF
              FIELD$NAME = 'ERR1'
              CALL CNSTAR(32,ERR$ONE,DATA$AREA)
              CALL SCREEN(PUT$FIELD,SCREEN$NAME,FIELD$NAME,
       *                  DATA$AREA,SCERR)
              IF (SCERR .NE. NO$SCREEN$ERROR)
       *         CALL SYERR(PUT$FIELD,SCREEN$NAME,FIELD$NAME,SCERR,
       *                    'PUT FIELD')
              ERR$MESSAGE = 'C'
C
C             ************* SET NUMERIC PAD *************
C
```

```
C
              FIELD$NAME = 'AS71'
              CALL SCREEN(NUMERIC$PAD,SCREEN$NAME,FIELD$NAME,
     *                    DATA$AREA,SCERR)
              IF (SCERR .EQ. 'NP')
     *          CALL SYERR(NUMERIC$PAD,SCREEN$NAME,FIELD$NAME,SCERR,
     *                     'NUMERIC PAD')
              NUM$PAD$VALUE = DATA$AREA(1)
C
C
C     ******** IF THE USER IS EXITING THE CUT OPERATION, ********
C     ******** THEN GET RID OF THE CURSOR AND THE BOX    ********
C     ******** FIND THE NEXT OBJECT                      ********
C
              IF (SCERR .EQ. SCREEN$ESCAPE)
     *        THEN
                DATA$AREA(1) = 76
                CALL SCREEN(GROUP$KILL$FIELD,SCREEN$NAME,FIELD$NAME,
     *                      DATA$AREA,SCERR)
                IF (SCERR .NE. NO$SCREEN$ERROR)
     *            CALL SYERR(GROUP$KILL$FIELD,SCREEN$NAME,FIELD$NAME,
     *                       SCERR,'GROUP KILL FIELD')
                FIELD$NAME = 'AS45'
                CALL SCREEN(UN$KILL$FIELD,SCREEN$NAME,FIELD$NAME,
     *                      DATA$AREA,SCERR)
                IF (SCERR .NE. NO$SCREEN$ERROR)
     *            CALL SYERR(UN$KILL$FIELD,SCREEN$NAME,FIELD$NAME,SCERR,
     *                       'UNKILL FIELD')
                FIELD$NAME = 'AS46'
                CALL SCREEN(UN$KILL$FIELD,SCREEN$NAME,FIELD$NAME,
     *                      DATA$AREA,SCERR)
                IF (SCERR .NE. NO$SCREEN$ERROR)
     *            CALL SYERR(UN$KILL$FIELD,SCREEN$NAME,FIELD$NAME,SCERR,
     *                       'UNKILL FIELD')
C
C            ************ DELETE THE CURSOR ************
C
                CALL SAQQ18(CURSOR$X$POS,CURSOR$Y$POS)
                CALL IMOVB$(HORIZ$LENGTH,SAVED$TOP(1),
     *                      IMAGEL(BOX$LEFT$POS,BOX$TOP$POS))
                CALL IMOVB$(HORIZ$LENGTH,SAVED$BOTTOM(1),
     *                      IMAGEL(BOX$LEFT$POS,BOX$BOTTOM$POS))
                CALL IMOVBH(VERT$LENGTH,SAVED$LEFT(1),
     *                      IMAGEL(BOX$LEFT$POS,BOX$TOP$POS))
                CALL IMOVBH(VERT$LENGTH,SAVED$RIGHT(1),
     *                      IMAGEL(BOX$RIGHT$POS,BOX$TOP$POS))
C
C      ****** COPY FROM IMAGE BUFFER 1 TO IMAGE BUFFER 2 ********
C
                CALL IMMAIN(IMAGE$COPY$1$2,IMERR)
                IF (IMERR .NE. ' ')
     *          THEN
                  FATAL$ERROR = .TRUE.
                  GOTO 600
                ENDIF
C
C     *************** FIND THE NEXT OBJECT ****************
C
                CALL SAQQ19(LOW$THRES,HIGH$THRES,X$STEP,Y$STEP,X$POS,Y$POS,
     *                      ADDR,XMIN,XMAX,YMIN,YMAX,END$FLAG,FATAL$ERROR)
                IF (FATAL$ERROR) GOTO 600
C
C   *  ****** CHECK TO SEE IF NO MORE OBJECT WERE FOUND IN THE IMAGE *****
C
                IF (END$FLAG)
     *          THEN
                  SAVE$DATA$FLAG = .TRUE.
C
C     *************** DISABLE FUNCTION KEYS ***************
C
                  CALL SCREEN(DISABLE$FUNCTION$KEYS,SCREEN$NAME,FIELD$NAME,
     *                        DATA$AREA,SCERR)
```

```
          IF (SCERR .NE. NO$SCREEN$ERROR)
*            CALL SYERR(DISABLE$FUNCTION$KEYS,SCREEN$NAME,FIELD$NAME,
*                      SCERR,'DISABLE FUNCTION KEYS')

C     ********** CLEAR AWAY ANY EXISITING ERROR MESSAGE *************
C
C
          IF (ERR$MESSAGE .EQ. 'C')
*         THEN
            ERR$ONE = ' '
            ERR$TWO = ' '
            FIELD$NAME = 'ERR1'
            CALL CNSTAR(32,ERR$ONE,DATA$AREA)
            CALL SCREEN(PUT$FIELD,SCREEN$NAME,FIELD$NAME,
*                       DATA$AREA,SCERR)
            IF (SCERR .NE. NO$SCREEN$ERROR)
*              CALL SYERR(PUT$FIELD,SCREEN$NAME,FIELD$NAME,SCERR,
*                         'PUT FIELD')
            FIELD$NAME = 'ERR2'
            CALL CNSTAR(32,ERR$TWO,DATA$AREA)
            CALL SCREEN(PUT$FIELD,SCREEN$NAME,FIELD$NAME,
*                       DATA$AREA,SCERR)
            IF (SCERR .NE. NO$SCREEN$ERROR)
*              CALL SYERR(PUT$FIELD,SCREEN$NAME,FIELD$NAME,SCERR,
*                         'PUT FIELD')
          ENDIF

C     **************** START IMAGE ACQUISITION ***************
C
C
          CALL IMMAIN(IMAGE$START$ACQ,IMERR)
          IF (IMERR .NE. ' ') FATAL$ERROR = .TRUE.
          RETURN
          ENDIF
          OBJECT$BOUNDARY(1,CURRENT$OBJECT) = YMIN
          OBJECT$BOUNDARY(2,CURRENT$OBJECT) = XMIN
          OBJECT$BOUNDARY(3,CURRENT$OBJECT) = YMAX
          OBJECT$BOUNDARY(4,CURRENT$OBJECT) = XMAX
          CELL$ADDR(CURRENT$OBJECT) = ADDR
          CELL$TYPE(CURRENT$OBJECT) = -1
          CELL$REJECTED(CURRENT$OBJECT) = .TRUE.
          MASS(CURRENT$OBJECT) = IM$PIXEL$SUM+
*                                TMP$AN$OFFSET
          AREA(CURRENT$OBJECT) = IM$PIXEL$COUNT

C     **************** PUT A BOX AROUND THE OBJECT ***************
C
C
          CALL SAQQ07(XMIN,XMAX,YMIN,YMAX,
*                     BOX$LEFT$POS,BOX$RIGHT$POS,BOX$TOP$POS,
*                     BOX$BOTTOM$POS,FATAL$ERROR)
          GOTO 600
        ENDIF

C     ******* IF THE KEYPAD VALUE IS ZERO, THEN REVERSE ******
C     ******* THE 'PEN' POSITION                         ******
C
C
        IF (NUM$PAD$VALUE .EQ. 0)
*       THEN
          PEN$DOWN = .NOT. PEN$DOWN
          GOTO 700

C     ******* IF THE KEYPAD VALUE IS FIVE, THEN PLACE     ******
C     ******* THE CURSOR TO THE CENTER OF THE BOX,        ******
C     ******* ASSUMING THE CENTER PIXEL VALUE IS IN RANGE ******
C
        ELSEIF (NUM$PAD$VALUE .EQ. 5)
*       THEN
          IF (CENTER$INVALID) GOTO 700
          NEW$CURSOR$X$POS = X$CENTER
          NEW$CURSOR$Y$POS = Y$CENTER
          CALL SAQQ18(CURSOR$X$POS,CURSOR$Y$POS)
          CURSOR$X$POS = NEW$CURSOR$X$POS
          CURSOR$Y$POS = NEW$CURSOR$Y$POS
```

```
            CALL SAQQ18(CURSOR$X$POS,CURSOR$Y$POS)
            CALL IMMAIN(IMAGE$PUT,IMERR)
            IF (IMERR .NE. ' ')
      *     THEN
              FATAL$ERROR = .TRUE.
              GOTO 600
            ENDIF
            GOTO 700
C
C
C     ****** IF THE KEYPAD VALUE IS IN THE RANGE 1 TO 9,    *******
C     ****** THEN MOVE THE CURSOR IN THE SPECIFIED DIRECTION, *******
C     ****** ASSUMING THE MOVEMENT IS VALID                 *******
C
            ELSEIF (NUM$PAD$VALUE .GE. 1 .AND. NUM$PAD$VALUE .LE. 9)
      *     THEN
              CALL SAQQ18(CURSOR$X$POS,CURSOR$Y$POS)
              NEW$CURSOR$X$POS = CURSOR$X$POS
              NEW$CURSOR$Y$POS = CURSOR$Y$POS
              STEP$SIZE = 0
              X$LOC = CURSOR$X$POS
              Y$LOC = CURSOR$Y$POS
C
C
C           ******** DETERMINE IF THE CURSOR IS GOING ********
C           ******** THROUGH INVALID PIXELS           ********
C
              DO 800 I=1,3
                X$LOC = X$LOC+X$DIR$CHANGE(NUM$PAD$VALUE)
                Y$LOC = Y$LOC+Y$DIR$CHANGE(NUM$PAD$VALUE)
                IF (X$LOC .LE. BOX$LEFT$POS .OR.
      *             X$LOC .GE. BOX$RIGHT$POS .OR.
      *             Y$LOC .LE. BOX$TOP$POS .OR.
      *             Y$LOC .GE. BOX$BOTTOM$POS)
      *             GOTO 900
                LGCL$VALUE = IMAGEL(X$LOC,Y$LOC)
                IF (L$VALUE .GT. 247) GOTO 900
                NEW$CURSOR$X$POS = X$LOC
                NEW$CURSOR$Y$POS = Y$LOC
                STEP$SIZE = I
 800          CONTINUE
C
 900          IF (STEP$SIZE .EQ. 0)
      *       THEN
                CALL SAQQ18(CURSOR$X$POS,CURSOR$Y$POS)
                GOTO 700
              ENDIF
C
C
C     ******* IF THE 'PEN' POSITION IS DOWN, THEN MOVE *******
C     ******* THE CURSOR WITHOUT CHANGING THE PIXELS   *******
C
              IF (.NOT. PEN$DOWN)
      *       THEN
                CURSOR$X$POS = NEW$CURSOR$X$POS
                CURSOR$Y$POS = NEW$CURSOR$Y$POS
                CALL SAQQ18(CURSOR$X$POS,CURSOR$Y$POS)
                CALL IMMAIN(IMAGE$PUT,IMERR)
                IF (IMERR .NE. ' ')
      *         THEN
                  FATAL$ERROR = .TRUE.
                  GOTO 600
                ENDIF
                GOTO 700
C
C
C     ******* IF THE 'PEN' POSITION IS UP, THEN MOVE         *******
C     ******* THE CURSOR AND CHANGE THE CORRESPONDING PIXELS *******
C
              ELSE
                DO 1000 I=1,STEP$SIZE
                  IF (STACK$PTR .EQ. 100)
      *           THEN
                    START = 99
                  ELSE
```

```
                        START = STACK$PTR
                     ENDIF
                     DO 1100 J=START,1,-1
                        STACK(1,J+1) = STACK(1,J)
                        STACK(2,J+1) = STACK(2,J)
                        STACK(3,J+1) = STACK(3,J)
1100                 CONTINUE
                     CURSOR$X$POS = CURSOR$X$POS+X$DIR$CHANGE(NUM$PAD$VALUE)
                     CURSOR$Y$POS = CURSOR$Y$POS+Y$DIR$CHANGE(NUM$PAD$VALUE)
                     LGCL$VALUE = IMAGEL(CURSOR$X$POS,CURSOR$Y$POS)
                     IF (STACK$PTR .LT. 100)
      *                 STACK$PTR = STACK$PTR+1
                     STACK(1,1) = L$VALUE
                     STACK(2,1) = CURSOR$X$POS
                     STACK(3,1) = CURSOR$Y$POS
                     L$VALUE = 247
                     IMAGEL(CURSOR$X$POS,CURSOR$Y$POS) = LGCL$VALUE
1000              CONTINUE
                  CALL SAQQ18(CURSOR$X$POS,CURSOR$Y$POS)
                  CALL IMMAIN(IMAGE$PUT,IMERR)
                  IF (IMERR .NE. ' ')
      *           THEN
                     FATAL$ERROR = .TRUE.
                     GOTO 600
                  ENDIF
                  GOTO 700
               ENDIF
C
C            ******* IF THE KEYPAD VALUE IS 12(I.E. THE 'ENTER' KEY), *******
C            ******* THEN UNCUT THE APPROPRIATE PIXELS                *******
C
C
            ELSEIF (NUM$PAD$VALUE .EQ. 12)
      *     THEN
               IF (STACK$PTR .EQ. 0) GOTO 700
               CALL SAQQ18(CURSOR$X$POS,CURSOR$Y$POS)
               IF (STACK$PTR .LT. 3)
      *        THEN
                  END = STACK$PTR
               ELSE
                  END = 3
               ENDIF
               DO 1200 I=1,END
                  L$VALUE = STACK(1,1)
                  X$LOC = STACK(2,1)
                  Y$LOC = STACK(3,1)
                  IMAGEL(X$LOC,Y$LOC) = LGCL$VALUE
                  DO 1300 J=1,STACK$PTR-1
                     STACK(1,J) = STACK(1,J+1)
                     STACK(2,J) = STACK(2,J+1)
                     STACK(3,J) = STACK(3,J+1)
1300              CONTINUE
                  CURSOR$X$POS = X$LOC
                  CURSOR$Y$POS = Y$LOC
                  STACK$PTR = STACK$PTR-1
                  IF (STACK$PTR .EQ. 0) GOTO 1400
1200           CONTINUE
1400           CALL SAQQ18(CURSOR$X$POS,CURSOR$Y$POS)
               CALL IMMAIN(IMAGE$PUT,IMERR)
               IF (IMERR .NE. ' ')
      *        THEN
                  FATAL$ERROR = .TRUE.
                  GOTO 600
               ENDIF
               GOTO 700
            ELSE
               GOTO 700
            ENDIF
         ENDIF
C***********************************************************************
C
                CODE TO HANDLE THE POINT COMMAND
```

```
C
C**************************************************************
            IF (SELECTED$FUNCTION .EQ. 'POINT')
          *    THEN
                 CURSOR$STEP = 5
                 CURSOR$X$POS = X$POS
                 CURSOR$Y$POS = Y$POS
                 CURRENT$OBJECT = LAST$OBJECT
C
C
C           ************* CREATE THE CURSOR **************
C
            CALL SAQQ18(CURSOR$X$POS,CURSOR$Y$POS)
            CALL IMMAIN(IMAGE$PUT,IMERR)
            IF (IMERR .NE. ' ')
          *    THEN
                 FATAL$ERROR = .TRUE.
                 GOTO 600
               ENDIF
            FIELD$NAME = 'AS45'
            CALL SCREEN(KILL$FIELD,SCREEN$NAME,FIELD$NAME,
          *             DATA$AREA,SCERR)
            IF (SCERR .NE. NO$SCREEN$ERROR)
          *    CALL SYERR(KILL$FIELD,SCREEN$NAME,FIELD$NAME,SCERR,
          *             'KILL FIELD')
            FIELD$NAME = 'AS46'
            CALL SCREEN(KILL$FIELD,SCREEN$NAME,FIELD$NAME,
          *             DATA$AREA,SCERR)
            IF (SCERR .NE. NO$SCREEN$ERROR)
          *    CALL SYERR(KILL$FIELD,SCREEN$NAME,FIELD$NAME,SCERR,
          *             'KILL FIELD')
            DATA$AREA(1) = 77
            CALL SCREEN(GROUP$UN$KILL$FIELD,SCREEN$NAME,FIELD$NAME,
          *             DATA$AREA,SCERR)
            IF (SCERR .NE. NO$SCREEN$ERROR)
          *    CALL SYERR(GROUP$UN$KILL$FIELD,SCREEN$NAME,FIELD$NAME,
          *             SCERR,'GROUP UNKILL FIELD')
            FIELD$NAME = 'AS73'
            CALL SCREEN(SET$CURSOR,SCREEN$NAME,FIELD$NAME,
          *             DATA$AREA,SCERR)
            IF (SCERR .NE. NO$SCREEN$ERROR)
          *    CALL SYERR(SET$CURSOR,SCREEN$NAME,FIELD$NAME,SCERR,
          *             'SET CURSOR')
C
C
C           ************* SET NUMERIC PAD **************
C
 1500       FIELD$NAME = 'AS73'
            CALL SCREEN(NUMERIC$PAD,SCREEN$NAME,FIELD$NAME,
          *             DATA$AREA,SCERR)
            IF (SCERR .EQ. 'NP')
          *    CALL SYERR(NUMERIC$PAD,SCREEN$NAME,FIELD$NAME,SCERR,
          *             'NUMERIC PAD')
            NUM$PAD$VALUE = DATA$AREA(1)
C
C           ******** IF THE USER IS EXITING THE CUT OPERATION, ********
C           ******** THEN GET RID OF THE CURSOR AND THE BOX    ********
C           ******** FIND THE NEXT OBJECT                      ********
C
            IF (SCERR .EQ. SCREEN$ESCAPE)
          *    THEN
                 DATA$AREA(1) = 77
                 CALL SCREEN(GROUP$KILL$FIELD,SCREEN$NAME,FIELD$NAME,
          *             DATA$AREA,SCERR)
                 IF (SCERR .NE. NO$SCREEN$ERROR)
          *         CALL SYERR(GROUP$KILL$FIELD,SCREEN$NAME,FIELD$NAME,
          *             SCERR,'GROUP KILL FIELD')
                 FIELD$NAME = 'AS45'
                 CALL SCREEN(UN$KILL$FIELD,SCREEN$NAME,FIELD$NAME,
          *             DATA$AREA,SCERR)
                 IF (SCERR .NE. NO$SCREEN$ERROR)
          *         CALL SYERR(UN$KILL$FIELD,SCREEN$NAME,FIELD$NAME,SCERR,
```

```
                        'UNKILL FIELD')
         FIELD$NAME = 'AS46'
         CALL SCREEN(UN$KILL$FIELD,SCREEN$NAME,FIELD$NAME,
*                    DATA$AREA,SCERR)
         IF (SCERR .NE. NO$SCREEN$ERROR)
            CALL SYERR(UN$KILL$FIELD,SCREEN$NAME,FIELD$NAME,SCERR,
*                       'UNKILL FIELD')
         X$POS = CURSOR$X$POS
         Y$POS = CURSOR$Y$POS
         ADDR = Y$POS*256+X$POS
```

C
C         *********** DELETE THE CURSOR **********
C
```
         CALL SAQQ18(CURSOR$X$POS,CURSOR$Y$POS)
```

C
C         ************ FIND THE NEXT OBJECT *************
C
```
         CALL SAQQ19(LOW$THRES,HIGH$THRES,X$STEP,Y$STEP,X$POS,Y$POS,
*                    ADDR,XMIN,XMAX,YMIN,YMAX,END$FLAG,FATAL$ERROR)
         IF (FATAL$ERROR) GOTO 600
```

C
C         * **** CHECK TO SEE IF NO MORE OBJECT WERE FOUND IN THE IMAGE ***
C
```
         IF (END$FLAG)
*        THEN
            CURRENT$OBJECT = LAST$OBJECT
            ADDR = CELL$ADDR(CURRENT$OBJECT)
            X$POS = MOD(ADDR$4,256)
            Y$POS = INT(ADDR$4/256.)
            YMIN = OBJECT$BOUNDARY(1,CURRENT$OBJECT)
            XMIN = OBJECT$BOUNDARY(2,CURRENT$OBJECT)
            YMAX = OBJECT$BOUNDARY(3,CURRENT$OBJECT)
            XMAX = OBJECT$BOUNDARY(4,CURRENT$OBJECT)
```

C
C         ************* PUT A BOX AROUND THE OBJECT *************
C
```
            CALL SAQQ07(XMIN,XMAX,YMIN,YMAX,
                        BOX$LEFT$POS,BOX$RIGHT$POS,BOX$TOP$POS,
*                       BOX$BOTTOM$POS,FATAL$ERROR)
            ERR$ONE = 'COULD NOT FIND ANY CELLS'
            ERR$TWO = 'AFTER THE CROSS HAIR POSITION.'
            ERR$MESSAGE = 'W'
            GOTO 600
         ENDIF
         OBJECT$BOUNDARY(1,CURRENT$OBJECT) = YMIN
         OBJECT$BOUNDARY(2,CURRENT$OBJECT) = XMIN
         OBJECT$BOUNDARY(3,CURRENT$OBJECT) = YMAX
         OBJECT$BOUNDARY(4,CURRENT$OBJECT) = XMAX
         CELL$ADDR(CURRENT$OBJECT) = ADDR
         CELL$TYPE(CURRENT$OBJECT) = -1
         CELL$REJECTED(CURRENT$OBJECT) = .TRUE.
         MASS(CURRENT$OBJECT) = IM$PIXEL$SUM+
*                               TMP$AN$OFFSET
         AREA(CURRENT$OBJECT) = IM$PIXEL$COUNT
```

C
C         ************* PUT A BOX AROUND THE OBJECT *************
C
```
         CALL SAQQ07(XMIN,XMAX,YMIN,YMAX,
                     BOX$LEFT$POS,BOX$RIGHT$POS,BOX$TOP$POS,
*                    BOX$BOTTOM$POS,FATAL$ERROR)
         GOTO 600
      ENDIF
```

C
C         ************ DETERMINE WHERE TO MOVE THE CURSOR ************
C
```
      IF (NUM$PAD$VALUE .EQ. 0)
*     THEN
         IF (CURSOR$STEP .EQ. 5)
*        THEN
            CURSOR$STEP = 15
         ELSE
```

```
                CURSOR$STEP = 5
              ENDIF
              GOTO 1500
            ELSEIF (NUM$PAD$VALUE .EQ. 1 .OR. NUM$PAD$VALUE .EQ. 2 .OR.
     *              NUM$PAD$VALUE .EQ. 3 .OR. NUM$PAD$VALUE .EQ. 4 .OR.
     *              NUM$PAD$VALUE .EQ. 6 .OR. NUM$PAD$VALUE .EQ. 7 .OR.
     *              NUM$PAD$VALUE .EQ. 8 .OR. NUM$PAD$VALUE .EQ. 9)
     *        THEN
              X$LOC = CURSOR$X$POS+X$DIR$CHANGE(NUM$PAD$VALUE)
     *                                      *CURSOR$STEP
              Y$LOC = CURSOR$Y$POS+Y$DIR$CHANGE(NUM$PAD$VALUE)
     *                                      *CURSOR$STEP
              IF (X$LOC .GT. 255)
     *        THEN
                X$LOC = 255
              ELSEIF (X$LOC .LT. 0)
     *        THEN
                X$LOC = 0
              ENDIF
              IF (Y$LOC .GT. 255)
     *        THEN
                Y$LOC = 255
              ELSEIF (Y$LOC .LT. 0)
     *        THEN
                Y$LOC = 0
              ENDIF
              CALL SAQQ18(CURSOR$X$POS,CURSOR$Y$POS)
              CURSOR$X$POS = X$LOC
              CURSOR$Y$POS = Y$LOC
              CALL SAQQ18(CURSOR$X$POS,CURSOR$Y$POS)
              CALL IMMAIN(IMAGE$PUT,IMERR)
              IF (IMERR .NE. ' ')
     *        THEN
                FATAL$ERROR = .TRUE.
                GOTO 600
              ENDIF
              GOTO 1500
            ELSEIF (NUM$PAD$VALUE .EQ. 5)
     *        THEN
              CALL SAQQ18(CURSOR$X$POS,CURSOR$Y$POS)
              CURSOR$X$POS = 127
              CURSOR$Y$POS = 127
              CALL SAQQ18(CURSOR$X$POS,CURSOR$Y$POS)
              CALL IMMAIN(IMAGE$PUT,IMERR)
              IF (IMERR .NE. ' ')
     *        THEN
                FATAL$ERROR = .TRUE.
                GOTO 600
              ENDIF
              GOTO 1500
            ELSE
              GOTO 1500
            ENDIF
          ENDIF
        ENDCC
CC                CELL ANALYSIS SYSTEMS, INC.
CC                    (C) COPYRIGHT 1986
CC****************************************************************
CC
CC      :PROGRAM NAME
CC      :SAQQ17
CC
CC      :SUBROUTINES
CC      :IMMAIN
CC      :SAQQ08
CC      :SAQQ09
CC
CC      :CALLING SEQUENCE
CC      :SAQQ17(LOW$THRES,HIGH$THRES,X$STEP,Y$STEP,X$POS,Y$POS,
CC              MASS,AREA,CELL$TYPE,CELL$ADDR,CELL$REJECTED,
CC              CURRENT$OBJECT,LAST$OBJECT,CELL$COUNT,FATAL$ERROR)
```

```
CC
CC      :PARAMETERS
CC      :LOW$THRES - LOW THRESHOLD VALUE
CC      :HIGH$THRES - HIGH THRESHOLD VALUE
CC      :X$STEP - X DIRECTION INCREMENT
CC      :Y$STEP - Y DIRECTION INCREMENT
CC      :X$POS - X COORDINATE OF THE CURRENT POSITION
CC      :Y$POS - Y COORDINATE OF THE CURRENT POSITION
CC      :MASS - ARRAY CONTAINING MASSES OF OBJECTS
CC      :AREA - ARRAY CONTAINING AREAS OF OBJECTS
CC      :CELL$TYPE - AN ARRAY CONTAINING THE TYPES OF THE OBJECTS
CC      :CELL$ADDR - ARRAY CONTAINING THE OBJECT ADDRESSES
CC      :CELL$REJECTED - A LOGICAL ARRAY THAT SPECIFIES IF AN OBJECT
CC                        WAS REJECTED
CC      :CURRENT$OBJECT - INDEX OF THE CURRENT OBJECT
CC      :LAST$OBJECT - INDEX OF THE LAST OBJECT
CC      :CELL$COUNT - CELL COUNT
CC      :FATAL$ERROR - A FLAG THAT SPECIFIES IF A 'FATAL'(I.E. SERIOUS) ERROR
CC                        OCCURRED WHILE IN SAQQ17
CC
CC
CC      :DESCRIPTION
CC      :SAQQ17 PERFORMS THE AUTOMATIC OPERATION
CC
CC**********************************************************************
CC********
        SUBROUTINE SAQQ17(LOW$THRES,HIGH$THRES,X$STEP,Y$STEP,
     *                    X$POS,Y$POS,MASS,AREA,
     *                    CELL$TYPE,
     *                    CELL$ADDR,CELL$REJECTED,CURRENT$OBJECT,
     *                    LAST$OBJECT,CELL$COUNT,FATAL$ERROR)
C
        INTEGER*2 LOW$THRES,HIGH$THRES,X$STEP,Y$STEP,X$POS,Y$POS,
     *            CURRENT$OBJECT,LAST$OBJECT,CELL$ADDR(*),
     *            CELL$COUNT,XMIN,XMAX,YMIN,CELL$TYPE(*),
     *            YMAX,ADDR
        INTEGER*4 MASS(*),AREA(*)
        LOGICAL*1 CELL$REJECTED(*),FATAL$ERROR,END$FLAG
C
        INCLUDE 'SAQCDT.FIN'
        INCLUDE 'IMAGED.FIN'
        INCLUDE 'SCREEN.FIN'
C
C       ************* INITIALIZE VARIABLES *****************
C
        FATAL$ERROR = .FALSE.
        END$FLAG = .FALSE.
        XMIN = 0
        XMAX = 0
        YMIN = 0
        YMAX = 0
        ADDR = 0
C
C       *************** FIND THE NEXT OBJECT ******************
C
100     IF (LAST$OBJECT .GT. 150)
     *  THEN
          RETURN
        ENDIF
        IM$X$DIM = 256
        IM$Y$DIM = 256
        IM$LINEAR$OFFSET = CELL$ADDR(CURRENT$OBJECT)
        IM$LOW$LIMIT = LOW$THRES
        IM$HIGH$LIMIT = HIGH$THRES
        IM$REPLACE$VALUE = 249
        IM$LABEL$TRACE = 0
        CALL IMMAIN(IMAGE$RELABEL,IMERR)
        IF (IMERR .NE. ' ')
     *  THEN
          FATAL$ERROR = .TRUE.
          RETURN
        ENDIF
```

```
            CELL$COUNT = CELL$COUNT+1
            CELL$TYPE(CURRENT$OBJECT) = 0
            CELL$REJECTED(CURRENT$OBJECT) = .FALSE.
C
C     ********** COPY IMAGE BUFFER 1 TO IMAGE BUFFER 2 *************
C
            CALL IMMAIN(IMAGE$COPY$1$2,IMERR)
            IF (IMERR .NE. ' ')
      *     THEN
               FATAL$ERROR = .TRUE.
               RETURN
            ENDIF
C
C     **************** PUT OUT THE IMAGE ****************
C
            CALL IMMAIN(IMAGE$PUT,IMERR)
            IF (IMERR .NE. ' ')
      *     THEN
               FATAL$ERROR = .TRUE.
               RETURN
            ENDIF
C
C     ****** CALL THE SUBROUTINE WHICH SEARCHES FOR THE NEXT OBJECT ******
C
            CALL SAQQ19(LOW$THRES,HIGH$THRES,X$STEP,Y$STEP,X$POS,Y$POS,
      *                 ADDR,XMIN,XMAX,YMIN,YMAX,END$FLAG,FATAL$ERROR)
            IF (FATAL$ERROR) RETURN
            IF (END$FLAG) RETURN
            CURRENT$OBJECT = CURRENT$OBJECT+1
            LAST$OBJECT = CURRENT$OBJECT
            CELL$ADDR(CURRENT$OBJECT) = ADDR
            CELL$TYPE(CURRENT$OBJECT) = -1
            CELL$REJECTED(CURRENT$OBJECT) = .TRUE.
            MASS(CURRENT$OBJECT) = IM$PIXEL$SUM+
      *                            TMP$AN$OFFSET
            AREA(CURRENT$OBJECT) = IM$PIXEL$COUNT
            GOTO 100
            ENDCC
CC              CELL ANALYSIS SYSTEMS, INC.
CC                 (C) COPYRIGHT 1986
CC***************************************************************
CC
CC    :PROGRAM NAME
CC    :SAQQ18
CC
CC    :SUBROUTINES
CC    :NONE
CC
CC    :CALLING SEQUENCE
CC    :SAQQ18(CURSOR$X$POS,CURSOR$Y$POS)
CC
CC    :PARAMETERS
CC    :CURSOR$X$POS - THE X COORDINATE OF THE CURRENT CURSOR LOCATION
CC    :CURSOR$Y$POS - THE Y COORDINATE OF THE CURRENT CURSOR LOCATION
CC
CC    :DESCRIPTION
CC    :SAQQ18 WILL CREATE A CURSOR IF NONE EXIST. IF A CURSOR EXISTS
CC    :THEN SAQQ18 WILL GET RID OF IT
CC
CC***************************************************************
CC########
            SUBROUTINE SAQQ18(CURSOR$X$POS,CURSOR$Y$POS)
            INTEGER*2 CURSOR$X$POS,CURSOR$Y$POS,START,END,
      *               I,L$VALUE
            LOGICAL*1 LGCL$VALUE
C
            EQUIVALENCE (L$VALUE,LGCL$VALUE)
C
            INCLUDE 'IMAGEL.FIN'
C
            START = 0
```

```
              END = 0
              L$VALUE = 0
C
C      ****** (CREATE/DELETE) THE HORIZONTAL LINE OF THE CURSOR ******
C
              START = CURSOR$X$POS-3
              IF (START .LT. 0) START=0
              END = CURSOR$X$POS+3
              IF (END .GT. 255) END=255
              DO 100 I=START,END
                LGCL$VALUE = IMAGEL(I,CURSOR$Y$POS)
                IF (L$VALUE+128 .GT. 255)
       *        THEN
                  L$VALUE = L$VALUE-128
                ELSE
                  L$VALUE = L$VALUE+128
                ENDIF
                IMAGEL(I,CURSOR$Y$POS) = LGCL$VALUE
   100        CONTINUE
C
C      ****** (CREATE/DELETE) THE VERTICAL LINE OF THE CURSOR ******
C
              START = CURSOR$Y$POS-3
              IF (START .LT. 0) START=0
              END = CURSOR$Y$POS+3
              IF (END .GT. 255) END=255
              DO 200 I=START,END
                LGCL$VALUE = IMAGEL(CURSOR$X$POS,I)
                IF (L$VALUE+128 .GT. 255)
       *        THEN
                  L$VALUE = L$VALUE-128
                ELSE
                  L$VALUE = L$VALUE+128
                ENDIF
                IMAGEL(CURSOR$X$POS,I) = LGCL$VALUE
   200        CONTINUE
              ENDCC
CC              CELL ANALYSIS SYSTEMS, INC.
CC                   (C) COPYRIGHT 1986
CC***************************************************************************
CC
CC      :PROGRAM NAME
CC      :SAQQ19
CC
CC      :SUBROUTINES
CC      :IMMAIN
CC      :IMOVBI
CC
CC      :CALLING SEQUENCE
CC      :SAQQ19(LOW$THRES,HIGH$THRES,X$STEP,Y$STEP,X$POS,Y$POS,ADDR,
CC              XMIN,XMAX,YMIN,YMAX,END$FLAG,FATAL$ERROR)
CC
CC      :PARAMETERS
CC      :LOW$THRES - THE LOW THRESHOLD VALUE
CC      :HIGH$THRES - THE HIGH THRESHOLD VALUE
CC      :X$STEP - THE PIXEL STEP IN THE X DIRECTION
CC      :Y$STEP - THE PIXEL STEP IN THE Y DIRECTION
CC      :X$POS - THE X COORDINATE OF THE LOCATION OF THE NEXT OBJECT
CC      :Y$POS - THE Y COORDINATE OF THE LOCATION OF THE NEXT OBJECT
CC      :ADDR - THE OFFSET OF THE NEXT OBJECT
CC      :XMIN - THE MINIMUM X POSITION OF THE NEXT OBJECT
CC      :XMAX - THE MAXIMUM X POSITION OF THE NEXT OBJECT
CC      :YMIN - THE MINIMUM Y POSITION OF THE NEXT OBJECT
CC      :YMAX - THE MAXIMUM Y POSITION OF THE NEXT OBJECT
CC      :END$FLAG - A FLAG THAT SPECIFIES IF NO MORE OBJECTS WERE FOUND
CC                    IN THE CURRENT IMAGE
CC      :FATAL$ERROR - A FLAG THAT SPECIFIES IF A "FATAL'(I.E. SERIOUS)
CC                    ERROR OCCURRED WHILE IN SAQQ19
CC
CC      :DESCRIPTION
CC      :SAQQ19 FINDS THE NEXT OBJECT IN THE IMAGE, IF ANY.
```

```
CC
CC****************************************************************
CC########
      SUBROUTINE SAQQ19(LOW$THRES,HIGH$THRES,X$STEP,Y$STEP,
     *                  X$POS,Y$POS,ADDR,XMIN,XMAX,YMIN,YMAX,
     *                  END$FLAG,FATAL$ERROR)
C
      INTEGER*2 LOW$THRES,HIGH$THRES,X$STEP,Y$STEP,X$POS,Y$POS,
     *          ADDR,XMIN,XMAX,YMIN,YMAX,I,IMG$LINE(256),VALUE,
     *          XLEN,YLEN
C
      LOGICAL*1 END$FLAG,FATAL$ERROR
C
      INCLUDE 'SAQCDT.FIN'
      INCLUDE 'IMAGED.FIN'
      INCLUDE 'IMAGEL.FIN'
      INCLUDE 'SCREEN.FIN'
C
C     ************ INITIALIZE THE APPROPRIATE VARIABLES ************
C
      ADDR = 0
      XMIN = 0
      XMAX = 0
      YMIN = 0
      YMAX = 0
      I = 0
      VALUE = 0
      XLEN = 0
      YLEN = 0
      END$FLAG = .FALSE.
      FATAL$ERROR = .FALSE.
C
C     ********** FIND THE NEXT OBJECT IN THE CURRENT IMAGE **********
C
 100  CALL IMOVBI(256,IMAGEL(0,Y$POS),IMG$LINE(0))
      DO 200 I=X$POS,255,X$STEP
         X$POS = I
         VALUE = IMG$LINE(I)
         IF (VALUE .GE. LOW$THRES .AND. VALUE .LE. HIGH$THRES)
     *   THEN
            ADDR = Y$POS*256+X$POS
            GOTO 300
         ENDIF
 200  CONTINUE
      X$POS = 2
      Y$POS = Y$POS+Y$STEP
      IF (Y$POS .GT. 255)
     *   THEN
            END$FLAG = .TRUE.
            RETURN
         ELSE
            GOTO 100
         ENDIF
C
C     ********** RELABEL THE OBJECT TO SEE IF IT'S THE RIGHT *********
C     ********** SIZE AND IT'S NOT TOUCHING A BOUNDARY       *********
C
 300  IM$X$DIM = 256
      IM$Y$DIM = 256
      IM$LINEAR$OFFSET = ADDR
      IM$LOW$LIMIT = LOW$THRES
      IM$HIGH$LIMIT = HIGH$THRES
      IM$REPLACE$VALUE = 248
      IM$LABEL$TRACE = 0
C
C     *************** RELABEL THE OBJECT ****************
C
      CALL IMMAIN(IMAGE$RELABEL,IMERR)
      IF (IMERR .NE. ' ')
     *   THEN
C
```

```
C
C         ********** CHECK FOR STACK OVERFLOW ERROR **********
C
          IF (IMERR .EQ. 'R1')
     *    THEN
             CALL IMMAIN(IMAGE$COPY$1$2,IMERR)
             IF (IMERR .NE. ' ')
     *       THEN
                FATAL$ERROR = .TRUE.
                RETURN
             ENDIF
             X$POS = X$POS+X$STEP
             GOTO 100
          ENDIF
          FATAL$ERROR = .TRUE.
          RETURN
       ENDIF
C
C         ********** CHECK SIZE AND BOUNDARY CRITERIA ***********]
C
          YMIN = IM$LABEL$BOUNDARY(1)
          XMIN = IM$LABEL$BOUNDARY(2)
          YMAX = IM$LABEL$BOUNDARY(3)
          XMAX = IM$LABEL$BOUNDARY(4)
          XLEN = (XMAX-XMIN)+1
          YLEN = (YMAX-YMIN)+1
          IF ((IM$EDGE$CODE .NE. 0) .OR.
     *        (XLEN .LT. PCSG$XDIM$MIN) .OR.
     *        (YLEN .LT. PCSG$YDIM$MIN) .OR.
     *        (XLEN .GT. PCSG$XDIM$MAX) .OR.
     *        (YLEN .GT. PCSG$YDIM$MAX) .OR.
     *        (2*XLEN+YLEN .LT. PCSG$DIAM$SUM$MIN) .OR.
     *        (2*XLEN+YLEN .GT. PCSG$DIAM$SUM$MAX))
     *    THEN
             CALL IMMAIN(IMAGE$COPY$1$2,IMERR)
             IF (IMERR .NE. ' ')
     *       THEN
                FATAL$ERROR = .TRUE.
                RETURN
             ENDIF
             X$POS = X$POS+X$STEP
             GOTO 100
          ENDIF
C
C         ********* COPY IMAGE BUFFER 2 TO IMAGE BUFFER 1 ***********
C
          CALL IMMAIN(IMAGE$COPY$2$1,IMERR)
          IF (IMERR .NE. ' ')
     *    THEN
             FATAL$ERROR = .TRUE.
             RETURN
          ENDIF
C
C         ***************** PUT OUT THE IMAGE ******************
C
          CALL IMMAIN(IMAGE$PUT,IMERR)
          IF (IMERR .NE. ' ')
     *    THEN
             FATAL$ERROR = .TRUE.
             RETURN
          ENDIF
       ENDCC
CC           CELL ANALYSIS SYSTEMS, INC.
CC              (C) COPYRIGHT 1986
CC***************************************************************
CC
CC      :PROGRAM NAME
CC      :SAQQ21
CC
CC      :SUBROUTINES
```

```
CC
CC      :CALLING SEQUENCE
CC      :SAQQ21(LOW$THRES,HIGH$THRES,X$STEP,Y$STEP,X$POS,Y$POS,ADDR,
CC              XMIN,XMAX,YMIN,YMAX,END$FLAG,FATAL$ERROR)
CC
CC      :PARAMETERS
CC      :LOW$THRES - THE LOW THRESHOLD VALUE
CC      :HIGH$THRES - THE HIGH THRESHOLD VALUE
CC      :X$STEP - THE PIXEL STEP IN THE X DIRECTION
CC      :Y$STEP - THE PIXEL STEP IN THE Y DIRECTION
CC      :X$POS - THE X COORDINATE OF THE LOCATION OF THE NEXT OBJECT
CC      :Y$POS - THE Y COORDINATE OF THE LOCATION OF THE NEXT OBJECT
CC      :ADDR - THE OFFSET OF THE NEXT OBJECT
CC      :XMIN - THE MINIMUM X POSITION OF THE NEXT OBJECT
CC      :XMAX - THE MAXIMUM X POSITION OF THE NEXT OBJECT
CC      :YMIN - THE MINIMUM Y POSITION OF THE NEXT OBJECT
CC      :YMAX - THE MAXIMUM Y POSITION OF THE NEXT OBJECT
CC      :END$FLAG - A FLAG THAT SPECIFIES IF NO MORE OBJECTS WERE FOUND
CC                  IN THE CURRENT IMAGE
CC      :FATAL$ERROR - A FLAG THAT SPECIFIES IF A "FATAL'(I.E. SERIOUS)
CC                     ERROR OCCURRED WHILE IN SAQQ21
CC
CC      :DESCRIPTION
CC      :SAQQ21 FINDS THE NEXT OBJECT IN THE IMAGE, IF ANY.
CC
CC*****************************************************************
CC########
        SUBROUTINE SAQQ21(LOW$THRES,HIGH$THRES,X$STEP,Y$STEP,
     *                   X$POS,Y$POS,ADDR,XMIN,XMAX,YMIN,YMAX,
     *                   END$FLAG,FATAL$ERROR)
C
        INTEGER*2 LOW$THRES,HIGH$THRES,X$STEP,Y$STEP,X$POS,Y$POS,
     *            ADDR,XMIN,XMAX,YMIN,YMAX,I,IMG$LINE(256),VALUE,
     *            XLEN,YLEN
C
        LOGICAL*1 END$FLAG,FATAL$ERROR
C
        INCLUDE 'SAQCCD.FIN'
        INCLUDE 'IMAGED.FIN'
        INCLUDE 'IMAGEL.FIN'
        INCLUDE 'SCREEN.FIN'
C
C       ************* INITIALIZE THE APPROPRIATE VARIABLES *************
C
        ADDR = 0
        XMIN = 0
        XMAX = 0
        YMIN = 0
        YMAX = 0
        I = 0
        VALUE = 0
        XLEN = 0
        YLEN = 0
        END$FLAG = .FALSE.
        FATAL$ERROR = .FALSE.
C
C       ********** FIND THE NEXT OBJECT IN THE CURRENT IMAGE **********
C
 100    CALL IMOVBI(256,IMAGEL(0,Y$POS),IMG$LINE(0))
        DO 200 I=X$POS,255,X$STEP
           X$POS = I
           VALUE = IMG$LINE(I)
           IF (VALUE .GE. LOW$THRES .AND. VALUE .LE. HIGH$THRES)
     *     THEN
              ADDR = Y$POS*256+X$POS
              GOTO 300
           ENDIF
 200    CONTINUE
        X$POS = 2
        Y$POS = Y$POS+Y$STEP
        IF (Y$POS .GT. 255)
```

```
      *     THEN
                ENDSFLAG = .TRUE.
                RETURN
              ELSE
                GOTO 100
              ENDIF
C
C           ********** RELABEL THE OBJECT TO SEE IF IT'S THE RIGHT *********
C           ********** SIZE AND IT'S NOT TOUCHING A BOUNDARY       *********
C
  300         IM$X$DIM = 256
              IM$Y$DIM = 256
              IM$LINEAR$OFFSET = ADDR
              IM$LOW$LIMIT = LOW$THRES
              IM$HIGH$LIMIT = HIGH$THRES
              IM$REPLACE$VALUE = 248
              IM$LABEL$TRACE = 0
C
C           *************** RELABEL THE OBJECT ****************
C
              CALL IMMAIN(IMAGE$RELABEL,IMERR)
              IF (IMERR .NE. ' ')
      *       THEN
C
C               ********** CHECK FOR STACK OVERFLOW ERROR **********
C
                IF (IMERR .EQ. 'R1')
      *         THEN
                  CALL IMMAIN(IMAGE$COPY$1$2,IMERR)
                  IF (IMERR .NE. ' ')
      *           THEN
                    FATAL$ERROR = .TRUE.
                    RETURN
                  ENDIF
                  X$POS = X$POS+X$STEP
                  GOTO 100
                ENDIF
                FATAL$ERROR = .TRUE.
                RETURN
              ENDIF
C
C           ********** CHECK SIZE AND BOUNDARY CRITERIA ***********]
C
              YMIN = IM$LABEL$BOUNDARY(1)
              XMIN = IM$LABEL$BOUNDARY(2)
              YMAX = IM$LABEL$BOUNDARY(3)
              XMAX = IM$LABEL$BOUNDARY(4)
              XLEN = (XMAX-XMIN)+1
              YLEN = (YMAX-YMIN)+1
              IF ((IM$EDGE$CODE .NE. 0) .OR.
      *          (IM$PIXEL$SUM .LT. 9000) .OR.
      *          (IM$PIXEL$SUM .GT. 17000) .OR.
      *          (IM$PIXEL$COUNT .LT. 75) .OR.
      *          (IM$PIXEL$COUNT .GT. 300) .OR.
      *          (XLEN .LT. PCCSG$XDIM$MIN) .OR.
      *          (YLEN .LT. PCCSG$YDIM$MIN) .OR.
      *          (XLEN .GT. PCCSG$XDIM$MAX) .OR.
      *          (YLEN .GT. PCCSG$YDIM$MAX) .OR.
      *          (2*XLEN+YLEN .LT. PCCSG$DIAM$SUM$MIN) .OR.
      *          (2*XLEN+YLEN .GT. PCCSG$DIAM$SUM$MAX))
      *       THEN
                CALL IMMAIN(IMAGE$COPY$1$2,IMERR)
                IF (IMERR .NE. ' ')
      *         THEN
                  FATAL$ERROR = .TRUE.
                  RETURN
                ENDIF
                X$POS = X$POS+X$STEP
                GOTO 100
              ENDIF
C
```

```
C .         ********** COPY IMAGE BUFFER 2 TO IMAGE BUFFER 1 **********
C
            CALL IMMAIN(IMAGE$COPY$2$1,IMERR)
            IF (IMERR .NE. ' ')
     *      THEN
               FATAL$ERROR = .TRUE.
               RETURN
            ENDIF
C
C           ***************** PUT OUT THE IMAGE *****************
C
            CALL IMMAIN(IMAGE$PUT,IMERR)
            IF (IMERR .NE. ' ')
     *      THEN
               FATAL$ERROR = .TRUE.
               RETURN
            ENDIF
            ENDCC
CC              CELL ANALYSIS SYSTEMS, INC.
CC              (C) COPYRIGHT 1986
CC******************************************************************
CC
CC      :PROGRAM NAME
CC      :SAQQ22
CC
CC      :SUBROUTINES
CC      :CNARST
CC      :CNSTAR
CC      :IMMAIN
CC      :SCREEN
CC      :SYERR
CC
CC      :CALLING SEQUENCE
CC      :SAQQ22(SCRN$NAME,XY$COUNTER,XY$COORDS,FATAL$ERROR)
CC
CC      :PARAMETERS
CC      :SCRN$NAME - SCREEN NAME OF THE CURRENT SCREEN
CC      :XY$COUNTER - A VARIABLES THAT SPECIFIES THE NUMBER OF XY COORDINATES
CC      :XY$COORDS - A TWO-DIMENSIONAL ARRAY THAT CONTAINS THE
CC                    COORDINATES DATA
CC      :FATAL$ERROR - A FLAG THAT SPECIFIES IF A 'FATAL'(I.E. SERIOUS)
CC                    ERROR OCCURRED INSIDE THIS SUBROUTINE
CC
CC      :DESCRIPTION
CC      :SAQQ22 DISPLAYS AND SORTS THE XY COORDINATES
CC
CC******************************************************************
CC########
        SUBROUTINESAQQ22(SCRN$NAME,XY$COUNTER,XY$COORDS,FATAL$ERROR)
        CHARACTER*1 ERR$MESSAGE
        CHARACTER*2 VAR$ENDING(48)
        CHARACTER*4 CURSOR$POSITION
        CHARACTER*6 XCHAR,YCHAR,SCRN$NAME
        CHARACTER*9 READ$INPUT$VALUE
        CHARACTER*20 CURR$XY$STRING
        CHARACTER*32 ERR$ONE,ERR$TWO
        INTEGER*2 XY$COUNTER,XY$COORDS(3,512)
        INTEGER*2 COORDS(3,512),END,I,J,TEMP$ID,TEMP$X,TEMP$Y,
     *            CURRENT$END,X,Y,CURRENT$INDEX
        REAL*4 EUCL$DIST(512),CURRENT$X,CURRENT$Y,TEMP$DIST
        LOGICAL*1 FATAL$ERROR
        INCLUDE 'IMAGED.FIN'
        INCLUDE 'SCREEN.FIN'
        DATA VAR$ENDING
     *       /'01','02','03','04','05','06','07','08',
     *        '09','10','11','12','13','14','15','16',
     *        '17','18','19','20','21','22','23','24',
     *        '25','26','27','28','29','30','31','32',
     *        '33','34','35','36','37','38','39','40',
     *        '41','42','43','44','45','46','47','48'/
C
```

```
C
C         ********** INITIALIZE THE APPROPRIATE VARIABLES **********
C
          ERR$MESSAGE = ' '
          CURSOR$POSITION = 'XY11'
          SCREEN$NAME = SCRN$NAME
          XCHAR = ' '
          YCHAR = ' '
          READ$INPUT$VALUE = ' '
          CURR$XY$STRING = ' '
          ERR$ONE = ' '
          ERR$TWO = ' '
          END = 0
          I = 0
          J = 0
          TEMP$ID = 0
          TEMP$X = 0
          TEMP$Y = 0
          CURRENT$END = 0
          X = 0
          Y = 0
          CURRENT$X = 0.0
          CURRENT$Y = 0.0
          TEMP$DIST = 0.0
          CURRENT$INDEX = 0
          FATAL$ERROR = .FALSE.
          DO 5 I=1,512
             EUCL$DIST(I) = 0.0
    5     CONTINUE
          DO 25 I=1,XY$COUNTER
             COORDS(1,I) = XY$COORDS(1,I)
             COORDS(2,I) = XY$COORDS(2,I)
             COORDS(3,I) = XY$COORDS(3,I)
   25     CONTINUE
C
C         ********** SORT THE XY COORDINATES BY ID NUMBER **********
C
          END = XY$COUNTER
          DO 100 I=1,XY$COUNTER-1
             DO 200 J=2,END
                IF (COORDS(1,J) .LT. COORDS(1,J-1))
     *          THEN
                   TEMP$ID = COORDS(1,J-1)
                   TEMP$X = COORDS(2,J-1)
                   TEMP$Y = COORDS(3,J-1)
                   COORDS(1,J-1) = COORDS(1,J)
                   COORDS(2,J-1) = COORDS(2,J)
                   COORDS(3,J-1) = COORDS(3,J)
                   COORDS(1,J) = TEMP$ID
                   COORDS(2,J) = TEMP$X
                   COORDS(3,J) = TEMP$Y
                ENDIF
  200        CONTINUE
             END = END-1
  100     CONTINUE
          CURRENT$INDEX = 1
          IF (XY$COUNTER .GT. 42)
     *    THEN
             CURRENT$END = 42
          ELSE
             CURRENT$END = XY$COUNTER
          ENDIF
C
C         ************ OUTPUT THE COORDINATE DATA *************
C
          DO 300 I=1,CURRENT$END
             FIELD$NAME = 'ID'//VAR$ENDING(I)
             DATA$AREA(1) = COORDS(1,I)
             CALL SCREEN(PUT$FIELD,SCREEN$NAME,FIELD$NAME,
     *                   DATA$AREA,SCERR)
             IF (SCERR .NE. NO$SCREEN$ERROR)
```

```
*              CALL SYERR(PUT$FIELD,SCREEN$NAME,FIELD$NAME,SCERR,
*                         'PUT FIELD')
           FIELD$NAME = 'XC'//VAR$ENDING(I)
           DATA$AREA(1) = COORDS(2,I)
           CALL SCREEN(PUT$FIELD,SCREEN$NAME,FIELD$NAME,
*                      DATA$AREA,SCERR)
           IF (SCERR .NE. NO$SCREEN$ERROR)
*              CALL SYERR(PUT$FIELD,SCREEN$NAME,FIELD$NAME,SCERR,
*                         'PUT FIELD')
           FIELD$NAME = 'YC'//VAR$ENDING(I)
           DATA$AREA(1) = COORDS(3,I)
           CALL SCREEN(PUT$FIELD,SCREEN$NAME,FIELD$NAME,
*                      DATA$AREA,SCERR)
           IF (SCERR .NE. NO$SCREEN$ERROR)
*              CALL SYERR(PUT$FIELD,SCREEN$NAME,FIELD$NAME,SCERR,
*                         'PUT FIELD')
300     CONTINUE
        IF (CURRENT$END .LT. 42)
*       THEN
           DO 400 I=CURRENT$END+1,42
             FIELD$NAME = 'ID'//VAR$ENDING(I)
             CALL SCREEN(KILL$FIELD,SCREEN$NAME,FIELD$NAME,
*                        DATA$AREA,SCERR)
             IF (SCERR .NE. NO$SCREEN$ERROR)
*                CALL SYERR(KILL$FIELD,SCREEN$NAME,FIELD$NAME,SCERR,
*                           'KILL FIELD')
             FIELD$NAME = 'XC'//VAR$ENDING(I)
             CALL SCREEN(KILL$FIELD,SCREEN$NAME,FIELD$NAME,
*                        DATA$AREA,SCERR)
             IF (SCERR .NE. NO$SCREEN$ERROR)
*                CALL SYERR(KILL$FIELD,SCREEN$NAME,FIELD$NAME,SCERR,
*                           'KILL FIELD')
             FIELD$NAME = 'YC'//VAR$ENDING(I)
             CALL SCREEN(KILL$FIELD,SCREEN$NAME,FIELD$NAME,
*                        DATA$AREA,SCERR)
             IF (SCERR .NE. NO$SCREEN$ERROR)
*                CALL SYERR(KILL$FIELD,SCREEN$NAME,FIELD$NAME,SCERR,
*                           'KILL FIELD')
400     CONTINUE
        ENDIF
C*************************************************************
C
C
C              ERROR MESSAGE HANDLING CODE
C
C*************************************************************
500     IF (ERR$MESSAGE .EQ. 'C')
*       THEN
           ERR$ONE = ' '
           ERR$TWO = ' '
        ENDIF
        IF (ERR$MESSAGE .EQ. 'C' .OR.
*           ERR$MESSAGE .EQ. 'W')
*       THEN
           FIELD$NAME = 'ERR1'
           CALL CNSTAR(32,ERR$ONE,DATA$AREA)
           CALL SCREEN(PUT$FIELD,SCREEN$NAME,FIELD$NAME,
*                      DATA$AREA,SCERR)
           IF (SCERR .NE. NO$SCREEN$ERROR)
*              CALL SYERR(PUT$FIELD,SCREEN$NAME,FIELD$NAME,SCERR,
*                         'PUT FIELD')
           FIELD$NAME = 'ERR2'
           CALL CNSTAR(32,ERR$TWO,DATA$AREA)
           CALL SCREEN(PUT$FIELD,SCREEN$NAME,FIELD$NAME,
*                      DATA$AREA,SCERR)
           IF (SCERR .NE. NO$SCREEN$ERROR)
*              CALL SYERR(PUT$FIELD,SCREEN$NAME,FIELD$NAME,SCERR,
*                         'PUT FIELD')
        ENDIF
        IF (ERR$MESSAGE .EQ. 'C') ERR$MESSAGE = ' '
        IF (ERR$MESSAGE .EQ. 'W') ERR$MESSAGE = 'C'
        IF (ERR$MESSAGE .NE. 'C') ERR$MESSAGE = ' '
```

```
C
C       ******* IF A 'FATAL' ERROR OCCURRED THEN EXIT THE SUBROUTINE *******
C
        IF (FATAL$ERROR)
     *  THEN
C
C           ************ KILL THE CURRENT SCREEN'S FIELDS ************
C
            DATA$AREA(1) = 90
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *          CALL SYERR(GROUP$KILL$FIELD,SCREEN$NAME,FIELD$NAME,SCERR,
     *                     'GROUP KILL FIELD')
            RETURN
        ENDIF
C
C       *************** SET CURSOR *******************
C
        FIELD$NAME = CURSOR$POSITION
        CALL SCREEN(SET$CURSOR,SCREEN$NAME,FIELD$NAME,
     *              DATA$AREA,SCERR)
        IF (SCERR .NE. NO$SCREEN$ERROR)
     *      CALL SYERR(SET$CURSOR,SCREEN$NAME,FIELD$NAME,SCERR,
     *                 'SET CURSOR')
C
C       ************** READ INPUT ****************
C
        CALL SCREEN(READ$INPUT,SCREEN$NAME,FIELD$NAME,
     *              DATA$AREA,SCERR)
        IF (SCERR .EQ. SCREEN$ESCAPE .OR.
     *      SCERR .EQ. SCREEN$FUNCTION .OR.
     *      SCERR .EQ. SCREEN$DATA)
     *  THEN
            CONTINUE
        ELSE
            CALL SYERR(READ$INPUT,SCREEN$NAME,FIELD$NAME,SCERR,
     *                 'READ INPUT')
        ENDIF
        CALL CNARST(9,DATA$AREA,READ$INPUT$VALUE)
        IF (SCERR .EQ. SCREEN$ESCAPE) READ$INPUT$VALUE = 'EXIT'
C****************************************************************
C
C              CODE TO HANDLE THE EXIT COMMAND
C
C****************************************************************
        IF (READ$INPUT$VALUE .EQ. 'EXIT')
     *  THEN
            IF (ERR$MESSAGE .EQ. 'C')
     *      THEN
                ERR$ONE = ' '
                ERR$TWO = ' '
                FIELD$NAME = 'ERR1'
                CALL CNSTAR(32,ERR$ONE,DATA$AREA)
                CALL SCREEN(PUT$FIELD,SCREEN$NAME,FIELD$NAME,
     *                      DATA$AREA,SCERR)
                IF (SCERR .NE. NO$SCREEN$ERROR)
     *              CALL SYERR(PUT$FIELD,SCREEN$NAME,FIELD$NAME,SCERR,
     *                         'PUT FIELD')
                FIELD$NAME = 'ERR2'
                CALL CNSTAR(32,ERR$TWO,DATA$AREA)
                CALL SCREEN(PUT$FIELD,SCREEN$NAME,FIELD$NAME,
     *                      DATA$AREA,SCERR)
                IF (SCERR .NE. NO$SCREEN$ERROR)
     *              CALL SYERR(PUT$FIELD,SCREEN$NAME,FIELD$NAME,SCERR,
     *                         'PUT FIELD')
            ENDIF
            DATA$AREA(1) = 90
            CALL SCREEN(GROUP$KILL$FIELD,SCREEN$NAME,FIELD$NAME,
     *                  DATA$AREA,SCERR)
            IF (SCERR .NE. NO$SCREEN$ERROR)
     *          CALL SYERR(GROUP$KILL$FIELD,SCREEN$NAME,FIELD$NAME,SCERR,
```

```
     *              'GROUP KILL FIELD')
              RETURN
            ENDIF
C*****************************************************************
C
C              CODE TO HANDLE THE XY COMMAND
C
C*****************************************************************
          IF (READ$INPUT$VALUE .EQ. 'XY')
     *    THEN
C
C          ********** READ CHANNEL VALUES **********
C
  600       CALL IMMAIN(IMAGE$CHANNELS,IMERR)
            IF (IMERR .NE. ' ')
     *      THEN
               FATAL$ERROR = .TRUE.
               GOTO 500
            ENDIF
C
C          ********** CONVERT CHANNEL VALUES TO INTEGER *********
C
            X = INT((IM$CHANNEL$ONE*0.125)+0.5)
            Y = INT((IM$CHANNEL$TWO*0.125)+0.5)
            WRITE(XCHAR,700)X
            WRITE(YCHAR,700)Y
  700       FORMAT(I6)
            CURR$XY$STRING = 'X='//XCHAR//'     '//'Y='//YCHAR
C
C          ******** PUT OUT THE X AND Y VALUES ********
C
            FIELD$NAME = 'ERR1'
            CALL CNSTAR(32,CURR$XY$STRING//'                ',
     *                  DATA$AREA)
            CALL SCREEN(PUT$FIELD,SCREEN$NAME,FIELD$NAME,
     *                  DATA$AREA,SCERR)
            IF (SCERR .NE. NO$SCREEN$ERROR)
     *         CALL SYERR(PUT$FIELD,SCREEN$NAME,FIELD$NAME,SCERR,
     *                    'PUT FIELD')
            ERR$MESSAGE = 'C'
C
C          **** CHECK TO SEE IF THE USER WANTS ANOTHER CHANNEL READING ****
C
            CALL SCREEN(READ$KEYBOARD,SCREEN$NAME,FIELD$NAME,
     *                  DATA$AREA,SCERR)
            IF (SCERR .EQ. READ$KEYBOARD) GOTO 600
            CURSOR$POSITION = 'XY11'
            GOTO 500
          ENDIF
C*****************************************************************
C
C              CODE TO HANDLE THE NEAREST COMMAND
C
C*****************************************************************
          IF (READ$INPUT$VALUE .EQ. 'NEAREST')
     *    THEN
C
C          ******** CALCULATE THE EUCLIDEAN DISTANCE FOR THE COORDINATES *****
C
            CALL IMMAIN(IMAGE$CHANNELS,IMERR)
            IF (IMERR .NE. ' ')
     *      THEN
               FATAL$ERROR = .TRUE.
               GOTO 500
            ENDIF
            CURRENT$X = IM$CHANNEL$ONE*0.125
            CURRENT$Y = IM$CHANNEL$TWO*0.125
            DO 800 I=1,XY$COUNTER
               EUCL$DIST(I) = SQRT(((CURRENT$X-COORDS(2,I))**2)+
     *                         ((CURRENT$Y-COORDS(3,I))**2))
  800       CONTINUE
```

```
C
C        ******* SORT THE COORDINATES BASED ON EUCLIDEAN DISTANCE ******
C
         END = XY$COUNTER
         DO 900 I=1,XY$COUNTER-1
           DO 1000 J=2,END
             IF (EUCL$DIST(J) .LT. EUCL$DIST(J-1))
     *       THEN
               TEMP$ID = COORDS(1,J-1)
               TEMP$X = COORDS(2,J-1)
               TEMP$Y = COORDS(3,J-1)
               TEMP$DIST = EUCL$DIST(J-1)
               COORDS(1,J-1) = COORDS(1,J)
               COORDS(2,J-1) = COORDS(2,J)
               COORDS(3,J-1) = COORDS(3,J)
               EUCL$DIST(J-1) = EUCL$DIST(J)
               COORDS(1,J) = TEMP$ID
               COORDS(2,J) = TEMP$X
               COORDS(3,J) = TEMP$Y
               EUCL$DIST(J) = TEMP$DIST
             ENDIF
1000       CONTINUE
           END = END-1
 900     CONTINUE
C
C        ************ PUT OUT THE COORDINATE DATA *************
C
         DO 1100 I=1,CURRENT$END
           J = CURRENT$INDEX+(I-1)
           FIELD$NAME = 'ID'//VAR$ENDING(I)
           DATA$AREA(1) = COORDS(1,J)
           CALL SCREEN(PUT$FIELD,SCREEN$NAME,FIELD$NAME,
     *                 DATA$AREA,SCERR)
           IF (SCERR .NE. NO$SCREEN$ERROR)
     *       CALL SYERR(PUT$FIELD,SCREEN$NAME,FIELD$NAME,SCERR,
     *                  'PUT FIELD')
           FIELD$NAME = 'XC'//VAR$ENDING(I)
           DATA$AREA(1) = COORDS(2,J)
           CALL SCREEN(PUT$FIELD,SCREEN$NAME,FIELD$NAME,
     *                 DATA$AREA,SCERR)
           IF (SCERR .NE. NO$SCREEN$ERROR)
     *       CALL SYERR(PUT$FIELD,SCREEN$NAME,FIELD$NAME,SCERR,
     *                  'PUT FIELD')
           FIELD$NAME = 'YC'//VAR$ENDING(I)
           DATA$AREA(1) = COORDS(3,J)
           CALL SCREEN(PUT$FIELD,SCREEN$NAME,FIELD$NAME,
     *                 DATA$AREA,SCERR)
           IF (SCERR .NE. NO$SCREEN$ERROR)
     *       CALL SYERR(PUT$FIELD,SCREEN$NAME,FIELD$NAME,SCERR,
     *                  'PUT FIELD')
1100     CONTINUE
         CURSOR$POSITION = 'XY07'
         GOTO 500
       ENDIF
C***********************************************************************
C
C           CODE TO HANDLE THE X COMMAND
C
C***********************************************************************
       IF (READ$INPUT$VALUE .EQ. 'X')
     * THEN
C
C        ******* SORT THE COORDINATES BASED ON X COORDINATE ******
C
         END = XY$COUNTER
         DO 1200 I=1,XY$COUNTER-1
           DO 1300 J=2,END
             IF ((COORDS(2,J) .LT. COORDS(2,J-1)) .OR.
     *           (COORDS(2,J) .EQ. COORDS(2,J-1) .AND.
     *            COORDS(3,J) .LT. COORDS(3,J-1)))
     *       THEN
```

```
                        TEMP$ID = COORDS(1,J-1)
                        TEMP$X = COORDS(2,J-1)
                        TEMP$Y = COORDS(3,J-1)
                        COORDS(1,J-1) = COORDS(1,J)
                        COORDS(2,J-1) = COORDS(2,J)
                        COORDS(3,J-1) = COORDS(3,J)
                        COORDS(1,J) = TEMP$ID
                        COORDS(2,J) = TEMP$X
                        COORDS(3,J) = TEMP$Y
                      ENDIF
 1300           CONTINUE
                END = END-1
 1200         CONTINUE
C
C             ************** PUT OUT THE COORDINATE DATA ***************
C
              DO 1400 I=1,CURRENT$END
                J = CURRENT$INDEX+(I-1)
                FIELD$NAME = 'ID'//VAR$ENDING(I)
                DATA$AREA(1) = COORDS(1,J)
                CALL SCREEN(PUT$FIELD,SCREEN$NAME,FIELD$NAME,
     *                      DATA$AREA,SCERR)
                IF (SCERR .NE. NO$SCREEN$ERROR)
     *            CALL SYERR(PUT$FIELD,SCREEN$NAME,FIELD$NAME,SCERR,
     *                       'PUT FIELD')
                FIELD$NAME = 'XC'//VAR$ENDING(I)
                DATA$AREA(1) = COORDS(2,J)
                CALL SCREEN(PUT$FIELD,SCREEN$NAME,FIELD$NAME,
     *                      DATA$AREA,SCERR)
                IF (SCERR .NE. NO$SCREEN$ERROR)
     *            CALL SYERR(PUT$FIELD,SCREEN$NAME,FIELD$NAME,SCERR,
     *                       'PUT FIELD')
                FIELD$NAME = 'YC'//VAR$ENDING(I)
                DATA$AREA(1) = COORDS(3,J)
                CALL SCREEN(PUT$FIELD,SCREEN$NAME,FIELD$NAME,
     *                      DATA$AREA,SCERR)
                IF (SCERR .NE. NO$SCREEN$ERROR)
     *            CALL SYERR(PUT$FIELD,SCREEN$NAME,FIELD$NAME,SCERR,
     *                       'PUT FIELD')
 1400         CONTINUE
              CURSOR$POSITION = 'XY08'
              GOTO 500
            ENDIF
C****************************************************************************
C
C           CODE TO HANDLE THE Y COMMAND
C
C****************************************************************************
            IF (READ$INPUT$VALUE .EQ. 'Y')
     *        THEN
C
C             ******* SORT THE COORDINATES BASED ON THE Y COORDINATE *******
C
              END = XY$COUNTER
              DO 1500 I=1,XY$COUNTER-1
                DO 1600 J=2,END
                  IF ((COORDS(3,J) .LT. COORDS(3,J-1)) .OR.
     *                (COORDS(3,J) .EQ. COORDS(3,J-1) .AND.
     *                 COORDS(2,J) .LT. COORDS(2,J-1)))
     *              THEN
                      TEMP$ID = COORDS(1,J-1)
                      TEMP$X = COORDS(2,J-1)
                      TEMP$Y = COORDS(3,J-1)
                      COORDS(1,J-1) = COORDS(1,J)
                      COORDS(2,J-1) = COORDS(2,J)
                      COORDS(3,J-1) = COORDS(3,J)
                      COORDS(1,J) = TEMP$ID
                      COORDS(2,J) = TEMP$X
                      COORDS(3,J) = TEMP$Y
                    ENDIF
 1600           CONTINUE
```

```
              END = END-1
1500       CONTINUE
C
C          ************** PUT OUT THE COORDINATE DATA ***************
C
           DO 1700 I=1,CURRENT$END
              J = CURRENT$INDEX+(I-1)
              FIELD$NAME = 'ID'//VAR$ENDING(I)
              DATA$AREA(1) = COORDS(1,J)
              CALL SCREEN(PUT$FIELD,SCREEN$NAME,FIELD$NAME,
     *                    DATA$AREA,SCERR)
              IF (SCERR .NE. NO$SCREEN$ERROR)
     *           CALL SYERR(PUT$FIELD,SCREEN$NAME,FIELD$NAME,SCERR,
     *                      'PUT FIELD')
              FIELD$NAME = 'XC'//VAR$ENDING(I)
              DATA$AREA(1) = COORDS(2,J)
              CALL SCREEN(PUT$FIELD,SCREEN$NAME,FIELD$NAME,
     *                    DATA$AREA,SCERR)
              IF (SCERR .NE. NO$SCREEN$ERROR)
     *           CALL SYERR(PUT$FIELD,SCREEN$NAME,FIELD$NAME,SCERR,
     *                      'PUT FIELD')
              FIELD$NAME = 'YC'//VAR$ENDING(I)
              DATA$AREA(1) = COORDS(3,J)
              CALL SCREEN(PUT$FIELD,SCREEN$NAME,FIELD$NAME,
     *                    DATA$AREA,SCERR)
              IF (SCERR .NE. NO$SCREEN$ERROR)
     *           CALL SYERR(PUT$FIELD,SCREEN$NAME,FIELD$NAME,SCERR,
     *                      'PUT FIELD')
1700       CONTINUE
           CURSOR$POSITION = 'XY09'
           GOTO 500
        ENDIF
C***********************************************************************
C
C          CODE TO HANDLE THE FIELD# COMMAND
C
C***********************************************************************
        IF (READ$INPUT$VALUE .EQ. 'FIELD#')
     *  THEN
C
C          ******** SORT THE COORDINATES BASED ON ID NUMBER *******
C
           END = XY$COUNTER
           DO 1800 I=1,XY$COUNTER-1
              DO 1900 J=2,END
                 IF (COORDS(1,J) .LT. COORDS(1,J-1))
     *           THEN
                    TEMP$ID = COORDS(1,J-1)
                    TEMP$X = COORDS(2,J-1)
                    TEMP$Y = COORDS(3,J-1)
                    COORDS(1,J-1) = COORDS(1,J)
                    COORDS(2,J-1) = COORDS(2,J)
                    COORDS(3,J-1) = COORDS(3,J)
                    COORDS(1,J) = TEMP$ID
                    COORDS(2,J) = TEMP$X
                    COORDS(3,J) = TEMP$Y
                 ENDIF
1900          CONTINUE
              END = END-1
1800       CONTINUE
C
C          ************** PUT OUT THE COORDINATE DATA *************
C
           DO 2000 I=1,CURRENT$END
              J = CURRENT$INDEX+(I-1)
              FIELD$NAME = 'ID'//VAR$ENDING(I)
              DATA$AREA(1) = COORDS(1,J)
              CALL SCREEN(PUT$FIELD,SCREEN$NAME,FIELD$NAME,
     *                    DATA$AREA,SCERR)
              IF (SCERR .NE. NO$SCREEN$ERROR)
     *           CALL SYERR(PUT$FIELD,SCREEN$NAME,FIELD$NAME,SCERR,
```

```
       *                          'PUT FIELD')
                 FIELD$NAME = 'XC'//VAR$ENDING(I)
                 DATA$AREA(1) = COORDS(2,J)
                 CALL SCREEN(PUT$FIELD,SCREEN$NAME,FIELD$NAME,
       *                     DATA$AREA,SCERR)
                 IF (SCERR .NE. NO$SCREEN$ERROR)
       *            CALL SYERR(PUT$FIELD,SCREEN$NAME,FIELD$NAME,SCERR,
       *                       'PUT FIELD')
                 FIELD$NAME = 'YC'//VAR$ENDING(I)
                 DATA$AREA(1) = COORDS(3,J)
                 CALL SCREEN(PUT$FIELD,SCREEN$NAME,FIELD$NAME,
       *                     DATA$AREA,SCERR)
                 IF (SCERR .NE. NO$SCREEN$ERROR)
       *            CALL SYERR(PUT$FIELD,SCREEN$NAME,FIELD$NAME,SCERR,
       *                       'PUT FIELD')
  2000      CONTINUE
            CURSOR$POSITION = 'XY10'
            GOTO 500
         ENDIF
C******************************************************************
C
C
C            CODE TO HANDLE THE PAGE-DOWN COMMAND
C
C******************************************************************
         IF (READ$INPUT$VALUE .EQ. 'PAGE-DOWN')
       *    THEN
C
C
C         ********* CHECK TO SEE IF THERE IS ANY MORE DATA ********
C         ********* TO PAGE DOWN TO                        ********
C
            IF (CURRENT$END .LT. 42 .OR.
       *        CURRENT$INDEX+41 .EQ. XY$COUNTER)
       *       THEN
              ERR$ONE = 'THERE IS NO MORE DATA.'
              ERR$TWO = ' '
              ERR$MESSAGE = 'W'
              CURSOR$POSITION = 'XY23'
              GOTO 500
            ENDIF
C
C         *********** UPDATE THE BEGINNING AND ENDING INDICES *********
C
            CURRENT$INDEX = CURRENT$INDEX+42
            IF (CURRENT$INDEX+41 .GT. XY$COUNTER)
       *       THEN
              CURRENT$END = (XY$COUNTER-CURRENT$INDEX)+1
            ELSE
              CURRENT$END = 42
            ENDIF
C
C         ********* PUT PUT THE NEXT PAGE OF DATA **********
C
            DO 2100 I=1,CURRENT$END
              J = CURRENT$INDEX+(I-1)
              FIELD$NAME = 'ID'//VAR$ENDING(I)
              DATA$AREA(1) = COORDS(1,J)
              CALL SCREEN(PUT$FIELD,SCREEN$NAME,FIELD$NAME,
       *                  DATA$AREA,SCERR)
              IF (SCERR .NE. NO$SCREEN$ERROR)
       *         CALL SYERR(PUT$FIELD,SCREEN$NAME,FIELD$NAME,SCERR,
       *                    'PUT FIELD')
              FIELD$NAME = 'XC'//VAR$ENDING(I)
              DATA$AREA(1) = COORDS(2,J)
              CALL SCREEN(PUT$FIELD,SCREEN$NAME,FIELD$NAME,
       *                  DATA$AREA,SCERR)
              IF (SCERR .NE. NO$SCREEN$ERROR)
       *         CALL SYERR(PUT$FIELD,SCREEN$NAME,FIELD$NAME,SCERR,
       *                    'PUT FIELD')
              FIELD$NAME = 'YC'//VAR$ENDING(I)
              DATA$AREA(1) = COORDS(3,J)
```

```
              CALL SCREEN(PUT$FIELD,SCREEN$NAME,FIELD$NAME,
     *                   DATA$AREA,SCERR)
              IF (SCERR .NE. NO$SCREEN$ERROR)
     *         CALL SYERR(PUT$FIELD,SCREEN$NAME,FIELD$NAME,SCERR,
     *                   'PUT FIELD')
2100      CONTINUE
C
C         ********,IF THERE IS NOT A FULL PAGE OF DATA ********
C         ********  THEN KILL THE NECESSARY FIELDS       ********
C
          IF (CURRENT$END .LT. 42)
     *    THEN
             DO 2200 I=CURRENT$END+1,42
                FIELD$NAME = 'ID'//VAR$ENDING(I)
                CALL SCREEN(KILL$FIELD,SCREEN$NAME,FIELD$NAME,
     *                      DATA$AREA,SCERR)
                IF (SCERR .NE. NO$SCREEN$ERROR)
     *            CALL SYERR(KILL$FIELD,SCREEN$NAME,FIELD$NAME,SCERR,
     *                       'KILL FIELD')
                FIELD$NAME = 'XC'//VAR$ENDING(I)
                CALL SCREEN(KILL$FIELD,SCREEN$NAME,FIELD$NAME,
     *                      DATA$AREA,SCERR)
                IF (SCERR .NE. NO$SCREEN$ERROR)
     *            CALL SYERR(KILL$FIELD,SCREEN$NAME,FIELD$NAME,SCERR,
     *                       'KILL FIELD')
                FIELD$NAME = 'YC'//VAR$ENDING(I)
                CALL SCREEN(KILL$FIELD,SCREEN$NAME,FIELD$NAME,
     *                      DATA$AREA,SCERR)
                IF (SCERR .NE. NO$SCREEN$ERROR)
     *            CALL SYERR(KILL$FIELD,SCREEN$NAME,FIELD$NAME,SCERR,
     *                       'KILL FIELD')
2200         CONTINUE
          ENDIF
          CURSOR$POSITION = 'XY23'
          GOTO 500
       ENDIF
C*******************************************************************
C
C           CODE TO HANDLE THE PAGE-UP COMMAND
C
C*******************************************************************
       IF (READ$INPUT$VALUE .EQ. 'PAGE-UP')
     * THEN
C
C      ******** CHECK TO SEE IF THERE IS ANY MORE DATA ********
C      ******** TO PAGE UP TO                          ********
C
       IF (CURRENT$INDEX .EQ. 1)
     * THEN
          ERR$ONE = 'THERE IS NO MORE DATA.'
          ERR$TWO = ' '
          ERR$MESSAGE = 'W'
          CURSOR$POSITION = 'XY22'
          GOTO 500
       ENDIF
C
C      ********* UPDATE THE STARTING AND ENDING INDICES **********
C
       IF (CURRENT$INDEX-42 .LE. 1)
     * THEN
          CURRENT$INDEX = 1
       ELSE
          CURRENT$INDEX = CURRENT$INDEX-42
       ENDIF
C
C      ******** IF THE OLD PAGE DID NOT HAVE 48 COORDINATES   ********
C      ******** THEN UNKILL THE KILLED FIELDS FOR THE NEW PAGE ********
C
       IF (CURRENT$END .LT. 42)
     * THEN
          DO 2300 I=CURRENT$END+1,42
```

```
              FIELD$NAME = 'ID'//VAR$ENDING(I)
              CALL SCREEN(UN$KILL$FIELD,SCREEN$NAME,FIELD$NAME,
     *                    DATA$AREA,SCERR)
              IF (SCERR .NE. NO$SCREEN$ERROR)
     *          CALL SYERR(UN$KILL$FIELD,SCREEN$NAME,FIELD$NAME,SCERR,
     *                     'UNKILL FIELD')
              FIELD$NAME = 'XC'//VAR$ENDING(I)
              CALL SCREEN(UN$KILL$FIELD,SCREEN$NAME,FIELD$NAME,
     *                    DATA$AREA,SCERR)
              IF (SCERR .NE. NO$SCREEN$ERROR)
     *          CALL SYERR(UN$KILL$FIELD,SCREEN$NAME,FIELD$NAME,SCERR,
     *                     'UNKILL FIELD')
              FIELD$NAME = 'YC'//VAR$ENDING(I)
              CALL SCREEN(UN$KILL$FIELD,SCREEN$NAME,FIELD$NAME,
     *                    DATA$AREA,SCERR)
              IF (SCERR .NE. NO$SCREEN$ERROR)
     *          CALL SYERR(UN$KILL$FIELD,SCREEN$NAME,FIELD$NAME,SCERR,
     *                     'UNKILL FIELD')
 2300       CONTINUE
          ENDIF
          CURRENT$END = 42
C
C
C         ********* PUT PUT THE NEXT PAGE OF DATA **********
C
          DO 2400 I=1,42
            J = CURRENT$INDEX+(I-1)
            FIELD$NAME = 'ID'//VAR$ENDING(I)
            DATA$AREA(1) = COORDS(1,J)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            FIELD$NAME = 'XC'//VAR$ENDING(I)
            DATA$AREA(1) = COORDS(2,J)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
            FIELD$NAME = 'YC'//VAR$ENDING(I)
            DATA$AREA(1) = COORDS(3,J)
            CALL SCREEN(PUT$FIELD,SCREEN$NAME,FIELD$NAME,
     *                  DATA$AREA,SCERR)
            IF (SCERR .NE. NO$SCREEN$ERROR)
     *        CALL SYERR(PUT$FIELD,SCREEN$NAME,FIELD$NAME,SCERR,
     *                   'PUT FIELD')
 2400     CONTINUE
          CURSOR$POSITION = 'XY22'

GOTO 500
        ENDIF
        END
CC
CC
CC              CELL ANALYSIS SYSTEMS, INC.
CC                 (C) COPYRIGHT 1986
CC*************************************************************************
CC
CC      :PROGRAM NAME
CC      :SAQQ23
CC
CC      :SUBROUTINES
CC      :SCREEN
CC
CC      :CALLING SEQUENCE
CC      :SAQQ23(SCRN$NAME,DNA$CONV$VALUE,ANALYSIS$TOTAL,PICO$HIST,TYPE$SELECTED,
CC              XSCALE$NUM,CURRENT$BIN,FIRST$PEAK$MASS,SEC$PEAK$MASS,
CC              SEC$PEAK$INDEX,SEC$PEAK$AREA,PICO$HIST)
CC
CC      :PARAMETERS
CC      :SCRN$NAME - THE CURRENT SCREEN NAME
CC      :DNA$CONV$VALUE - THE DNA CONVERSION VALUE
```

```
CC       :ANALYSIS$TOTAL - THE NUMBER OF CELLS THAT HAVE BEEN MEASURED
CC       :PICO$HIST - AN ARRAY THAT CONTAINS THE RAW HISTOGRAM OF THE
CC                 CELL MASS DATA
CC       :TYPE$SELECTED - A LOGICAL ARRAY THAT SPECIFIES THE TYPES SELECTED
CC       :XSCALE$NUM - THE X AXIS SCALE NUMBER(I.E. 16,32, OR 64)
CC       :CURRENT$BIN - THE CURRENT BIN NUMBER
CC       :FIRST$PEAK$MASS - THE MASS OF THE FIRST PEAK
CC       :SEC$PEAK$MASS - THE MASS OF THE SECOND PEAK
CC       :SEC$PEAK$INDEX - THE INDEX OF THE SECOND PEAK
CC       :SEC$PEAK$AREA - THE AREA OF THE SECOND PEAK
CC       :PICO$HIST - AN ARRAY CONTAINING THE GREY LEVEL COUNTS OF THE CELL
CC                 MASSES
CC
CC       :DESCRIPTION
CC       :SAQQ23 CALCULATES THE DATA FOR THE SECOND PEAK
CC
CC************************************************************************
CC#########
      SUBROUTINE SAQQ23(SCRN$NAME,DNA$CONV$VALUE,ANALYSIS$TOTAL,
     *                  PICO$HIST,TYPE$SELECTED,XSCALE$NUM,
     *                  CURRENT$BIN,FIRST$PEAK$MASS,SEC$PEAK$MASS,
     *                  SEC$PEAK$INDEX,SEC$PEAK$AREA)
      CHARACTER*6 SCRN$NAME
      INTEGER*2 XSCALE$NUM,CURRENT$BIN,ANALYSIS$TOTAL,
     *          PICO$HIST(*),START,END,MAX,MAX$VALUE,I,J,
     *          AREA$VALUE1
      INTEGER*4 AREA$VALUE2
      REAL*4 FIRST$PEAK$MASS,SEC$PEAK$MASS,SEC$PEAK$INDEX,
     *       SEC$PEAK$AREA,LOW,HIGH,COUNT,DIFF,DNA$CONV$VALUE
      REAL*8 ASUM,AREA$CONV
      LOGICAL*1 TYPE$SELECTED(*)
C
      EQUIVALENCE (AREA$VALUE2,AREA$VALUE1)
C
      INCLUDE 'SAQCCD.FIN'
      INCLUDE 'SAQCDT.FIN'
      INCLUDE 'SCREEN.FIN'
C
      SCREEN$NAME = SCRN$NAME
      BUCKET = 0
      START = 0
      END = 0
      MAX = 0
      MAX$VALUE = 0
      DIFF = 0.0
      I = 0
      J = 0
      AREA$VALUE1 = 0
      AREA$VALUE2 = 0
      LOW = 0.0
      HIGH = 0.0
      ASUM = 0.0
      AREA$CONV = 31.8*((40.0/100.0)**2)
      WIDTH = INT(0.1*PCCD$PICOMASS)
      HALF$WIDTH = WIDTH/2
      IF (XSCALE$NUM .EQ. 16)
     *  THEN
        HIGH = (0.5*CURRENT$BIN)
        LOW = HIGH - 0.5
      ELSEIF (XSCALE$NUM .EQ. 32)
     *  THEN
        HIGH = CURRENT$BIN
        LOW = HIGH - 1.0
      ELSE
        HIGH = (2.0*CURRENT$BIN)
        LOW = HIGH - 2.0
      ENDIF
      END = INT(HIGH*10)
      START = INT(LOW*10)
      IF (START .EQ. 0) START=1
      IF (XSCALE$NUM .EQ. 16 .AND. END .NE. 160)
```

```
      IF (SCERR .NE. NO$SCREEN$ERROR)
   *    CALL SYERR(PUT$FIELD,SCREEN$NAME,FIELD$NAME,
   *               SCERR,'PUT FIELD')
      ENDCC
CC              CELL ANALYSIS SYSTEMS, INC.
CC              (C) COPYRIGHT 1986
CC************************************************************************
CC
CC      :PROGRAM NAME
CC      :SAQQ24
CC
CC      :SUBROUTINES
CC      :SCREEN
CC
CC      :CALLING SEQUENCE
CC      :SAQQ24(SCRN$NAME,AREA$STATUS)
CC
CC      :PARAMETERS
CC      :SCRN$NAME - THE CURRENT SCREEN NAME
CC      :AREAS$STATUS - AN INTEGER ARRAY THAT KEEPS TRACK OF WHERE
CC                     AREA 1 AND AREA 2 ARE LOCATED
CC
CC      :DESCRIPTION
CC      :SAQQ24 KILLS AND UNKILLS THE APPROPRIATE HISTOGRAM VERTICAL FIELDS
CC
CC************************************************************************
CC#######
      SUBROUTINE SAQQ24(SCRN$NAME,AREA$STATUS)
      CHARACTER*2 VAR$ENDING1(39),VAR$ENDING3(32)
      CHARACTER*4 FIELD1,FIELD2,FIELD3
      CHARACTER*(*) SCRN$NAME
      INTEGER*2 I,AREA$STATUS(*)
C
      INCLUDE 'SCREEN.FIN'
C
      DATA VAR$ENDING1
     *   /'25','26','27','28','29','30','31','32','33','34',
     *    '35','36','37','38','39','40','41','42','43','44',
     *    '45','46','47','48','49','50','51','52','53','54',
     *    '55','56','57','58','59','60','61','62','63'/,
     *   VAR$ENDING3
     *   /'01','02','03','04','05','06','07','08','09','10',
     *    '11','12','13','14','15','16','17','18','19','20',
     *    '21','22','23','24','25','26','27','28','29','30',
     *    '31','32'/
C
      FIELD1 = ' '
      FIELD2 = ' '
      FIELD3 = ' '
      SCREEN$NAME = SCRN$NAME
      I = 0
C
C
C     ************ DISPLAY THE APPROPRIATE VERTICLE FIELDS ************
      DO 100 I=1,32
        IF (AREA$STATUS(I) .EQ. 0)
     *    THEN
          FIELD1 = 'CS'//VAR$ENDING1(I+7)
          FIELD2 = 'AB'//VAR$ENDING3(I)
          FIELD3 = 'AC'//VAR$ENDING3(I)
        ELSEIF (AREA$STATUS(I) .EQ. 1)
     *    THEN
          FIELD1 = 'AB'//VAR$ENDING3(I)
          FIELD2 = 'CS'//VAR$ENDING1(I+7)
          FIELD3 = 'AC'//VAR$ENDING3(I)
        ELSE
          FIELD1 = 'AC'//VAR$ENDING3(I)
          FIELD2 = 'CS'//VAR$ENDING1(I+7)
          FIELD3 = 'AB'//VAR$ENDING3(I)
        ENDIF
```

```
              FIELD$NAME = FIELD1
              CALL SCREEN(UN$KILL$FIELD,SCREEN$NAME,FIELD$NAME,
     *                    DATA$AREA,SCERR)
              IF (SCERR .NE. NO$SCREEN$ERROR)
     *          CALL SYERR(UN$KILL$FIELD,SCREEN$NAME,FIELD$NAME,
     *                     SCERR,'UNKILL FIELD')
              FIELD$NAME = FIELD2
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,
     *                     SCERR,'KILL FIELD')
              FIELD$NAME = FIELD3
              CALL SCREEN(KILL$FIELD,SCREEN$NAME,FIELD$NAME,
     *                    DATA$AREA,SCERR)
              IF (SCERR .NE. NO$SCREEN$ERROR)
     *          CALL SYERR(KILL$FIELD,SCREEN$NAME,FIELD$NAME,
     *                     SCERR,'KILL FIELD')
 100      CONTINUE
          ENDCC
CC                CELL ANALYSIS SYSTEMS, INC.
CC                (C) COPYRIGHT 1986
CC*************************************************************
CC
CC        :PROGRAM NAME
CC        :SAQQ25
CC
CC        :SUBROUTINES
CC.       :IMMAIN
CC        :SCREEN
CC
CC        :CALLING SEQUENCE
CC        :SAQQ25(SCRN$NAME,CAL$LIGHT$LEVEL,FATAL$ERROR)
CC
CC        :PARAMETERS
CC        :SCRN$NAME - THE CURRENT SCREEN NAME
CC        :CAL$LIGHT$LEVEL - THE CURRENT PEAK LIGHT LEVEL VALUE
CC        :FATAL$ERROR - A LOGICAL VARIABLE THAT SPECIFIES IF A 'FATAL'
CC                      (I.E. SERIOUS) ERROR OCCURRED WHILE IN SAQQ25
CC
CC        :DESCRIPTION
CC        :SAQQ25 PERFORMS THE CK-LIGHT FUNCTION FOR THE ANALYSIS SCREEN
CC
CC*************************************************************
CC#########
          SUBROUTINE SAQQ25(SCRN$NAME,CAL$LIGHT$LEVEL,FATAL$ERROR)
C
          CHARACTER*(*) SCRN$NAME
          INTEGER*2 CAL$LIGHT$LEVEL
          LOGICAL*1 FATAL$ERROR
C
          INTEGER*2 I
C
          INCLUDE 'IMAGED.FIN'
          INCLUDE 'SCREEN.FIN'
C
          SCREEN$NAME = SCRN$NAME
          CAL$LIGHT$LVEL = 0
          I = 0
          FATAL$ERROR = .FALSE.
          CAL$LIGHT$LEVEL = 0
C
C         ************** SELECT THE FIRST TABLES ***************
C
          IM$TABLE$NUM = 1
          DO 100 I=1,4
```

```
          IM$GROUP$NUM = I
          CALL IMMAIN(IMAGE$SELECT$TABLE,IMERR)
          IF (IMERR .NE. ' ')
     *    THEN
             FATAL$ERROR = .TRUE.
             RETURN
          ENDIF
 100   CONTINUE
C
C      ************* START IMAGE ACQUISITION **************
C
       CALL IMMAIN(IMAGE$START$ACQ,IMERR)
       IF (IMERR .NE. ' ')
     * THEN
          FATAL$ERROR = .TRUE.
          RETURN
       ENDIF
C
C      ************ GET AN AVERAGED IMAGE **************
C
       CALL IMMAIN(IMAGE$GET$AVERAGE,IMERR)
       IF (IMERR .NE. ' ')
     * THEN
          FATAL$ERROR = .TRUE.
          RETURN
       ENDIF
C
C      ************* GET THE HISTOGRAM **************
C
       IM$HIST$SAMPLE = 1
       CALL IMMAIN(IMAGE$HISTOGRAM,IMERR)
       IF (IMERR .NE. ' ')
     * THEN
          FATAL$ERROR = .TRUE.
          RETURN
       ENDIF
C
C      ************ SMOOTH THE HISTOGRAM TO FIND THE PEAK ***********
C
       IM$SMOOTH$LOW$LIM = 0
       IM$SMOOTH$HIGH$LIM = 255
       IM$PKS$WANTED = 4
       CALL IMMAIN(IMAGE$SMOOTH$HIST,IMERR)
       IF (IMERR .NE. ' ')
     * THEN
          FATAL$ERROR = .TRUE.
          RETURN
       ENDIF
C
C      ********** PUT OUT THE PEAK LIGHT LEVEL VALUE **********
C
       I = IM$PKS$FOUND*2
       CAL$LIGHT$LEVEL = IM$VALLS$PKS(I)-1
       FIELD$NAME = 'AS42'
       DATA$AREA(1) = CAL$LIGHT$LEVEL
       CALL SCREEN(PUT$FIELD,SCREEN$NAME,FIELD$NAME,
     *             DATA$AREA,SCERR)
       IF (SCERR .NE. NO$SCREEN$ERROR)
     *    CALL SYERR(PUT$FIELD,SCREEN$NAME,FIELD$NAME,SCERR,
     *               'PUT FIELD')
C
C      ************** SELECT THE SECOND TABLES **************
C
       IM$TABLE$NUM = 2
       DO 200 I=1,4
          IM$GROUP$NUM = I
          CALL IMMAIN(IMAGE$SELECT$TABLE,IMERR)
          IF (IMERR .NE. ' ')
     *    THEN
```

```
              FATAL$ERROR = .TRUE.
              RETURN
           ENDIF
  200   CONTINUE
C
C        ************ START IMAGE ACQUISITION *************
C
        CALL IMMAIN(IMAGE$START$ACQ,IMERR)
        IF (IMERR .NE. ' ')
       * THEN
            FATAL$ERROR = .TRUE.
            RETURN
         ENDIF
         ENDCC
CC              CELL ANALYSIS SYSTEMS, INC.
CC                  (C) COPYRIGHT 1986
CC*******************************************************************
CC
CC      :PROGRAM NAME
CC      :SAQQ26
CC
CC      :SUBROUTINES
CC      :SAQQ24
CC      :SCREEN
CC
CC      :CALLING SEQUENCE
CC      :SAQQ26(SCRN$NAME,CURRENT$BIN,HIST$STRING,AREAS$STATUS,AREA1$COUNT,
CC              AREA2$COUNT)
CC
CC      :PARAMETERS
CC      :SCRN$NAME    - THE CURRENT SCREEN NAME
CC      :CURRENT$BIN  - BUCKET NUMBER OF SECOND PEAK. THIS VALUE WILL BE
CC                      ZERO IF THE SECOND PEAK HAS NOT BEEN SELECTED
CC      :HIST$STRING  - A CHARACTER STRING THAT STORES THE SYMBOLS FOR
CC                      THE HISTOGRAM BUCKETS
CC      :AREAS$STATUS - AN INTEGER ARRAY THAT KEEPS TRACK OF WHERE
CC                      AREA 1 AND AREA 2 ARE LOCATED
CC      :AREA1$COUNT  - THE CELL COUNT IN AREA 1
CC      :AREA2$COUNT  - THE CELL COUNT IN AREA 2
CC
CC      :DESCRIPTION
CC      :SAQQ26 CLEARS AWAY AREA 1 AND AREA 2 DATA
CC
CC*******************************************************************
CC********
        SUBROUTINE SAQQ26(SCRN$NAME,CURRENT$BIN,HIST$STRING,
       *                  AREAS$STATUS,AREA1$COUNT,AREA2$COUNT)
C
        CHARACTER*(*) SCRN$NAME
        CHARACTER*(*) HIST$STRING
        INTEGER*2 AREAS$STATUS(*),AREA1$COUNT,AREA2$COUNT,CURRENT$BIN
        CHARACTER*1 UP$ARROW
C
        INTEGER*2 I
C
        INCLUDE 'SCREEN.FIN'
C
        DATA UP$ARROW/Z'5E'/
C
C        *************** INITIALIZE VARIABLES ******************
C
        SCREEN$NAME = SCRN$NAME
        HIST$STRING = ' '
        I = 0
        AREA1$COUNT = 0
        AREA2$COUNT = 0
        DO 100 I=1,32
           AREAS$STATUS(I) = 0
  100   CONTINUE
C
C        **************** UPDATE THE SCREEN'S FIELDS ****************
```

```
C
              IF (CURRENT$BIN .NE. 0)
       *      THEN
                 HIST$STRING(CURRENT$BIN:CURRENT$BIN) = UP$ARROW
              ENDIF
              FIELD$NAME = 'AS79'
              CALL CNSTAR(32,HIST$STRING,DATA$AREA)
              CALL SCREEN(PUT$FIELD,SCREEN$NAME,FIELD$NAME,
       *                  DATA$AREA,SCERR)
              IF (SCERR .NE. NO$SCREEN$ERROR)
       *         CALL SYERR(PUT$FIELD,SCREEN$NAME,FIELD$NAME,SCERR,
       *                    'PUT FIELD')
              FIELD$NAME = 'AS76'
              DATA$AREA(1) = 0
              CALL SCREEN(PUT$FIELD,SCREEN$NAME,FIELD$NAME,
       *                  DATA$AREA,SCERR)
              IF (SCERR .NE. NO$SCREEN$ERROR)
       *         CALL SYERR(PUT$FIELD,SCREEN$NAME,FIELD$NAME,SCERR,
       *                    'PUT FIELD')
              FIELD$NAME = 'AS77'
              DATA$AREA(1) = 0
              CALL SCREEN(PUT$FIELD,SCREEN$NAME,FIELD$NAME,
       *                  DATA$AREA,SCERR)
              IF (SCERR .NE. NO$SCREEN$ERROR)
       *         CALL SYERR(PUT$FIELD,SCREEN$NAME,FIELD$NAME,SCERR,
       *                    'PUT FIELD')
C
C         ********* CALL THE SUBROUTINE THAT KILLS AND         **********
C         ********* AND UNKILLS THE APPROPRIATE VERTICAL FIELDS **********
C
              CALL SAQQ24(SCREEN$NAME,AREAS$STATUS)
              ENDC
CC                 CELL ANALYSIS SYSTEMS, INC.
CC                    (C) COPYRIGHT 1986
CC***************************************************************************
CC
CC        :PROGRAM NAME
CC        :SAQQ27
CC
CC        :SUBROUTINES
CC
CC***************************************************************************
CC#########
              SUBROUTINE SAQQ27()
C
              CHARACTER*4 CURSOR$POSITION
              CHARACTER*6 READ$INPUT$VALUE
C
              INCLUDE 'SAQCCD.FIN'
              INCLUDE 'SAQCDT.FIN'
              INCLUDE 'SCREEN.FIN'
C
C
C         ****************** GET THE SCREEN ******************
C
              SCREEN$NAME = 'QEN002'
              CALL SCREEN(GET$SCREEN,SCREEN$NAME,FIELD$NAME,
       *                  DATA$AREA,SCERR)
              IF (SCERR .NE. NO$SCREEN$ERROR)
       *         CALL SYERR(GET$SCREEN,SCREEN$NAME,FIELD$NAME,SCERR,
       *                    'GET SCREEN')
              READ$INPUT$VALUE = ' '
              CURSOR$POSITION = 'ZF02'
C
C         *************** PUT OUT VALUES ****************
C
              FIELD$NAME = 'ZC02'
              DATA$AREA(1) = PCCSG$LO$THRES
              CALL SCREEN(PUT$FIELD,SCREEN$NAME,FIELD$NAME,
       *                  DATA$AREA,SCERR)
              IF (SCERR .NE. NO$SCREEN$ERROR)
```

```
    *       CALL SYERR(PUT$FIELD,SCREEN$NAME,FIELD$NAME,SCERR,
    *                  'PUT FIELD')
            FIELD$NAME = 'ZC04'
            DATA$AREA(1) = PCCSG$HI$THRES
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                  'PUT FIELD')
            FIELD$NAME = 'ZC06'
            DATA$REAL = TMP$CAL$OFFSET
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                  'PUT FIELD')
            FIELD$NAME = 'ZC08'
            DATA$REAL = PCCD$CALIB$CELL$DNA
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                  'PUT FIELD')
            FIELD$NAME = 'ZA02'
            DATA$AREA(1) = PCSG$LO$THRES
            CALL SCREEN(PUT$FIELD,SCREEN$NAME,FIELD$NAME,
    *                  DATA$AREA,SCERR)
            IF (SCERR .NE. NO$SCREEN$ERROR)
CC      :SUBROUTINES
CC
CC*****************************************************************
CC#########
            SUBROUTINE SAQQ27()
C
            CHARACTER*4 CURSOR$POSITION
            CHARACTER*6 READ$INPUT$VALUE
C
            INCLUDE 'SAQCCD.FIN'
            INCLUDE 'SAQCDT.FIN'
            INCLUDE 'SCREEN.FIN'
C
C
C       ****************** GET THE SCREEN ******************
C
            SCREEN$NAME = 'QEN002'
            CALL SCREEN(GET$SCREEN,SCREEN$NAME,FIELD$NAME,
    *                  DATA$AREA,SCERR)
            IF (SCERR .NE. NO$SCREEN$ERROR)
    *          CALL SYERR(GET$SCREEN,SCREEN$NAME,FIELD$NAME,SCERR,
    *                  'GET SCREEN')
            READ$INPUT$VALUE = ' '
            CURSOR$POSITION = 'ZF02'
C
C       *************** PUT OUT VALUES ****************
C
            FIELD$NAME = 'ZC02'
            DATA$AREA(1) = PCCSG$LO$THRES
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                  'PUT FIELD')
            FIELD$NAME = 'ZC04'
            DATA$AREA(1) = PCCSG$HI$THRES
            CALL SCREEN(PUT$FIELD,SCREEN$NAME,FIELD$NAME,
    *                  DATA$AREA,SCERR)
            IF (SCERR .NE. NO$SCREEN$ERROR)
    *          CALL SYERR(PUT$FIELD,SCREEN$NAME,FIELD$NAME,SCERR,
    *                  'PUT FIELD')
            FIELD$NAME = 'ZC06'
```

```
            CALL SCREEN(PUT$FIELD,SCREEN$NAME,FIELD$NAME,
     *                 DATA$AREA,SCERR)
            IF (SCERR .NE. NO$SCREEN$ERROR)
     *         CALL SYERR(PUT$FIELD,SCREEN$NAME,FIELD$NAME,SCERR,
     *                    'PUT FIELD')
            FIELD$NAME = 'ZC08'
            DATA$REAL = PCCD$CALIB$CELL$DNA
            CALL SCREEN(PUT$FIELD,SCREEN$NAME,FIELD$NAME,
     *                 DATA$AREA,SCERR)
            IF (SCERR .NE. NO$SCREEN$ERROR)
     *         CALL SYERR(PUT$FIELD,SCREEN$NAME,FIELD$NAME,SCERR,
     *                    'PUT FIELD')
            FIELD$NAME = 'ZA02'
            DATA$AREA(1) = PCSG$LO$THRES
            CALL SCREEN(PUT$FIELD,SCREEN$NAME,FIELD$NAME,
     *                 DATA$AREA,SCERR)
            IF (SCERR .NE. NO$SCREEN$ERROR)

*         CALL SYERR(PUT$FIELD,SCREEN$NAME,FIELD$NAME,SCERR,
     *                    'PUT FIELD')
            FIELD$NAME = 'ZA04'
            DATA$AREA(1) = PCSG$HI$THRES
            CALL SCREEN(PUT$FIELD,SCREEN$NAME,FIELD$NAME,
     *                 DATA$AREA,SCERR)
            IF (SCERR .NE. NO$SCREEN$ERROR)
     *         CALL SYERR(PUT$FIELD,SCREEN$NAME,FIELD$NAME,SCERR,
     *                    'PUT FIELD')
            FIELD$NAME = 'ZA06'
            DATA$REAL = TMP$AN$OFFSET
            CALL SCREEN(PUT$FIELD,SCREEN$NAME,FIELD$NAME,
     *                 DATA$AREA,SCERR)
            IF (SCERR .NE. NO$SCREEN$ERROR)
     *         CALL SYERR(PUT$FIELD,SCREEN$NAME,FIELD$NAME,SCERR,
     *                    'PUT FIELD')
C ***********************************************************************
C
C
C              *************** SET CURSOR *****************
C
C
C ***********************************************************************
 100        FIELD$NAME = CURSOR$POSITION
            CALL SCREEN(SET$CURSOR,SCREEN$NAME,FIELD$NAME,
     *                 DATA$AREA,SCERR)
            IF (SCERR .NE. NO$SCREEN$ERROR)
     *         CALL SYERR(SET$CURSOR,SCREEN$NAME,FIELD$NAME,SCERR,
     *                    'SET CURSOR')
C ***********************************************************************
C
C              *************** READ INPUT *********************
C
C
C ***********************************************************************
            CALL SCREEN(READ$INPUT,SCREEN$NAME,FIELD$NAME,
     *                 DATA$AREA,SCERR)
            IF (SCERR .EQ. SCREEN$ESCAPE .OR.
     *          SCERR .EQ. SCREEN$FUNCTION .OR.
     *          SCERR .EQ. SCREEN$DATA)
     *      THEN
              CONTINUE
            ELSE
              CALL SYERR(READ$INPUT,SCREEN$NAME,FIELD$NAME,SCERR,
     *                   'READ INPUT')
            ENDIF
            CALL CNARST(6,DATA$AREA,READ$INPUT$VALUE)
            IF (READ$INPUT$VALUE .EQ. 'MAIN') RETURN
C***********************************************************************
C
C       CODE FOR SELECT FUNCTION
C
C***********************************************************************
            IF (READ$INPUT$VALUE .EQ. 'SELECT' .AND.
     *          SCERR .EQ. SCREEN$DATA)
```

```
  *    THEN
            FIELD$NAME = 'ZC02'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            PCCSG$LO$THRES = DATA$AREA(1)
            FIELD$NAME = 'ZC04'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            PCCSG$HI$THRES = DATA$AREA(1)
            FIELD$NAME = 'ZC06'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            TMP$CAL$OFFSET = DATA$REAL
            FIELD$NAME = 'ZC08'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            PCCD$CALIB$CELL$DNA = DATA$REAL
            FIELD$NAME = 'ZA02'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            PCSG$LO$THRES = DATA$AREA(1)
            FIELD$NAME = 'ZA04'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            PCSG$HI$THRES = DATA$AREA(1)
            FIELD$NAME = 'ZA06'
            CALL SCREEN(GET$FIELD,SCREEN$NAME,FIELD$NAME,
  *                     DATA$AREA,SCERR)
            IF (SCERR .NE. NO$SCREEN$ERROR)
  *           CALL SYERR(GET$FIELD,SCREEN$NAME,FIELD$NAME,SCERR,
  *                      'GET FIELD')
            TMP$AN$OFFSET = DATA$REAL
            CURSOR$POSITION = 'ZF02'
            GOTO 100
         ENDIF
         END
CC
CC              CELL ANALYSIS SYSTEMS, INC.
CC                  (C) COPYRIGHT 1986
CC****************************************************************
CC
CC       :PROGRAM NAME
CC       :SAQQ28
CC
CC       :SUBROUTINES
CC       :IMMAIN
CC       :SCREEN
CC
CC       :CALLING SEQUENCE
CC       :SAQQ28(SCRN$NAME,FATAL$ERROR)
```

```
CC
CC      :PARAMETER
CC      :SCRN$NAME - THE CURRENT SCREEN NAME
CC      :FATAL$ERROR - A LOGICAL FLAG THAT SPECIFIES IF A 'FATAL'(I.E SERIOUS)
CC                    ERROR OCCURRED WHILE IN SAQQ28
CC      :DESCRIPTION
CC      :SAQQ28 INITIALIZES THE COMMON BLOCK VARIABLES
CC·
CC*****************************************************************************
CC#########
        SUBROUTINE SAQQ28(SCRN$NAME,FATAL$ERROR)
        CHARACTER*6 SCRN$NAME
        LOGICAL*1 FATAL$ERROR
C
        INTEGER*2 I,K,IO$STATUS,TABLE(0:127)
C
        INCLUDE 'SAQCCD.FIN'
        INCLUDE 'SAQCDT.FIN'
        INCLUDE 'IMAGED.FIN'
        INCLUDE 'SCREEN.FIN'
C
        SCREEN$NAME = SCRN$NAME
        I = 0
        K = 0
        IO$STATUS = 0
C
        FATAL$ERROR = .FALSE.
        DO 100 I=1,512
           PCCD$CELLDATA(I) = 0
           PCCD$AREA(I) = 0
 100    CONTINUE
C
C       ************* INITIALIZE COMMON BLOCK VARIABLES **************
C
        PCCSG$LO$THRES = 35
        PCCSG$HI$THRES = 200
        PCCSG$XDIM$MIN = 5
        PCCSG$YDIM$MIN = 8
        PCCSG$XDIM$MAX = 50
        PCCSG$YDIM$MAX = 50
        PCCSG$DIAM$SUM$MAX = 768
        PCCSG$DIAM$SUM$MIN = 4
        PCCSG$X$STEP = 3
        PCCSG$Y$STEP = 5
        PCCSG$OD = 12.9
C
        PCCD$CELLCNT = 0
        PCCD$MEAN = 0.
        PCCD$PICOMASS = 0.0
        PCCD$CALIB$CELL$DNA = 5.959
C
        PCSG$STATE = 0
        PCSG$LO$THRES = 13
        PCSG$HI$THRES = 200
        PCSG$XDIM$MIN = 5
        PCSG$YDIM$MIN = 8
        PCSG$XDIM$MAX = 200
        PCSG$YDIM$MAX = 200
        PCSG$DIAM$SUM$MAX = 768
        PCSG$DIAM$SUM$MIN = 0
        PCSG$X$STEP = 3
        PCSG$Y$STEP = 5
        DO 200 I=1,6
           PCDT$COUNT(I) = 0
           PCDT$OFF$SCALE(I) = 0
 200    CONTINUE
        DO 300 I=1,6
           PCDT$MASS(I) = 0
           PCDT$AREA(I) = 0
           PCDT$CLASS(I) = -1
```

```
            PCDT$640(I) = 0
  300  CONTINUE
       TMP$CAL$OFFSET = 0.
       TMP$AN$OFFSET = 0.
C
C      ************** STOP IMAGE ACQUISITION *****************
C
       CALL IMMAIN(IMAGE$STOP$ACQ,IMERR)
       IF (IMERR .NE. ' ')
     * THEN
          FATAL$ERROR = .TRUE.
          RETURN
       ENDIF
C
C      ************ INITIALIZE THE IMAGE BOARD TABLES **************
C
       CALL IMMAIN(IMAGE$INIT$BOARD,IMERR)
       IF (IMERR .NE. ' ')
     * THEN
          FATAL$ERROR = .TRUE.
          RETURN
       ENDIF
C
C      *************** READ IN THE OPTICAL DENSITY TABLES ***************
C
       K = 1
       OPEN(50,FILE='C:\MICROPTH\FILES\OPTICAL.QDA',IOSTAT=IO$STATUS,
     *      STATUS='OLD',RECL=2,ACCESS='DIRECT',FORM='UNFORMATTED')
       IF (IO$STATUS .NE. 0)
     * THEN
          FATAL$ERROR = .TRUE.
          RETURN
       ENDIF
       DO 400 I=1,127,2
          READ(50,REC=K,IOSTAT=IO$STATUS) TABLE(I)
          IF (IO$STATUS .NE. 0)
     *    THEN
             FATAL$ERROR = .TRUE.
             RETURN
          ENDIF
          K = K+1
  400  CONTINUE
       DO 500 I=0,126,2
          READ(50,REC=K,IOSTAT=IO$STATUS) TABLE(I)
          K = K+1
  500  CONTINUE
       CLOSE(50)
       IM$TABLE$NUM = 2
       IM$GROUP$NUM = 4
       DO 600 I=0,127
         IM$TABLE(I+1) = TABLE(I)
  600  CONTINUE
       CALL IMMAIN(IMAGE$PUT$TABLE,IMERR)
       IF (IMERR .NE. ' ')
     * THEN
          FATAL$ERROR = .TRUE.
          RETURN
       ENDIF
       IM$TABLE$NUM = 1
       DO 700 I=1,4
          IM$GROUP$NUM = I
          CALL IMMAIN(IMAGE$SELECT$TABLE,IMERR)
          IF (IMERR .NE. ' ')
     *    THEN
             FATAL$ERROR = .TRUE.
             RETURN
          ENDIF
  700  CONTINUE
       CALL IMMAIN(IMAGE$GET,IMERR)
       IF (IMERR .NE. ' ')
```

```
    *     THEN
              FATAL$ERROR = .TRUE.
              RETURN
          ENDIF
          CALL IMMAIN(IMAGE$START$ACQ,IMERR)
          IF (IMERR .NE. ' ')
    *     THEN
              FATAL$ERROR = .TRUE.
              RETURN
          ENDIF
          END
CC
CC              CELL ANALYSIS SYSTEMS, INC.
CC                (C) COPYRIGHT 1986
CC*******************************************************************
CC
CC      :PROGRAM NAME
CC      :SAQQ29
CC
CC      :SUBROUTINES
CC      :SCREEN
CC
CC      :CALLING SEQUENCE
CC      :SAQQ29(SCRN$NAME,CAL$LIGHT$LEVEL,ANALYSIS$TOTAL,FIRST$PEAK$MASS,
CC              FIRST$PEAK$INDEX,SEC$PEAK$MASS,SEC$PEAK$INDEX)
CC
CC      :PARAMETERS
CC      :SCRN$NAME - THE CURRENT SCREEN NAME
CC      :CAL$LIGHT$LEVEL - THE LIGHT LEVEL
CC      :ANALYSIS$TOTAL - THE NUMBER OF CELLS THAT WERE CLASSFIED IN THE
CC                       ANALYSIS SCREEN
CC      :FIRST$PEAK$MASS - THE MASS OF THE FIRST PEAK
CC      :FIRST$PEAK$INDEX - THE INDEX OF THE FIRST PEAK
CC      :SEC$PEAK$MASS - THE MASS OF THE SECOND PEAK
CC      :SEC$PEAK$INDEX - THE INDEX OF THE SECOND PEAK
CC
CC      :DESCRIPTION
CC      :SAQQ29 UPDATES THE CALIBRATION AND ANALYSIS DATA ON THE MAIN SCREEN
CC
CC*******************************************************************
CC#########
          SUBROUTINE SAQQ29(SCRN$NAME,CAL$LIGHT$LEVEL,ANALYSIS$TOTAL,
    *                      FIRST$PEAK$MASS,FIRST$PEAK$INDEX,
    *                      SEC$PEAK$MASS,SEC$PEAK$INDEX)
          CHARACTER*6 SCRN$NAME
          INTEGER*2 ANALYSIS$TOTAL,CAL$LIGHT$LEVEL
          REAL*4 FIRST$PEAK$MASS,FIRST$PEAK$INDEX,SEC$PEAK$MASS,
    *          SEC$PEAK$INDEX
C
          INCLUDE 'SAQCCD.FIN'
          INCLUDE 'SAQCDT.FIN'
          INCLUDE 'SCREEN.FIN'
C
          SCREEN$NAME = SCRN$NAME
C
C         ********** UPDATE THE MAIN SCREEN'S STATUS FIELDS **********
C
          FIELD$NAME = 'MS10'
          DATA$AREA(1) = PCCD$CELLCNT
          CALL SCREEN(PUT$FIELD,SCREEN$NAME,FIELD$NAME,
    *                DATA$AREA,SCERR)
          IF (SCERR .NE. NO$SCREEN$ERROR)
    *        CALL SYERR(PUT$FIELD,SCREEN$NAME,FIELD$NAME,SCERR,
    *                   'PUT FIELD')
          FIELD$NAME = 'MS12'
          DATA$INTEGER$4 = PCCD$MEAN
          CALL SCREEN(PUT$FIELD,SCREEN$NAME,FIELD$NAME,
    *                DATA$AREA,SCERR)
          IF (SCERR .NE. NO$SCREEN$ERROR)
    *        CALL SYERR(PUT$FIELD,SCREEN$NAME,FIELD$NAME,SCERR,
    *                   'PUT FIELD')
```

```
       FIELD$NAME = 'MS14'
       DATA$AREA(1) = CAL$LIGHT$LEVEL
       CALL SCREEN(PUT$FIELD,SCREEN$NAME,FIELD$NAME,
*                  DATA$AREA,SCERR)
       IF (SCERR .NE. NO$SCREEN$ERROR)
*         CALL SYERR(PUT$FIELD,SCREEN$NAME,FIELD$NAME,SCERR,
*                    'PUT FIELD')
       FIELD$NAME = 'MS17'
       DATA$AREA(1) = ANALYSIS$TOTAL
       CALL SCREEN(PUT$FIELD,SCREEN$NAME,FIELD$NAME,
*                  DATA$AREA,SCERR)
       IF (SCERR .NE. NO$SCREEN$ERROR)
*         CALL SYERR(PUT$FIELD,SCREEN$NAME,FIELD$NAME,SCERR,
*                    'PUT FIELD')
       FIELD$NAME = 'MS19'
       DATA$REAL = FIRST$PEAK$MASS
       CALL SCREEN(PUT$FIELD,SCREEN$NAME,FIELD$NAME,
*                  DATA$AREA,SCERR)
       IF (SCERR .NE. NO$SCREEN$ERROR)
*         CALL SYERR(PUT$FIELD,SCREEN$NAME,FIELD$NAME,SCERR,
*                    'PUT FIELD')
       FIELD$NAME = 'MS21'
       DATA$REAL = FIRST$PEAK$INDEX
       CALL SCREEN(PUT$FIELD,SCREEN$NAME,FIELD$NAME,
*                  DATA$AREA,SCERR)
       IF (SCERR .NE. NO$SCREEN$ERROR)
*         CALL SYERR(PUT$FIELD,SCREEN$NAME,FIELD$NAME,SCERR,
*                    'PUT FIELD')
       FIELD$NAME = 'MS23'
       DATA$REAL = SEC$PEAK$MASS
       CALL SCREEN(PUT$FIELD,SCREEN$NAME,FIELD$NAME,
*                  DATA$AREA,SCERR)
       IF (SCERR .NE. NO$SCREEN$ERROR)
*         CALL SYERR(PUT$FIELD,SCREEN$NAME,FIELD$NAME,SCERR,
*                    'PUT FIELD')
       FIELD$NAME = 'MS25'
       DATA$REAL = SEC$PEAK$INDEX
       CALL SCREEN(PUT$FIELD,SCREEN$NAME,FIELD$NAME,
*                  DATA$AREA,SCERR)
       IF (SCERR .NE. NO$SCREEN$ERROR)
*         CALL SYERR(PUT$FIELD,SCREEN$NAME,FIELD$NAME,SCERR,
*                    'PUT FIELD')
       END
```

What is claimed is:

1. An interactive method for selecting a subpopulaion of cell objects from a population of cell objects and or measuring a subpopulation of malignant cell objects or a given measured parameter with a digital image rocessing means, said method comprising the steps of:

providing in real time an enlarged view of a field containing a plurality of malignant cell objects from the population of cell objects to a user-observer through the digital image processing means, visually selecting which of the plurality of cell objects have visual parameters identifying them for being placed into a selected subpopulation of malignant cell objects to be measured and rejecting from the subpopulation those cells objects being viewed and lacking the visual parameters, measuring only the selected malignant cell objects in the selected subpopulation for the measured parameter with a digital image processing means, and generating with a digital image processing means a quantitation based on the measured parameter for the selected malignant cell object subpopulation, including the generation of a parameter distribution of the measured parameter for the malignant cells showing a first peak and/or second peak for the selected subpopulation.

2. A method in accordance with claim 1 in which the step of selecting includes the step of gating the malignant cell objects into the subpopulation and in which the measuring step includes the measurement of DNA in the gated cell objects into a normal cell object subpopulation and into one of several malignant cell object subpopulations.

3. A method in accordance with claim 1 in which the classifying step includes the user classifying the cell objects into a normal cell object subpopulation and into one of several abnormal cell object subpopulations.

4. A method in accordance with claim 1 in which said subpopulation of the cell objects is a small fraction of the total population of cell objects.

* * * * *